US011057991B2

(12) United States Patent
Rogers et al.

(10) Patent No.: US 11,057,991 B2
(45) Date of Patent: Jul. 6, 2021

(54) WATERPROOF STRETCHABLE OPTOELECTRONICS

(71) Applicants: THE BOARD OF TRUSTEES OF THE UNIVERSITY OF ILLINOIS, Urbana, IL (US); TRUSTEES OF TUFTS COLLEGE, Medford, MA (US)

(72) Inventors: John A. Rogers, Wilmette, IL (US); Rak-Hwan Kim, Champaign, IL (US); Dae-Hyeong Kim, Urbana, IL (US); David L. Kaplan, Concord, MA (US); Fiorenzo G. Omenetto, Wakefield, MA (US)

(73) Assignees: The Board of Trustees of the University of Illinois, Urbana, IL (US); Trustees of Tufts College, Medford, MA (US)

( * ) Notice: Subject to any disclaimer, the term of this patent is extended or adjusted under 35 U.S.C. 154(b) by 0 days.

(21) Appl. No.: 15/942,242

(22) Filed: Mar. 30, 2018

(65) Prior Publication Data
US 2018/0359850 A1 Dec. 13, 2018

Related U.S. Application Data

(63) Continuation of application No. 13/046,191, filed on Mar. 11, 2011, now Pat. No. 9,936,574, which is a
(Continued)

(51) Int. Cl.
*H05K 1/02* (2006.01)
*A61B 5/00* (2006.01)
(Continued)

(52) U.S. Cl.
CPC ......... *H05K 1/0283* (2013.01); *A61B 5/6867* (2013.01); *A61B 5/6883* (2013.01);
(Continued)

(58) Field of Classification Search
CPC ......... H01L 2924/0002; H01L 2924/00; H01L 23/3121; H01L 23/3192; H01L 27/1218;
(Continued)

(56) References Cited

U.S. PATENT DOCUMENTS 3,949,410 A 4/1976 Bassous
4,058,418 A 11/1977 Lindmayer
(Continued)

FOREIGN PATENT DOCUMENTS

CN 1222758 A 7/1999
CN 1454045 A 11/2003
(Continued)

OTHER PUBLICATIONS

U.S. Appl. No. 11/001,689, filed Dec. 1, 2004.
(Continued)

*Primary Examiner* — Jonathan T Kuo
(74) *Attorney, Agent, or Firm* — Leydig, Voit & Mayer, Ltd.

(57) ABSTRACT

Described herein are flexible and stretchable LED arrays and methods utilizing flexible and stretchable LED arrays. Assembly of flexible LED arrays alongside flexible plasmonic crystals is useful for construction of fluid monitors, permitting sensitive detection of fluid refractive index and composition. Co-integration of flexible LED arrays with flexible photodetector arrays is useful for construction of flexible proximity sensors. Application of stretchable LED arrays onto flexible threads as light emitting sutures provides novel means for performing radiation therapy on wounds.

23 Claims, 74 Drawing Sheets

Related U.S. Application Data continuation-in-part of application No. 12/968,637, filed on Dec. 15, 2010, now Pat. No. 10,918,298, and a continuation-in-part of application No. PCT/US2010/060425, filed on Dec. 15, 2010, and a continuation-in-part of application No. 12/892,001, filed on Sep. 28, 2010, now Pat. No. 8,666,471, and a continuation-in-part of application No. PCT/US2010/050468, filed on Sep. 28, 2010.

(60) Provisional application No. 61/388,529, filed on Sep. 30, 2010, provisional application No. 61/313,397, filed on Mar. 12, 2010, provisional application No. 61/314,739, filed on Mar. 17, 2010, provisional application No. 61/286,921, filed on Dec. 16, 2009.

(51) Int. Cl.
| | |
|---|---|
| *H01L 23/31* | (2006.01) |
| *A61N 1/05* | (2006.01) |
| *A61N 1/18* | (2006.01) |
| *F21K 9/00* | (2016.01) |
| *H01L 27/12* | (2006.01) |
| *H01L 29/786* | (2006.01) |
| *H05K 1/14* | (2006.01) |
| *H05K 3/32* | (2006.01) |
| *A61B 5/287* | (2021.01) |

(52) U.S. Cl.
CPC .......... *H01L 23/3192* (2013.01); *A61B 5/287* (2021.01); *A61B 5/6806* (2013.01); *A61B 2562/02* (2013.01); *A61B 2562/0233* (2013.01); *A61B 2562/0257* (2013.01); *A61B 2562/0271* (2013.01); *A61B 2562/066* (2013.01); *A61B 2562/12* (2013.01); *A61B 2562/164* (2013.01); *A61N 1/05* (2013.01); *A61N 1/18* (2013.01); *F21K 9/00* (2013.01); *H01L 23/3121* (2013.01); *H01L 27/1218* (2013.01); *H01L 29/7869* (2013.01); *H01L 29/78603* (2013.01); *H01L 2924/0002* (2013.01); *H01L 2924/09701* (2013.01); *H01L 2924/12044* (2013.01); *H01L 2924/19041* (2013.01); *H01L 2924/3011* (2013.01); *H01L 2924/3025* (2013.01); *H05K 1/147* (2013.01); *H05K 3/323* (2013.01); *H05K 2201/09263* (2013.01); *H05K 2201/10106* (2013.01); *H05K 2203/1316* (2013.01); *Y10T 29/49128* (2015.01)

(58) Field of Classification Search
CPC . H01L 2924/09701; H01L 2924/12044; H01L 2924/19041; H01L 2924/3011; H01L 2924/3025; H01L 29/78603; H01L 29/7869; A61B 2562/02; A61B 2562/0233; A61B 2562/0257; A61B 2562/0271; A61B 2562/066; A61B 2562/12; A61B 2562/164; A61B 5/0422; A61B 5/6806; A61B 5/6867; A61B 5/6883; A61N 1/05; A61N 1/18; A61N 1/36; A61N 5/06–2005/073; F21K 9/00; H05K 1/0283; H05K 1/147; H05K 2201/09263; H05K 2201/10106; H05K 2203/1316; H05K 3/323; Y10T 29/49128; G04G 21/00–21/025
USPC ...................... 361/679.01–679.03
See application file for complete search history.

(56) References Cited

U.S. PATENT DOCUMENTS

| | | |
|---|---|---|
| 4,392,451 A | 7/1983 | Mickelsen et al. |
| 4,471,003 A | 9/1984 | Cann |
| 4,487,162 A | 12/1984 | Cann |
| 4,663,828 A | 5/1987 | Hanak |
| 4,715,235 A | 12/1987 | Fukui et al. |
| 4,761,335 A | 8/1988 | Aurichio et al. |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,118,400 A | 6/1992 | Wollam |
| 5,178,957 A | 1/1993 | Kolpe et al. |
| 5,204,144 A | 4/1993 | Cann et al. |
| 5,313,094 A | 5/1994 | Beyer et al. |
| 5,339,180 A | 8/1994 | Katoh |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattnger |
| 5,469,845 A | 11/1995 | Delonzor et al. |
| 5,501,893 A | 3/1996 | Laernner et al. |
| 5,525,815 A | 6/1996 | Einset |
| 5,545,291 A | 8/1996 | Smith et al. |
| 5,625,471 A | 4/1997 | Smith |
| 5,648,148 A | 7/1997 | Simpson |
| 5,687,737 A | 11/1997 | Branham et al. |
| 5,691,245 A | 11/1997 | Bakhit |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,817,242 A | 10/1998 | Biebuyck et al. |
| 5,824,186 A | 10/1998 | Smith et al. |
| 5,904,545 A | 5/1999 | Smith et al. |
| 5,907,189 A | 5/1999 | Mertol |
| 5,915,180 A | 6/1999 | Hara et al. |
| 5,917,534 A | 6/1999 | Rajeswaran |
| 5,928,001 A | 7/1999 | Gilette et al. |
| 5,955,781 A | 9/1999 | Joshi et al. |
| 5,976,683 A | 11/1999 | Liehrr et al. |
| 5,997,569 A | 12/1999 | Chen |
| 5,998,291 A | 12/1999 | Bakhit et al. |
| 6,024,702 A | 2/2000 | Iverson |
| 6,049,727 A * | 4/2000 | Crothall ............. A61B 5/14532 600/310 |
| 6,057,212 A | 5/2000 | Chan et al. |
| 6,080,608 A | 6/2000 | Nowak |
| 6,097,984 A | 8/2000 | Douglas |
| 6,165,391 A | 12/2000 | Vedamuttu |
| 6,171,730 B1 | 1/2001 | Kuroda et al. |
| 6,225,149 B1 | 5/2001 | Gan et al. |
| 6,236,883 B1 | 5/2001 | Ciaccio et al. |
| 6,265,326 B1 | 7/2001 | Ueno |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,334,960 B1 | 1/2002 | Wilson et al. |
| 6,380,729 B1 | 4/2002 | Smith |
| 6,403,397 B1 | 6/2002 | Katz |
| 6,413,790 B1 | 7/2002 | Duthaler et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |

(56) References Cited

U.S. PATENT DOCUMENTS

| | | |
|---|---|---|
| 6,468,638 B2 | 10/2002 | Jacobsen et al. |
| 6,479,395 B1 | 11/2002 | Smith et al. |
| 6,517,995 B1 | 2/2003 | Jacobson et al. |
| 6,527,964 B1 | 3/2003 | Smith et al. |
| 6,555,408 B1 | 4/2003 | Jacobsen et al. |
| 6,559,905 B1 | 5/2003 | Akiyama |
| 6,566,744 B2 | 5/2003 | Gengel |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |
| 6,731,353 B1 | 5/2004 | Credelle et al. |
| 6,743,982 B2 | 6/2004 | Biegelsen et al. |
| 6,780,696 B1 | 8/2004 | Schatz |
| 6,784,450 B2 | 8/2004 | Pan et al. |
| 6,787,052 B1 | 9/2004 | Vaganov |
| 6,814,898 B1 | 11/2004 | Deeman et al. |
| 6,816,380 B2 | 11/2004 | Credelle et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |
| 6,887,450 B2 | 5/2005 | Chen et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whiteford |
| 6,950,220 B2 | 9/2005 | Abramson et al. |
| 6,984,934 B2 | 1/2006 | Moller et al. |
| 6,989,285 B2 | 1/2006 | Ball |
| 7,029,951 B2 | 4/2006 | Chen et al. |
| 7,033,961 B1 | 4/2006 | Smart et al. |
| 7,067,903 B2 | 6/2006 | Tachibana et al. |
| 7,116,318 B2 | 10/2006 | Amundson et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,195,733 B2 | 3/2007 | Rogers et al. |
| 7,223,609 B2 | 5/2007 | Anvar et al. |
| 7,253,442 B2 | 8/2007 | Huang et al. |
| 7,255,919 B2 | 8/2007 | Sakata et al. |
| 7,291,540 B2 | 11/2007 | Mech et al. |
| 7,374,968 B2 | 5/2008 | Kornlivich et al. |
| 7,425,523 B2 | 9/2008 | Ikemizu et al. |
| 7,431,696 B1 * | 10/2008 | Brady .......... A61B 5/02055 600/300 |
| 7,521,292 B2 | 4/2009 | Rogers et al. |
| 7,521,727 B2 * | 4/2009 | Khanarian .......... H01L 33/22 257/100 |
| 7,557,367 B2 | 7/2009 | Rogers et al. |
| 7,622,367 B1 | 11/2009 | Nuzzo et al. |
| 7,629,691 B2 | 12/2009 | Roush et al. |
| 7,635,755 B2 | 12/2009 | Kaplan et al. |
| 7,674,882 B2 | 3/2010 | Kaplan et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,575 B2 | 6/2010 | Kaplan et al. |
| 7,799,699 B2 | 9/2010 | Nuzzo et al. |
| 7,842,780 B2 | 11/2010 | Kaplan et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,562,095 B2 | 10/2013 | Alleyne et al. |
| 8,679,888 B2 | 3/2014 | Rogers et al. |
| 8,722,458 B2 | 5/2014 | Rogers et al. |
| 8,865,489 B2 | 10/2014 | Rogers et al. |
| 9,936,574 B2 | 4/2018 | Rogers et al. |
| 2001/0003043 A1 | 6/2001 | Metspalu et al. |
| 2002/0004251 A1 | 1/2002 | Roberts et al. |
| 2002/0021445 A1 | 2/2002 | Bozhevolnyi et al. |
| 2002/0055666 A1 | 5/2002 | Hunter |
| 2002/0110766 A1 | 8/2002 | Tsai et al. |
| 2003/0006527 A1 | 1/2003 | Rabolt et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0138704 A1 | 7/2003 | Mei et al. |
| 2003/0149456 A1 | 8/2003 | Rottenberg et al. |
| 2003/0178316 A1 | 9/2003 | Jacobs et al. |
| 2003/0222282 A1 | 12/2003 | Fjelstad et al. |
| 2003/0227116 A1 | 12/2003 | Halik et al. |
| 2003/0236452 A1 * | 12/2003 | Melker .......... A61B 5/0873 600/323 |
| 2004/0005723 A1 | 1/2004 | Empedocles et al. |
| 2004/0026684 A1 | 2/2004 | Empedocles et al. |
| 2004/0079464 A1 | 4/2004 | Kumakura |
| 2004/0081384 A1 | 4/2004 | Datesman et al. |
| 2004/0095658 A1 | 5/2004 | Buretea et al. |
| 2004/0112964 A1 | 6/2004 | Empedocles et al. |
| 2004/0136866 A1 | 7/2004 | Pontis et al. |
| 2004/0146560 A1 | 7/2004 | Whiteford et al. |
| 2004/0155290 A1 | 8/2004 | Mech et al. |
| 2004/0178390 A1 | 9/2004 | Whiteford |
| 2004/0188531 A1 | 9/2004 | Gengel |
| 2004/0192082 A1 | 9/2004 | Wagner et al. |
| 2004/0200734 A1 | 10/2004 | Co et al. |
| 2004/0206448 A1 | 10/2004 | Dubrow |
| 2004/0211458 A1 | 10/2004 | Gui et al. |
| 2004/0211459 A1 | 10/2004 | Suenaga et al. |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0038498 A1 | 2/2005 | Dubrow et al. |
| 2005/0082526 A1 | 4/2005 | Bedell et al. |
| 2005/0124712 A1 | 6/2005 | Anderson et al. |
| 2005/0133954 A1 | 6/2005 | Homola |
| 2005/0187608 A1 | 8/2005 | O'Hara |
| 2005/0214962 A1 | 9/2005 | Daniels et al. |
| 2005/0227389 A1 | 10/2005 | Bhattacharya et al. |
| 2005/0233546 A1 | 10/2005 | Oohata et al. |
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1 | 2/2006 | Rogers et al. |
| 2006/0049485 A1 | 3/2006 | Pan et al. |
| 2006/0052678 A1 | 3/2006 | Drinan et al. |
| 2006/0076561 A1 | 4/2006 | Hioki et al. |
| 2006/0084012 A1 | 4/2006 | Nuzzo et al. |
| 2006/0085976 A1 | 4/2006 | Eldridge et al. |
| 2006/0102525 A1 | 5/2006 | Volkel et al. |
| 2006/0119853 A1 | 6/2006 | Baumberg et al. |

(56) References Cited

U.S. PATENT DOCUMENTS

| | | |
|---|---|---|
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0159837 A1 | 7/2006 | Kaplan et al. |
| 2006/0169989 A1 | 8/2006 | Bhattacharya |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0244105 A1 | 11/2006 | Forbes et al. |
| 2006/0255341 A1 | 11/2006 | Pinnington et al. |
| 2006/0273279 A1 | 12/2006 | Kaplan et al. |
| 2006/0279191 A1 | 12/2006 | Gehegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0187862 A1 | 8/2007 | Kaplan et al. |
| 2007/0212730 A1 | 9/2007 | Vepari et al. |
| 2007/0227586 A1 | 10/2007 | Zapalac |
| 2007/0233208 A1 | 10/2007 | Kurtz et al. |
| 2007/0284601 A1* | 12/2007 | Khanarian ............... H01L 33/52 257/98 |
| 2008/0000871 A1 | 1/2008 | Suh et al. |
| 2008/0038236 A1 | 2/2008 | Gimble et al. |
| 2008/0041617 A1 | 2/2008 | Chen et al. |
| 2008/0055581 A1 | 3/2008 | Rogers et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0152281 A1 | 6/2008 | Lundquist et al. |
| 2008/0157235 A1 | 7/2008 | Rogers |
| 2008/0183076 A1 | 7/2008 | Witte et al. |
| 2008/0203431 A1 | 8/2008 | Garcia et al. |
| 2008/0212102 A1 | 9/2008 | Nuzzo et al. |
| 2008/0239755 A1 | 10/2008 | Parker et al. |
| 2008/0280360 A1 | 11/2008 | Kaplan et al. |
| 2008/0288037 A1 | 11/2008 | Neysmith et al. |
| 2008/0293919 A1 | 11/2008 | Kaplan et al. |
| 2009/0004737 A1 | 1/2009 | Borenstein et al. |
| 2009/0028910 A1 | 1/2009 | Desimone et al. |
| 2009/0078990 A1 | 3/2009 | Yasuda |
| 2009/0085214 A1 | 4/2009 | Wada et al. |
| 2009/0149930 A1 | 6/2009 | Schecnk |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0289246 A1 | 11/2009 | Schneider et al. |
| 2009/0294803 A1 | 12/2009 | Nuzzo et al. |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0176705 A1 | 7/2010 | Van Herpen et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0252840 A1 | 10/2010 | Ibbetson et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0317132 A1 | 12/2010 | Rogers et al. |
| 2011/0021885 A1* | 1/2011 | Ma ..................... A61B 5/0084 600/301 |
| 2011/0068672 A1 | 3/2011 | Hasnain |
| 2011/0147715 A1 | 6/2011 | Rogers et al. |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0316120 A1 | 12/2011 | Rogers et al. |
| 2012/0157804 A1 | 6/2012 | Rogers et al. |

FOREIGN PATENT DOCUMENTS

| | | |
|---|---|---|
| CN | 101772348 A | 7/2010 |
| DE | 4241045 C1 | 5/1994 |
| DE | 19748173 A1 | 5/1999 |
| EP | 0929097 A2 | 7/1999 |
| EP | 1357773 A2 | 10/2003 |
| EP | 1467224 A1 | 10/2004 |
| EP | 1477230 A1 | 11/2004 |
| EP | 1498456 A1 | 1/2005 |
| EP | 1511096 A2 | 3/2005 |
| EP | 1558444 A2 | 8/2005 |
| EP | 1613796 A2 | 1/2006 |
| EP | 1726329 A1 | 11/2006 |
| EP | 1773240 A2 | 4/2007 |
| EP | 1915436 A2 | 4/2008 |
| EP | 2086749 A2 | 8/2009 |
| EP | 2101975 A2 | 9/2009 |
| EP | 2107964 A2 | 10/2009 |
| EP | 2109634 A2 | 10/2009 |
| EP | 2129772 A2 | 12/2009 |
| EP | 2206017 A1 | 7/2010 |
| EP | 2221876 A1 | 8/2010 |
| EP | 2249886 A2 | 11/2010 |
| EP | 2544598 A1 | 1/2013 |
| JP | 06-118441 A | 4/1994 |
| JP | 6-163365 A | 6/1994 |
| JP | 11-026344 A | 1/1999 |
| JP | 1126344 A | 1/1999 |
| JP | 11-142878 A | 5/1999 |
| JP | 2001-007340 A | 1/2001 |
| JP | 2002-092984 A | 3/2002 |
| JP | 2006-504450 A | 2/2006 |
| JP | 2006-186294 A | 7/2006 |
| JP | 2007-515391 A | 6/2007 |
| JP | 2008-502739 A | 1/2008 |
| JP | 2010-508852 A | 3/2010 |
| JP | 2010-509593 A | 3/2010 |
| JP | 2010-509644 A | 3/2010 |
| JP | 2010-509645 A | 3/2010 |
| JP | 2010-522583 A | 7/2010 |
| JP | 2010-529230 A | 8/2010 |
| KR | 2008-0069553 A | 7/2008 |
| TW | 367570 B | 8/1999 |
| TW | 494257 B | 7/2002 |
| TW | 200836353 A | 9/2008 |
| WO | WO 1996021245 A1 | 7/1996 |
| WO | WO 1998049936 A1 | 11/1998 |
| WO | WO 1999045860 A1 | 9/1999 |
| WO | WO 2000046854 A1 | 8/2000 |
| WO | WO 2000049421 A1 | 8/2000 |
| WO | WO 2000049658 A1 | 8/2000 |
| WO | WO 2000055915 A1 | 9/2000 |
| WO | WO 2000055916 A1 | 9/2000 |
| WO | WO 2001031082 A1 | 5/2001 |
| WO | WO 2001033621 A2 | 5/2001 |
| WO | WO 2001066833 A1 | 9/2001 |
| WO | WO 2001098838 A2 | 12/2001 |
| WO | WO 2002027701 A2 | 4/2002 |

(56) References Cited

FOREIGN PATENT DOCUMENTS

| | | |
|---|---|---|
| WO | WO 2002043032 A2 | 5/2002 |
| WO | WO 2002045160 A1 | 6/2002 |
| WO | WO 2002071137 A1 | 9/2002 |
| WO | WO 2002073699 A2 | 9/2002 |
| WO | WO 2002092778 A2 | 11/2002 |
| WO | WO 2002097708 A2 | 12/2002 |
| WO | WO 2002097724 A1 | 12/2002 |
| WO | WO 2003030194 A1 | 4/2003 |
| WO | WO 2003032240 A2 | 4/2003 |
| WO | WO 2003049201 A1 | 6/2003 |
| WO | WO 2003063211 A1 | 7/2003 |
| WO | WO 2003085700 A2 | 10/2003 |
| WO | WO 2003085701 A2 | 10/2003 |
| WO | WO 2003092073 A2 | 11/2003 |
| WO | WO 2004000915 A2 | 12/2003 |
| WO | WO 2004001103 A2 | 12/2003 |
| WO | WO 2004003535 A1 | 1/2004 |
| WO | WO 2004022637 A2 | 3/2004 |
| WO | WO 2004022714 A2 | 3/2004 |
| WO | WO 2004023527 A2 | 3/2004 |
| WO | WO 2004024407 A1 | 3/2004 |
| WO | WO 2004027822 A2 | 4/2004 |
| WO | WO 2004032190 A2 | 4/2004 |
| WO | WO 2004032191 A2 | 4/2004 |
| WO | WO 2004032193 A2 | 4/2004 |
| WO | WO 2004034025 A2 | 4/2004 |
| WO | WO 2004062697 A2 | 7/2004 |
| WO | WO 2004086289 A2 | 10/2004 |
| WO | WO 2004094303 A2 | 11/2004 |
| WO | WO 2004099068 A2 | 11/2004 |
| WO | WO 2004100252 A1 | 11/2004 |
| WO | WO 2004105456 A1 | 12/2004 |
| WO | WO 2004107973 A1 | 12/2004 |
| WO | WO 2005000483 A1 | 1/2005 |
| WO | WO 2005005679 A2 | 1/2005 |
| WO | WO 2005012606 A2 | 2/2005 |
| WO | WO 2005015480 A2 | 2/2005 |
| WO | WO 2005017962 A2 | 2/2005 |
| WO | WO 2005022120 A2 | 3/2005 |
| WO | WO 2005029578 A1 | 3/2005 |
| WO | WO 2005033786 A2 | 4/2005 |
| WO | WO 2005033787 A1 | 4/2005 |
| WO | WO 2005054119 A2 | 6/2005 |
| WO | WO 2005099310 A2 | 10/2005 |
| WO | WO 2005104756 A2 | 11/2005 |
| WO | WO 2005106934 A1 | 11/2005 |
| WO | WO 2005122285 A2 | 12/2005 |
| WO | WO 2005123114 A2 | 12/2005 |
| WO | WO 2006028996 A2 | 3/2006 |
| WO | WO 2006042287 A2 | 4/2006 |
| WO | WO 2006076711 A2 | 7/2006 |
| WO | WO 2006104069 A1 | 10/2006 |
| WO | WO 2006130558 A2 | 12/2006 |
| WO | WO 2006130721 A2 | 12/2006 |
| WO | WO 2007000037 A1 | 1/2007 |
| WO | WO 2007016524 A2 | 2/2007 |
| WO | WO 2007028003 A2 | 3/2007 |
| WO | WO 2007056183 A1 | 5/2007 |
| WO | WO 2007126412 A2 | 11/2007 |
| WO | WO 2008030666 A2 | 3/2008 |
| WO | WO 2008030960 A2 | 3/2008 |
| WO | WO 2008036837 A2 | 3/2008 |
| WO | WO 2008055054 A2 | 5/2008 |
| WO | WO 2008085904 A1 | 7/2008 |
| WO | WO 2008103464 A1 | 8/2008 |
| WO | WO 2008106485 A2 | 9/2008 |
| WO | WO 2008108838 A2 | 9/2008 |
| WO | WO 2008118133 A2 | 10/2008 |
| WO | WO 2008118211 A2 | 10/2008 |
| WO | WO 2008127401 A2 | 10/2008 |
| WO | WO 2008127402 A2 | 10/2008 |
| WO | WO 2008127403 A2 | 10/2008 |
| WO | WO 2008127404 A2 | 10/2008 |
| WO | WO 2008127405 A2 | 10/2008 |
| WO | WO 2008/137851 A1 | 11/2008 |
| WO | WO 2008140562 A2 | 11/2008 |
| WO | WO 2008143635 A1 | 11/2008 |
| WO | WO 2008150861 A1 | 12/2008 |
| WO | WO 2009011709 A1 | 1/2009 |
| WO | WO 2009023615 A1 | 2/2009 |
| WO | WO 2009061823 A1 | 5/2009 |
| WO | WO 2009075625 A1 | 6/2009 |
| WO | WO 2009076088 A1 | 6/2009 |
| WO | WO 2009090398 A2 | 7/2009 |
| WO | WO 2009100280 A1 | 8/2009 |
| WO | WO 2009111641 A1 | 9/2009 |
| WO | WO 2009114115 A1 | 9/2009 |
| WO | WO 2009114689 A1 | 9/2009 |
| WO | WO 2009118678 A1 | 10/2009 |
| WO | WO 2009126689 A2 | 10/2009 |
| WO | WO 2009140588 A1 | 11/2009 |
| WO | WO 2009155397 A2 | 12/2009 |
| WO | WO 2010005707 A1 | 1/2010 |
| WO | WO 2010036807 A1 | 4/2010 |
| WO | WO 2010036992 A2 | 4/2010 |
| WO | WO 2010040528 A1 | 4/2010 |
| WO | WO 2010042798 A2 | 4/2010 |
| WO | WO 2010049881 A1 | 5/2010 |
| WO | WO 2010057142 A2 | 5/2010 |
| WO | WO 2010065957 A2 | 6/2010 |
| WO | WO 2010126640 A2 | 11/2010 |
| WO | WO 2010132552 A1 | 11/2010 |
| WO | WO 2010141133 A2 | 12/2010 |
| WO | WO 2011005381 A2 | 1/2011 |
| WO | WO 2011006133 A2 | 1/2011 |
| WO | WO 2011008842 A2 | 1/2011 |
| WO | WO 2011011347 A2 | 1/2011 |
| WO | WO 2011026101 A2 | 3/2011 |
| WO | WO 2011038401 A2 | 3/2011 |
| WO | WO 2011041395 A2 | 4/2011 |
| WO | WO 2011046652 A2 | 4/2011 |
| WO | WO 2011084450 A1 | 7/2011 |
| WO | WO 2011112931 A1 | 9/2011 |
| WO | WO 2011115643 A1 | 9/2011 |

OTHER PUBLICATIONS

U.S. Appl. No. 11/115,954, filed Apr. 27, 2005.
U.S. Appl. No. 11/145,574, filed Jun. 2, 2005.
U.S. Appl. No. 12/564,566, filed Sep. 22, 2009.
U.S. Appl. No. 13/113,504, filed May 23, 2011.
U.S. Appl. No. 11/145,542, filed Jun. 2, 2005.
U.S. Appl. No. 11/423,287, filed Jun. 9, 2006.
U.S. Appl. No. 12/405,475, filed Mar. 17, 2009.
U.S. Appl. No. 11/675,659, filed Feb. 16, 2007.
U.S. Appl. No. 11/465,317, filed Aug. 17, 2006.
U.S. Appl. No. 11/423,192, filed Jun. 9, 2006.
U.S. Appl. No. 11/421,654, filed Jun. 1, 2006.
U.S. Appl. No. 12/844,492, filed Jul. 27, 2010.
U.S. Appl. No. 11/851,182, filed Sep. 6, 2007.
U.S. Appl. No. 11/858,788, filed Sep. 20, 2007.
U.S. Appl. No. 13/071,027, filed Mar. 24, 2011.
U.S. Appl. No. 13/228,041, filed Sep. 8, 2011.
U.S. Appl. No. 11/981,380, filed Oct. 31, 2007.
U.S. Appl. No. 13/100,774, filed May 4, 2011.
U.S. Appl. No. 12/669,28, filed Jan. 15, 2010.
U.S. Appl. No. 12/418,071, filed Apr. 3, 2009.
U.S. Appl. No. 12/398,811, filed Mar. 5, 2009.
U.S. Appl. No. 12/996,924, filed Dec. 8, 2010.
U.S. Appl. No. 13/120,486, filed Aug. 4, 2011.
U.S. Appl. No. 12/778,588, filed May 12, 2010.
U.S. Appl. No. 12/968,637, filed Dec. 15, 2010.
U.S. Appl. No. 12/947,120, filed Nov. 16, 2010.
U.S. Appl. No. 12/892,001, filed Sep. 28, 2010.
U.S. Appl. No. 12/916,934, filed Nov. 1, 2010.
U.S. Appl. No. 13/046,191, filed Mar. 11, 2011.
Abbaschian et al., "High Pressure-High Temperature Growth of Diamond Crystals Using Split Sphere Apparatus", *Diamond Relat. Mater.*, 14(11-12):1916-1919 (Dec. 2005).
Adachi et al., "Chemical Etching of InGaAsP/InP DH Wafer", *J. Electrochem. Soc.*, 129:1053-1062 (1982).

(56) References Cited

OTHER PUBLICATIONS

Adachi et al., "Chemical Etching Characteristics of (001)GaAs," *J. Electrochem. Soc,*. 130:2427-2435 (1983).
Adrega et al., "Stretchable Gold Conductors Embedded in PDMS and Patterned by Photolithography: Fabrication and Electromechanical Characterization", *J. Micromech. Microeng,*. 20:055025 (2010).
Ago et al., "Aligned Growth of Isolated Single-Walled Carbon Nanotubes Programmed by Atomic Arrangement of Substrate Surface", *Chem. Phys. Lett.* 408:433-438 (2005).
Ago et al., "Synthesis of Horizontally-Aligned Single-Walled Carbon Nanotubes with Controllable Density on Sapphire Surface and Polarized Raman Spectroscopy", *Chem. Phys. Lett.*, 421:399-403 (2006).
Ahmed et al., "Extending the 3ω-Method to the MHz Range for Thermal Conductivity Measurements of Diamond Thin Films," *Diamond Relat. Mater.* 15(2-3):389-393 (Web Release Oct. 11, 2005).
Ahn et al., "Bendable Integrated Circuits on Plastic Substrates by Use of Printed Ribbons of Single-Crystalline Silicon", *Appl. Phys. Lett.*, 90:213501 (2007).
Ahn et al., "Heterogeneous Three-Dimensional Electronics by Use of Printed Semiconductor Nanomaterials", *Science*, 314:1754-1757 (2006).
Ahn et al., "High-Speed Mechanically Flexible Single-Crystal Silicon Thin-Film Transistors on Plastic Substrates", *IEEE Electron Dev. Lett.*, 27(6):460-462 (2006).
Al-Halhouli et al., "Nanoindentation Testing of SU-8 Photoresist Mechanical Properties", *Microelectronic Eng.*, 85:942-944 (2008).
Aliot et al., "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)", *Europace*, 11:771-817 (2009).
Alivisatos et al., "Semiconductor Clusters, Nanocrystals, and Quantum Dots", *Science*, 271:933-937 (1996).
Alivisatos et al., "From Molecules to Materials: Current Trends and Future Directions", *Adv. Mater.*, 10:1297-1336 (1998).
Allen et al., "Nanomaterial Transfer Using Hot Embossing for Flexible Electronic Devices", *Appl. Phys. Lett.*, 88:083112 (2006).
Al-Sarawi et al., "A Review of 3-D Packaging Technology", *IEEE Trans. Comp. Packag. Manufac. Technol.*, 21(1):2-14 (1998).
Altman et al., "Silk-Based Biomaterials", *Biomaterials*, 24:401-416 (2003).
Amano et al., "Metalorganic Vapor Phase Epitaxial Growth of a High Quality GaN Film Using an AIN Buffer Layer", *Appl. Phys. Lett.*, 48(5):353-355 (1986).
Ambrosy et al., "Silicon Motherboards for Multichannel Optical Modules", *IEEE Trans. Compon. Pack. A.*, 19:34-40 (1996).
Amir et al., "The Influence of Helium-Neon Irradiation on the Viability of Skin Flaps in the Rat", *Br. J. Plast. Surg.*, 53:58-62 (2000).
Amsden et al., "Spectral Analysis of Induced Color Change on Periodically Nanopatterned Silk Films", *Opt. Expres,s* 17(23):21271-21279 (2009).
Andersen et al., "Selecting the Signals for a Brain-Machine Interface", *Curr. Opin. Neurobiol.*, 14:720-726 (2004).
Andersson et al., "Active Matrix Displays Based on All-Organic Electrochemical Smart Pixels Printed on Paper", *Adv. Mater.*, 14:1460-1464 (2002).
Ando et al., "Self-Aligned Self-Assembly Process for Fabricating Organic Thin-Film Transistors", *Appl. Phys. Lett.*, 85:1849-1851 (2004).
Angadi et al., "Thermal Transport and Grain Boundary Conductance in Ultrananocrystalline Diamond Thin Films", *J. Appl. Phys.*, 99:114301 (Web Release Jun. 1, 2006).
Aoki et al., "Microassembly of Semiconductor Three Dimensional Photonic Crystals", *Nat. Mater.*, 2:117-121(2003).
Arnold et al., "Field-Effect Transistors Based on Single Semiconducting Oxide Nanobelts", *J. Phys. Chem B.*, 107(3):659-663 (2003).
Ayón et al., "Characterization of a Time Multiplexed Inductively Coupled Plasma Etcher", *J. Electrochem. Soc.*, 146(1):339-349 (1999).
Baca et al., "Semiconductor Wires and Ribbons for High-Performance Flexible Electronics", *Angew. Chem. Int. Ed.*, 47:5524-5542 (2008).
Bachtold et al., "Logic Circuits with Carbon Nanotube Transistors", *Science*, 294:1317-1320 (2001).
Bae et al., "Single-Crystalline Gallium Nitride Nanobelts", *Appl. Phys. Lett.*, 81(1):126-128 (2002).
Ball et al., "Towards an Implantable Brain-Machine Interface Based on Epicortical Field Potentials", *Biomed. Tech.*, 49:756-759 (2004).
Balmer et al., "Diffusion of Alkanethiols in PDMS and Its Implications on Microcontact Printing (μCP)", *Langmuir* 21(2):622-632 (2005).
Banerjee et al., "3-D ICs: A Novel Chip Design for Improving Deep-Submicrometerinterconnect Performance and Systems-on-Chip Integration", *Proc. IEEE*, 89(5):602-633 (2001).
Bao et al., "High-Performance Plastic Transistors Fabricated by Printing Techniques", *Chem. Mater.*, 9:1299-1301 (1997).
Bao et al., "Printable Organic and Polymeric Semiconducting Materials and Devices", *J. Mater. Chem.*, 9:1895-1904 (1999).
Barquins, "Adherence, Friction and Wear of Rubber-Like Materials", *Wear*, 158:87-117(1992).
Bates, "Polymer-Polymer Phase Behavior", *Science*, 251:898-905(1991).
Battaglia et al., "Colloidal Two-Dimensional Systems: CdSe Quantum Shells and Wells", *Angew. Chem. Int. Ed.*, 442:5035-5039 (2003).
Bauer et al., "Biological Applications of High Aspect Ratio Nanoparticles", *J. Mater. Chem.*, 14:517-526 (2004).
Berg et al., "Tailored Micropatterns Through Weak Polyelectrolyte Stamping", *Langmuir*, 19:2231-2237(2003).
Bernard et al., "Printing Patterns of Proteins", *Langmuir*, 14(9):2225-2229 (1998).
Bett et al., "III-V Compounds for Solar Cell Applications", *Appl. Phys. A. Mater. Sci.*, 69(2):119-129 (1999).
Bhunia et al., "Free-Standing and Vertically Aligned InP Nanowires Grown by Metalorganic Vapor Phase Epitaxy", *Physica E.*, 21:583-587 (2004).
Bhushan et al., "Multiwalled Carbon Nanotube AFM Probes for Surface Characterization of Micro/Nanostructures", *Microsyst. Technol.*, 10(8-9):633-639 (2004).
Bietsch et al., "Conformal Contact and Pattern Stability of Stamps Used for Soft Lithography", *J. Appl. Phys.*, 88(7):4310-4318 (2000).
Bioflex—Biocompatible Flexible Electronic Circuits. Available at http://tfcg.elis.ugent.be/projects/bioflex. (Accessed Feb. 8, 2012).
Bishay et al., "Temperature Coefficient of the Surface Resistivity of Two-Dimensional Island Gold Films", *J. Phys. D. Appl. Phys.*, 33(18):2218-2222 (2000).
Blanchet et al., "Large Area, High Resolution, Dry Printing of Conducting Polymers for Organic Electronics", *Appl. Phys. Lett.*, 82:463-465 (2003).
Blanchet et al., "Printing Techniques for Plastic Electronics", *J. Imag. Sci. Tech.*, 47(4):296-303 (2003).
Blazdell et al., "Preparation of Ceramic Inks for Solid Freeforming Using a Continuous Jet Printer", *J. Mat. Syn. Process.*, 7(6):349-356 (1999).
Boltau et al., "Surface-Induced Structure Formation of Polymer Blends on Patterned Substrates", *Nature*, 391:877-879 (1998).
Boncheva et al., "Magnetic Self-Assembly of Three-Dimensional Surfaces from Planar Sheets", *Proc. Natl. Acad. Sci. USA*, 102(11):3924-3929 (2005).
Boncheva et al., "Templated Self-Assembly: Formation of Folded Structures by Relaxation of Pre-Stressed, Planar Tapes", *Adv. Mater.*, 17(5):553-557 (2005).
Bourzac, K. "TR10: Implantable Electronics", Technology Review, Published by MIT, http://www.technologyreview.com/biomedicine/25086/?a=f (May/Jun. 2010).
Bowden et al., "Self Assembly of Mesoscale Objects into Ordered Two-Dimensional Arrays", *Science*, 276:233-235 (1997).

(56) References Cited

OTHER PUBLICATIONS

Bowden et al., "Spontaneous Formation of Ordered Structures in Thin Films of Metals Supported on an Elastomeric Polymer", *Nature*, 393:146-149 (1998).
Bowden et al., "Molecule-Mimetic Chemistry and Mesoscale Self-Assembly", *Acc. Chem. Res.*, 34:231-238 (2001).
Bracher et al., "Shaped Films of Ionotropic Hydrogels Fabricated Using Templates of Patterns Paper", *Adv. Mater.*, 21:445-450 (2009).
Bradley et al., "Flexible Nanotube Electronics", *Nano Lett.*, 3(10):1353-1355 (2003).
Braun et al., "Electrochemically Grown Photonic Crystals", *Nature*, 402:603-604 (1999).
Britton et al., "Microstructural Defect Characterization of a Si:H Deposited by Low Temperature HW-CVD on Paper Substrates", *Thin Solid Films*, 501(1-2):79-83 (Web Release Oct. 25, 2005).
Brown et al., "Heterogeneous Materials Integration: Compliant Substrates to Active Device and Materials Packaging", *Mater. Sci. Eng. B.*, 87(3):317-322 (2001).
Brown et al., "Evaluation of Polydimethylsiloxane Scaffolds with Physiologically-Relevant Elastic Moduli: Interplay of Substrate Mechanics and Surface Chemistry Effects on Vascular Smooth Muscle Cell Response", *Biomaterials*, 26(16):3123-3129 (2005).
Brown, "The Adhesion Between Polymers", *Ann. Rev. Mater. Sci.*, 21:463-489 (1991).
Bruschi et al., "Micromachined Silicon Suspended Wires With Submicrometric Dimensions", *Microelectron. Eng.*, 57-58:959-965 (2001).
Buma et al., "High-Frequency Ultrasound Array Element Using Thermoelastic Expansion in an Elastomeric Film", *Appl. Phys. Lett.*, 79:548-550 (2001).
Burdinski et al., "Single Etch Patterning of Stacked Silver and Molybdenum Alloy Layers on Glass Using Microcontact Wave Printing", *J. Am. Chem. Soc.*, 27(31):10786-10787 (2005).
Burdinski, "Soft Lithography and Microcontact Wave Printing", http://www.research.philips.com/technologies/light_dev_microsys/softlitho/index.html, (Downloaded May 23, 2007).
Burge et al., "X-Ray Holography for VLSI Using Synthetic Bilevel Holograms", *Proc. Int. Soc. Opt. Eng.*, 3183:2-13 (1997).
Burgin et al., "Large Area Submicrometer Contact Printing Using a Contact Aligner", *Langmuir*, 16:5371-5375 (2000).
Burns et al., "Printing of Polymer Thin-Film Transistors for Active-Matrix-Display Applications", *J. Soc. Inf. Display*, 11:599-604 (2003).
Campbell et al., "Fabrication of Photonic Crystals for the Visible Spectrum by Holographic Lithography", *Nature*, 404:53-56 (2000).
Cao et al., "Bilayer Organic-Inorganic Gate Dielectrics for High-Performance, Low-Voltage, Single-Walled Carbon Nanotube Thin-Film Transistors, Complementary Logic Gates, and p-n Diodes on Plastic Substrates", *Adv. Fund. Mater.*, 16:2355-2362 (2006).
Cao et al., "Highly Bendable,Transparent Thin-Film Transistors That Use Carbon-Nanotube-Based Conductors and Semiconductors with Elastomeric Dielectrics", *Adv. Mater.*, 18(3):304-309 (2006).
Cao et al., "Transparent flexible organic thin-film transistors that use printed single-walled carbon nanotube electrodes", *Applied Physics Letters*, 88:113511 (2006).
Cao et al., "Ultrathin Films of Single-Walled Carbon Nanotubes for Electronics and Sensors: A Review of Fundamental and Applied Aspects", *Adv. Mater.*, 21(1):29-53 (2009).
Cao et al., "Medium-Scale Carbon Nanotube Thin-Film Integrated Circuits on Flexible Plastic Substrates", *Nature*, 454:495-500 (2008).
Carr et al., "Measurement of Nanomechanical Resonant Structures in Single-Crystal Silicon", *J. Vac. Sci. Technol. B.*, 16:3821-3824 (1998).
Chadhury et al., "Direct Measurement of Interfacial Interactions Between Semispherical Lenses and Flat Sheets of Poly(dimethylsiloxane) and their Chemical Derivatives", *Langmuir*, 7:1013-1025 (1991).
Chang et al., "Process Techniques," "Lithography," and "Device-Related Physics and Principles", In; GaAs High-Speed Devices: Physics, Technology and Circuit Application, John Wiley and Sons, New York, pp. 115-278 (1994).
Chen et al., "Characterization of Pd—GaAs Schottly Diodes Prepared by the Electrodes Plating Technique", *Semiconductor. Sci. Technol.*, 18:620-626 (2003).
Chen et al., "Electronic Paper: Flexible Active-Matrix Electronics Ink Display", *Nature*, 423:136 (2003).
Chen et al., "InGaN Nanorings and Nanodots by Selective Area Epitaxy", *Appl. Phys. Lett.*, 87:143111(2005).
Chen et al., "The Role of Metal-Nanotube Contact in the Performance of Carbon Nanotube Field-Effect Transistors", *Nano Lett.*, 5(7):1497-1502 (2005).
Chen et al., "Complementary Carbon Nanotube-Gated Carbon Nanotube Thin-Fim Transistor", *Appl. Phys. Lett.*, 88:093502 (2006).
Chen et al., "Effect of Process Parameters on the Surface Morphology and Mechanical Performance of Silicon Structures After Deep Reactive Ion Etching (DRIE)", *J. Microelectromech. Syst.*, 11(3):264-275 (2002).
Chen et al., "A Family of Herringbone Patterns in Thin Films", *Scripta Materialia*, 50(6):797-801 (2004).
Chen et al., "An Integrated Logic Circuit Assembled on a Single Carbon Nanotube", *Science*, 311:1735 (2006).
Chen et al., "Herringbone Buckling Patterns of Compressed Thin Films on Compliant Substrates", *J. Appl. Mech.*, 71:597-603 (2004).
Cheng et al., "Ink-Jet Printing, Self-Assembled Polyelectrolytes, and Electroless Plating: Low Cost Fabrication of Circuits on a Flexible Substrate at Room Temperature", *Macromol. Rapid Commun.*, 26:247-264 (2005).
Chiang et al., "An ultrathin (~ 100 µm thick) flexible light plate fabricated using self-alignment and lift-off techniques", *Applied Physics Letters*, 91.18 (2007): 181108. DOI: 10.1063/1.2804001.
Childs et al., "Decal Transfer Microlithography: A New Soft-Lithographic Patterning Method", *J. Am. Chem. Soc.*, 124:13583-13596 (2002).
Childs et al., "Masterless Soft-Lithography: Patterning UV/Ozone-Induced Adhesion on Poly(dimethylsiloxane) Surfaces", *Langmuir*, 21:10096-10105 (2005).
Childs et al., "Patterning of Thin-Film Microstructures on Non-Planar Substrate Surfaces Using Decal Transfer Lithography", *Adv. Mater.*, 16(15):1323-1327 (2004).
Choi et al., "Biaxially Stretchable 'Wavy' Silicon Nanomembranes", *Nano Lett.*, 7(6):1655-1663 (2007).
Choi et al., "Simple Detachment Patterning of Organic Layers and Its Applications to Organic Light-Emitting Diodes", *Adv. Mater.*, 17(2):166-171 (Web Release Jan. 25, 2005).
Chou et al., "An Orientation-Controlled Pentacene Film Aligned by Photoaligned Polyimide for Organic Thin-Film Transistor Applications", *Adv. Func. Mater.*, 14:811-815 (2004).
Chou et al., "Micromachining on (111)-Oriented Silicon", *Sens. Actuators A.*, 75(3):271-277 (1999).
Chu et al., "High-Performance Organic Thin-Film Transistors with Metal Oxide/Metal Bilayer Electrode", *Appl. Phys. Lett.*, 87:193508 (2005).
Chung et al., "Silicon Nanowire Devices", *Appl. Phys. Lett.*, 76(15):2068-2070 (2000).
Chung et al., "A Study on Formation of Al and $Al_2O_3$ on the Porous Paper by DC Magnetron Sputtering", *Surf. Coat. Technol.*, 171(1-3):65-70 (2003).
Clerc, "Directional Differences of Impulse Spread in Trabecular Muscle from Mammalian Heart", *J. Physiol.*, 255:335-346 (1976).
Cohen-Karni et al., "Flexible Electrical Recording from Cells Using Nanowire Transistor Arrays", *Proc. Natl. Acad. Sci. USA*, 106:7309-7313 (2009).
Cole et al., "Patterned Growth and Transfer of ZnO Micro- and Nanocrystals with Size and Location Control", *Adv. Mater.*, 20:1474-1478 (2008).
Collins et al., "Engineering Carbon Nanotubes and Nanotube Circuits Using Electrical Breakdown", *Science*, 292:706-709 (2001).
Corazza et al., "Photobiomodulation on the Angiogenesis of Skin Wounds in Rats Using Different Light Sources", *Photomedicine Laser Surg.*, 25:102-106 (2007).

(56) References Cited

OTHER PUBLICATIONS

Cox, "The Elasticity and Strength of Paper and Other Fibrous Materials", *Br. J. Appl. Phys.*, 3:72-79 (1952).
Creagh et al., "Design and Performance of Inkjet Print Heads for Non-Graphic-Arts Applications", *MRS Bull.*, 28:807-811 (2003).
Crone et al., "Large-Scale Complementary Integrated Circuits Based on Organic Transistors", *Nature*, 403:521-523 (2000).
Crowder et al., "Low-Temperature Single-Crystal Si TFTs Fabricated on Si Films Processed via Sequential Lateral Solidification", *IEEE Electron. Dev. Lett.*, 19:306-308 (1998).
Cui et al., "Nanowire Nanosensors for Highly Sensitive and Selective Detection of Biological and Chemical Species", *Science*, 293:1289-1292 (2001).
Dai et al., "Gallium Oxide Nanoribbons and Nanosheets", *J. Phys. Chem B.*, 106(5):902-904 (2002).
Dai et al., "Novel Nanostructures of Functional Oxides Synthesized by Thermal Evaporation", *Adv. Funct. Mater.*, 13:9-24 (2003).
Davidson et al., "Supercritical Fluid-Liquid-Solid Synthesis of Gallium Arsenide Nanowires Seeded by Alkanethiol-Stabilized Gold Nanocrystals", *Adv. Mater.*, 16:646-649 (2004).
De Gans, "Inkjet Printing of Polymers: State of the Art and Future Developments", *Adv. Mater.*, 16(3):203-213 (2004).
De Sio et al., "Electro-Optical Response of a Single-Crystal Diamond Ultraviolet Photoconductor in Transverse Configuration", *Appl. Phys. Lett.*, 86:213504 (Web Release May 18, 2005).
Deboer et al., "Organic Single-Crystal Field-Effect Transistors", *Phys. Stat. Sol.*, 201:1302-1331 (2004).
Deen et al., "Electrical Characterization of Polymer-Based FETs Fabricated by Spin-Coating Poly(3-alkylthiophene)s", *IEEE Trans. Electron Devices*, 51:1892-1901 (2004).
Delmerche et al., "Stability of Molded Polydimethylsiloxane Microstructures", *Adv. Mat.*, 9:741-746 (1997).
Deruelle et al., "Adhesion at the Solid-Elastomer Interface: Influence of Interfacial Chains", *Macromol.*, 28:7419-7428 (1995).
Derycke et al., "Carbon Nanotube Inter- and Intramolecular Logic Gates", *Nano Lett.*, 1(9):453-456 (2001).
Desai et al., "Nanopore Technology for Biomedical Applications", *Biomed. Microdevices*, 2(1):11-40 (1999).
Dick et al., "Synthesis of Branched 'Nanotrees' by Controlled Seeding of Multiple Branching Events", *Nat. Mater.*, 3:380-384 (2004).
Dimroth et al., "High Efficiency Multijunction Solar Cells", *MRS Bull.*, 32:230-235 (2007).
Ding et al., "Self Catalysis and Phase Transformation in the Formation of CdSe Nanosaws", *Adv. Mater.*, 16(19):1740-1743 (2004).
Dinsmore et al., "Colloidosomes: Selectively Permeable Capsules Composed of Colloidal Particles", *Science*, 298:1006-1009 (2002).
Divliansky et al., "Fabrication of Three-Dimensional Polymer Photonic Crystal Structures Using Single Diffraction Element Interference Lithography", *Appl. Phys. Lett.*, 82(11):1667-1669 (2003).
Dodabalapur, "Organic and Polymer Transistors for Electronics", *Mater. Today*, 9(4):24-30 (2006).
Dodabalapur et al., "Organic Transistors: Two-Dimensional Transport and Improved Electrical Characteristics", *Science*, 268:270-271 (1995).
Duan et al., "General Synthesis of Compound Semiconductor Nanowires", *Adv. Mater.*, 12(4):298-302 (2000).
Duan et al., "High-performance Thin-Film Transistors Using Semiconductor Nanowires and Nanoribbons", *Nature*, 425:274-278 (2003).
Duan, "Semiconductor Nanowires: From Nanoelectronics to Macroelectronics", Abstract from a presentation given at the 11th Foresight Conference on Molecular Nanotechnology, Oct. 10-20, Burlingame, CA (2003).
Duboz et al., "Transistors and Detectors Based on GaN-Related Materials", In; Group III Nitride Semiconductor Compounds, Gill, B. ed., Clarendon, Oxford, pp. 343-387 (1998).
Duesberg et al., "Polarized Raman Spectroscopy on Isolated Single-Wall Carbon Nanotubes", *Phys. Rev. Lett.*, 85(25): 5436-5439 (2000).

Duffy et al., "Rapid Prototyping of Microfluidic Systems in Poly(dimethylsiloxane)", *Anal. Chem.*, 70:4974-4984 (1998).
Dupuis et al., "History, Development, and Applications of High-Brightness Visible Light-Emitting Diodes", *IEEE J. Lightwave Tech.*, 26:1154-1171 (2008).
Durkop et al., "Extraordinary Mobility in Semiconducting Carbon Nanotube", *Nano Lett.*, 4(1):35-39 (2004).
Eder et al., "Organic Electronics on Paper", *Appl. Phys. Lett.*, 84(14):2673-2675 (2004).
Edrington et al., "Polymer-Based Photonic Crystals," *Adv. Mater.* 13:421-425 (2001).
Efimenko et al., "Surface Modification of Sylgard-184 Poly(dimethyl Siloxane) Networks by Ultraviolet and Ultraviolet/Ozone Treatment", *J. Colloid Interface Sci.*, 254(2):306-315 (2002).
Eftekhari, Variation in the Effective Richardson Constant of Metal-GaAs and Metal-InP Contacts Due to the Effect of Processing Parameters, *Phys. Status Solid A-Appl. Res.*, 140:189-194 (1993).
Ensell, "Free Standing Single-Crystal Silicon Microstructures", *J. Micromech. Microeng.*, 5:1-4 (1995).
Faez et al., "An Elastomeric Conductor Based on Polyaniline Prepared by Mechanical Mixing", *Polymer*, 40:5497-5503 (1999).
Felgner et al., "Flexural Rigidity of Microtubules Measured with the Use of Optical Tweezers", *J. Cell Sci.*, 109:509-516 (1996).
Fink et al., "Block Copolymers as Photonic Bandgap Materials", *J. Lightwave Tech.*, 17:1963-1969 (1999).
Flewitt et al., "Low-Temperature Deposition of Hydrogenated Amorphous Silicon in an Electron Cyclotron Resonance Reactor for Flexible Displays", *Proc. IEEE*, 93:1364-1373 (2005).
Folch et al., "Wafer-Level In-Registry Microstamping", *J. Microelectromech. Syst.*, 8:85-89 (1999).
Forment et al., "Influence of Hydrogen Treatment and Annealing Processes Upon the Schottky Barrier Height of Au/n-GaAs and Ti/n-GaAs Diodes", *Semicond. Sci. Technol.*, 19:1391-1396 (2004).
Forrest et al., "The Path to Ubiquitous and Low-Cost Organic Electronic Appliances on Plastic", *Nature*, 428:911-918 (2004).
Fortunato et al., "Flexible a-Si: H Position-Sensitive Detectors", *Proc. IEEE*, 93:1281-1286 (2005).
Fortunato et al., "High-Performance Flexible Hybrid Field-Effect Transistors Based on Cellulose Fiber Paper", *IEEE Electron. Dev. Lett.*, 29(9):988-990 (2008).
Freeman et al., "Spatial Spectral Analysis of Human Electrocardiograms Including the Alpha and Gamma Bands", *J. Neurosci. Methods*, 95:111-121 (2000).
Freire et al., "Thermal Stability of Polyethylene Terephthalate (PET): Oligomer Distribution and Formation of Volatiles," Packag. Technol. Sci. 12:29-36 (1999).
Freund, "The Mechanics of Electronic Materials," *Int. J. Solids Struct.* 37:185-196 (2000).
Friedman et al., "High-Speed Integrated Nanowire Circuits," *Nature* 434:1085 (2005).
Fu et al., "Patterning of Diamond Microstructures on Si Substrate by Bulk and Surface Micromachining", *J. Mater. Process. Technol.*, 132(1-3):73-81 (2003).
Furneaux et al., "The Formation of Controlled-Porosity Membranes from Anodically Oxidized Aluminum," *Nature* 337:147-149 (1989).
Gan et al., "Preparation of Thin-Film Transistors With Chemical Bath Deposited CdSe and CdS Thin Films", *IEEE Trans. Electron. Dev.*, 49:15-18 (2002).
Gao et al., "Conversion of Zinc Oxide Nanobelts into Superlattice-Structures Nanohelices", *Science*, 309:1700-1704 (2005).
Garcia et al., "Etchant Anisotropy Controls the Step Bunching Instability in KOH Etching of Silicon", *Phys. Rev. Lett.*, 93(16):166102 (2004).
Gardner et al., "Physical Aspects of the Internal Water Relations of Plant Leaves", *Plant Physiol.*, 40:705-710 (1965).
Garnier et al., "All-Polymer Field-Effect Transistor Realized by Printing Techniques", *Science*, 265:1684-1686 (1994).
Geim et al., "The Rise of Graphene", *Nature Mater.*, 6:183-191 (2007).
Geissler et al., "Fabrication of Metal Nanowires Using Microcontact Printing", *Langmuir*, 19(15):6301-6311 (2003).

(56) References Cited

OTHER PUBLICATIONS

Geissler et al., "Selective Wet-Etching of Microcontact-Printed Cu Substrates with Control Over the Etch Profile", *Microelec. Eng.*, 67-68:326-332 (2003).
Gelinck et al., "High-Performance All-Polymer Integrated Circuits", *Appl. Phys. Lett.*, 77:1487-1489 (2000).
Gelinck et al., "Flexible Active-Matrix Displays and Shift Registers Based on Solution-Processed Organic Transistors", *Nat. Mater.*, 3:106-110 (2004).
Georgakilas et al., "Wafer-Scale Integration of GaAs Optoelectronic Devices with Standard Si Integrated Circuits Using a Low-Temperature Bonding Procedure", *Appl. Phys. Lett.*, 81:5099-5101 (2002).
Givargizov, E.I., "Applications", In; Oriented Crystallization on Amorphous Substrates, Plenum Press, New York, pp. 341-363 (1991).
Goetting et al., "Microcontact Printing of Alkanephosphonic Acids on Aluminum: Pattern Transfer by Wet Chemical Etching", *Langmuir*, 15:1182-1191(1999).
Goldman et al., "Correlation of Buffer Strain Relaxation Modes with Transport Properties of Two-Dimensional Electron Gases", *J. Appl. Phys.*, 80:6849-6854 (1996).
Goldmann et al., "Hole Mobility in Organic Single Crystals Measured by a "Flip-Crystal" Field-Effect Technique", *J. Appl. Phys.*, 96:2080-2086 (2004).
Goldsmith, "Optimization, Constraint, and History in the Evolution of Eyes", *Quart. Rev. Biol.*, 65(3):281-322 (1990).
Gratz et al., "Atomic Force Microscopy of Atomic-Scale Ledges and Etch Pits Formed During Dissolution of Quartz", *Science*, 251:1343-1346 (1991).
Gray et al., "Screen Printed Organic Thin Film Transistors (OTFTs) on a Flexible Substrate", *Proc. SPIE*, 4466:89-94 (2001).
Gray et al., "High-Conductivity Elastomeric Electronics", *Adv. Mater.*, 16(5):393-397 (2004).
Grayson, "Curved Focal Plane Wide Field of View Telescope Design", *Proc. SPIE*, 4849:269-274 (2002).
Gruen et al., "Fullerenes as Precursors for Diamond Film Growth Without Hydrogen or Oxygen Additions", *Appl. Phys. Lett.*, 65(12):1502-1504 (1994).
Gudiksen et al., "Synthetic Control of the Diameter and Length of Single Crystal Semiconductor Nanowires", *J. Phys. Chem B.*, 105:4062-4064 (Web Release Apr. 18, 2001).
Guo et al., "Metal-Insulator-Semiconductor Electrostatics of Carbon Nanotubes", *Appl. Phys. Lett.*, 81(8):1486-1488 (2002).
Gur et al., "Air-Stable All-Inorganic Nanocrystal Solar Cells Processed from Solution", *Science*, 310:462-465 (2005).
Gurbuz et al., "Diamond Semiconductor Technology for RF Device Applications", *Solid State Electron.*, 49(7):1055-1070 (2005).
Haisma et al., "Contact Bonding, Including Direct-Bonding in a Historical and Recent Context of Materials Science and Technology, Physics and Chemistry", *Mater. Sci Eng.*, 37:1-60 (2002).
Halik et al., "Low-Voltage Organic Transistors with an Amorphous Molecular Gate Dielectric", *Nature*, 431:963-966 (2004).
Hamedi et al., "Towards Woven Logic from Organic Electronic Fibres", *Nat. Mater.*, 6:357-362 (2007).
Hamilton et al., "Field-Effect Mobility of Organic Polymer Thin-Film Transistors", *Chem. Mater.*, 16:4699-4704 (2004).
Han et al., "Template-Free Directional Growth of Single-Walled Carbon Nanotues on a- and r-Plane Sapphire", *J. Am. Chem. Soc.*, 127:5294-5295 (2005).
Harada et al., "Catalytic Amplification of the Soft Lithographic Patterning of Si. Nonelectrochemical Orthogonal Fabrication of Photoluminescent Porous Si Pixel Arrays", *J. Am. Chem. Soc.*, 123:8709-8717 (2001).
Harkonen et al., "4 W Single-Transverse Mode VECSEL Utilizing Intra-Cavity Diamond Heat Spreader", *Electron Lett.*, 42(12):693-694 (2006).
Hayase et al., "Photoangioplasty with Local Motexafin Lutetium Delivery Reduces Macrophages in a Rabbit Post-Balloon Injury Model", *Cardiovascular Res.*, 49:449-455 (2001).

He et al., "Si Nanowire Bridges in Microtrenches: Integration of Growth into Device Fabrication", *Adv. Mater.*, 17:2098-2102 (2005).
Heffelfinger et al., "Steps and the structure of the (0001) α-alumina surface", *Surf. Sci.*, 370:L168-L172 (1997).
Hillbrog et al., "Nanoscale Hydrophobic Recovery: A Chemical Force Microscopy Study of UV/Ozone-Treated Cross-Linker Poly(dimethylsiloxane)", *Langmuir*, 20(3):785-794 (Web Release Dec. 30, 2003).
Hines et al., "Nanotransfer Printing of Organic and Carbon Nanotube Thin-Film Transistors on Plastic Substrates", *Appl. Phys. Lett.*, 86:163101 (2005).
Hollenberg et al., "A MEMS Fabricated Flexible Electrode Array for Recording Surface Field Potentials",*J. Neurosci. Methods*, 153:147-153 (2006).
Holmes et al., "Control of Thickness and Orientation of Solution-Grown Silicon Nanowires", *Science*, 287:1471-1473 (2000).
Horan et al., "In Vitro Degradation of Silk Fibroin", *Biomaterials*, 26(17):3385-3393 (2005).
Horn et al., "Contact Electrification and Adhesion Between Dissimilar Materials", *Science*, 256:362-364 (1992).
Hoyer, P., "Semiconductor Nanotube Formation by a Two-Step Template Process", *Adv. Mater.*, 8:857-859 (1996).
Hsia et al., "Collapse of Stamps for Soft Lithography Due to Interfacial Adhesion", *Appl. Phys. Lett.*, 86:154106 (2005).
Hsu et al., "Amorphous Si TFTs on Plastically Deformed Spherical Domes", *J. Non-Crystalline Solids*, 299-302:1355-1359 (2002).
Hsu et al., "Nature of Electrical Contacts in a Metal-Molecule-Semiconductor System", *J. Vac. Sci. Technol. B.*, 21(4):1928-1935 (2003).
Hsu et al., "Spherical Deformation of Compliant Substrates with Semiconductor Device Islands", *J. Appl. Phys.*, 95(2):705-712 (2004).
Hsu et al., "Effects of Mechanical Strain on TFT's on Spherical Domes", *IEEE Trans. Electron Dev.*, 51(3):371-377 (2004).
Hu et al., "Using Soft Lithography to Fabricate GaAs/AlGaAs Heterostructure Field Effect Transistors", *Appl. Phys. Lett.*, 71:2020-2022 (1997).
Hu et al., Chemistry and Physics in One Dimension: Synthesis and Properties of Nanowires and Nanotubes, *Acc. Chem. Res.*, 32:435-445 (1999).
Hu et al., "Percolation in Transparent and Conducting Carbon Nanotube Networks", *Nano Lett.*, 4(12): 2513-2517 (2004).
Hu et al., "Highly Conductive Paper for Energy-Storage Devices", *Proc. Natl. Acad. Sci. USA*, 106:21490-21494 (2009).
Hu et al., "Stretchable, Porous, and Conductive Energy Textiles", *Nano Lett.*, 10:708-714 (2010).
Huang et al., "Directed Assembly of One-Dimensional Nanostructures into Functional Networks", *Science*, 291:630-633 (2001).
Huang et al., "Room-Temperature Ultraviolet Nanowire Nanolasers", *Science*, 292:1897-1899 (2001).
Huang et al., "Growth of Millimeter-Long and Horizontally Aligned Single-Walled Carbon Nanotubes on Flat Substrates", *J. Am. Chem. Soc.*, 125:5636-5637 (2003).
Huang et al., "Long and Oriented Single-Walled Carbon Nanotubes Grown by Ethanol Chemical Vapor Deposition", *J. Phys. Chem. B.*, 108:16451-16456 (2004).
Huang et al., "Self-Organizing High-Density Single-Walled Carbon Nanotube Arrays from Surfactant Suspensions", *Nanotechnol.*, 15:1450-1454 (2004).
Huang et al., "Nanomechanical Architecture of Strained Bilayer Thin Films: From Design Principles to Experimental Fabrication", *Adv. Mater.*, 17(23):2860-2864 (2005).
Huang et al., "Nanowires for Integrated Multicolor Nanophotonics", *Small*, 1(1):142-147 (2005).
Huang et al., "Nonlinear Analyses of Wrinkles in a Film Bonded to a Compliant Substrate",*J. Mech. Phys. Solids*, 53:2101-2118 (2005).
Huang et al., "Stamp Collapse in Soft Lithography", *Langmuir*, 21:8058-8068 (2005).
Huang et al., "Catalytic Growth of Zinc Oxide Nanowires by Vapor Transport", *Adv. Mater.*, 13(2):113-116 (2001).
Huck et al., "Ordering of Spontaneously Formed Buckles on Planar Surfaces", *Langmuir*, 16:3497-3501 (2000).

(56) References Cited

OTHER PUBLICATIONS

Huie, "Guided Molecular Self Assembly: A review of Recent Efforts," *Smart Mater. Struct.* 12:264-271 (2003).
Huitema et al., "Plastic Transistors in Active-Matrix Displays", *Nature*, 414:599 (2001).
Hur et al., "Organic Nanodielectrics for Low Voltage Carbon Nanotube Thin Film Transistors and Complementary Logic Gates", *J. Am. Chem. Soc.*, 127:13808-13809 (2005).
Hur et al., "Printed thin-film transistors and complementary logic gates that use polymer-coated single-walled carbon nanotube networks", *J. Appl. Phys.*, 98: 114302 (2005).
Hur et al., "Nanotransfer Printing by Use of Noncovalent Surface Forces: Applications to Thin-Film Transistors that Use Single-Walled Carbon Nanotube Networks and Semiconducting Polymers", *Appl. Phys. Lett.*, 85(23):5730-5732 (2004).
Hur et al., "Extreme Bendability of Single Walled Carbon Nanotube Networks Transferred From High-Temperature Growth Substrates to Plastic and Their Use in Thin-Film Transistors", *Appl. Phys. Lett.*, 86: 243502 (2005).
Hutchinson et al., "Mixed Mode Cracking in Layered Materials", *Adv. Appl. Mech.*, 29:63-191 (1992).
Imparato et al., "Excimer Laser Induced Crystallization of Amorphous Silicon on Flexible Polymer Substrates", *Thin Solid Films*, 487:58-62 (2005).
Isberg et al., "High Carrier Mobility in Single-Crystal Plasma-Deposited Diamond", *Science*, 297:1670-1672 (2002).
Islam et al., "High Weight Fraction Surfactant Solubilization of Single-Wall Carbon Nanotubes in Water", *Nano Lett.*, 3(2):269-273 (2003).
Ismach et al., "Atomic-Step-Tern plated Formation of Single Wall Carbon Nanotube Patterns", *Angew. Chem. Int. Ed.*, 43:6140-6143 (2004).
Itoh et al., "Cathodoluminescence Properties of Undoped and Zn-Doped $Al_xGa_{1-x}N$ Grown by Metalorganic Vapor Phase Epitaxy", *Jap. J. Appl. Phys.*, 30:1604-1608 (1991).
Jabbour et al., "Screen Printing for the Fabrication of Organic Light-Emitting Devices", *IEEE J. Select. Top. Quantum. Electron.*, 7:769-773 (2001).
Jackman et al., "Fabrication of Submicrometer Features on Curved Substrates by Microcontact Printing", *Science*, 269:664-666 (1995).
Jacobs et al., "Submicrometer Patterning of Charge in Thin-Film Electrets", *Science*, 291:1763-1766 (2001).
Jacobs et al., "Fabrication of a Cylindrical Display by Patterned Assembly", *Science*, 296:323-325 (2002).
Jain et al., "III-Nitrides: Growth, Characterization, and Properties", *J. Appl. Phys.*, 87:965-1006 (2000).
Jain et al., "Flexible Electronics and Displays: High-Resolution, Roll-to-Roll, Projection Lithography and Photoablation Processing Technologies for High-Throughput Production", *Proc. IEEE*, 93:1500-1510 (2005).
James et al., "Patterned Protein Layers on Solid Substrates by This Stamp Microcontact Printing", *Langmuir*, 14:742-744 (1998).
Jang et al., "Lateral Growth of Aligned Multiwalled Carbon Nanotubes Under Electric Fields", *Solid State Commun.*, 126:305-308 (2003).
Jang et al., "Low-Voltage and High-Field-Effect Mobility Organic Transistors with a Polymer Insulator", *Appl. Phys. Lett.*, 88:072101 (2006).
Javey et al., "High-K Dielectrics for Advanced Carbon-Nanotube Transistors and Logic Gates", *Nature* Mater., 1:241-246 (2002).
Javey et al., "High Performance n-Type Carbon Nanotube Field-Effect Transistors with Chemically Doped Contacts", *Nano Lett.*, 5(2): 345-348 (2005).
Javey et al., "Ballistic Carbon Nanotube Field-Effect Transistors", *Nature*, 424:654-657 (2003).
Jenkins et al., "Gallium Arsenide Transistors: Realization Through a Molecularly Designed Insulator", *Science*, 263:1751-1753 (1994).
Jeon et al., "Patterning of Dielectric Oxide Thin Layers by Microcontact Printing of Self-Assembled Monolayers", *J. Mater. Res.* 10:2996-2999 (1995).

Jeon et al., "Structural and Mechanical Properties of Woven Fabrics Employing Peirce's Model," *Textile Res. J.*, 73:929-933 (2003).
Jeon et al., "Fabricating Complex Three-Dimensional Nanostructures with High Resolution Conformable Phase Masks", *Proc. Natl. Acad. Sci. USA*, 101:12428-12433 (2004).
Jeon et al., "Three Dimensional Nanofabrication with Rubber Stamps and Conformable Photomasks", *Adv. Mater.*, 16:593-600 (2004).
Jeon et al., "Three Dimensional Nanofabrication with Rubber Stamps and Conformable Photomasks", *Adv. Mater.*, 16(15):1369-1375 (2004).
Jiang et al., "Preparation of Macroporous Metal Films from Colloidal Crystals", *J. Am. Chem. Soc.*, 121:7957-7958 (1999).
Jiang et al., "Polymer-on-Polymer Stamping: Universal Approaches to Chemically Patterned Surfaces", *Langmuir*, 18:2607-2615 (2002).
Jiang et al., "Mechanical Properties of Robust Ultrathin Silk Fibroin Films," *Adv. Funct. Mater.*, 17:2229-2237 (2007).
Jiang et al., "Finite Deformation Mechanics in Buckled Thin Films on Compliant Supports", *Proc. Natl. Acad. Sci. USA*, 104(40):15607-15612 (2007).
Jin et al., "Scalable Interconnection and Integration of Nanowire Devices Without Registration", *Nano Lett.*, 4:915-919 (2004).
Jin et al., "Soft Lithographic Fabrication of an Image Sensor Array on a Curved Substrate", *J. Vac. Sci. Technol. B.*, 22(5):2548-2551 (2004).
Jin et al., "Water-Stable Silk Films with Reduced β-Sheet Content", *Adv. Funct. Mater.*, 15(8):1241-1247 (2005).
Jin et al., "Biomaterial Films of Bombyx mori Silk Fibroin with Poly(ethylene oxide)", *Biomacromolecules*, 5(3):711-717 (Web Release Jan. 23, 2004).
Jiyun, "Guided Molecular Self-Assembly: A Review of Recent Efforts", *Smart Mater. Struct.*, 12:264-271 (2003).
Joachim et al., "Electronics Using Hybrid-Molecular and Mono-Molecular Devices", *Nature*, 408:541-548 (2000).
Johnson et al., "Ordered Mesoporous Polymers of Tunable Pore Size from Colloidal Silica Templates", *Science*, 283:963-965 (1999).
Jones et al., "Stretchable Wavy Metal Interconnects", *J. Vac. Sci. Technol. A.*, 22(4):1723-1725 (2004).
Joo et al., "Low-Temperature Solution-Phase Synthesis of Quantum Well Structures CdSe Nanoribbons", *J. Am. Chem. Soc.*, 128(17):5632-5633 (2006).
Jortner et al., "Nanostructured Advanced Materials Perspectives and Directions", *Pure Appl. Chem.*, 74(9):1491-1506 (2002).
Joselevich, "Vectorial Growth of Metallic and Semiconducting Single-Wall Carbon Nanotubes", *Nano Lett.*, 2(10): 1137-1141 (2002).
Kadish et al., "Interaction of Fiber Orientation and Direction of Impulse Propagation with Anatomic Barriers in Anisotropic Canine Myocardium", *Circulation*, 78:1478-1494 (1988).
Kagan, "Organic-Inorganic Hybrid Materials as Semiconducting Channels in Thin-Film Field-Effect Transistors", *Science*, 286:945-947 (1999).
Kagan et al., "Patterning Organic-Inorganic Thin-Film Transistors Using Microcontact Printed Templates", *Appl. Phys Lett.*, 79(21):3536-3538 (2001).
Kagan et al., "Thin Film Transistors", Dekker, New York, pp. 1-34 (2003).
Kane et al., "Analog and Digital Circuits Using Organic Thin-Film Transistors on Polyester Substrates", *IEEE Electron. Dev. Lett.*, 21:534-536 (2000).
Kang et al., "Printed Multilayer Superstructures of Aligned Single-Walled Carbon Nanotubes for Electronic Applications", *Nano Lett.*, 7(11):3343-3348 (2007).
Kang et al., "High-Performance Electronics Using Dense, Perfectly Aligned Arrays of Single-Walled Carbon Nanotubes", *Nat. Nanotechnol.*, 2(4):230-236 (2007).
Kar et al., "Controlled Synthesis and Photoluminescence Properties of ZnS Nanowires and Nanoribbons", *J. Phys. Chem B.*, 109(8):3298-3302 (2005).
Kar et al., "Synthesis and Optical Properties of CdS Nanoribbons", *J. Phys. Chem. B.*, 109(41):19134-19138 (2005).

(56) References Cited

OTHER PUBLICATIONS

Kar et al., "Shape Selective Growth of CdS One-Dimensional Nanostructures by a Thermal Evaporation Process", *J. Phys. Chem B.*, 110(10):4542-4547 (2006).
Karnik et al., "Lateral Polysilicon p$^+$-p-n$^+$ and p$^+$-n-n$^+$ Diodes", *Solid-State Electronics*, 47:653-659 (2003).
Karnik et al., "Multiple Lateral Polysilicon Diodes as Temperature Sensors for Chemical Microreaction Systems", *Jpn. J. Appl. Phys.*, 42:1200-1205 (2003).
Kato et al., "The Characteristic Improvement of Si(111) Metal-Oxide-Semiconductor Field-Effect Transistor by Long-Time Hydrogen Annealing", *Jpn. J. Appl. Phys.*, 43(10):6848-6853 (2004).
Katz et al., "Synthetic Chemistry for Ultrapure, Processable, and High-Mobility Organic Transistor Semiconductors", *Acc. Chem. Res.*, 34:359-369 (2001).
Katz, "Recent Advances in Semiconductor Performance and Printing Processes for Organic Transistor-Based Electronics", *Chem. Mater.*, 16:4748-4756 (2004).
Kawata et al., "Finer Features for Functional Microdevices", *Nature*, 412:697-698 (2001).
Kellis et al., "Human Neocortical Electrical Activity Recorded on Nonpenetrating Microwire Arrays: Applicability for Neuroprostheses", *Neurosurg. Focus*, 27(1):E9 (2009).
Kendall, "Vertical Etching of Silicon at Very High Apect Ratios", *Ann. Rev. Mater. Sci.*, 9:373-403 (1979).
Khakani et al., "Lateral Growth of Single Wall Carbon Nanotubes on Various Substrates by Means of an 'All-Laser' Synthesis Approach", *Diamond Relat. Mater.*, 15:1064-1069 (2006).
Khan et al., "High Electron Mobility Transistor Based on a GaN—Al$_x$Ga$_{1-x}$N Heterojunction", *Appl. Phys. Lett.*, 63:1214-1215 (1993).
Khang et al., "A Stretchable Form of Single-Crystal Silicon for High-Performance Electronics on Rubber Substrates", *Science*, 311:208-212 (2006).
Kilby, "Invention of the Integrated Circuit", *IEEE Trans. Electron. Dev.*, 23:648-654 (1976).
Kim et al., "Field Emission from Carbon Nanotubes for Displays", *Diamond and Related Mater.*, 9(3-6):1184-1189 (2000).
Kim et al., "Nanolithography Based on Patterned Metal Transfer and Its Application to Organic Electronic Devices", *Appl. Phys. Lett.*, 80:4051-4053 (2002).
Kim et al., "Epitaxial Self-Assembly of Block Copolymers on Lithographically Defined Nanopatterned Substrates", *Nature*, 424:411-414 (2003).
Kim et al., "Stretchable Electronics: Materials Strategies and Devices", *Adv. Mater.*, 20:4887-4892 (2008).
Kim et al., "Integrated Wireless Neural Interface Based on the Utah Electrode array", *Biomed. Microdevices*, 11:453-466 (2009).
Kim et al., "Optimized Structural Designs for Stretchable Silicon Integrated Circuits", *Small*, 5(24):2841-2847 (2009).
Kim et al., "Stretchable and Foldable Silicon Integrated Circuits", *Science*, 320:507-511 (2008).
Kim et al., "Materials and Noncoplanar Mesh Designs for Integrated Circuits with Linear Elastic Responses to Extreme Mechanical Deformations", *Proc. Natl. Acad. Sci. USA*, 105(48):18675-18680 (2008).
Kim et al., "Complementary Logic Gates and Ring Oscillators Plastic Substrates by Use of Printed Ribbons Single-Crystalline Silicon", *IEEE Electron. Dev. Lett.*, 29(1):73-76 (2008).
Kim et al., "Direct Observation of Electron Emission Site on Boron-Doped Polycrystalline Diamond Thin Films Using an Ultra-High-Vacuum Scanning Tunneling Microscope", *Appl. Phys. Lett.*, 75(20):3219-3221 (1999).
Kim et al., "Waterproof AlInGaP optoelectronics on stretchable substrates with applications in biomedicine and robotics", *Nature Materials*, 9:929-937 (2010).
Kim et al., "Organic TFT Array on a Paper Substrate", *IEEE Electron. Dev. Lett.*, 25(10):702-704 (2004).
Kim et al., "Dissolvable Films of Silk Fibroin for Ultrathin Conformal Bio-Integrated Electronics", *Nature Materials*, 9:511-517 (Web Release Apr. 18, 2010).
Kim et al., "Highly Emissive Self-Assembled Organic Nanoparticles Having Dual Color Capacity for Targeted Immunofluorescence Labeling", *Adv. Mater.*, 20(6):1117-1121 (Web Release Feb. 29, 2008).
Kim et al., "Complementary Metal Oxide Silicon Integrated Circuits Incorporating Monolithically Integrated Stretchable Wavy Interconnects", *Appl. Phys. Lett.*, 93(4):044102 (Web Release Jul. 31, 2008).
Kim et al., "Ultrathin Silicon Circuits with Strain-Isolation Layers and Mesh Layouts for High-Performance Electronics on Fabric, Vinyl, Leather and Paper", *Adv. Mater.*, 21(36):3703-3707 (Web Release Jul. 6, 2009).
Kim et al., "Silicon Electronics on Silk as a Path to Bioresorbable, Implantable Devices", *Appl. Phys. Lett.*, 95:133701-133703 (Web Release Sep. 29, 2009).
Kim, "Microheater-Integrated Single Gas Sensor Array Chip Fabricated on Flexible Polyimide Substrate", *Sens. Actuators B.*, 114(1):410-417 (Web Release Aug. 9, 2005).
Klauk et al., "High-Mobility Polymer Gate Dielectric Pentacene Thin Film Transistors", *J. Appl. Phys.*, 92:5259-5263 (2002).
Klein-Wiele et al., "Fabrication of Periodic Nanostructures by Phase-Controlled Multiple-Beam Interference", *Appl. Phys. Lett.*, 83(23):4707-4709 (2003).
Knipp et al., "Pentacine Thin Film Transistors on Inorganic Dielectrics: Morphology, Structural Properties, and Electronic Transport", *Appl. Phys. Lett.*, 93:347-355 (2003).
Ko et al., "Bulk Quantities of Single-Crystal Silicon Micro-/Nanoribbons Generated from Bulk Wafers", *Nano Lett.*, 6(10):2318-2324 (2006).
Ko et al., "Flexible Carbon Nanofiber Connectors with Anisotropic Adhesion Properties", *Small*, 6:22-26 (2010).
Ko et al., "A Hemispherical Electronic Eye Camera Based on Compressible Silicon Optoelectronics", *Nature*, 454:748-753 (2008).
Ko et al., "Curvilinear Electronics Formed Using Silicon Membrane Circuits and Elastomeric Transfer Elements", *Small*, 5(23):2703-2709 (Web Release Oct. 28, 2009).
Kocabas et al., "Aligned Arrays of Single-Walled Carbon Nanotubes Generated from Random Networks by Orientationally Selective Laser Ablation", *Nano Lett.*, 4(12): 2421-2426 (2004).
Kocabas et al., "Guided Growth of Large-Scale, Horizontally Aligned Arrays of Single-Walled Carbon Nanotubes and Their Use in Thin-Film Transistors", *Small*, 1(11):1110-1116 (2005).
Kocabas et al., "Large Area Aligned Arrays of SWNTs for High Performance Thin Film Transistors", American Physical Society, APS March Meeting, Mar. 13-17, Abstract # W31.004 (2006).
Kocabas et al., "Spatially Selective Guided Growth of High-Coverage Arrays and Random Networks of Single-Walled Carbon Nanotubes and Their Integration into Electronic Devices", *J. Am. Chem. Soc.*, 128:4540-4541 (2006).
Kocabas et al., "Experimental and Theoretical Studies of Transport Through Large Scale, Partially Aligned Arrays of Single-Walled Carbon Nanotubes in Thin Film Type Transistors", *Nano Lett.*, 7(5):1195-1202 (2007).
Kocabas et al., "Radio Frequency Analog Electronics Based on Carbon Nanotube Transistors", *Proc. Natl. Acad. Sci. USA*, 105(5):1405-1409 (2008).
Kodambaka et al., "Control of Si Nanowire Growth by Oxygen", *Nano Lett.*, 6(6):1292-1296 (2006).
Koide et al., "Patterned Luminescence of Organic Light-Emitting Diodes by Hot Microcontact Printing (HμCP) of Self-Assembled Monolayers", *J. Am. Chem. Soc.*, 122:11266-11267(2000).
Konagai et al., "High Efficiency GaAs Thin Film Solar Cells by Peeled Film Technology", *J. Cryst. Growth*, 45:277-280 (1978).
Kong et al., "Single-Crystal Nanorings Formed by Epitaxial Self-Coating of Polar Nanobelts", *Science*, 303:1348-1351 (2004).
Kong et al., "Nanotube Molecular Wires as Chemical Sensors", *Science*, 287:622-625 (2000).
Kong et al., "Structure of Indium Oxide Nanobelts", *Solid State Commun.*, 128(1):1-4 (2003).
Kong et al., "Synthesis of Individual Single-Walled Carbon Nonotubes on Patterned Silicon Wafers", *Nature*, 395:878-881 (1998).

(56) References Cited

OTHER PUBLICATIONS

Kudo et al., "A Flexible and Wearable Glucose Sensor Based on Functional Polymers with Soft-MEMS Techniques", *Biosens. Bioelectron.*, 22:558-562 (Web Release Jun. 13, 2006).
Kulkarni et al., "Mesoscale Organization of Metal Nanocrystals," *Pure Appl. Chem* ,74(9):1581-1591 (2002).
Kumar et al., "Features of Gold Having Micrometer to Centimeter Dimensions can be Formed Through a Combination of Stamping with an Elastomeric Stamp and an Alkanethiol "Ink" Followed by Chemical Etching", *Appl. Phys. Lett.*, 63(4):2002-2004 (1993).
Kumar et al., "Patterning Self-Assembled Monolayers: Applications in Materials Science", *Langmuir*, 10:1498-1511 (1994).
Kumar et al., "Thermally-Stable Low-Resistance Ti/Al/Mo/Au Multilayer Ohmic Contacts on n-GaN", *J. Appl. Phys.*, 92:1712-1714 (2002).
Kumar et al., "Percolating in Finite Nanotube Networks", *Phys. Rev. Lett.*, 95, 066802 (2005).
Kuo et al., "Effect of Mismatch Strain on Band Gap in III-V Semiconductors", *J. Appl. Phys.*, 57:5428-5432 (1985).
Kuykendall et al., "Crystallographic Alignment of High Density Gallium Nitride Nanowire Arrays", *Nat. Mater,.* 3:524-528 (2004).
Lacour et al., "Stretchable Interconnects for Elastic Electronic Surfaces", *Proc. IEEE*, 93:1459-1467 (2005).
Lacour et al., "Flexible and Stretchable Micro-Electrodes for in Vitro and n Vivo Neural Interfaces", *Med. Biol. Eng. Comput.*, 48:945-954 (2010).
Lacour et al., "Stretchable Gold Conductors on Elastomeric Substrates", *Appl. Phys. Lett.*, 82(15):2404 (2003).
Lacour et al., "Design and Performance of Thin Metal Film Interconnects for Skin-Like Electronic Circuits", *IEEE Electron. Dev. Lett.*, 25(4):179-181 (2004).
Lacour et al., "An Elastically Stretchable TFT Circuit", *IEEE Electron Dev. Lett.*, 25(12):792-794 (2004).
Lacour et al., "Stiff Subcircuit Islands of Diamondlike Carbon for Stretchable Electronics", *J. Appl. Phys.*, 100:014913 (Web Release Jul. 14, 2006).
Lacour et al., "Mechanisms of Reversible Stretchability of Thin Metal Films on Elastomeric Substrates", *Appl. Phys. Lett.*, 88:204103 (Web Release May 16, 2006).
Laimer et al., "Diamond Growth in a Direct-Current Low-Pressure Supersonic Plasmajet", *Diamond Relat. Mater.*, 6:406-410 (1997).
Lambacher et al., "Electrical Imaging of Neuronal Activity by Multi-Transistor-Array (MTA) Recording at 7.8 μm Resolution", *Appl. Phys. A.*, 79:1607-1611 (2004).
Landes et al., "Some Properties of Spherical and Rod-Shaped Semiconductor and Metal Nanocrystals", *Pure Appl. Chem.*, 74(9):1675-1692 (2002).
Law et al., "Semiconductor Nanowires and Nanotubes", *Ann. Rev. Mater. Res.*, 34:83-122 (2004).
Law et al., "Nanoribbon Waveguides for Subwavelength Photonics Integration", *Science*, 305:1269-1273 (2004).
Lawrence et al., "Bioactive Silk Protein Biomaterial Systems for Optical Devices", *Biomacromolecules*, 9:1214-1220 (2008).
Lay et al., "Simple Route to Large-Scale Ordered Arrays of Liquid-Deposited Carbon Nanotubes", *Nano Lett.*, 4(4): 603-606 (2004).
Leclercq et al., "III-V Micromachined Devices for Microsystems", *Microelectronics J.*, 29:613-619 (1998).
Lecomte et al., "Degradation Mechanism of Diethylene Glycol Units in a Terephthalate Polymer", *Polym. Degrade. Stab.*, 91(4):681-689 (2006).
Lee et al., "Thin Film Transistors for Displays on Plastic Substrates", *Solid State Electron.*, 44:1431-1434 (2000).
Lee et al., "High-Performance Poly-Si TFTs on Plastic Substrates Using a Nano-Structured Separation Layer Approach", *IEEE Elec. Dev. Lett.*, 24:19-21 (2003).
Lee et al., "Organic Light-Emitting Diodes Formed by Soft Contact Lamination", *Proc. Natl. Acad. Sci. USA*, 101(2):429-433 (2004).
Lee et al., "A Printable Form of Single-Crystalline Gallium Nitride for Flexible Optoelectronic Systems", *Small*, 1:1164-1168 (2005).

Lee et al., "Large-Area, Selective Transfer of Microstructured Silicon (μs-Si): A Printing-Based Approach to High-Performance Thin-Film Transistors Supported on Flexible Substrates", *Adv. Mater.*, 17:2332-2336 (2005).
Lee et al., "Micron and Submicron Patterning of Polydimethylsiloxane Resists on Electronic Materials by Decal Transfer Lithography and Reactive Ion-Beam Etching: Application to the Fabrication of High-Mobility, Thin-Film Transistors", *Appl. Phys. Lett.*, 100:084907/1-7 (2006).
Lee et al., "Fabrication of Stable Metallic Patterns Embedded in Poly(dimethylsiloxane) and Model Applications in Non-Planar Electronic and Lab-on-a-Chip Device Patterning", *Adv. Funct. Mater.*, 15(4):557-566 (2005).
Lee et al., "The Surface/Bulk Micromachining (SBM) Process: A New Method for Fabricating Released MEMS in Single Crystal Silicon", *J. Microelectromech. Syst.*, 8(4):409-416 (1999).
Lee et al., "Application of Carbon Nanotubes to Field Emission Displays", *Diamond and Related Mater.*, 10(2):265-270 (2001).
Lee et al., "Weave Patterned Organic Transistors on Fiber for E-Textiles", *IEEE Trans. Electron. Dev.*, 52(2):269-275 (2005).
Leong et al., "Tetherless Thermobiochemicall Actuated Microgrippers", *Proc. Natl. Acad. Sci. USA*, 106:703-709 (2009).
Létant et al., "Functionalized Silicon Membranes for Selective Bio-Organisms Capture", *Nat. Mater.*, 2:391-395 (2003).
Li et al., "High-Resolution Contact Printing with Dendrimers", *Nano Lett.*, 2(4):347-349 (2002).
Li et al., "Ultrathin Single-Crystalline-Silicon Cantilever Resonators: Fabrication Technology and Significant Specimen Size effect on Young's Modulus", *Appl. Phys. Lett.*, 83:3081-3083 (2003).
Li et al., "Electrospinning of Nanofibers: Reinventing the Wheel", *Adv. Mater.*, 16(14):1151-1170 (2004).
Li et al., "Catalyst-Assisted Formation of Nanocantilever Arrays on ZnS Nanoribbons by Post-Annealing Treatment", *J. Phys. Chem B.*, 110(13):6759-6762 (2006).
Li et al., "Compliant Thin Film Patterns of Stiff Materials as Platforms for Stretchable Electronics", *J. Mater. Res.*, 20(12):3274-3277 (2005).
Li et al., "ZnO Nanobelts Grown on Si Substrate", *Appl. Phys. Lett.*, 81:144-146 (2002).
Lieber, "The Incredible Shrinking Circuit", *Sci. Am.*, 285(3):58-64 (2001).
Lieber, "Nanoscale Science and Technology: Building a Big Future from Small Things", *MRS Bull.*, 28:486-491 (2003).
Lim et al., "Flexible Membrane Pressure Sensor", *Sens. Act. A.*, 119:332-335 (2005).
Lima et al., "Creating Micro- and Nanostructures on Tubular and Spherical Surfaces", *J. Vac. Sci. Technol. B.*, 25(6):2412-2418 (2007).
Lin et al., "High-Performance Carbon Nanotube Field-Effect Transistor With Tunable Polarities", *IEEE Trans. Nano*, 4(5):481-489 (2005).
Linder et al., "Fabrication Technology for Wafer Through-Hole Interconnections and Three-Dimensional Stacks of Chips and Wafers", *Proc. IEEE Micro. Electro Mech. Syst.*, 349-354 (1994).
Ling et al., "Thin Film Deposition, Patterning, and Printing in Organic Thin Film Transistors", *Chem. Mater.*, 16:4824-4840 (2004).
Liu et al., "Controlled deposition of individual single-walled carbon nanotubes on chemically functionalized templates", *Chem. Phys. Lett.*, 303:125-129 (1999).
Long et al., "Heterostructure FETs and Bipolar Transistors", In; Gallium Arsenide Digital Integrated Circuit Design, McGraw-Hill, New York, pp. 58-69 (1990).
Loo et al., "Additive, Nanoscale Patterning of Metal Films with a Stamp and a Surface Chemistry Mediated Transfer Process: Applications in Plastic Electronics", *Appl. Phys. Lett.*, 81:562-564 (2002).
Loo et al., "High-Resolution Transfer Printing on GaAs Surfaces Using Alkane Dithiol Monolayers", *J. Vac. Sci. Technol. B.*, 20(6):2853-2856 (2002).
Loo et al., "Interfacial Chemistries for Nanoscale Transfer Printing", *J. Am. Chem. Soc.*, 124:7654-7655 (2002).
Loo et al., "Soft, Conformable Electrical Contacts for Organic Semiconductors: High-Resolution Plastic Circuits by Lamination," *Proc. Natl. Acad. Sci. USA* 99(16):10252-10256 (2002).

(56) References Cited

OTHER PUBLICATIONS

Loo et al., "Electrical Contacts to Molecular Layers by Nanotransfer Printing", *Nano Lett.*, 3(7):913-917 (2003).
Loo et al., "Progress and challenges in commercialization of organic electronics," *MRS Bull.* 33(7): 653-662 (2008).
Lopes et al., "Thermal Conductivity of PET/(LDPE/Al) Composites Determined by MDSC", *Polym. Test.*, 23(6):637-643 (2004).
Lu et al., "Water-Insoluble Silk Films with Silk I Structure", *Acta Biomater.*, 6(4):1380-1387 (2010).
Lu et al., "Electronic Materials-Buckling Down for Flexible Electronics", *Nat. Nanotechnol.*, 1:163-164 (2006).
Lu et al., "One Dimensional Hole Gas in Germanium/Silicon Nanowire Heterostructures", *Proc. Nat. Acad. Sci. USA*, 102(29):10046-10051 (2005).
Lu et al., "Nanowire Transistor Performance Limits and Applications", *IEEE Trans Electron Dev.*, 55(11):2859-2876 (2008).
Luan et al., "An Experimental Study of the Source/Drain Parasitic Resistance Effects in Amorphous Silicon Thin Film Transistors", *J. Appl. Phys.*, 72:766-772 (1992).
Ma et al., "Single-Crystal CdSe Nanosaws", *J. Am. Chem. Soc.*, 126(3):708-709 (2004).
Mack et al., "Mechanically Flexible Thin-Film Transistors that Use Ultrathin Ribbons of Silicon Derived from Bulk Wafers", *Appl. Phys. Lett.*, 88:213101 (2006).
Madou, M., "Etch-Stop Techniques," In; Fundamentals of Microfabrication, CRC Press, New York, pp. 193-199 (1997).
Maikap et al., "Mechanically Strained-Si NMOSFETs", *IEEE Electron. Dev. Lett.*, 25:40-42 (2004).
Maldovan et al., "Diamond-Structured Photonic Crystals", *Nature Materials*, 3:593-600 (2004).
Mandlik et al., "Fully Elastic Interconnects on Nanopatterned Elastomeric Substrates", *IEEE Electron Dev. Lett.*, 27(8):650-652 (2006).
Manna et al., Controlled Growth of Tetrapod-Branched Inorganic Nanocrystals, *Nat. Mater.*, 2:382-385 (Web Release May 25, 2003).
Markovich et al., "Architectonic Quantum Dot Solids", *Acc. Chem. Res.*, 32:415-423 (1999).
Marquette et al., "Conducting Elastomer Surface Texturing: A Path to Electrode Spotting Application to the Biochip Production", *Biosens. Bioelectron.*, 20:197-203 (2004).
Martensson et al., "Nanowire Arrays Defined by Nanoimprint Lithography", *Nano Lett.*, 4:699-702 (2004).
Martin, "Template Synthesis of Electronically Conductive Polymer Nanostructures", *Acc. Chem. Res.*, 28:61-68 (1995).
Mas-Torrent et al., "Large Photoresponsivity in High-Mobility Single-Crystal Organic Field-Effect Phototransistors", *ChemPhysChem*, 7:86-88 (2006).
Masuda et al., "Fabrication of Ordered Diamonds/Metal Nanocomposite Structures", *Chem. Lett.*, 10:1112-1113 (2000).
Matsunaga et al., "An Improved GaAs Device Model for the Simulation of Analog Integrated Circuit", *IEEE Trans. Elect. Dev.*, 50:1194-1199 (2003).
McAlpine et al., "High-Performance Nanowire Electronics and Photonics on Glass and Plastic Substrates", *Nano Lett.*, 3:1531-1535 (2003).
McAlpine et al., "High-Performance Nanowire Electronics and Photonics and Nanoscale Patterning on Flexible Plastic Substrates", *Proc. IEEE*, 93:1357-1363 (2005).
McCaldin et al., "Diffusivity and Solubility of Si in the Al Metallization of Integrated Circuits", *Appl. Phys. Lett.*, 19:524-517 (1971).
McCoy et al., "Triggered drug delivery from biomaterials", *Expert Opinion on Drug Delivery*, 7(5): 605-616 (2010).
Mehring et al., Inference of hand movements from local field potentials in monkey motor cortex., *Nature Neurosci.*, 6, 1253-1254 (2003).
Meisel et al., "Three-Dimensional Photonic Crystals by Holographic Lithography Using the Umbrella Configuration: Symmetries and Complete Photonic Band Gaps", *Phys. Rev. B.*, 70:165101:1-10 (2004).

Meitl et al., "Solution Casting and Transfer Printing Single-Walled Carbon Nanotube Films", *Nano Lett.*, 4:1643-1647 (2004).
Meitl et al., "Transfer Printing by Kinetic Control of Adhesion to an Elastomeric Stamp", *Nat. Mater.*, 5:33-38 (2006).
Meitl et al., "Stress Focusing for Controlled Fracture in Microelectromechanical Systems", *Appl. Phys. Lett.*, 90:083110 (Web Release Feb. 22, 2007).
Melosh et al., "Ultrahigh-Density Nanowire Lattices and Circuits", *Science*, 300:112-115 (2003).
Menard et al., "A Printable Form of Silicon for High Performance Thin Film Transistors on Plastic Substrates", *Appl. Phys. Lett.*, 84:5398-5400 (2004).
Menard et al., "High-Performance n- and p-Type Single-Crystal Organic Transistors with Free-Space Gate Dielectrics", *Adv. Mat.*, 16:2097-2101 (2004).
Menard et al., "Improved Surface Chemistries, Thin Film Deposition Techniques, and Stamp Designs for Nanotransfer Printing", *Langmuir*, 20:6871-6878 (2004).
Menard et al., "Bendable Single Crystal Silicon Thin Film Transistors Formed by Printing on Plastic Substrates", *Appl. Phys. Lett.*, 86(093507):1-3 (2005).
Menard et al., "Micro- and Nanopatterning Techniques for Organic Electronic and Optoelectronic Systems", *Chem. Rev.*, 107:1117-1160 (2007).
Meng et al., "Plasma removal of Parylene C", *Journal of Micromechanics and Microengineering,*, 18(4 ): 045004 (2008).
Miao et al., "Micromachining of Three-Dimensional GaAs Membrane Structures Using High-Energy Nitrogen Implantation", *J. Micromech. Microeng.*, 13:35-39 (2003).
Michalske et al., "Closure and Repropagation of Healed Cracks in Silicate Glass", *J. Am. Ceram. Soc.*, 68:586-590 (1985).
Michel et al., "Printing Meets Lithography: Soft Approaches to High-Resolution Printing", *IBM J. Res. Dev.*, 45:697-719 (2001).
Miller et al., "Direct Printing of Polymer Microstructures on Flat and Spherical Surfaces Using a Letterpress Technique", *J. Vac. Sci. Technol. B.*, 20(6):2320-2327 (2002).
Milliron et al., "Colloidal Nanocrystal Heterostructures with Linear and Branched Topology", *Nature*, 430:190-195 (2004).
Min, "Plastic Electronics and Their Packaging Technologies", *Syn. Metals.*, 135:141-143 (2003).
Minev et al., "Impedance Spectroscopy on Stretchable Microelectrode Arrays", *Appl. Phys. Lett.*, 97:043707 (2010).
Mirkin et al., "Emerging Methods for Micro- and Nanofabrication", *MRS Bulletin*, 26(7):506-507 (2001).
Misewich et al., "Electronically Induced Optical Emission from a Carbon Nanotube FET", *Science*, 300:783-786 (2003).
Mishra et al., "AlGaN/GaN HEMTs—an Overview of Device Operation and Applications", *Proc. IEEE*, 90:1022-1031 (2002).
Mitzi et al., "High-Mobility Ultrathin Semiconducting Films Prepared by Spin Coating", *Nature*, 428:299-303(2004).
Moon et al., "Ink-Jet Printing of Binders for Ceramic Components", *J. Am. Ceram. Soc.*, 85:755-762 (2002).
Moore et al., "Individually Suspended Single-Walled Carbon Nanotubes in Various Surfactants", *Nano Lett.*, 3(10):1379-1382 (2003).
Morales et al., "A Laser Ablation Method for the Synthesis of Crystalline Semiconductor Nanowires", *Science*, 279:208-211(1998).
Morent et al., "Adhesion Enhancement by a Dielectric Barrier Discharge of PDMS used for Flexible and Stretchable Electronics", *J. Phys. D. Appl. Phys.*, 40:7392-7401 (2007).
Mori et al., "A New Etching Solution System, $H_3PO_4$—$H_2O_2$—$H_2O$, for GaAs and Its Kinetics", *J. Electrochem. Soc.*, 125:1510-1514 (1978).
Morkoc et al., "High-Luminosity Blue and Blue-Green Gallium Nitride Light-Emitting Diodes", *Science*, 267:51-55 (1995).
Morkved et al., "Mesoscopic Self-Assembly of Gold Islands on Diblock-Copolymer Films", *Appl. Phys. Lett.*, 64:422-424 (1994).
Morra et al., "On the Aging of Oxygen Plasma-Treated Polydimthylsiloxane Surfaces", *J. Colloid Interface Sci.*, 137:11-24 (1990).
Murakami et al., "Polarization Dependence of the Optical Absorption of Single-Walled Carbon Nanotubes", *Phys. Rev. Lett.*, 94, 087402 (2005).

(56) References Cited

OTHER PUBLICATIONS

Murphy et al., "Modification of Silk Fibroin Using Diazonium Coupling Chemistry and the Effects on hMSC Proliferation and Differentiation", *Biomaterials*, 29:2829-2838 (2008).
Namazu et al., "Evaluation of Size Effect on Mechanical Properties of Single Crystal Silicon by Nanoscale Bending Test Using AFM", *J. MEMS*, 9:450-459 (2000).
Nath et al., "Nanotubes of the Disulfides of Groups 4 and 5 Metals", *Pure Appl. Chem.*, 74(9):1545-1552 (2002).
Nathan et al., "Amorphous Silicon Detector and Thin Film Transistor Technology for Large-Area Imaging of X-Rays", *Microelectron J.*, 31:883-891(2000).
Nathan et al., "Amorphous Silicon Technology for Large Area Digital X-Ray and Optical Imaging", *Microelectronics Reliability*, 42:735-746 (2002).
Newman et al., "Introduction to Organic Thin Film Transistors and Design of n-Channel Organic Semiconductors", *Chem. Mater.*, 16:4436-4451(2004).
Nirmal et al., "Luminescence Photophysics in Semiconductor Nanocrystals", *Acc. Chem. Res.*, 32:407-414 (1999).
Noda et al., "New Realization Method for Three-Dimensional Photonic Crystal in Optical Wavelength Region", *Jpn. J. Appl. Phys.*, 35:L909-L912 (1996).
Nomura et al., "Room-Temperature Fabrication of Transparent Flexible Thin-Film Transistors Using Oxide Semiconductors", *Nature*, 432:488-492(2004).
Novoselov et al., "Electric Field Effect in Atomically Thin Carbon Films", *Science*, 306:666-669 (2004).
O'Connell et al., "Bang Gap Fluorescence from Individual Single-Walled Carbon Nanotubes", *Science*, 297:593-596 (2002).
Odom et al., "Improved Pattern Transfer in Soft Lithography Using Composite Stamps", *Langmuir*, 18(13):5314-5320 (2002).
Ohzono et al., "Ordering of Microwrinkle Patterns by Compressive Strain", *Phys. Rev. B.*, 69(13):132202 (2004).
Ohzono et al., "Geometry-Dependent Stripe Rearrangement Processes Induced by Strain on Preordered Microwrinkle Patterns", *Langmuir*, 21(16):7230-7237 (Web Release Jul. 7, 2005).
Omenetto et al., "A New Route for Silk", *Nature Photon,.* 2:641-643 (2008).
Ong et al., "High-Performance Semiconducting Polythiophenes for Organic Thin-Film Transistors", *J. Am. Chem. Soc.*, 126:3378-3379 (2004).
Ong et al., "Design of High-Performance Regioregular Polythiophenes for Organic Thin-Film Transistors", *Proc. IEEE*, 93:1412-1419 (2005).
Onoe, et al., "Temperature-controlled transfer and self-wiring for multi-color light-emitting diode arrays", *Journal of Micromechanics and Microengineering*, 19(7): 075015 (2009).
Origin Energy "Fact Sheet—Sliver Cells," www.orginenergy.com.au/sliver (May 2004).
O'Riordan et al., "Field Configured Assembly: Programmed Manipulation and Self-Assembly at the Mesoscale", *Nano Lett.*, 4:761-765 (2004).
Ouyang et al., "High-Performance, Flexible Polymer Light-Emitting Diodes Fabricated by a Continuous Polymer Coating Process," *Adv. Mat.*, 14:915-918 (2002).
Ouyang et al., "High Frequency Properties of Electro-Textiles for Wearable Antenna Applications", *IEEE Trans. Antennas Propag.*, 56(2):381-389 (2008).
Ouyang et al., "Conversion of Some Siloxane Polymers to Silicon Oxide by UV/Ozone Photochemical Processes", *Chem. Mater.*, 12(6):1591-1596 (Web Release Mar. 20, 2000).
Overholt et al., "Photodynamic Therapy for Esophageal Cancer using a 180° Windowed Esophageal Balloon", *Lasers in Surg. Med.*, 14:27-33 (2005).
Pan et al., "Nanobelts of Semiconducting Oxides", *Science*, 291:1947-1949 (2001).
Panev et al., "Sharp Excitation from Single InAs Quantum Dots in GaAs Nanowires", *Appl. Phys. Lett.*, 83:2238-2240.(2003).

Pardo et al., "Application of Screen Printing in the Fabrication of Organic Light-Emitting Devices", *Adv. Mater.*, 12(17):1249-1252 (2000).
Park et al., "Block Copolymer Lithography: Periodic Arrays of ~$10^{11}$ Holes in 1 Square Centimeter", *Science*, 276:1401-1404 (1997).
Park et al., "Fabrication of Three-Dimensional Macroporous Membranes with Assemblies of Microspheres as Templates", *Chem. Mater.*, 10:1745-1747 (1998).
Park et al., "Printed Assemblies of Inorganic Light-Emitting Diodes for Deformable and Semitransparent Displays", *Science*, 325:977-981 (2009).
Park et al., "Biodegradable Luminescent Porous Silicon Nanoparticles for in Vivo Applications", *Nature Mater.*, 8:331-336 (Web Release Feb. 22, 2009).
Parker et al., "Biocompatible Silk Printed Optical Waveguides", *Adv. Mater.*, 21:2411-2415 (2009).
Patolsky et al., "Stimulation, and Inhibition of Neuronal Signals with High-Density Nanowire Transistor Arrays", *Science*, 313:1100-1104 (2006).
Patton et al., "Effect of Diamond like Carbon Coating and Surface Topography on the Performance of Metal Evaporated Magnetic Tapes", *IEEE Trans Magn.*, 34(2):575-587 (1998).
Paul et al., "Patterning Spherical Surfaces at the Two Hundred Nanometer Scale Using Soft Lithography", *Adv. Func. Mater.*, 13(4):259-263 (2003).
Pearton et al., "GaN: Processing, Defects, and Devices", *J. Appl. Phys.*, 86:1-78 (1999).
Peng et al., "Shape Control of CdSe Nanocrystals", *Nature*, 404:59-61 (2000).
Perry et al., "Nano- and Micropatterning of Optically Transparent, Mechanically Robust, Biocompatible Silk Fibroin Films", *Adv. Mater.*, 20:3070-3072 (2008).
Piazza et al., "Protective Diamond-Like Carbon Coatings for Future Optical Storage Disks", *Diamond Relat. Mater.*, 14:994-999 (2005).
Pimparkar et al., "Current-Voltage Characteristics of Long-Channel Nanobundle Thin-Film Transistors: A 'Bottom-Up' Perspective", *IEEE Electron Dev. Lett.*, 28(2):157-160 (2007).
Podzorov et al., "Hall Effect in the Accumulation Layers on the Surface of Organic Semiconductors", *Phys. Rev. Lett.*, 95:226601 (2005).
Pushpa et al., "Stars and Stripes. Nanoscale Misfit Dislocation Patterns on Surfaces", *Pure Appl. Chem.*, 74(9):1663-1671 (2002).
Qian et al., "Scaling Effects of Wet Adhesion in Biological Attachment Systems", *Acta Biomaterialia*, 2:51-58 (2006).
Quake et al., "From Micro- to Nanofabrication with Soft Materials", *Science*, 290:1536-1540 (2000).
Radtke et al., "Laser-Lithography on Non-Planar Surfaces", *Opt. Exp.*, 15(3):1167-1174 (2007).
Raman et al., "Study of Mesa Undercuts Produced in GaAs with $H_3PO_4$-Based Etchants", *J. Electrochem. Soc.*, 136:2405-2410 (1989).
Randall et al., "Permeation-driven flow in poly(dimethylsiloxane) microfluidic devices", *Proc. Nat. Acad. Sci. USA*, 102(31):10813-10818 (2005).
Rao et al., "Large-scale assembly of carbon nanotubes", *Nature*, 425:36-37 (2003).
Razavi et al., "Three Dimensional Nanopillar Array Photovoltaics on Low Cost and Flexible Substrates", *Nature Materials*, 8:648-653 (2009).
Razeghi et al., "High-Power Laser Diode Based on InGaAsP Alloys", *Nature*, 369:631-633 (1994).
Razouk et al., "Dependence of Interface State Density on Silicon Thermal Oxidation Process Variables", *J. Electrochem. Soc.*, 126(9):1573-1581(1979).
Reuss et al., "Macroelectronics: Perspectives on Technology and Applications", *Proc. IEEE*, 93(7):1239-1256 (2005).
Reuss et al., "Macroelectronics", *MRS Bull.*, 31:447-454 (2006).
Ribas et al., "Bulk Micromachining Characterization of 1.2 µm HEMT MMIC Technology for GaAs MEMS Design", *Mater. Sci. Eng. B.*, 51:267-273 (1998).
Ridley et al., "All-Inorganic Field Effect Transistors Fabricated by Printing", *Science*, 286:746-749 (1999).

(56) References Cited

OTHER PUBLICATIONS

Roberts et al., "Looking at Rubber Adhesion", *Rubber Chem. Technol.*, 52:23-42 (1979).
Roberts et al., "Elastically Relaxed Free-Standing Strained-Silicon Nanomembranes", *Nat. Mater.*, 5:388-393 (2006).
Robinson et al., "GaAs Readied for High-Speed Microcircuits", *Science*, 219:275-277 (1983).
Roelkens et al., "Integration of InP/InGaAsP Photodetectors onto Silicon-on-Insulator Waveguide Circuits", *Optics Express*, 13(25):10102-10108 (2005).
Rogers et al., "Using an Elastomeric Phase Mask for Sub-100 nm Photolithography in the Optical Near Field", *Appl. Phys. Lett.*, 70:2658-2660 (1997).
Rogers et al., "Generating ~90 Nanometer Features Using Near Field Contact Mode Photolithography with an Elastomeric Phase Mask", *J. Vac. Sci. Technol.*, 16(1):59-68 (1998).
Rogers et al., "Quantifying Distortions in Soft Lithography", *J. Vac. Sci. Technol.*, 16:88-97 (1998).
Rogers et al., "Using Printing and Molding Techniques to Produce Distributed Feedback and Bragg Reflector Resonators for Plastic Lasers",*Appl. Phys. Lett.*, 73:1766-1768 (1998).
Rogers et al., "Printing Process Suitable for Reel-to-Reel Production of High-Performance Organic Transistors and Circuits", *Adv. Mater.*, 11(9):741-745 (1999).
Rogers et al., "Paper-Like Electronic Displays: Large-Area Rubber-Stamped Plastic Sheets of Electronics and Microencapsulated Electrophoretic Inks", *Proc. Nat. Acad. Sci. USA*, 98:4835-4840 (2002).
Rogers et al., "Printed Plastic Electronics and Paperlike Displays", *J. Polym. Sci. Part A. Polym. Chem.*, 40:3327-3334 (2002).
Rogers et al., "Organic Smart Pixels and Complementary Inverter Circuits Formed on Plastic Substrates by Casting and Rubber Stamping", *IEEE Electron Dev. Lett.*, 21(3):100-103 (2000).
Rogers, "Farewell to Flatland", *Science*, 329:138-139 (2010).
Rogers, "Rubber Stamping for Plastic Electronics and Fiber Optics", *MRS Bulletin*, 26(7):530-534 (2001).
Rogers, "Toward Paperlike Displays", *Science*, 291:1502-1503 (2001).
Rosenblatt et al., "High Performance Electrolyte Gated Carbon Nanotube Transistors", *Nano Lett.*, 2(8):869-872 (2002).
Rotkin et al., "Universal Description of Channel Conductivity for Nanotube and Nanowire Transistors", *Appl. Phys. Lett.*, 83:1623-1625 (2003).
Roundy et al., "Photonic Crystal Structure with Square Symmetry within Each Layer and a Three-Dimensional Band Gap", *Appl. Phys Lett.*, 82:3835-3837 (2003).
Rubehn et al., "A MEMS based Flexible Multichannel ECoG-Electrode Array", *J. Neural Eng.*, 6:036003 (2009).
Ruchehoeft et al., "Optimal Strategy for Controlling Linewidth on Spherical Focal Surface Arrays",*J. Vac. Sci. Technol. B.*, 18(6):3185-3189 (2000).
Ryu et al., "Human Cortical Prostheses: Lost in Translation?", *Neurosurg Focus*, 27(1):E5 (2009).
Samuelson et al., "Semiconductor Nanowires for Novel One-Dimensional Devices", *Physica E.*, 21:560-567(2004).
Sangwal et al., "Nature of multilayer steps on the {100} cleavage planes of MgO single crystals", *Surf. Sci.*, 383:78-87 (1997).
Santin et al., "In vitro Evaluation of the Inflammatory Potential of the Silk Fibroin", *J. Biomed. Mater. Res.*, 46:382-389 (1999).
Sanyal et al., "Morphology of Nanostructured Materials", *Pure Appl. Chem.*, 74(9):1553-1570 (2002).
Sazonov et al., "Low-Temperature Materials and Thin-Film Transistors for Flexible Electronics", *Proc. IEEE*, 93:1420-1428 (2005).
Scherlag et al., "Catheter Technique for Recording His Bundle Activity in Man", *Circulation*, 39:13-18 (1969).
Schermer et al., "Thin-Film GaAs Epitaxial Lift-Off Solar Cells for Space Applications", *Prog. Photovoltaics: Res. Applic.*, 13:587-596 (Web Release Apr. 28, 2005).
Schermer et al., "Photon Confinement in High-Efficiency, Thin-Film III-V Solar Cells Obtained by Epitaxial Lift-Off", *Thin Solid Films*, 511-512:645-653 (Web Release Jan. 19, 2006.

Schindl et al., "Direct Stimulatory Effect of Low-Intensity 670-nm Laser Irradiation on Human Endothelial Cell Proliferation", *Br. J. Dermatol.*, 148:334-336 (2003).
Schlegel et al., "Structures of quartz (1010)- and (1011)-water interfaces determined by X-ray reflectivity and atomic force microscopy of natural growth surfaces", *Geochim. Cosmochim. Acta,*, 66(17): 3037-3054 (2002).
Schmid et al., "Preparation of Metallic Films on Elastomeric Stamps and Their Application on Contact Processing and Contact Printing", *Adv. Fund. Mater.*, 13:145-153 (2003).
Schmid et al., "Siloxane Polymers for High-Resolution, High-Accuracy Soft Lithography", *Macromolecules*, 33(8):3042-3049 (2000).
Schmid et al., "Light-Coupling Masks for Lensless, Sub-wavelength Optical Lithography", *Appl. Phys. Lett.*, 72(19):2379-2381 (1998).
Schmidt et al., "Thin Solid Films Roll up into Nanotubes", *Nature*, 410:168 (2001).
Schnable et al., "Aluminum Metallization; Advantages and Limitations for Integrated Circuit Applications", *IEEE*, 57:1570-1580 (1969).
Schneider et al., "Mechanical Properties of Silicones for MEMS", *J. Micromech. Microeng.*, 18:065008 (2008).
Schon et al., "Ambipolar Pentacene Field-Effect Transistors and Inverters", *Science*, 287:1022-1023 (1995).
Schrieber et al., "The Effectiveness of Silane Adhesion Promotors in the Performance of Polyurethane Adhesives", *J. Adhesion*, 68:31-44 (1998).
Scorzoni et al., "On the Relationship Between the Temperature Coefficient of Resistance and the Thermal Conductance of Integrated Metal Resistors", *Sens Actuators A.*, 116(1):137-144 (2004).
Seidel et al., "High-Current Nanotube Transistors", *Nano Lett.*, 4(5):831-834 (2004).
Sekitani et al., "Bending Experiment on Pentacene Field-Effect Transistors on Plastic Films", *Appl. Phys. Lett.*, 86:073511 (2005).
Sekitani et al., "Stretchable Active-Matrix Organic Light-Emitting Diode Display Using Printable Elastic Conductors", *Nature Mater.*, 8:494-499 (2009).
Sekitani et al., "A Rubberlike Stretchable Active Matrix Using Elastic Conductors", *Science*, 321:1468-1472 (2008).
Sen et al., "Nonequilibrium Processes for Generating Silicon Nanostructures in Single-Crystalline Silicon", *Pure Appl. Chem.*, 74(9):1631-1641 (2002).
Serikawa et al., "High-Mobility Poly-Si Thin Film Transistors Fabricated on Stainless-Steel Foils by Low-Temperature Processes Using Sputter-Depositions", *Jpn. J. Appl. Phys.*, 39:L393-L395 (2000).
Servanti et al., "Functional Pixel Circuits for Elastic AMOLED displays", *Proc. IEEE*, 93:1257-1264 (2005).
Service, "Electronic Textiles Charge Ahead", *Science*, 301:909-911 (2003).
Shan et al., "From Si Source Gas Directly to Positioned, Electrically Contained Si Nanowires: The Self-Assembling 'Grow-in-Place' Approach", *Nano Lett.*, 4(11):2085-2089 (2004).
Sharp et al., "Holographic Photonic Crystals with Diamond Symmetry", *Phys. Rev. B.*, 68:205102/1-205102/6 (2003).
Sheraw et al., "Organic Thin-Film Transistor-Driven Polymer-Dispersed Liquid Crystal Displays on Flexible Polymeric Substrates", *Appl. Phys. Lett.*, 80:1088-1090 (2002).
Shetty et al., "Formation and Characterization of Silicon Films on Flexible Polymer Substrates", *Mater. Lett.*, 59:872-875 (2005).
Shi et al., "Free-Standing Single Crystal Silicon Nanoribbons", *J. Am. Chem. Soc.*, 123(44):11095-11096 (2001).
Shi et al., "Synthesis of Large Areas of Highly Oriented, Very Long Silicon Nanowires", *Adv. Mater.*, 12(18):1343-1345 (2000).
Shin et al., "PDMS-Based Micro PCR Chip with Parylene Coating", *J. Micromech. Microeng.*, 13:768-774 (2003).
Shtein et al., "Direct Mask-Free Patterning of Molecular Organic Semiconductors Using Organic Vapor Jet Printing", *J. Appl. Phys.*, 96(8):4500-4507 (2004).
Shull et al., "Axisymmetric Adhesion Tests of Soft Materials", *Macromol. Chem. Phys.*, 199:489-511 (1998).

(56) References Cited

OTHER PUBLICATIONS

Siegel et al., "Lightweight, Foldable Thermochromic Displays on Paper", *Lab Chip*, 9:2775-2781 (2009).
Siegel et al., "Foldable Printed Circuit Boards on Paper Substrates", *Adv. Funct. Mater.*, 20:28-35 (2010).
Siegel et al., "Microsolidics: Fabrication of Three-Dimensional Metallic Microstructures in Poly(dimethylsiloxane)", *Adv. Mater.*, 19(5):727-733 (Web Release Feb. 7, 2007).
Sim et al., "An Analytical Back-Gate Bias Effect Model for Ultrathin SOI CMOS Devices", *IEEE Trans. Elec. Dev.*, 40:755-765 (1993).
Sirringhaus et al., "Inkjet Printing of Functional Materials", *MRS Bull.*, 28:802-806 (2003).
Sirringhaus et al., "High-Resolution Inkjet Printing of All-Polymer Transistor Circuits", *Science*, 290:2123-2126 (2000).
Sirringhaus, H., "Device Physics of Solution-Processed Organic Field-Effect Transistors", *Adv. Mater.*, 17:2411-2425 (2005).
Smay et al., "Colloidal Inks for Directed Assembly of 3-D Periodic Structures", *Langmuir*, 18:5429-5437 (2002).
Smith et al., "Electric-Field Assisted Assembly and Alignment of Metallic Nanowires", *Appl. Phys. Lett.*, 77(9):1399-1401 (2000).
Snow et al., "Random networks of carbon nanotubes as an electronic material", *Appl. Phys. Lett.*, 82(13): 2145-2147 (2003).
Snow et al., "High-mobility carbon-nanotube transistors on a polymeric substrate", *Appl. Phys. Lett.*, 86, 033105 (2005).
So et al., "Organic Light-Emitting Devices for Solid-State Lighting", *MRS Bull.*, 33:663-669 (2008).
Sofia et al., "Functionalized Silk-Based Biomaterials for Bone Formation", *J. Biomed. Mater. Res.*, 54:139-148 (2001).
Someya et al., "Conformable, Flexible, Large-Area Networks of Pressure and Thermal Sensors with Organic Transistor Active Matrixes", *Proc. Nat. Acad. Sci. USA*, 102:12321-12325 (2005).
Someya et al., "Integration of Organic FETs with Organic Photodiodes for a Large Area, Flexible, and Lightweight Sheet Image Scanners", *IEEE Trans. Electron Devices*, 52:2502-2511 (2005).
Someya et al., "A Large-Area, Flexible, Pressure Sensor Matrix with Organic Field-Effect Transistors for Artificial Skin Applications", *Proc. Nat. Acad. Sci. USA*, 101(27):9966-9970 (2004).
Someya, "Electronic Eyeballs", *Nature*, 454:703-704 (2008).
Soole et al., "InGaAs Metal-Semiconductor-Metal Photodetectors for Long Wavelength Optical Communications", *IEEE J. Quantum Electron.*, 27(3):737-752 (1991).
Soong et al., "Adverse Reactions to Virgin Silk Sutures in Cataract Surgery", *Ophthalmology*, 91:479-483 (1984).
Srinivasan et al., "Piezoelectric/Ultrananocrystalline Diamond Heterostructures for High-Performance Multifunctional Micro/Nanoelectromechanical Systems", *Appl. Phys. Lett.*, 90:134101 (Web Release Mar. 26, 2007).
Stafford et al., "A Buckling-Based Metrology for Measuring the Elastic Moduli of Polymeric Thin Films", *Nature Mater.*, 3:545-550 (2004).
Star et al., "Nanotube Optoelectric Memory Devices", *Nano Lett.,*, 4(9):1587-1591 (2004).
Stella Project—Stretchable Electronics for Large-Area Applications. Available at www.stella-project.de. (Accessed Feb. 8, 2012).
Storm et al., "Fabrication of Solid-State Nanopores with Single-Nanometre Precision", *Nat. Mater.*, 2:537-540 (2003).
Streetman et al., "Intrinsic Material", In; Solid State Electronic Devices, 5th Ed., Prentice Hall; Upper Saddle River, NJ; pp. 74-75 (2000).
Strukov et al., "CMOL FPGA: A Reconfigurable Architecture for Hybrid Digital Circuits with Two-Terminal Nanodevices", *Nanotechnology*, 16:888-900 (2005).
Su et al., "Lattice-Oriented Growth of Single-Walled Carbon Nanotubes", *J. Phys. Chem B.*, 104(28):6505-6508 (2000).
Sum et al., "Near-Infrared Spectroscopy for the Detection of Lipid Core Coronary Plaques", *Curr. Cardiovasc. Imag. Rep.*, 2:307-315 (2009).
Sumant et al., "Toward the Ultimate Tribological Interface: Surface Chemistry and Nanotribology of Ultrananocrystalline Diamond", *Adv. Mater.*, 17(8):1039-1045 (2005).
Sun et al., "Fabricating Semiconductor Nano/Microwires and Transfer Printing Ordered Arrays of Them onto Plastic Substrates", *Nano Lett.*, 4:1953-1959 (2004).
Sun et al., "Advances in Organic Field-Effect Transistors", *J. Mater. Chem.*, 15:53-65 (2005).
Sun et al., "Bendable GaAs Metal-Semiconductor Field-Effect Transistors Formed with Printed GaAs Wire Arrays on Plastic Substrates", *Appl. Phys. Lett.*, 87:083501 (2005).
Sun et al., "Photolithographic Route to the Fabrication of Micro/Nanowires of III-V Semiconductors", *Adv. Fuct. Mater.*, 15:30-40 (2005).
Sun et al., "Controlled Buckling of Semiconductor Nanoribbons for Stretchable Electronics", *Nat. Nanotechnol.*, 1:201-207 (2007).
Sun et al., "Structural Forms of Single Crystal Semiconductor Nanoribbons for High-Performance Stretchable Electronics", *J. Mater Chem.*, 17:832-840 (2007).
Sun et al., "Inorganic Semiconductors for Flexible Electronics", *Adv. Mater.*, 19(15):1897-1916 (2007).
Sun et al., "Buckled and Wavy Ribbons of GaAs for High-Performance Electronics on Elastomeric Substrates", *Adv. Mater.*, 18(21):2857-2862 (2006).
Sundar et al., "Elastomeric Transistor Stamps: Reversible Probing of Charge Transport in Organic Crystals", *Science*, 303:1644-1646 (2004).
Suo et al., "Mechanics of Rollable and Foldable Film-on-Foil Electronics", *Appl. Phys. Lett.*, 74(8):1177-1179 (1999).
Swain et al., "Curved CCD Detector Devices and Arrays for Multi-Spectral Astrophysical Application and Terrestrial Stereo Panoramic Cameras", *Proc. SPIE*, 5499:281-301 (2004).
SWEET: Stretchable and Washable Electronics for Embedding Textiles. Available at http://tfcg.elis.ugent.be/projects/sweet. Accessed Feb. 8, 2012.
Sze et al., Semiconductor Devices, Physics and Technology, 2nd ed., Wiley, New York, pp. 190-192 (1985).
Sze, Semiconductor Devices: Physics and Technology, New York: Wiley, pp. 428-467 (1985).
Sze, VLSI Technology, Mcgraw-Hill, 327-374, 566-611 (1988).
Sze, Semiconductor Sensors, John Wiley and Sons: New York, pp. 17-95 (1994).
Takamoto et al., "Over 30% Efficient InGaP/GaAs Tandem Solar Cells", *Appl. Phys. Lett.*, 70(3):381-383 (1997).
Talapin et al., "PbSe Nanocrystal Solids for n- and p-Channel Thin Film Field-Effect Transistors", *Science*, 310:86-89 (2005).
Tan et al., "Performance Enhancement of InGaN Light Emitting Diodes by Laser-Lift-off and Transfer from Sapphire to Copper Substrate", *Appl. Phys. Lett.*, 84(15):2757-2759 (2004).
Tanase et al., "Magnetic Trapping and Self-Assembly of Multicomponent Nanowires", *J. Appl. Phys.*, 91:8549-8551 (2002).
Tang et al., "One-Dimensional Assemblies of Nanoparticles: Preparation, Properties, and Promise", *Adv. Mater.*, 17:951-962 (2005).
Tao et al., "Langmuir-Blodgett Silver Nanowire Monolayers for Molecular Sensing Using Surface-Enhanced Raman Spectroscopy", *Nano Lett.*, 3:1229-1233 (2003).
Tate et al., "Anodization and Microcontact Printing on Electroless Silver: Solution-Based Fabrication Procedures for Low-Voltage Electronic Systems with Organic Active Components", *Langmuir*, 16:6054-6060 (2000).
Teshima et al., "Room-Temperature Deposition of High-Purity Silicon Oxide Films by RF Plasma-Enhanced CVD", *Surf. Coat. Technol.*, 146-147:451-456 (2001).
Theiss et al., "PolySilicon Thin Film Transistors Fabricated at 100° C. on a Flexible Plastic Substrate", *IEDM*, 98:257-260 (1998).
Thornwood et al., "Utilizing Olptical Lithography in the Sub-Micron Dimensional Regime", *IBM Tech. Disc. Bull.*, 33(5):187-188 (1990).
Timko et al., "Electrical Recording from Hearts with Flexible Nanowire Device Arrays", *Nano Lett.*, 9:914-918 (2009).
Toader et al., "Photonic Band Gap Architectures for Holographic Lithography", *Phy. Rev. Lett.*, 043905/1-043905/4 (2004).
Toader et al., "Photonic Band Gaps Based on Tetragonal Lattices of Slanted Pores", *Phys. Rev. Lett.*, 90:233901/1-233901/4 (2004).
Tong, "Semiconductor Wafer Bonding": Science and Technology, John Wiley; New York, pp. 187-221 (1999).

(56) References Cited

OTHER PUBLICATIONS

Trau et al., "Microscopic Patterning of Orientated Mesoscopic Silica Through Guided Growth", *Nature*, 390:674-676 (1997).
Trentler et al., "Solution-Liquid-Solid Growth of Crytalline III-V Semiconductors: An Analogy to Vapor-Liquid-Solid Growth", *Science*, 270:1791-1794 (1995).
Tseng et al., "Monolithic Integration of Carbon Nanotube Devices with Silicon MOS Technology", *Nano Lett.*, 4(1):123-127 (Web Release Dec. 19, 2003).
Ucjikoga, "Low-Temperature Polycrystalline Silicon Thin-Film Transistor Technologies for System-on-Glass Displays", *MRS Bull.*, 27:881-886 (2002).
Urruchi et al., "Etching of DLC Films Using a Low Intensity Oxygen Plasma Jet", *Diamond Relat. Mater.*, 9:685-688 (2000).
Vanfleteren, "SWEET: Stretchable and Washable Electronics for Embedding Textiles", Available at ftp://ftp.cordis.europa.eu/pub/ist/docs/mnd/ws-sfit_en.pdf. (1991) (Accessed Feb. 8, 2012).
Vanhollenbeke et al., "Compliant Substrate Technology: Integration of Mismatched Materials for Opto-Electronic Applications", *Prog. Cryst. Growth Charact. Mater.*, 41(1-4):1-55 (2000).
Velev et al., "Porous silica via colloidal crystallization", *Nature*, 389:447-448 (1997).
Vepari et al., "Silk as a Biomaterial", *Prog. Polym. Sci.*, 32(8-9):991-1007 (2007).
Vilan et al., "Molecular Control Over Au/GaAs Diodes", *Nature*, 404:166-168 (2000).
Vinck et al., "Increased Fibroblast Proliferation Induced by Light Emitting Diode and Low Power Laser Irradiation", *Lasers Med. Sci.*, 18:95-99 (2003).
Viventi et al., "A Conformal, Bio-Interfaced Class of Silicon Electronics for Mapping Cardiac Electrophysiology", *Sci. Trans. Med.*, 2(24):24ra22 (Mar. 2010).
Vlasov et al., "On-Chip Natural Assembly of Silicon Photonic Bandgap Crystals", *Nature*, 414:289-293 (2001).
Voss, "Cheap and Cheerful Circuits", *Nature*, 407:442-444 (2000).
Wagner et al., "Silicon for Thin-Film Transistors", *Thin Solid Films* 430:15-19 (2003).
Wagner et al., "Electronic Skin: Architecture and Components", *Physica E.*, 25:326-334 (2005).
Wagner et al., "Vapor-Liquid-Solid Mechanism of Single Crystal Growth", *Appl. Phys. Lett.*, 4(5):89-90 (1964).
Waksman et al., "Photopoint Photodynamic Therapy Promotes Stabilization of Atherosclerotic Plaques and Inhibits Plaque Progression", *J. Am. Coll. Cardiol.*, 52:1024-1032 (2008).
Wang et al., "A Solution-Phase, Precursor Route to Polycrystalline $SnO_2$ Nanowires that can be Used for Gas Sensing under Ambient Conditions", *J. Am. Chem. Soc.*, 125:16176-16177 (2003).
Wang et al., "Electronically Selective Chemical Functionalization of Carbon Nanotubes: Correlation between Raman Spectral and Electrical Responses", *J. Am. Chem. Soc.*, 127:11460-11468 (2005).
Wang et al., "Oxidation Resistant Germanium Nanowires: Bulk Synthesis, Long Chain Alkanethiol Functionalization, and Langmuir-Blodgett Assembly", *J. Am. Chem. Soc,.* 127(33):11871-11875 (2005).
Wang et al., "Direct Synthesis and Characterization of CdS Nanobelts", *Appl. Phys. Lett.*, 89:033102 (2006).
Wang et al., "In Vivo Degradation of Three-Dimensional Silk Fibroin Scaffolds", *Biomaterials*, 29(24-25):3415-3428 (2008).
Waxman et al., "In vivo Validation of a Catheter-Based Near-Infrared Spectroscopy System for Detection of Lipid Core Coronary Plaques: Initial Results of the Spectacl Study", *J. Am. Coll. Cardiol. Img.*, 2:858-868 (2009).
Waxman, "Near-Infrared Spectroscopy for Plaque Characterization", *J. Interv. Cardiol.*, 21:452-458 (2008).
Weber et al., "A Novel Low-Cost, High Efficiency Micromachined Silicon Solar Cell", *IEEE Electron Device Lett.*, 25(1):37-39 (2004).
Wen et al., "Controlled Growth of Large-Area, Uniform, Vertically Aligned Arrays of $\alpha$-$Fe_2O_2$ Nanobelts and Nanowires", *J. Phys. Chem B.* 109(1):215-220 (Web Release Dec. 4, 2004).

Whang et al., "Large-Scale Hierarchical Organization of Nanowire Arrays for Integrated Nanosystems", *Nano Lett.*, 3(9):1255-1259 (2003).
Williams et al., "Growth and Properties of Nanocrystalline Diamond Films", *Phys. Stat. Sol. A.*, 203(13):3375-3386 (2006).
Williams et al., "Comparison of the Growth and Properties of Ultrananocrystalline Diamond and Nanocrystalline Diamond", *Diamond Relat. Mater.*, 15:654-658 (Web Release Jan. 23, 2006).
Willner et al., "Functional Nanoparticle Architectures for Senoric, Optoelectronic, and Bioelectronic Applications", *Pure Appl. Chem.*, 74(9):1773-1783 (2002).
Wilson et al., "ECoG Factors Underlying Multimodal Control of a Brain-Computer Interface", *IEEE Trans. Neural Syst. Rehabil. Eng.*, 14:246-250 (2006).
Wind et al., "Vertical Scaling of Carbon Nanotube-Field-Effect Transitors Using Top Gate Electrodes", *Appl. Phys. Lett.*, 80(20):3871-3819 (2002).
Wise et al., "Microelectrodes, Microelectronics, and Implantable Neural Microsystems", *Proc. IEEE*, 96(7):1184-1202 (2008).
Won et al., "Effect of Mechanical and Electrical Stresses on the Performance of an a-Si:H TFT on Plastic Substrate", *J. Electrochem. Soc.*, 151:G167-G170 (2004).
Wong-Riley et al., "Photobiomodulation Directly Benefits Primary Neurons Functionally Inactivated by Toxins", *J. Biol. Chem.*, 280:4761-4771 (2005).
Woodburn et al., "Phototherapy of Cancer and Atheromatous Plaque with Texaphyrins", *J. Clin. Laser Med. Surg.*, 14:343-348 (1996).
Wu et al., "Amorphous Silicon Crystallization and Polysilicon Thin Film Transistors on $SiO2$ Passivated Steel Foil Substrates", *Appl. Surf. Sci.*, 175-176:753-758 (2001).
Wu et al., "Direct Observation of Vapor-Liquid-Solid Nanowire Growth", *J. Am. Chem. Soc.*, 123(13):3165-3166 (2001).
Wu et al., "Thermal Oxide of Polycrystalline Silicon on Steel Foil as a Thin-Film Transitor Gate Dielectric", *Appl. Phys. Lett.*, 78:3729-2731 (2001).
Wu et al., "Block-by-Block Growth of Single-Crystalline Si/SiGe Superlattice Nanowires", *Nano Lett.*, 2(2):83-86 (2002).
Wu et al., "Growth of Au-Catalyzed Ordered GaAs Nanowire Arrays by Molecular-Beam Epitaxy", *Appl. Phys. Lett.*, 81:5177-5179 (2002).
Wu et al., "Inorganic Semiconductor Nanowires: Rational Growth, Assembly, and Novel Properties", *Chem. Eur. J.*, 8(6):1261-1268 (2002).
Wu et al., "Growth, Branching, and Kinking of Molecular-Beam Epitaxial (110) GaAs Nanowires", *Appl. Phys. Lett.*, 83:3368-3370 (2003).
Wu et al., "Single-Crystal Metallic Nanowires and Metal/Semiconductor Nanowire Heterostructures", *Nature*, 430:61-65 (2004).
Wu et al., "Complementary Metal-Oxide-Semiconductor Thin-Film Transistor Circuits from a High-Temperature Polycrystalline Silicon Process on Steel Foil Substrates", *IEEE Trans. Electr. Dev.*, 49(11):1993-2000 (2002).
Xia, "Soft Lithography", *Angew. Chem. Int. Ed.*, 37:551-575 (1998).
Xia et al., "Shadowed Sputtering of Gold on V-Shaped Microtrenches Etched in Silicon and Applications in Microfabrication", *Adv. Mater.*, 8(9):765-768 (1996).
Xia et al., "Soft Lithography", *Annu. Rev. Mater. Sci.*, 28:153-184 (1998).
Xia et al., "Unconventional Methods for Fabricating and Patterning Nanostructures", *Chem. Rev.*, 99:1823-1848 (1999).
Xia et al., "One-Dimensional Nanostructures: Synthesis, Characterization and Applications", *Adv. Mater.*, 15:353-389 (2003).
Xia et al., "Complex Optical Surfaces Formed by Replica Molding Against Elastomeric Masters", *Science*, 273:347-349 (1996).
Xiang et al., "Ge/Si Nanowire Heterostructures as High-Performance Field-Effect Transistors", *Nature*, 441:489-493 (2006).
Xiao et al., "High-mobility thin-film transistors based on aligned carbon nanotubes", *Appl. Phys. Lett.*, 83(1): 150-152 (2003).
Xie et al., "Polymer-Controlled Growth of $Sb_2Se_3$ Nanoribbons Via a Hydrothermal Process", *J. Cryst. Growth*, 252(4):570-574 (2003).
Yang et al., "Mesoporous Silica with Micrometer-Scale Designs", *Adv. Mater.*, 9:811-814 (1997).

(56) References Cited

OTHER PUBLICATIONS

Yang et al., "Stability of Low-Temperature Amorphous Silicon Thin Film Transistors Formed on Glass and Transparent Plastic Substrates", *J. Vac. Sci. Technol. B*., 18:683-689 (2000).
Yang et al., "Creating Periodic Three-Dimensional Structures by Multibeam Interface of Visible Laser", *Chem. Mater.*, 14:2831-2833 (2002).
Yang et al., "RFID Tag and RF Structures on a Paper Substrate Using Injket-Printing Technology", *IEEE Trans. Microw. Theory Tech.*, 55(12):2894-2901 (2007).
Yang, "The Chemistry and Physics of Semiconductor Nanowires", *MRS Bull.*, 30:85-91 (2005).
Yanina et al., "Terraces and ledges on (001) spinel surfaces", *Surf. Sci.*, 513:L402-L412 (2002).
Yao et al., "Seeing Molecules by Eye: Surface Plasmon Resonance Imaging at Visible Wavelengths with High Spatial Resolution and Submonolayer Sensitivity", *Angew. Chem.*, 47:5013-5017 (2008).
Yao et al., "Functional Nanostructured Plasmonic Materials", *Adv. Mater.*, 22:1102-1110 (2010).
Yao et al., "High-Field Effect Electrical Transport in Single-Walled Carbon Nanotubes", *Phys. Rev. Lett.*, 84(13):2941-2944 (2000).
Yeager et al., "Characterization of Flexible ECoG Electrode Arrays for Chronic Recording in Awake Rats", *J. Neurosci. Methods*, 173(2):279-285 (2008).
Yeh et al., "Fluidic Self-Assembly for the Integration of GaAs Light Emitting Diodes on Si Substrates", *IEEE Photon. Techn. Lett.*, 6:706-708 (1994).
Yin et al., "A Soft Lithography Approach to the Fabrication of Nanostructures of Single Crystalline Silicon with Well-Defined Dimensions and Shapes", *Adv. Mater.*, 12:1426-1430 (2000).
Yin et al., "Colloidal Nanocrystal Synthesis and the Organic-Inorganic Interface", *Nature*, 437:664-670 (2005).
Yoon et al., "Low-Voltage Organic Field-Effect Transistors and Inverters Enabled by Ultrathin Cross-Linked Polymers as Gate Dielectrics", *J. Am. Chem. Soc.*, 127:10388-10395 (2005).
Yu et al., "Silicon Nanowires: Preparation, Device Fabrication, and Transport Properties", *J. Phys. Chem B.*, 104(50):11864-11870 (2000).
Yu et al., "Solution-Liquid-Solid Growth of Soluble GaAs Nanowires", *Adv. Mater.*, 15:416-419. (2003).
Yu et al., "Two-Versus Three-Dimensional Quantum Confinement in Indium Phosphide Wires and Dots", *Nat. Mater.*, 2:517-520 (2003).
Yu et al., "The Yield Strength of Thin Copper Films on Kapton", *J. Appl. Phys.*, 95:2991-2997 (2004).
Yuan et al., "High-Speed Strained-Single-Crystal-Silicon Thin-Film Transistors on Flexible Polymers", *J. Appl. Phys.*, 100:013708 (2006).
Yurelki et al. "Small-Angle Neutron Scattering from Surfactant-Assisted Aqueous Dispersions of Carbon Nanotubes", *J. Am. Chem. Soc.*, 126(32):9902-9903 (2004).
Zakhidov et al., "Carbon Structure with Three-Dimensional Periodicity at Optical Wavelengths", *Science*, 282:897-901 (1998).
Zaumseil et al., "Nanoscale Organic Transistors that use Source/Drain Electrodes Supported by High Resolution Rubber Stamps", *Appl. Phys. Lett.*, 82(5):793-795 (2003).
Zaumseil et al., "Three-Dimensional and Multilayer Nanostructures Formed by Nanotransfer Printing", *Nano Lett.*, 3(9):1223-1227 (2003).
Zhang et al., "Electric-field-directed growth of aligned single-walled carbon nanotubes", Appl. Phys. Lett., 79(19): 3155-3157 (2001).
Zhang et al., "Low-Temperature Growth and Photoluminescence Property of ZnS Nanoribbons", *J. Phys. Chem B.*, 109(39):18352-18355 (2005).
Zhang et al., "Anomalous Coiling of SiGe/Si and SiGe/Si/Cr Helical Nanobelts", *Nano Lett.*, 6(7):1311-1317 (2006).
Zhang et al., "Oxide-Assisted Growth of Semiconducting Nanowires", *Adv. Mater.*, 15(7-8):635-640 (2003).
Zhang et al., "Structure and Photoiluminescence of ZnSe Nanoribbons Grown by Metal Organic Chemical Vapor Deposition", *Appl. Phys. Lett.*, 84(14):2641-2643 (2004).
Zhang et al., "Electronic Transport in Nanometre-Scale Silicon-on-Insulator Membranes", *Nature*, 439:703-706 (2006).
Zhao et al., "Improved Field Emission Properties from Metal-Coated Diamond Films", *Diamond Relat Mater.*, 16(3):650-653 (2007).
Zheng et al., "Sudden Cardiac Death in the United States, 1989 to 1998", *Circulation*, 104, 2158-2163 (1998).
Zheng et al., "Shape-and Solder-Directed Self-Assembly to Package Semiconductor Device Segments", *Appl. Phys. Lett.*, 85:3635-3637 (2004).
Zheng et al., "Sequential Shape-and-Solder-Directed Self Assembly of Functional Microsystems", *Proc. Natl. Acad. Sci. USA*, 101(35):12814-12817 (2004).
Zhou et al., "An Efficient Two-Photon-Generated Photoacid Applied to Positive-Tone 3D Microfabrication", *Science*, 296:1106-1109 (2002).
Zhou et al., "p-Channel, n-Channel Thin Film Transistors and p-n Diodes Based on Single Wall Carbon Nanotube Networks", *Nano Lett.*, 4:2031-2035 (2004).
Zhou et al., "Band Structure, Phonon Scattering, and the Performance Limit of Single-Walled Carbon Nanotube Transistors", *Phys. Rev. Lett.*, 95:146805 (2005).
Zhou et al., "Mechanism for Stamp Collapse in Soft Lithography", *Appl. Phys. Lett.*, 87:251925 (2005).
Zhu et al., "Spin on Dopants for High-Performance Single Crystal Silicon Transistors on Flexible Plastic Substrates", *Appl. Phys. Lett.*, 86(133507)1-3 (2005).
Zipes et al., "ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death", *Circulatio,n* 114:385-484 (2006).
Communication pursuant to Article 94(3) and Rule 71 (1) EPC dated Jul. 17, 2017, for European Patent Application No. 11754158.1.
Examination Report, Written Opinion and Response to Written Opinion, Corresponding to Singapore Patent Application No. 2007/18082-1 (dated Jan. 15, 2009).
Examination Report and Response, Corresponding to Malaysian Patent Application No. PI 20062672 (dated Aug. 28, 2009).
Examination Report, Corresponding to European Application No. EP 05 756 327.2 (dated Jan. 20, 2010).
Examination Report, Corresponding to Malaysian Patent Application No. PI 20092343 (dated Jun. 15, 2010).
Examination Report, Corresponding to Malaysian Patent Publication No. PI 20052553 (dated Mar. 13, 2009).
Examination Report, Corresponding to Singapore Patent Application No. 200608359-6 (dated Aug. 27, 2008).
Examination Report, Response and Search Report, Corresponding to Malaysian Patent Application No. PI 20062537 (dated Nov. 20, 2009).
Final Rejection corresponding to U.S. Appl. No. 12/968,637 dated Jun. 13, 2006, 28 pages.
International Search Report and Written Opinion dated Jul. 30, 2012, corresponding to International Patent Application No. PCT/US12/37973.
International Search Report and Written Opinion, Corresponding to International Application No. PCT/2005/014449, dated Jul. 3, 2008.
International Search Report and Written Opinion, Corresponding to International Application No. PCT/US04/40192, dated Jul. 6, 2005.
International Search Report and Written Opinion, Corresponding to International Application No. PCT/US07/74293, dated Jul. 24, 2008.
International Search Report and Written Opinion, Corresponding to International Application No. PCT/US07/77217, dated Jun. 3, 2008.

(56) References Cited

OTHER PUBLICATIONS

International Search Report and Written Opinion, Corresponding to International Application No. PCT/US07/82633, dated May 16, 2008.
International Search Report and Written Opinion, Corresponding to International Application No. PCT/US09/47442, dated Sep. 21, 2009.
International Search Report and Written Opinion, Corresponding to International Application No. PCT/US10/50468, dated Jan. 6, 2011.
International Search Report and Written Opinion, Corresponding to International Application No. PCT/US10/60425, dated May 25, 2011.
International Search Report and Written Opinion, Corresponding to International Application No. PCT/US2006/032125, dated Mar. 21, 2008.
International Search Report and Written Opinion, Corresponding to International Application No. PCT/US2009/036192, dated Jul. 6, 2009.
International Search Report and Written Opinion, Corresponding to International Application No. PCT/US2009/058231, dated Nov. 17, 2009.
International Search Report and Written Opinion, Corresponding to International Application No. PCT/US2010/034520, dated Sep. 24, 2010.
International Search Report and Written Opinion, Corresponding to International Application No. PCT/US2010/042585, dated May 25, 2011.
International Search Report and Written Opinion, Corresponding to International Application No. PCT/US2011/028094, dated Jul. 14, 2011.
International Search Report and Written Opinion, Corresponding to International PCT Application No. PCT/US05/19354, dated Apr. 18, 2007.
International Search Report and Written Opinion, Corresponding to International PCT Application No. PCT/US2006/021161, dated Feb. 28, 2008.
International Search Report and Written Opinion, Corresponding to International PCT Application No. PCT/US2007/022959, dated Oct. 14, 2008.
International Search Report and Written Opinion, Corresponding to International PCT Application No. PCT/US2007/077759, dated Apr. 11, 2008.
International Search Report and Written Opinion, Corresponding to International PCT Application No. PCT/US2007/079070, dated Apr. 23, 2008.
Notice of Reasons for Rejection corresponding to Japanese Patent Application No. P2006-165159, Dispatched Apr. 24, 2012—includes English translation.
Notice of Reasons for Rejection corresponding to Japanese Patent Application No. P2008-514820, Dispatched May 8, 2012—includes English translation.
Notice of Reasons for Rejection corresponding to Japanese Patent Application No. P2009-546361, Dispatched Jul. 3, 2012—includes English translation.
Office Action and Response, Corresponding to Malaysian Patent Publication No. PI 20052553, dated Mar. 13, 2009 and Dec. 8, 2009.
Office Action and Response, Corresponding to U.S. Appl. No. 11/421,654, dated Sep. 29, 2009.
Office Action and Response, Corresponding to U.S. Appl. No. 11/423,287, dated Feb. 13, 2008.
Office Action and Response, Corresponding to U.S. Appl. No. 11/858,788, dated Beginning Jan. 28, 2011.
Office Action Corresponding to Chinese Patent Application No. 200780041127.6, dated Apr. 8, 2011.
Office Action Corresponding to Chinese Patent Application No. 200780049982.1, dated May 12, 2010.
Office Action Corresponding to Chinese Patent Application No. 201010519400.5 dated Nov. 3, 2011.
Office action Corresponding to Korean Patent Application No. 10-2006-7010632, dated Nov. 22, 2007.
Office Action Corresponding to U.S. Appl. No. 11/851,182, dated Apr. 1, 2010.
Office Action corresponding to U.S. Appl. No. 12/968,637, dated Aug. 7, 2015.
Office Action corresponding to U.S. Appl. No. 13/046,191, dated Jan. 6, 2017.
Office Action corresponding to U.S. Appl. No. 15/942,242, dated May 24, 2019.
Office Action dated Jun. 12, 2017 for Taiwan Patent Application No. 100108416.
Office Action, Corresponding to Chinese Patent Application No. 200580013574.1, dated May 11, 2010.
Office Action, Corresponding to Chinese Patent Application No. 200780048002.6, dated Apr. 13, 2010.
Office Action, Corresponding to Taiwan Patent Application No. 095121212, dated May 7, 2010.
Office Action, Corresponding to U.S. Appl. No. 11/981,380, dated Sep. 23, 2010.
Office Actions and Responses, Corresponding to U.S. Appl. No. 11/145,542, dated between Apr. 5, 2007 and Dec. 23, 2008.
Office Actions and Responses, Corresponding to U.S. Appl. No. 11/981,380, dated Beginning Sep. 23, 2010.
Office Actions Corresponding to Chinese Patent Application No. 200480035731.4, dated Mar. 27, 2009 and Dec. 3, 2010.
Office Action, Corresponding to EP Patent Application No. 11 754 158.1, dated Aug. 4, 2014.
Office Actions, Corresponding to Chinese Patent Application No. 200580018159.5, dated Jan. 23, 2009 and Feb. 12, 2010.
Office Action, Corresponding to EP Patent Application No. 11 754 158.1, dated May 9, 2016.
Office Action, Corresponding to Taiwan Patent Application No. 100108416, dated Jun. 14, 2016.
Office Action, Corresponding to EP Patent Application No. 11 754 158.1, dated Mar. 6, 2018.
Search and Examination Report, Corresponding to Singapore Application No. 200904208-6, dated Dec. 17, 2010.
Search Report and Examination Report Corresponding to Singapore Patent Application No. 200901178-4, dated Mar. 13, 2010.
Search Report and First Written Opinion, Corresponding to Singapore Patent Application No. 200902530-5, dated Sep. 23, 2010.
Search Report and Written Opinion, Corresponding to Singapore Application No. 200901451-5, dated Dec. 22, 2010.
Search Report Corresponding to Singapore Patent Application No. SG 200607372-0, dated Oct. 17, 2007.
Search Report Corresponding to Taiwanese Patent Application No. 095121212, dated Oct. 8, 2010.
Search Report, Corresponding to Republic of China (Taiwan) Patent Application No. 094118507, dated Feb. 24, 2007.
Supplementary European Search Report Corresponding to European Patent Application No. 07 84 1968, Completed Mar. 31, 2011.
Supplementary European Search Report dated Jun. 15, 2012, corresponding to European Patent Application No. 09 71 6695.
Supplementary European Search Report, Corresponding to European Application No. 04 81 2651, Completed Oct. 19, 2010.
Supplementary European Search Report, Corresponding to European Application No. 05 75 6327, Completed Sep. 25, 2009.
Supplementary European Search Report, Corresponding to European Application No. 11 75 4158, Completed Nov. 11, 2013.
Extended European Search Report, dated Jul. 10, 2020, corresponding to European Patent Application No. 20168313.3, 7 pp.

* cited by examiner

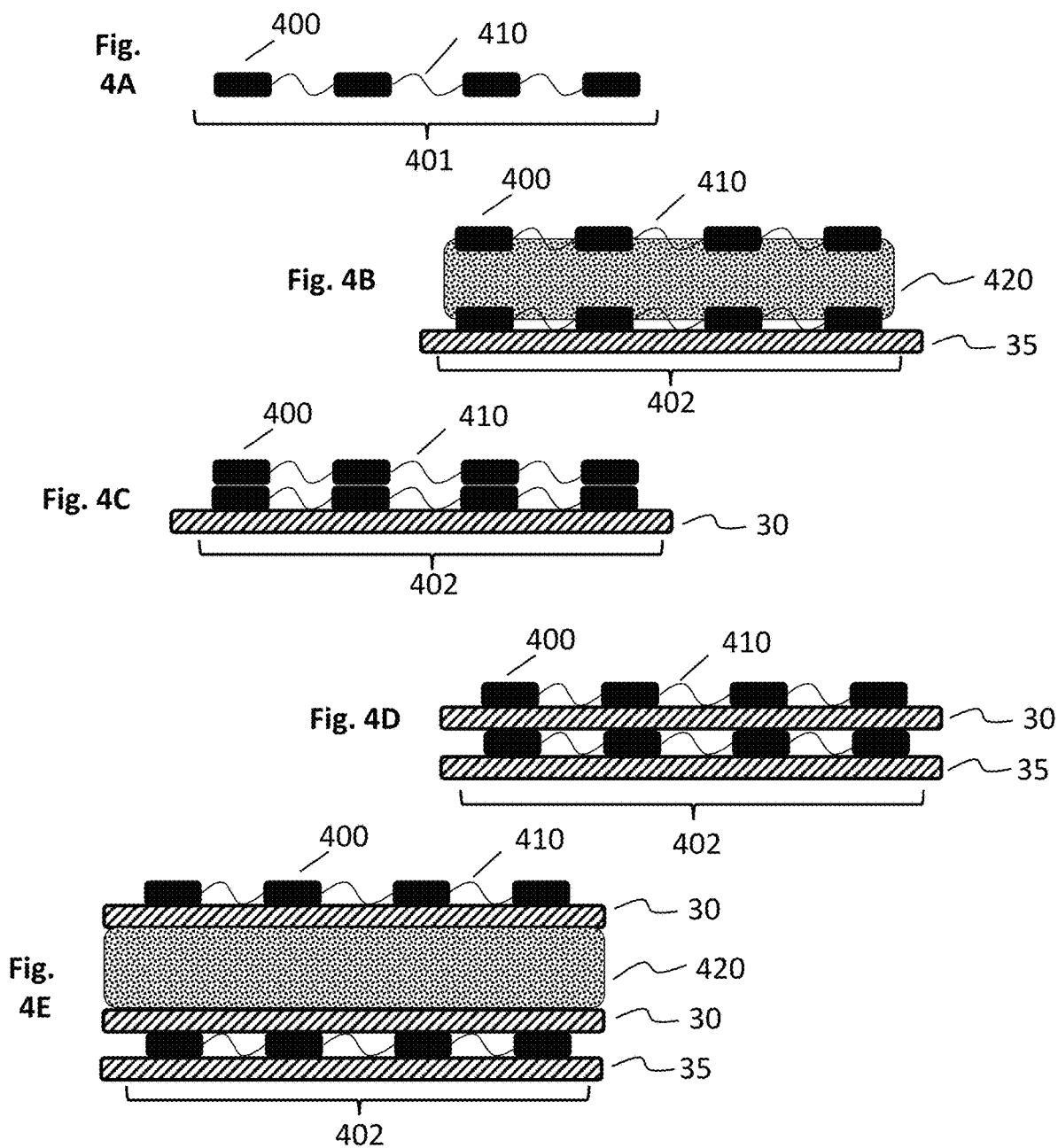

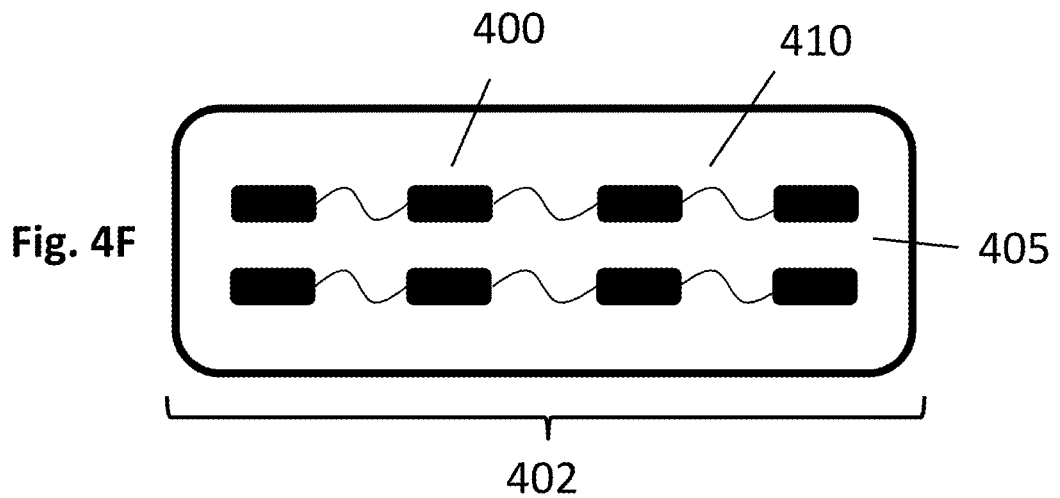
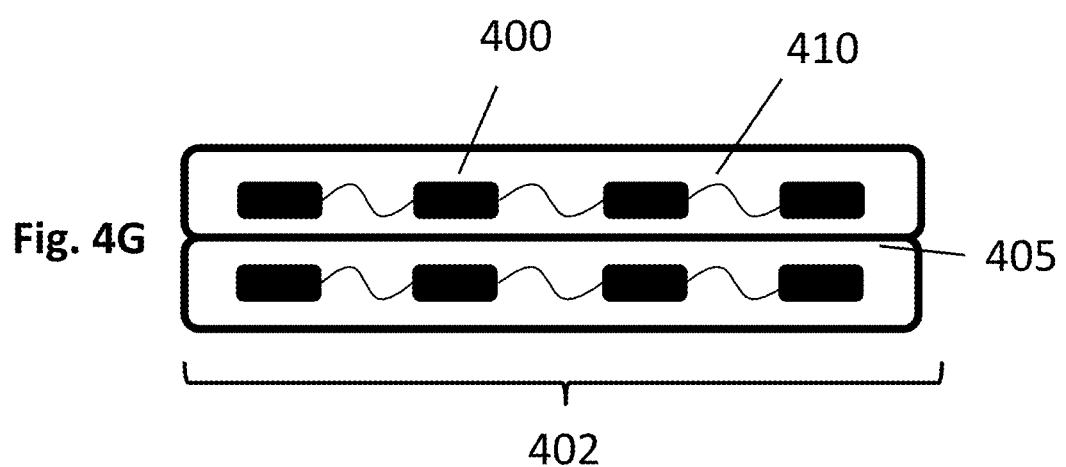
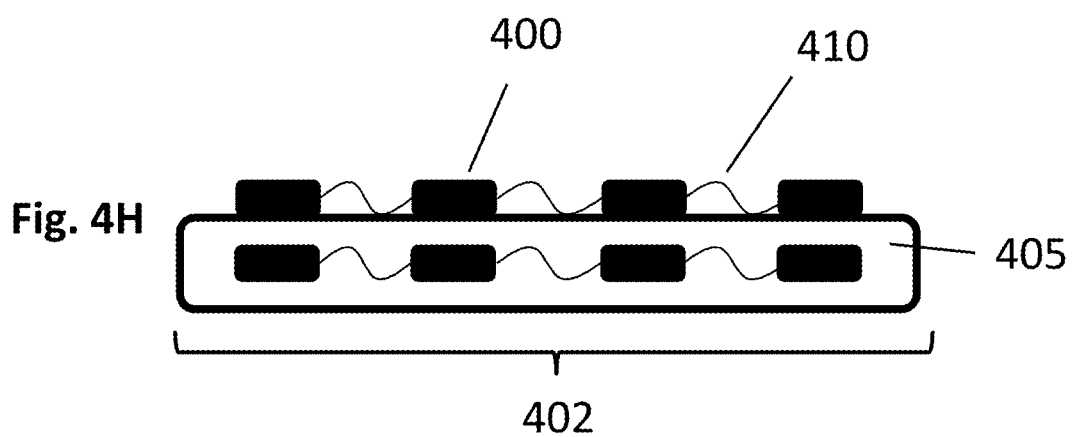

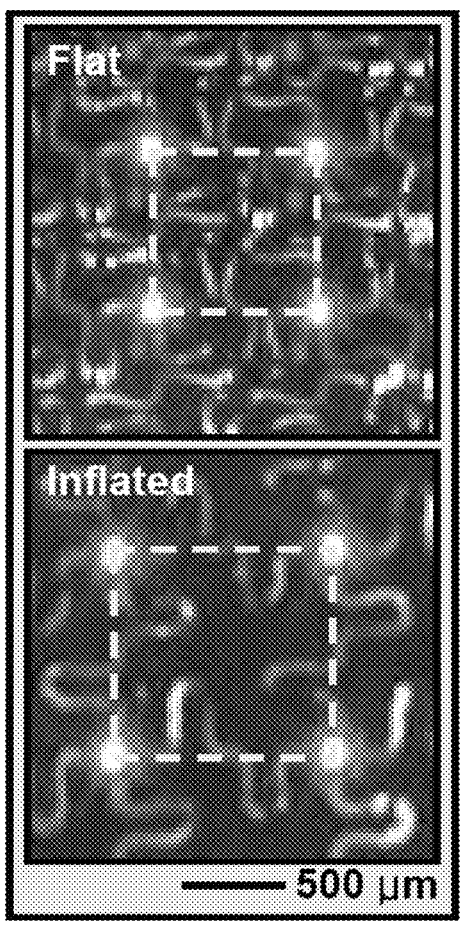
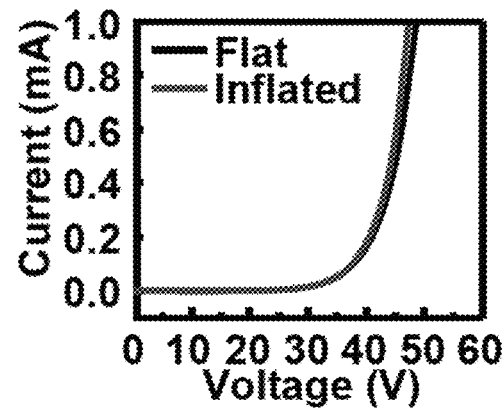
Fig. 11F
Fig. 11E
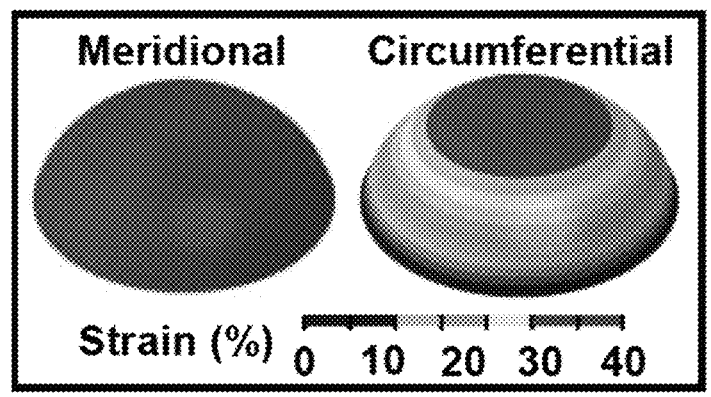
Fig. 11G

PDMS 1 mm

Fig. 18A Device fabrication on a glass
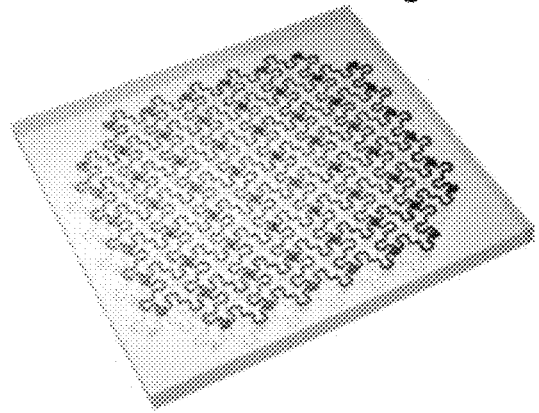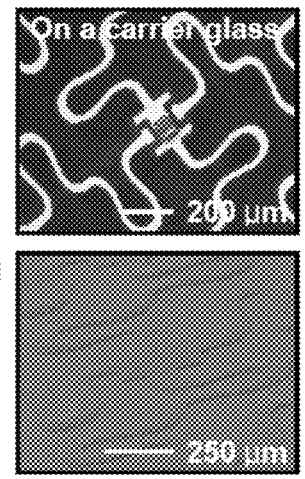
Fig. 18B Deposition of Cr / SiO₂ through a shadow mask after pickup
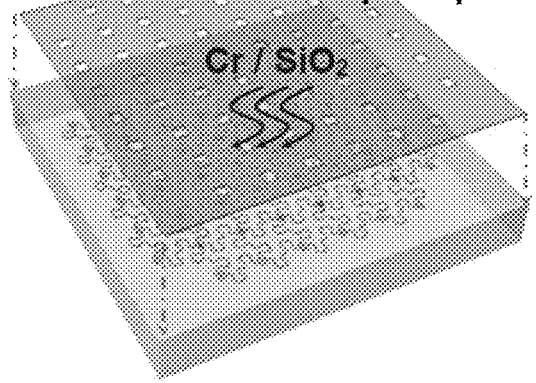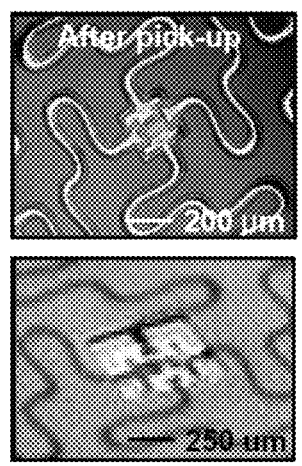
Fig. 18C Transfer printing
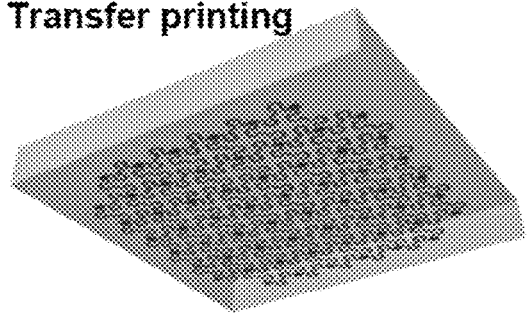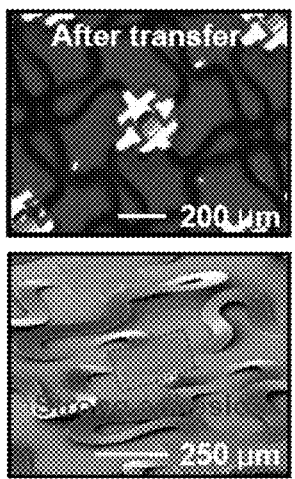

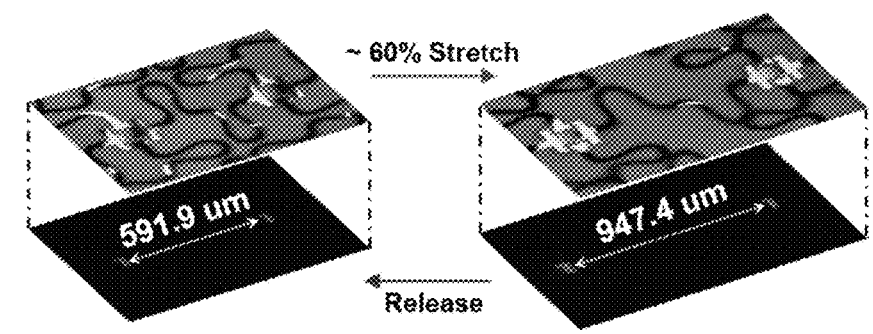
Fig. 21A
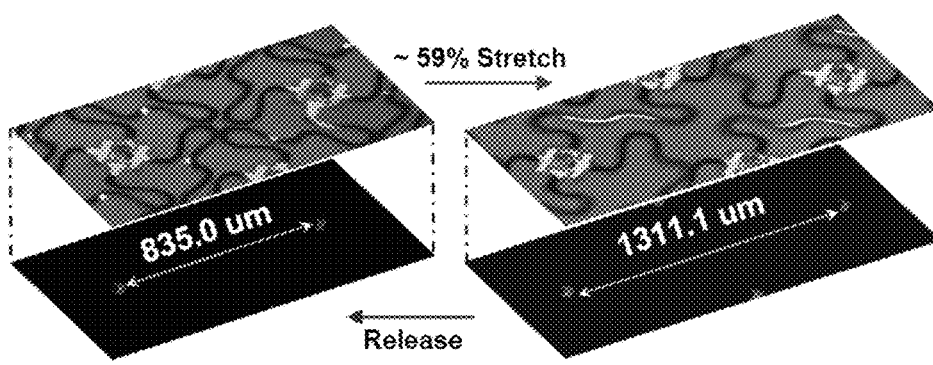
Fig. 21B
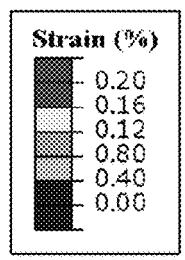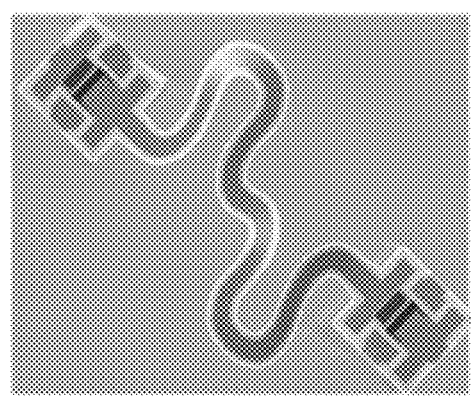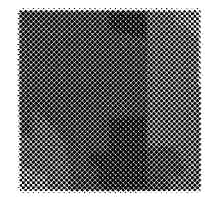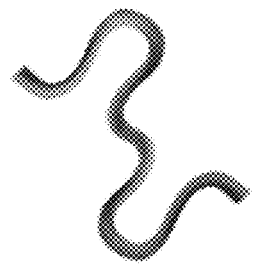
Fig. 21C

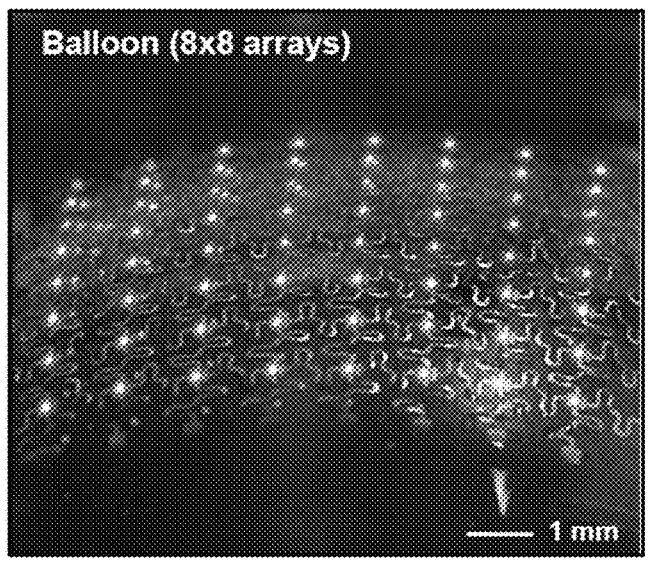
Fig. 23A
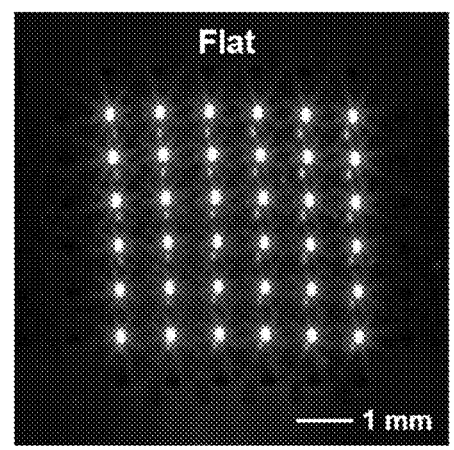 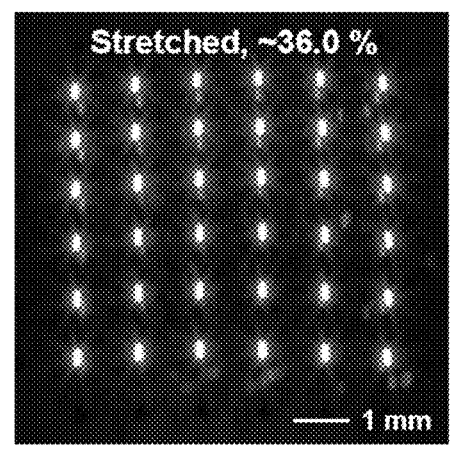
Fig. 23B
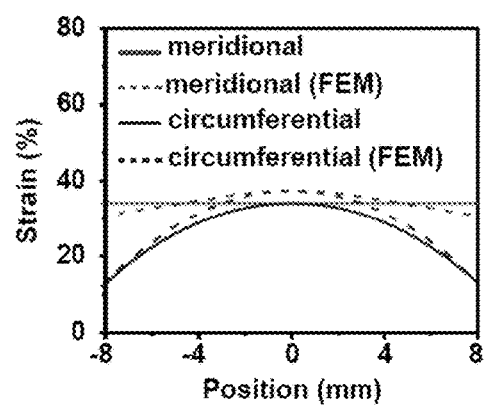
Fig. 23C

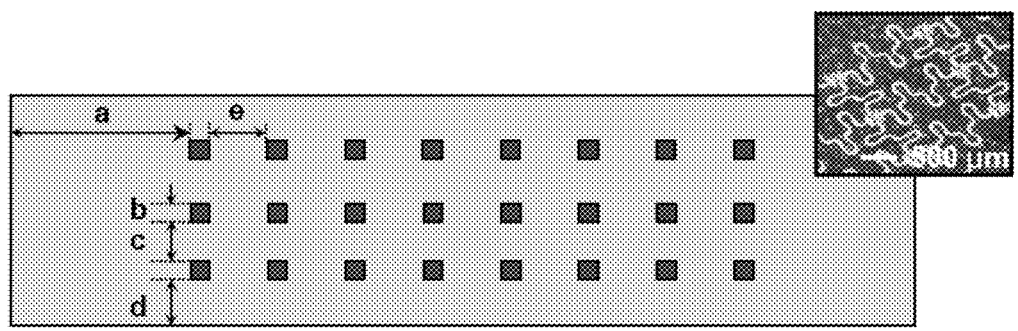
$a = 5$ mm / $b = 277$ um / $c = 695.5$ um / $d = \sim 1.5$ mm / $e = 1.2676$ mm
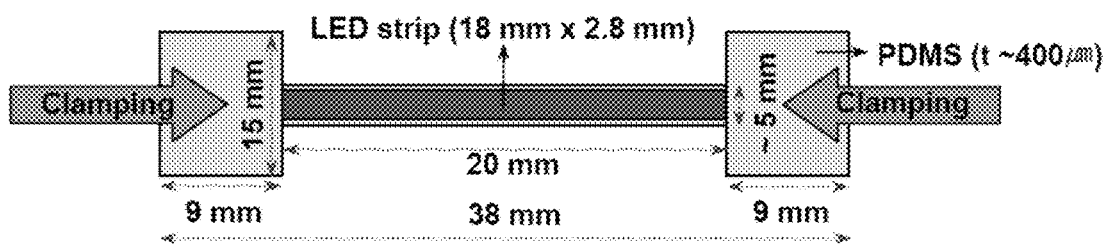
Fig. 24A
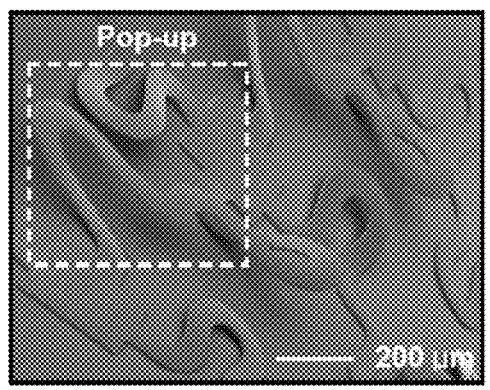
Fig. 24B
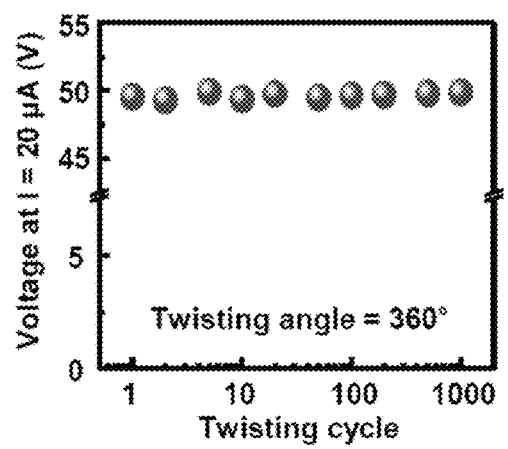
Fig. 24C

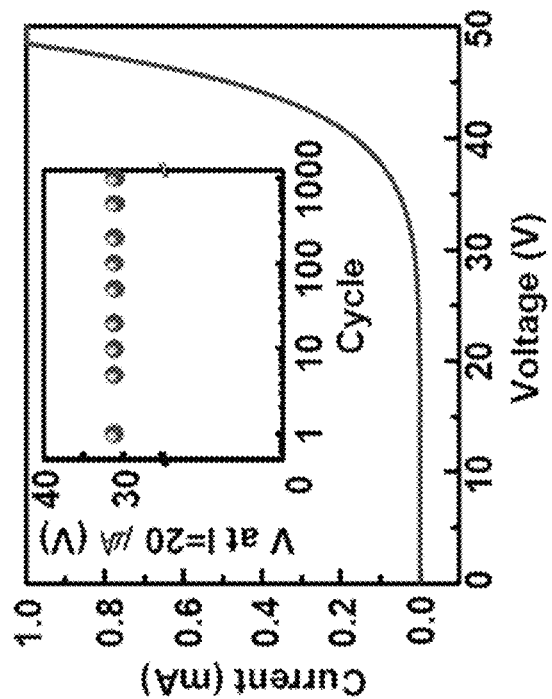
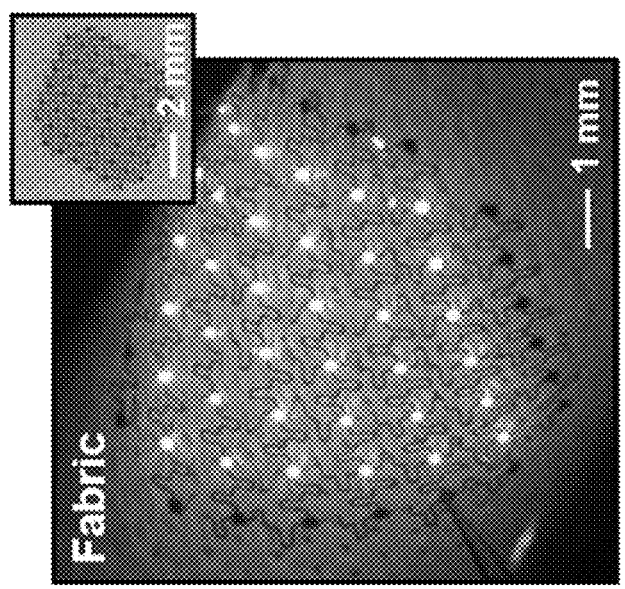
Fig. 29B
Fig. 29A

Fig. 31A
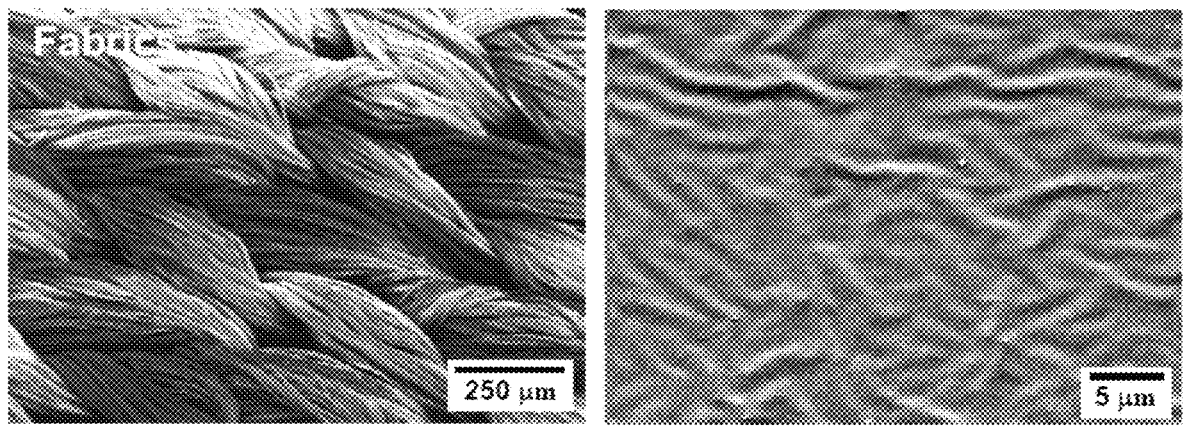
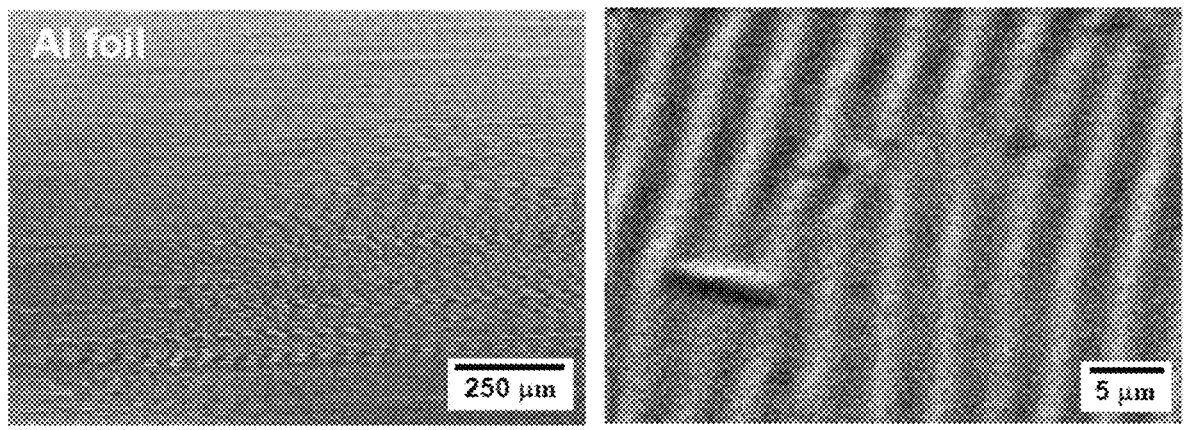
Fig. 31B

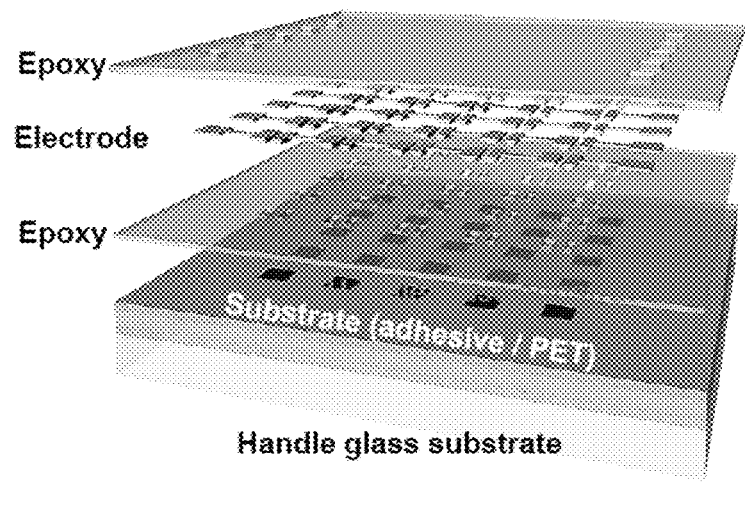
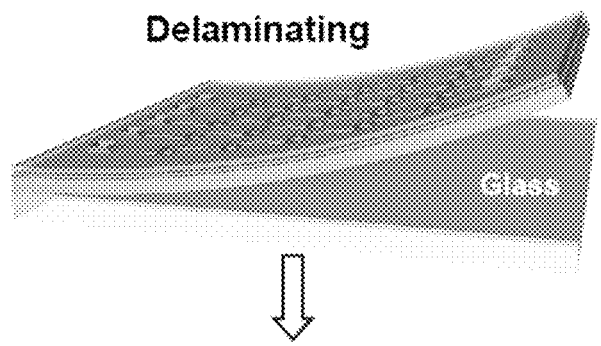
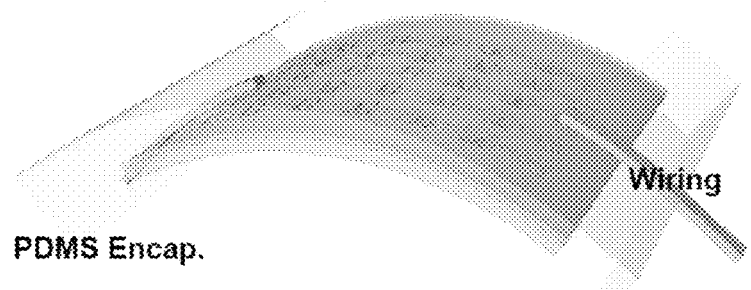
Fig. 33

8 Point Pt temperature sensing from both sides

WATERPROOF STRETCHABLE OPTOELECTRONICS

CROSS REFERENCE TO RELATED APPLICATION

This application is a continuation of U.S. patent application Ser. No. 13/046,191, filed Mar. 11, 2011, which claims the benefit of and priority to U.S. Provisional Application No. 61/388,529 filed on Sep. 30, 2010; U.S. Provisional Application No. 61/313,397 filed on Mar. 12, 2010; U.S. Provisional Application No. 61/314,739 filed on Mar. 17, 2010. U.S. patent application Ser. No. 13/046,191 is also a continuation-in-part of U.S. spplication Ser. No. 12/968,637 filed on Dec. 15, 2010; International Application No. PCT/US10/60425 filed Dec. 15, 2010; U.S. patent application Ser. No. 12/892,001 filed on Sep. 28, 2010, now U.S. Pat. No. 8,666,471 and International Application No. PCT/US10/50468 filed Sep. 28, 2010. U.S. application Ser. No. 12/968,637 and International Application No. PCT/US10/60425 also claim the benefit of priority to U.S. Provisional Application No. 61/313,397; U.S. Provisional Application No. 61/286,921 and U.S. Provisional Application No. 61/388,529 filed on Sep. 30, 2010. U.S. patent application Ser. No. 12/892,001, now U.S. Pat. No. 8,666,471, and International Application No. PCT/US10/50468 also claim the benefit of priority to U.S. Provisional Application No. 61/314,739. Each of the above-identified applications is hereby incorporated by reference in its entirety to the extent not inconsistent herewith.

STATEMENT REGARDING FEDERALLY SPONSORED RESEARCH OR DEVELOPMENT

This invention was made with United States governmental support from the National Science Foundation under grant DMI-0328162, the U.S. Department of Energy under Award No. DE-FG02-07ER46471, the U.S. Army Research Laboratory and the U.S. Army Research Office under contract number W911 NF-07-1-0618 and by the DARPA-DSO and the National Institutes of Health P41 Tissue Engineering Resource Center under award number P41 EB002520. The U.S. government has certain rights in the invention.

BACKGROUND

This invention is in the field of stretchable and flexible electronics. This invention relates generally to flexible and stretchable electronics adapted for use in biomedical, sensing and robotics applications.

Many established forms of inorganic light emitting diodes (LEDs) and photodetectors (PDs) incorporate rigid, flat and brittle semiconductor wafers as supporting substrates, thereby restricting the ways that these devices can be used. Research in organic optoelectronic materials is motivated, in part, by the potential for alternative applications enabled by integration of thin film devices on flexible sheets of plastic. Many impressive results have been achieved in recent years, several of which are moving toward commercialization.

There is growing interest in the use of organic and inorganic micro/nanomaterials and devices in similarly unusual forms on plastic, paper, textile, rubber, and other flat or curved substrates. For example, European Patent Application EP 1467224 discloses a flexible optical proximity detector which utilizes organic semiconductor elements.

Additionally, sealing of electronic devices permits a variety of uses in biological environments. For example, International Patent Application Publication WO 2009/076088 discloses an implantable optical sensor device which is hermetically sealed.

A variety of platforms are available for printing structures on device substrates and device components supported by device substrates, including nanostructures, microstructures, flexible electronics, and a variety of other patterned structures. For example, a number of patents and patent applications describe different methods and systems for making and printing a wide range of structures, including U.S. Pat. Nos. 7,705,280, 7,195,733, 7,557,367, 7,622,367 and 7,521,292, U.S. Patent Application Publication Nos. 2009/0199960, 2007/0032089, 2008/0108171, 2008/0157235, 2010/0059863, 2010/0052112, 2010/0283069 and 2010/0002402, U.S. patent application Ser. No. 12/968,637 filed Dec. 15, 2010 and Ser. No. 12/892,001 filed Sep. 28, 2010; all of which are hereby incorporated by reference in their entireties to the extent not inconsistent herewith.

SUMMARY

Provided herein are a variety of stretchable and flexible optical devices incorporating micro-scale inorganic semiconductor elements, and methods utilizing stretchable and flexible devices incorporating micro-scale inorganic semiconductor elements. The devices described herein are useful in biomedical applications, for example in applications for sensing, treating, repairing and actuating biological tissue. A number of the devices described herein permit interaction with biological tissues by incorporating a waterproof component protecting device elements from exposure to water from the biological environment, for example presenting an electrical short circuit caused by contact of water from the biological environment. A number of the devices described herein permit interaction with biological tissues by incorporating a barrier layer component for limiting a net leakage current from the flexible or stretchable electronic circuit to the biological environment to an amount that to an amount which does not adversely affect the tissue and/or biological environment. The unique substrates and applications disclosed further permit novel uses as sensors and actuators in robotics, medical and biomedical applications.

In embodiments, the devices described herein provide multiple component integrated device configurations, for example devices including combinations of active sensing components, active actuating components and/or passive components. Useful active and passive components include flexible or stretchable electronic devices. Useful passive device components include structural device elements, for example sutures, threads, flexible substrates, stretchable substrates, barrier layers, encapsulation layers, microstructured or nanostructured elements and optical elements. Multiple component device integration is achieved in some embodiments by contacting one device component, such as a flexible or stretchable electronic device on a first substrate with a second device component. In certain embodiments, adhesives or adhesive layers are provided between the individual components in a multiple component device to unite the components a single integrated device. Optionally, an individual component in a multiple component device has an internal adhesive layer. In certain embodiments, the individual components are each provided on individual substrates with an adhesive layer provided between the substrates to unite the components into a single integrated device. In certain embodiments, the individual components are encapsulated to unite the components into a single integrated device. In certain embodiments, one component is laminated on top of another component to unite the components into a single integrated device. In certain embodiments, one component is printed on top of another component to unite the components into a single integrated device. In certain embodiments, one component is printed on top of an encapsulated component to unite the components into a single integrated device. Multiple component device integration is achieved in some embodiments by processing in which a component, such as a lenses array, optical filter, polarizer, etc., is molded or embossed directly into another component or molded onto a layer provided on another component such as on a layer laminated on another layer. In an embodiment, an optical component is molded into an intermediate elastomer layer provided on a flexible or stretchable electronic device, for example, via a replica molding or nano-imprinting molding technique.

In a first aspect, a multiple component integrated device is a biomedical device. In one embodiment, provided are biomedical devices useful for treating a tissue in a biological environment, such as an in-vivo biological environment and/or a biological environment comprising a conductive ionic solution. Such devices are useful, for example, for performing therapy on a tissue, for closing openings or wounds in a tissue, for treating medical conditions and for tissue sensing and actuation applications. Devices of this aspect include sutures incorporating electronic devices or electronic circuits for interaction with tissues in biological environments.

In a specific embodiment, a device of this aspect comprises a suture having an external surface, a flexible or stretchable electronic circuit supported by the external surface of the suture, and a barrier layer at least partially encapsulating the flexible or stretchable electronic circuit. In a specific embodiment, the flexible or stretchable electronic circuit comprises one or more inorganic semiconductor elements, such as inorganic semiconductor elements having an average thickness less than or equal to 100 µm. In a specific embodiment, a device of this aspect further comprises a controller in electrical communication with the flexible or stretchable electronic circuit. In a specific embodiment, a device of this aspect further comprises a flexible or stretchable substrate positioned between the external surface of the suture and the flexible or stretchable electronic circuit, for example a substrate comprising an elastomer, such as PDMS. In an embodiment, the components of the biomedical device, such as the flexible or stretchable electronic device are encapsulated by a barrier layer comprising an elastomer material.

In embodiments, one component of a multiple component integrated device is a flexible or stretchable substrate, for example a stretchable or flexible substrate positioned in contact with another component of a multiple component integrated device. In specific embodiments, devices described herein further comprise an additional flexible or stretchable substrate positioned between a flexible or stretchable electronic device and the supporting surface, for example a PDMS substrate. In specific embodiments, a flexible or stretchable substrate has an average thickness selected over the range of 0.25 µm to 1000 µm, or an average thickness less than or equal to 100 µm. Useful flexible or stretchable substrates include those having an average modulus selected over the range of 0.5 KPa to 10 GPa. In a specific embodiment, a flexible or stretchable substrate has a substantially uniform thickness over a flexible or stretchable electronic circuit. In embodiments, a flexible or stretchable substrate has a thickness that varies selectively along one or more lateral dimensions over a flexible or stretchable electronic circuit. Optionally a flexible or stretchable substrate is a flexible or stretchable mesh structure. Useful flexible or stretchable substrates include those comprising a biocompatible material, a bioinert material, a bioresorbable material or any combination thereof. Specific materials useful for flexible or stretchable substrates of this aspect include those comprising material selected from the group consisting of a polymer, an inorganic polymer, an organic polymer, a plastic, an elastomer, a biopolymer, a thermoset, a rubber, fabric, paper and any combination of these. In specific embodiments, the flexible or stretchable substrate comprises an elastomer, PDMS, parylene, or polyimide.

In embodiments, one component of a multiple component integrated device is a suture. In embodiments, sutures useful with the devices and methods described herein include sutures comprising a fiber or a thread. Useful sutures also include those comprising a biocompatible material, a bioinert material or a combination of biocompatible and bioinert materials. In a specific embodiment, a suture comprises a bioresorbable material. Specific sutures useful with the devices and methods described herein include those comprising a material selected from the group consisting of a biopolymer, a synthetic polymer, a natural fiber, a synthetic fiber, a protein, a polysaccharide, silk and any combination of these. Useful sutures further include sutures used in medical procedures. In a specific embodiment, useful sutures include those comprising a polymer such as polyglycolic acid (Biovek), polylactic acid, polydioxanone, or caprolactone. In a specific embodiment, a suture comprises silk. In a specific embodiment, a suture comprises polypropylene, polyester or nylon. In a specific embodiment, a suture comprises stainless steel.

In specific embodiments, a suture has an average diameter over its length less than or equal to 1000 µm, such as those having average diameters selected over the range of 1 µm to 1000 µm, optionally 10 µm to 1000 µm, optionally 100 µm to 1000 µm or any sub-ranges thereof. Suture in the present devices include those having a tensile strength selected over the range of 50 MPa to 1000 MPa, preferably for some embodiments 100 MPa to 1000 MPa, and preferably for some embodiments 200 MPa to 1000 MPa In an embodiment, a suture has a length selected over the range of 1 cm to 100 m. Useful sutures include those which are stretchable or flexible, for example those having an average modulus selected over the range of 0.5 kPa to 10 GPa, those having a net flexural rigidity less than or equal to $1\times10^{-4}$ Nm, those having a net bending stiffness less than or equal to $1\times10^8$ GPa um$^4$, or any combination of these properties.

In an exemplary embodiment, a device, such as a suture, has an external surface which is nanostructured or microstructured. In embodiments, an external surface of a device is patterned using replica molding or nano-imprint lithography. Nanostructured and microstructured sutures include those having a plurality of nanostructures or microstructures which accommodate a flexible or stretchable electronic circuit or a component thereof. In an embodiment, the external surface of a suture is provided in conformal contact with at least a portion of a flexible or stretchable electronic circuit. In an embodiment, the external surface of a suture is provided in physical contact with at least a portion of a flexible or stretchable electronic circuit. Optionally, sutures useful with the devices and methods described herein have external surfaces having one or more microstructured or nanostructured openings, channels, vias, receiving surfaces, relief features, optically transmissive regions, optically opaque regions or selectively permeable regions that are permeable to one or more target molecules.

In embodiments, one component of a multiple component integrated device is a layer, such as a barrier layer, having a nanostructured or microstructured surface, optionally exposed to the tissue and/or biological environment. In an embodiment, for example, a multiple component integrated device comprises a barrier layer having a microstructured or nanostructure external surface providing a plurality of raised or recessed features exposed to the tissue or biological environment, such as channels, vias, pores, opening, windows, etc. Useful nanostructured or microstructured components include those patterned using replica molding or nano-imprint lithography techniques. In certain embodiments, a nanostructured or microstructured component provides useful properties to a device, for example a surface that promotes cell growth, a surface that inhibits cell growth, a surface with enhanced wetting properties, a surface with reduced wetting properties, a surface with altered optical properties.

Optionally, an adhesive layer is provided between a flexible or stretchable electronic circuit and a surface, such as the external surface of a suture. In embodiments, for example, an adhesive layer is deposited over at least a portion of a surface, such as an external surface of a suture, for example an elastomeric layer such as a PDMS layer. In embodiments, an adhesive layer deposited on a surface is patterned using replica molding or nano-imprint lithography. Adhesive layers are further useful for enhancing the attachment of elements to a surface during a printing process, such as dry transfer contact printing. In some embodiments, adhesives improve the structural or mechanical integrity of a device, for example by preventing, reducing or limiting motion between two device elements in contact with the adhesive. In some embodiments, the adhesive layer functions to laminate one or more layers in a multilayer device, such as a 3D multilayer LED array comprising individually encapsulated 2D LED arrays. In some embodiments, the adhesive layer functions to at least partially encapsulate one or more device components.

Also provided are methods of making biomedical devices. A method of this aspect comprises the steps of providing a flexible or stretchable suture having an external surface, rolling the flexible or stretchable suture over a plurality of inorganic semiconductor elements such that one or more inorganic semiconductor elements are transferred to an external surface of the flexible or stretchable suture, and encapsulating at least a portion of the one or more transferred inorganic semiconductor elements with a barrier layer. In another embodiment, a method of this aspect comprises the steps of: providing a flexible or stretchable suture having an external surface, assembling a plurality of printable inorganic semiconductor elements on an external surface of the flexible or stretchable suture using dry transfer contact printing, and encapsulating at least a portion of the one or more transferred inorganic semiconductor elements with a barrier layer. Another method of this aspect comprises the steps of providing a flexible or stretchable suture, transfer printing one or more inorganic semiconductor elements to an external surface of the flexible or stretchable suture, and encapsulating at least a portion of the one or more transfer printed inorganic semiconductor elements with a barrier layer. Optionally, methods of this aspect further comprise providing an adhesive layer on an external surface of the suture, for example, wherein the adhesive layer comprises an elastomer layer such as a PDMS layer. In specific embodiments of these aspects, the barrier layer comprises a bioresorbable material, a biocompatible material, or a combination of bioresorbable and biocompatible materials.

In another aspect, methods are provided for treating a tissue in a biological environment. A method of this aspect comprises the steps of providing the tissue and contacting the tissue with a biomedical device, such as a device described herein, for example a biomedical device comprising a suture. In embodiments of this aspect, the tissue has an opening, a wound, or a surgical incision and the step of contacting the tissue with the biomedical device comprises closing the opening, wound or surgical incision, for example by stitching or otherwise sewing up the opening. A specific method of treating a tissue comprises thermally, optically or electrically activating a barrier layer of a biomedical device to release one or more pharmaceutical compositions at least partially encapsulated by or otherwise incorporated into the barrier layer into a biological environment, for example including the tissue. In a specific embodiment, actuation of one or more inorganic semiconductor elements changes a permeability of, degrades or melts at least a portion of a barrier layer, thereby releasing at least a portion of the one or more pharmaceutical compositions into a biological environment.

A specific method for performing therapy on a wound of a tissue comprises the steps of providing the tissue having the wound, contacting the wound with a biomedical device, such as a biomedical device comprising a suture having an external surface, a flexible or stretchable array of light emitting diodes supported by the external surface of the suture, and a barrier layer at least partially encapsulating the flexible or stretchable electronic circuit, and exposing the wound to electromagnetic radiation generated by the flexible or stretchable array of light emitting diodes.

Some methods of these aspects further comprise a step of actuating or sensing the tissue in contact with the biomedical device. For embodiments of this aspect where the biomedical device comprises an array of light emitting diodes, the array of light emitting diodes generate electromagnetic radiation and the method further comprises a step of exposing the tissue to the electromagnetic radiation or visualizing the electromagnetic radiation.

In an embodiment, a biomedical device further comprises one or more sensors supported by the external surface of the suture, such as one or more thermal sensors (e.g., thermocouple, thermistor, etc.), optical sensors (e.g., photodetector or photodetector array), or electronic sensors (e.g., measurement of current or voltage), optionally provided in a partially or completely encapsulated configuration, such as having an elastomeric encapsulating layer. In an embodiment, for example, a device of this aspect further comprises one or more temperature sensors and/or or heaters supported by the external surface of the suture. In an embodiment, a device of this aspect further comprises one or more optical components supported by the external surface of the suture and optionally provided on top of the flexible or stretchable electronic device. In an embodiment, for example, the device further comprises one or more molded or embossed optical components in optical communication with the flexible electronic device, such as lenses, diffusers or arrays thereof. A method for sensing or actuation of a tissue comprises the steps of providing the tissue, contacting the tissue with a biomedical device comprising a flexible or stretchable array of light emitting diodes (LEDs) and a flexible or stretchable array of photodetectors (PDs), actuating at least a portion of the flexible or stretchable array of LEDs to generate and expose the tissue electromagnetic radiation to expose and sensing electromagnetic radiation scattered, reflected or emitted by the tissue with at least a portion of the flexible or stretchable PD array. In specific embodiments, the electromagnetic radiation has a wavelength or wavelength range within the Optical window or therapeutic window of the biological tissue. As used herein "optical window" or "therapeutic window" of a biological tissue refers to a region of the electromagnetic spectrum over which electromagnetic radiation has a substantial penetration depth in the biological tissue, such as a wavelength range of 650 nm to 1300 nm. In specific embodiments, the electromagnetic radiation has a wavelength of 680 nm or a wavelength range including 680 nm. In specific embodiments, the electromagnetic radiation has a wavelength of 940 nm or a wavelength range including 940 nm. In specific embodiments, the electromagnetic radiation has a wavelength useful for sensing the extent of oxygenation of blood in the tissue.

In another aspect, a multiple component integrated device is provided in electrical communication with a controller. Useful controllers include those comprising a microprocessor. Controllers useful with the devices and methods described herein include controllers which perform one or more specific functions such as a diagnostic and/or therapeutic function. In a specific embodiment, a controller provides, directly or indirectly, a current or a voltage to an electronic circuit. In a specific embodiment, a controller receives, directly or indirectly, a current or a voltage from an electronic circuit or information corresponding to or derived from a current or voltage, for example a current generated by a photodetector in response to receipt of electromagnetic radiation. Useful controllers permit automatic, autonomous or manual operation of the devices described herein. In one embodiment, a controller receives information corresponding to an intensity of electromagnetic radiation received by a photodetector and provides to an electronic circuit a current or voltage having a magnitude derived from the intensity of the electromagnetic radiation received by the photodetector. In one embodiment, a controller receives information corresponding to an intensity of electromagnetic radiation received by a photodetector and provides to an electronic circuit a current or voltage that actuates at least a portion of an electronic circuit, for example a light emitting diode or a microelectromechanical device.

In embodiments, a multiple component integrated device comprises one or more conductive electrical interconnects providing electrical communication between an electronic circuit of a multiple component integrated device and a controller. Useful electrical interconnects include, but are not limited to, wire bonded interconnects, interconnects comprising a ribbon cable, interconnects comprising lithographically patterned conductors and combinations of these. In embodiments, the controller is provided in wired or wireless, one-way or two-way communication with an electronic circuit.

Devices described herein include those having one or more components comprising one or more bioresorbable materials. For example, provided are biomedical devices wherein the suture component is a bioresorbable material; and/or wherein the barrier layer comprises a bioresorbable material; and/or wherein the flexible or stretchable substrate component comprises a bioresorbable material. A variety of bioresorbable materials are useful in the present devices, including materials that are efficiently processed and/or remodeled without formation of biologically active, toxic and/or harmful byproducts upon contact with a biological environment. Useful bioresorbable materials include, for example, a biopolymer (e.g., protein, peptide, carbohydrate, polynucleotide, etc.), a synthetic polymer, a protein, a polysaccharide, silk, poly(glycerol-sebacate) (PGS), polydioxanone, poly(lactic-co-glycolic acid) (PLGA), polylactic acid (PLA), collagen, chitosan, fibroin, and combinations of these. Useful silk materials for components of the devices described herein include, for example, silkworm fibroin, modified silkworm fibroin, spider silk, insect silk, recombinant silk, and any combination of these. As used herein, modified silkworm fibroin refers to a polymer composition that is derived via chemical modification of silkworm fibroin.

The physical dimensions and physical properties of components comprising a bioresorbable material are important parameters for supporting a range of device functionalities and compatibility with different tissue types. In some embodiments, the component comprising a bioresorbable material has a thickness less than or equal to 10,000 µm, and optionally in some embodiments less than or equal to 1000 µm, and optionally in some embodiments less than or equal to 100 µm, and optionally in some embodiments less than or equal to 10 µm; and optionally in some embodiments less than or equal to 1 µm. Use of a thin component comprising a bioresorbable material (e.g., thickness less than or equal to 100 µm, optionally less than or equal to 10 µm and optionally less than or equal to 1 µm) is useful for providing a flexible, or otherwise deformable device capable of establishing conformal contact with a wide range of tissue types, including tissues having complex, highly contoured surfaces. In some embodiments, the component comprising a bioresorbable material has a thickness selected over the range of 100 nm and 10000 µm, optionally for some applications selected over the range of 1 µm and 1000 µm, and optionally for some embodiments selected over the range of 1 µm and 10 µm. In some embodiments, the composition and physical properties (e.g., Young's modulus, net bending stiffness, toughness, etc.) of the component comprising a bioresorbable material are selected to provide sufficient structural support for the electronic device component, while also providing an ability to achieve a high degree of conformal contact upon deployment. In some embodiments, the component comprising a bioresorbable material is a low modulus layer. Alternatively, useful devices include those having a component comprising a bioresorbable material that is a high modulus layer. In some embodiments, for example, the component comprising a bioresorbable material has a Young's modulus less than or equal to 10 GPa, preferably for some applications a Young's modulus less than or equal to 100 MPa, optionally for some applications less than or equal to 10 MPa. In some embodiments, for example, the component comprising a bioresorbable material has a Young's modulus selected over the range of 0.5 MPa and 10 GPa, and optionally for some applications selected over the range of 0.5 MPa and 100 MPa, and optionally for some applications selected over the range of 0.5 MPa and 10 MPa. In some embodiments, for example, the component comprising a bioresorbable material has a net bending stiffness less than or equal to $1 \times 10^9$ GPa µm$^4$, optionally for some applications less than or equal to $1 \times 10^7$ GPa µm$^4$ and optionally for some applications less than or equal to $1 \times 10^6$ GPa µm$^4$. In some embodiments, for example, the component comprising a bioresorbable material has a net bending stiffness selected over the range of $0.1 \times 10^4$ GPa µm$^4$ and $1 \times 10^9$ GPa µm$^4$, and optionally for some applications between $0.1 \times 10^4$ GPa µm$^4$ and $5 \times 10^5$ GPa µm$^4$.

In some biological environments, such as an in vivo biological environment, the degradation of the bioresorbable material occurs via enzymatic degradation, for example, via protease mediated degradation. In addition, degradation occurs in some embodiments from the surfaces of the bioresorbable material that are exposed to the biological environment having degradation enzymes present, such as at the interface with a tissue and/or biological fluid. Accordingly, certain parameters of the bioresorbable material may be selected to effectively control the resorption rate. In an embodiment, the chemical composition, physical state and/or thickness of the bioresorbable material is selected so as to control the resorption rate. In an embodiment, for example, the bioresorbable material comprises a biopolymer exhibiting a useful resorption rate for a selected biological environment, such as a silk biopolymer exhibiting a useful resorption rate. Useful bioresorbable materials include those comprising amorphous materials, crystalline materials, partially amorphous materials and partially crystalline materials. In an embodiment, devices described herein include an at least partially crystalline material, wherein the extent of crystallinity of the bioresorbable material is selected to provide a useful and/or preselected resorption rate for a selected biological environment and device application. In some embodiments, the larger the degree of crystallinity of the bioresorbable material the slower the resorption rate when provided in contact with the target tissue. For example, devices described herein include those having a bioresorbable material with a degree of crystallinity less than or equal to 55%, and optionally a degree of crystallinity less than or equal to 30% and optionally a degree of crystallinity less than or equal to 20%, and optionally a degree of crystallinity less than or equal to 5%. For example, devices described herein include those having a bioresorbable material with a degree of crystallinity selected over the range of 0 to 55%, and optionally for some embodiments a degree of crystallinity selected over the range of 1 to 30%, and optionally for some embodiments a degree of crystallinity selected over the range of 5 to 20%. As used herein, 0% crystallinity refers to an entirely amorphous material and the given degree of crystallinity corresponds to the amount of a material provided in a crystalline state relative to the total amount of material. In some embodiments, for example those having a silk bioresorbable material, the degree of crystallinity refers to the beta sheet content of the silk bioresorbable material.

In some embodiments, implantable biomedical devices advantageously utilize silk as a bioresorbable material. Silk is biocompatible, FDA-approved, optically transparent, mechanically robust (high mechanical modulus and toughness), and flexible in thin film form. It is also compatible with aqueous processing, which preserves sensitive electronic functions, and amenable to chemical and biological functionalization. The presence of diverse amino acid side chains facilitates coupling chemistry for functionalizing silks. Silk is also water soluble with programmable rates of proteolytic biodegradation (yielding non-inflammatory amino acids) over a range from minutes to hours to years.

Some other natural polymers that exhibit properties similar to or analogous to silk include, but are not limited to, chitosan, collagen, gelatin, agarose, chitin, polyhydroxyalkanoates, pullan, starch (amylose amylopectin), cellulose, hyaluronic acid, or any combination of these.

Silk may be obtained from various natural sources, for example, from the silkworm *Bombyx mori* or from the spider *Nephila clavipes*. Silk solutions used in accordance with embodiments described herein may be obtained, for example, from a solution containing a dissolved silkworm silk (e.g. from *Bombyx mori*), a dissolved spider silk (e.g. from *Nephila clavipes*), or from a solution containing a recombinant silk, such as from bacteria, yeast, mammalian cells, transgenic animals, or transgenic plants.

In an embodiment, the silk of the bioresorbable material may be silk fibroin protein, which consists of layers of antiparallel beta sheets and has a primary structure consisting mainly of the recurrent amino acid sequence (Gly-Ser-Gly-Ala-Gly-Ala)$_n$. Fibroin is known to arrange itself in three structures, called silk I, II, and III. Silk I is the natural, amorphous form of fibroin, as emitted from the *Bombyx mori* silk glands. Silk II refers to the crystalline arrangement of fibroin molecules in spun silk, which has greater strength. Silk III is formed principally in solutions of fibroin at an interface (i.e. air-water interface, water-oil interface, etc.). In the disclosed implantable biomedical devices, silk I, II and/or III may be used.

In another aspect, a multiple component integrated device is a proximity sensor device. Proximity sensor devices are useful, for example, in methods for sensing a distance between two objects, for example in a biological environment. A device of this aspect comprises a flexible or stretchable substrate, one or more flexible or stretchable light emitting diode (LED) arrays supported by the flexible or stretchable substrate, one or more flexible or stretchable photodetector (PD) arrays supported by the flexible or stretchable substrate, and one or more barrier layers at least partially encapsulating the one or more flexible or stretchable LED arrays, at least part of the one or more flexible or stretchable PD arrays, or at least parts of both. In embodiments, the one or more flexible or stretchable LED arrays comprise a large area array. In embodiments, the one or more flexible or stretchable PD arrays comprise a large area array. In a specific embodiment, a device of this aspect further comprises a controller in electrical communication with the one or more flexible or stretchable LED arrays and/or PD arrays. Optionally, the one or more flexible or stretchable LED arrays and the one or more flexible or stretchable PD arrays are provided in one or more individually encapsulated layers in a multilayer stacked geometry.

A method of this latter aspect for sensing a distance between two objects comprises the steps of providing a first object having a first surface, providing a proximity sensor on the first surface, the proximity sensor comprising: a flexible or stretchable substrate, one or more flexible or stretchable LED arrays supported by the flexible or stretchable substrate, each flexible or stretchable LED array comprising one or more inorganic LEDs having an average thickness less than or equal to 100 μm, and one or more flexible or stretchable PD arrays supported by the flexible or stretchable substrate, each flexible or stretchable PD array comprising one or more inorganic semiconductor elements having an average thickness less than or equal to 100 μm, one or more barrier layers at least partially encapsulating the one or more flexible or stretchable LED arrays and the one or more flexible or stretchable PD arrays, wherein the barrier layer prevents water from a biological environment from contacting at least a portion of the inorganic LEDs of the one or more flexible or stretchable LED arrays and at least a portion of the inorganic semiconductor elements of the one or more flexible or stretchable PD arrays; providing a current, voltage or electromagnetic energy to the one or more flexible or stretchable LED arrays, thereby producing electromagnetic radiation from the one or more flexible or stretchable LED arrays; providing a second object at a distance from the first object, the second object positioned in optical communication with at least one of the one or more flexible or stretchable LED arrays and at least one of the one or more flexible or stretchable PD arrays; wherein the second object receives at least a portion of the electromagnetic and thereby generates scattered, emitted or reflected electromagnetic radiation; and detecting at least a portion of the scattered, emitted or reflected electromagnetic radiation with at least one of the one or more flexible or stretchable PD arrays.

In embodiments, the proximity sensor device further comprises one or more inorganic semiconductor elements supported by the flexible or stretchable substrate. Optionally, the one or more inorganic semiconductor elements are provided in an individually encapsulated layer, provided in a multilayer stacked geometry. In embodiments, the proximity sensor device further comprises a barrier layer encapsulating at least a portion of the one or more flexible or stretchable LED arrays, at least a portion of the one or more flexible or stretchable PD arrays, or at least portions of both the one or more flexible or stretchable LED array and the one or more flexible or stretchable PD arrays. In embodiments, the barrier layer comprises a bioresorbable material, a biocompatible material, or a combination of bioresorbable and biocompatible materials.

In embodiments, a flexible or stretchable LED array comprises one or more individually encapsulated LED array layers provided in a multilayer stacked geometry, for example 2 to 1000 individually encapsulated LED array layers in a multilayer laminated geometry. In embodiments, a flexible or stretchable PD array comprises one or more individually encapsulated PD array layers provided in a multilayer stacked geometry, for example 2 to 1000 individually encapsulated PD array layers in a multilayer laminated geometry. In one embodiment, the one or more flexible or stretchable LED arrays and the one or more flexible or stretchable PD arrays are provided in a multilayer laminated geometry.

In embodiments, each flexible or stretchable LED array comprises one or more inorganic LEDs having an average thickness less than or equal to 100 µm. In embodiments, each inorganic LED has one or more lateral dimensions selected over the range of 250 nm to 1000 µm. Optionally, each inorganic LED in a flexible or stretchable LED array is independently selected from the group consisting of AlInGaP LEDs, GaN LEDs, stacked inorganic LEDs, inorganic LEDs incorporating a phosphor and any combination of these. Optionally, each LED independently produces infrared electromagnetic radiation, visible electromagnetic radiation, ultraviolet electromagnetic radiation, broadband electromagnetic radiation or narrowband electromagnetic radiation. Optionally, each LED independently produces electromagnetic radiation having a wavelength selected over the range of 100 nm to 5000 nm.

In embodiments, each flexible or stretchable PD array comprises one or more inorganic semiconductor elements having an average thickness less than or equal to 100 µm. In embodiments, each inorganic semiconductor element in a flexible PD array has one or more lateral dimensions selected over the range of 250 nm to 1000 µm. In embodiments, each flexible or stretchable PD array comprises one or more inorganic LEDs operated in reverse bias mode. In embodiments, each flexible or stretchable PD array comprises one or more GaAs diode.

In one embodiment, the flexible or stretchable substrate of a proximity sensor device comprises a surgical glove. Optionally, the one or more flexible or stretchable LED arrays and the one or more flexible or stretchable PD arrays are positioned on a fingertip region of the surgical glove. In another embodiment, the flexible substrate comprises a surgical instrument. In embodiments, a proximity sensor is incorporated into a robotic device for autonomous sensing of distances between objects.

In embodiments, the one or more flexible or stretchable LED arrays and the one or more flexible or stretchable PD arrays are positioned proximate to one another on the flexible or stretchable substrate. In embodiments, the one or more flexible or stretchable LED arrays and the one or more flexible or stretchable PD arrays are positioned in physical contact with one another on the flexible or stretchable substrate. In embodiments, the one or more flexible or stretchable LED arrays and the one or more flexible or stretchable PD arrays are positioned to overlap one another on the flexible or stretchable substrate. In other embodiments, the one or more flexible or stretchable LED arrays and the one or more flexible or stretchable PD array are spatially separated from one another on the flexible or stretchable substrate a distance selected over the range of 10 nm to 10 mm, 100 nm to 1 mm or 1 µm to 100 µm.

In certain embodiments, at least a portion of the one or more flexible or stretchable LED arrays is positioned proximate to a neutral mechanical surface of the proximity sensor device. In embodiments, at least a portion of the one or more flexible or stretchable PD arrays is positioned proximate to a neutral mechanical surface of the proximity sensor device. Optionally, portions of the one or more LED arrays are positioned at a distance selected over the range of 0 nm to 100 µm from a neutral mechanical plane of the proximity sensor device. Optionally, portions of the one or more PD arrays are positioned at a distance selected over the range of 0 nm to 100 µm from a neutral mechanical plane of the proximity sensor device.

In embodiments, one component of a multiple component integrated device is a flexible or stretchable electronic circuit. In embodiments, flexible or stretchable electronic circuits, such as flexible or stretchable LED arrays or flexible or stretchable PD arrays, are useful with the devices and methods described herein. One embodiment of a flexible or stretchable electronic circuit comprises a plurality of inorganic semiconductor elements having an average thickness selected over the range of 250 nm to 100 µm. Useful flexible or stretchable electronic circuits include those comprising one or more single crystalline semiconductor elements. Optionally, inorganic semiconductor elements useful with the flexible or stretchable electronic circuits of the devices and methods described herein include semiconductor nanoribbons, semiconductor membranes, semiconductor nanowires and any combination of these. In embodiments, a flexible or stretchable electronic circuit comprises a large area array.

In specific embodiments, a flexible or stretchable electronic circuit useful in the devices and methods described herein comprises one or more flexible or stretchable single crystalline inorganic semiconductor elements. Useful flexible or stretchable semiconductor elements include those having lateral dimensions selected over the range of 250 nm to 100000 µm, optionally for some applications 1 µm to 10000 µm, and optionally for some applications 10 µm to 1000 µm. Optionally, each inorganic semiconductor element in a flexible or stretchable electronic circuit has a net flexural rigidity less than or equal to $1 \times 10^{-4}$ N·m. Optionally, each inorganic semiconductor element in a flexible or stretchable electronic circuit has a net bending stiffness less than or equal to $1 \times 10^{8}$ GPa µm$^{4}$.

Useful inorganic semiconductor elements include those selected from the group consisting of a transistor, a diode, an amplifier, a multiplexer, a light emitting diode, a laser, a temperature sensor (e.g., thermistor), a heater (e.g., semiconductor resistive heater), a photodiode, a photodetector, an integrated circuit, a sensor and an actuator. In an embodiment, the inorganic semiconductor elements of the device include one or more temperature sensors, such as a thermocouple, thermistor, silicon diode temperature sensor or platinum resistor temperature sensor. In an embodiment, the inorganic semiconductor elements of the device include one or more heaters, such as resistive heaters. Use of a combination of a temperature sensor and heater is beneficial in embodiments providing drug delivery functionality, including controlled release drug delivery. Optionally, an inorganic LED element of any device described herein can be substituted with an inorganic laser diode element. Useful laser diode elements include those having an average thickness less than or equal to 100 μm. Optionally, the flexible or stretchable electronic circuits comprise one or more semiconductor elements arranged to form an active circuit, for example, a circuit which performs one or more discrete functions, such an amplifier circuit or a multiplexing circuit.

In specific embodiments, flexible or stretchable electronic circuits used with the devices and methods described herein comprise a plurality of electronically interconnected island-bridge structures. In a specific embodiment, an island structure of an island-bridge structure comprises a semiconductor circuit element. In a specific embodiment, a bridge structure of an island-bridge structure comprises a flexible or stretchable electrical interconnection, such as an electrical interconnection having a serpentine geometry.

In embodiments, a component of a multiple component integrated device is a flexible or stretchable LED array. In embodiments, a flexible or stretchable electronic circuit component of a multiple component integrated device is a flexible or stretchable LED array. In some embodiments, a multiple component integrated device comprises multiple flexible or stretchable LED arrays. In certain embodiments, a flexible or stretchable electronic circuit useful for the devices and methods described herein comprise a flexible or stretchable array of light emitting diodes (LEDs). In one embodiment, a flexible or stretchable array of light emitting diodes comprises a plurality of light emitting diodes in electrical communication with a plurality of stretchable or flexible electrical interconnects. In a specific embodiment, a flexible or stretchable array of light emitting diodes is an island-bridge structure, for example where an island structure comprises a light emitting diode element and where a bridge structure comprises a flexible or stretchable electrical interconnection. Certain embodiments provide a density of light emitting diodes in a flexible or stretchable array of light emitting diodes selected over the range of 1 LED mm$^{-2}$ to 1000 LEDs mm$^{-2}$. Useful light emitting diodes with the devices and methods described herein include, but are not limited to AlInGaP LEDs, GaN LEDs, stacked inorganic LEDs, inorganic LEDs incorporating a phosphor or any combination of these. In embodiments, an ON/OFF state of an inorganic LED within the LED array is independent from ON/OFF states of other inorganic LEDs within the array.

In embodiments, each LED in an array independently produces electromagnetic radiation having a wavelength selected over the range of 1000 nm to 5000 nm. In embodiments, each LED in the array independently produces infrared electromagnetic radiation, visible electromagnetic radiation, ultraviolet electromagnetic radiation, broadband electromagnetic radiation or narrowband electromagnetic radiation. Optionally, one or more LEDs in an array comprise stacked LEDs, for example one or more LED elements in a stacked configuration. In embodiments, a stacked LED comprises two or more LED elements that emit light of two or more specific wavelengths or wavelength ranges. In a specific embodiment, a stacked LED element comprises an LED that emits red light, and LED that emits green light and an LED that emits blue light, all provided in a stacked configuration. In another embodiment, multiple LED arrays are provided in a multilayer stacked geometry. In one embodiment, a multilayer stacked LED array comprises a first layer comprising an array of LEDs that emit light of a first wavelength or wavelength range and a second layer comprising an array of LEDs that emit light of a second wavelength or wavelength range. Additional embodiments contemplated further comprise an additional layer comprises an array of LEDs that emit light of an additional wavelength or wavelength range. In a specific embodiment, a first LED array in a multilayer stack emits red light, a second LED array in a multilayer stack emits green light and a third LED array in a multilayer stack emits blue light. Additional embodiments include LED arrays that emit white light or light of a broad wavelength range.

In embodiments, a flexible or stretchable LED array generates an intensity of electromagnetic radiation that is sufficient for visualization, for actuating a tissue, for detection, for transmission through a plasmonic crystal, for detection by a flexible or stretchable PD array, or sufficient for any combination of these.

In exemplary embodiments, a flexible or stretchable electronic circuit comprises a multilayer structure. In embodiments, one or more flexible or stretchable electronic circuits are provided in individually encapsulated layers in a multilayer stacked geometry. In a specific embodiment, a multilayer structure of this aspect comprises a plurality of individually encapsulated LED array layers provided in multilayer laminated geometries. In specific embodiments, multilayer structures include those comprising 2 to 1000 individual layers. Flexible or stretchable electronic circuits comprising a multilayer structure are useful, for example, for providing flexible or stretchable electronic circuits exhibiting a variety of fill factors, such as fill factors selected over the range of $1 \times 10^{-6}$ to $1 \times 10^{-3}$. In one embodiment, individually encapsulated LED array layers are provided in a laterally offset configuration; such a configuration is useful for providing fill factors greater than $1 \times 10^{-6}$. As used herein, the expression "laterally offset" refers to a multilayer geometry wherein at least a portion of the LEDs in different layers of the device are positioned such that they do not reside on top of each other. As used in this context, the term "fill factor" refers to the fraction of the area of the footprint of the device that is occupied by the LED structures. In certain embodiments, adhesives or adhesive layers are provided between individual layers of a multilayer structure to unite the components a single multilayer device. Optionally, an individual layer in a multilayer structure has an internal adhesive layer. In certain embodiments, the individual layers of a multilayer structure are each provided on individual substrates with an adhesive layer provided between the substrates to unite the individual layers into a single multilayer device. In certain embodiments, the individual layers are encapsulated to unite the layers into a single multilayer device. In certain embodiments, one layer is laminated on top of another layer to unite the layers into a single multilayer device.

In certain embodiments, a flexible or stretchable electronic circuit supported by an external surface of a suture or a flexible or stretchable substrate covers a percentage of the external surface of the suture or the flexible or stretchable substrate, for example a percentage selected over the range of 1% to 100%, optionally for some applications selected over the range of 10% to 100%, optionally for some embodiments selected over the range of 10% to 60% and optionally for some applications selected over the range of 40% to 100%. In certain embodiments, a flexible or stretchable electronic circuit supported by an external surface of a suture or a flexible or stretchable substrate covers a percentage of the external surface of the suture or the flexible or stretchable substrate, for example a percentage that is 10% or more, optionally for some embodiments 20% or more, and optionally for some embodiments 40% or more. In specific embodiments, a flexible or stretchable electronic circuit covers an area of the external surface of a suture selected over the range of 1 mm$^2$ to 10,000 mm$^2$, selected over the range of 100 mm$^2$ to 1000 mm$^2$, greater than or equal to 100 mm$^2$ or greater than or equal to 1 mm$^2$. In an embodiment, a flexible or stretchable electronic circuit is a large area device.

For some embodiments, a flexible or stretchable electronic circuit is positioned proximate to a neutral mechanical surface of a device. In some embodiment, a thickness of a barrier layer and a thickness of a substrate are selected so as to position one or more semiconductor circuit elements in a flexible or stretchable electronic circuit proximate to a neutral mechanical surface of a device.

Optionally, a flexible or stretchable electronic circuit is assembled via transfer printing, for example via dry transfer contact printing. U.S. Pat. No. 7,557,367 describes useful transfer printing methods. A range of transfer printing methods are useful for assembly of a flexible or stretchable electronic circuit, including those using a conformable transfer device. In an embodiment, a step of assembling a flexible or stretchable electronic circuit comprises the steps of: contacting one or more contact surfaces of semiconductor components and/or electrodes with a transfer surface of a conformable transfer device, thereby generating a conformable transfer device having the semiconductor components and/or electrodes disposed on a transfer surface; contacting the transfer surface of the conformable transfer device having the semiconductor components and/or electrodes with the receiving surface of a flexible or stretchable substrate in a manner to establish conformal contact between the transfer surface of the conformal transfer device and the receiving surface of the flexible or stretchable substrate; and separating the conformable transfer device and the semiconductor components and/or electrodes, thereby transferring the semiconductor components and/or electrodes to the receiving surface of the flexible or stretchable substrate. In an embodiment, the semiconductor components and/or electrodes are at least partially encapsulated by a barrier layer and the transfer surface of the conformable transfer device contacts the barrier layer provided on the contact surfaces of the semiconductor components or electrodes. In an embodiment, the conformal transfer device is a stamp, such as an elastomer stamp or a composite elastomer stamp.

A specific method of making a flexible or stretchable electronic device comprises the steps of providing a substrate having a sacrificial layer; applying a first dielectric layer on the sacrificial layer of the substrate; providing one or more inorganic semiconductor components on the first dielectric layer; covering a portion of the one or more inorganic semiconductor components with a second dielectric layer, thereby generating a covered inorganic semiconductor component having an exposed distal end; providing an electrode that physically contacts the exposed distal end of an inorganic semiconductor component; removing at least a portion of the first dielectric layer, the second dielectric layer or both, thereby generating a mesh structure; removing the sacrificial layer on the substrate to leave a mesh structure; and transferring the mesh structure to a receiving surface of a flexible or stretchable substrate. In an embodiment, the step of removing at least a portion of the first dielectric layer and the second dielectric layer to generate the mesh structure comprises etching, for example, oxygen reactive ion etching. In an embodiment, the step of providing one or more inorganic semiconductor components on the first dielectric layer is carried out via transfer printing, for example, via dry contact transfer printing. In an embodiment, the step of transferring the mesh structure to a receiving surface of a flexible or stretchable substrate is carried out via transfer printing, for example, via dry contact transfer printing.

In some embodiments, the geometry of electronic devices may be used to provide stretchability, flexibility, conformability and/or compressibility. In an embodiment, the devices may exploit inorganic semiconductor materials configured into structural shapes that can geometrically accommodate large mechanical deformations without imparting significant strain in the materials themselves. For example, bridges connecting rigid device islands may be wavy, buckled, serpentine or meandering as further described in U.S. Patent Application Publication Nos. US 2008/0157235 and US 2010/059863. In an aspect, devices disclosed herein comprise one or more stretchable components, such as disclosed in U.S. Patent Application Publication Nos. US 2008/0157235, US 2010/059863 and US 2010/0002402, and are made by one or more of the processes disclosed therein. U.S. Patent Application Publication Nos. US 2008/0157235, US 2010/059863 and US 2010/0002402 are hereby incorporated by reference in their entireties to the extent not inconsistent herewith.

In embodiments, one component of a multiple component integrated device is a barrier layer, for example a barrier layer comprising a polymer or elastomer. In exemplary embodiments, barrier layers used in the devices and methods described herein prevent water from a biological environment or a non-biological environment from contacting at least a portion of a flexible or stretchable electronic circuit or components thereof. For example, a barrier layer of one embodiment provides a net permeability with respect to transport of water low enough to prevent an electrical short circuit in a flexible or stretchable electronic circuit. Useful barrier layers include, but are not limited to barrier layers which limit a leakage current between a biological environment and a flexible or stretchable electronic circuit or a component thereof, barrier layers which limit a temperature difference between a biological environment and a flexible or stretchable electronic circuit or a component thereof, barrier layers which selectively permit transmission of electromagnetic radiation between a biological environment and a flexible or stretchable electronic circuit or a component thereof, barrier layers which selectively permit transport of one or more compositions to or from a biological environment, and any combination of these.

In a specific embodiment, a barrier layer provides or limits a net leakage current from a flexible or stretchable electronic to 10 µA or less, and for some applications 0.01 pA/cm$^2$ or less, and for some applications 0.001 µA/cm$^2$ or less. In some embodiments, a barrier layer has an electrical resistivity of $10^{14}$ Ω·m or greater, for example an electrical resistivity selected over the range of $10^{15}$ to $10^{17}$ Ω·m. In some embodiments, the barrier layer prevents the rate at which charge is leaked from the electronic device; for example, one barrier layer embodiment limits electrical discharge from a device to 10 µC or less over a period of 1 second. In some embodiments, the barrier layer limits leakage current or average leakage current from the device to 10 µA or less or 5 µA or less over a long period of time, such as 3 hours or more or 5 hours or more.

Barrier layers which selectively permit transmission of electromagnetic radiation include those having at least portions which are optically transparent and those having at least portions which are optically opaque. Certain barrier layers include at least portions which have specific wavelength regions which are at least partially transparent, such as wavelength regions selected over the range of 100 nm to 300 µm or any sub-range therein. Useful barrier layers further include those layers in which the transmission properties are modulated by an electronic circuit in contact with the barrier layer or a component thereof.

Barrier layers which selectively permit transport of one or more compositions to or from a biological environment include those having at least portions which have an increased permeability for one or more compositions. Barrier layers of this class are useful, for example for permitting introduction of one or more pharmaceutical compositions to a biological environment from within the barrier layer or from an electronic circuit in contact with the barrier layer. In some embodiments, the permeability of portions of a barrier layer is modulated by an electronic circuit or a component thereof in contact with the barrier layer.

In specific embodiments, a barrier layer has an average thickness over a flexible or stretchable electronic circuit less than or equal to 1000 µm, optionally for some embodiments less than or equal to 100 µm and optionally for some embodiments less than or equal to 10 µm. Optionally, a barrier layer has a thickness over at least a portion of a flexible or stretchable electronic circuit selected over the range of 250 nm to 1000 µm, optionally for some embodiments selected over the range of 1 µm to 500 µm, and optionally for some embodiments selected over the range of 10 µm to 100 µm. In some embodiments, a barrier layer comprises a plurality of individual layers, for example where each layer has a thickness selected over the range of 250 nm to 1000 µm and/or where the total thickness of the multiple layers is less than or equal to 1000 µm. In embodiments, a barrier layer is a stretchable or flexible layer. In embodiments, a barrier layer has an average modulus selected over the range of 0.5 kPa to 10 GPa, optionally for some application selected over the range of 1 KPa to 1 GPa, optionally for some application selected over the range of 1 KPa to 100 MPa, optionally for some application selected over the range of 1 KPa to 1 MPa. As will be generally understood by one skilled in the art, use of a barrier layer with a relatively high modulus (e.g., greater than 1 GPa) in some embodiments may require a small thickness (e.g., less than 100 µm or optionally less than 10 µm) to provide net device mechanical properties (e.g., bending stiffness or flexural rigidity) useful for some therapeutic and diagnostic applications. In embodiments, a barrier layer has net flexural rigidity less than or equal to $1 \times 10^{-4}$ Nm. In embodiments, a barrier layer has a net bending stiffness less than or equal to $1 \times 10^8$ GPa µm$^4$, optionally for some applications less than or equal to $1 \times 10^7$ GPa µm$^4$, and optionally for some applications less than or equal to $1 \times 10^6$ GPa µm$^4$.

Optionally, barrier layers useful with the devices and methods described herein comprise a biocompatible material, a bioinert material or a combination of biocompatible and bioinert materials. In one embodiment, a barrier layer comprises a bioresorbable material. Useful barrier layers include those comprising a material selected from the group consisting of a polymer, an inorganic polymer, an organic polymer, an elastomer, a biopolymer, a ceramic and any combination of these. Specific barrier layers include those comprising PDMS, polyimide, SU-8, parylene, parylene C, silicon carbide (SiC), or $Si_3N_4$. Optionally, barrier layers useful with the devices and methods described herein include barrier layers which are microstructured or nanostructured layers having one or more microstructured or nanostructured openings, channels, vias, receiving surfaces, relief features, optically transmissive regions, optically opaque regions or selectively permeable regions that are permeable to one or more target molecules. Optionally, an adhesive layer is provided adjacent to a barrier layer, for example a PDMS layer.

Optionally, a barrier layer may completely or partially encapsulate inorganic semiconductor components or electrodes of a flexible or stretchable electronic device. In an embodiment, the barrier layer comprises a mesh structure. Such a mesh structure may be formed, for example, by removing material from selected regions of the barrier layer, for example, via wet or dry etching (e.g., reactive oxygen etching).

Optionally, devices described herein further comprise one or more pharmaceutical compositions, for example pharmaceutical compositions at least partially encapsulated by a barrier layer or pharmaceutical compositions incorporated into the barrier layer material. The term "pharmaceutical composition" is used herein interchangeably with the term "drug." Useful pharmaceutical compositions include, but are not limited to antibiotics, antiseptics, proteins, nucleic acids, anti-inflammatories, carbohydrates, analgesics, antipyretics, anti-fungals, antihistamines, hormones, antivirals, vitamins, antibodies, photosensitizers and any combination of these. In a specific embodiment, the barrier layer comprises a bioresorbable material and the device further comprises one or more pharmaceutical compositions. In these embodiments, when the bioresorbable material is at least partially resorbed or dissolved by a biological environment, at least a portion of a pharmaceutical composition is released into the biological environment.

Optionally, when a device comprises a pharmaceutical composition, the flexible or stretchable electronic circuit comprises a thermal, electrical or optical actuator, such that a portion of the pharmaceutical composition is released to the biological environment upon actuation of the flexible or stretchable electronic circuit. In embodiments, actuation of a flexible or stretchable electronic circuit thermally, optically, or electrically actuates the barrier layer such that the pharmaceutical composition is released. In embodiments, actuation of a flexible or stretchable electronic circuit changes a permeability of at least a portion of the barrier layer, permitting release of a portion of the pharmaceutical composition to a biological environment. In embodiments, actuation of a flexible or stretchable electronic circuit melts, photolytically degrades or otherwise renders porous at least a portion of the barrier layer, thereby releasing at least a portion of the pharmaceutical composition to a biological environment. In certain embodiments, when a pharmaceutical composition is released to a biological environment it is exposed to electromagnetic radiation generated by a flexible or stretchable electronic circuit to photoactivate the pharmaceutical composition. In certain embodiments, heating of a barrier layer by actuation of a flexible or stretchable electronic circuit partially degrades the barrier layer to release portions of a pharmaceutical composition contained therein.

In embodiments, components of a multiple component integrated device are optical elements. For example, in certain embodiments, devices described herein further comprise one or more optical elements. Optical elements useful in the devices and methods described herein include coatings, reflectors, windows, optical filters, collecting optics, diffusing optics, concentrating optics and combinations of these. In embodiments, optical elements comprise molded structures. In embodiments, the optical elements are positioned in optical communication with other device components, for example a flexible or stretchable electronic circuit, a flexible or stretchable LED array, a flexible or stretchable PD array, a flexible or stretchable substrate, a detector, a plasmonic crystal and any combination of these. In certain embodiments, an optical element comprises a molded structure, such as a replica molded structure. In embodiments, an optical element comprises a lithographically patterned structure, for example patterned by a conventional lithographic method known in the art of microfabrication. In a specific embodiment, an optical element comprises a structure patterned by nano-imprint lithography. In one embodiment, a method of making an optical element comprises the steps of providing a prepolymer layer, molding or patterning the prepolymer layer and curing the prepolymer layer. Useful optical elements include those provided in optical communication with one or more semiconductor device elements, for example LEDs or PDs.

In another aspect, a multiple component integrated device is a fluid delivery monitor. Fluid delivery monitors are useful, for example, in methods for monitoring flowing fluids. A device of this aspect comprises a tube for delivery of a fluid, a flexible or stretchable plasmonic crystal device conformally positioned on a surface of the tube, and a detector positioned in optical communication with the plasmonic crystal device to receive electromagnetic radiation. In one embodiment, the tube accommodates the plasmonic crystal device. In one embodiment, the tube and plasmonic crystal device comprise a unitary structure. In one embodiment, the plasmonic crystal device is provided in an aperture in the tube, for example such that a sensing surface of a plasmonic crystal is provided in physical contact with a fluid in the tube. In an embodiment, the flexible or stretchable plasmonic crystal device is fabricated into the tube.

A method of this aspect for monitoring a fluid flowing in a tube comprises the steps of flowing the fluid through the tube, providing a flexible or stretchable plasmonic crystal device conformally on a surface of the tube, passing electromagnetic radiation from the plasmonic crystal device through the flowing fluid and detecting at least a portion of the electromagnetic radiation which passes through the flowing fluid with a detector.

In specific embodiments, the flexible or stretchable plasmonic crystal device comprises a flexible or stretchable light emitting diode (LED) array supported by a first flexible or stretchable substrate and a plasmonic crystal positioned in optical communication with the flexible or stretchable LED array. Optionally the plasmonic crystal is supported by a separate substrate, for example a substrate positioned between a plasmonic crystal and a flexible or stretchable LED array. Optionally, the device may further comprise one or more inorganic semiconductor elements supported by the first flexible substrate, for example in individually encapsulated layers provided in a multilayer stacked geometry. In a specific embodiment, the plasmonic crystal is positioned in optical communication with a detector. In a specific embodiment, the plasmonic crystal is provided in physical contact with the fluid being monitored. In a specific embodiment, a sensing surface of the plasmonic crystal is provided in physical contact with the fluid.

In embodiments, the flexible or stretchable LED array produces electromagnetic radiation and the plasmonic crystal receives at least a portion of the electromagnetic radiation and transmits at least a portion of the electromagnetic radiation to produce transmitted electromagnetic radiation. In these embodiments, the detector receives and detects at least a portion of the transmitted electromagnetic radiation. Optionally, the detector detects an intensity of the transmitted electromagnetic radiation, for example, as a function of time, as a function of wavelength, or as a function of position, for example as a function of the position of the plasmonic crystal that the electromagnetic radiation is transmitted through. In some embodiments, a property of the flowing fluid is determined from the detected intensity. For example, useful properties determined from the detected intensity include, but is not limited to, a refractive index of the fluid, a composition of the fluid, a presence or absence of a pharmaceutical composition in the fluid, a concentration of a pharmaceutical composition in the fluid, a density of the fluid, a flow rate of the fluid and any combination of these.

In embodiments, the flexible or stretchable LED array comprises a plurality of inorganic LEDs having a thickness less than or equal to 100 µm. Optionally each individual inorganic LED in the flexible or stretchable LED array has one or more lateral dimensions selected over the range of 250 nm to 1000 µm. In embodiments, the inorganic LEDS are AlInGaP LEDs, GaN LEDs, stacked inorganic LEDs, inorganic LEDs incorporating a phosphor or any combination of these. In embodiments, an ON/OFF state of an inorganic LED within the LED array is independent from ON/OFF states of other inorganic LEDs within the array. In embodiments, each LED in the array independently produces electromagnetic radiation having a wavelength selected over the range of 1000 nm to 5000 nm. In embodiments, each LED in the array independently produces infrared electromagnetic radiation, visible electromagnetic radiation, ultraviolet electromagnetic radiation, broadband electromagnetic radiation or narrowband electromagnetic radiation.

Optionally the flexible or stretchable LED array comprises an encapsulation layer provided over the individual inorganic LEDs in the array, such as an encapsulation layer which prevents fluid from making direct contact with the LEDs. The flexible or stretchable LED array may optionally comprise a plurality of individually encapsulated LED array layers provided in a multilayer stacked geometry. In a specific embodiment, the flexible or stretchable LED array comprises 2 to 1,000 individually encapsulated LED array layers provided in a multilayer laminated geometry. Optionally, the LED array is assembled by transfer printing. In a specific embodiment, the LED array is an island-bridge structure, for example where islands of the island-bridge structure are provided by a plurality of inorganic LEDs and bridges of the island-bridge structure are provided by a plurality of flexible electrical interconnects positioned in electrical communication with the plurality of inorganic LEDs. In one embodiment, a plasmonic crystal comprises a molded or embossed structure on a flexible or stretchable LED array, for example a molded or embossed encapsulation layer. In a specific embodiment, a plasmonic crystal and a flexible or stretchable LED array of a flexible or stretchable plasmonic crystal device are provided in a multilayer laminated geometry.

Useful plasmonic crystals include those fabricated by replica molding methods or nano-imprint lithography methods. U.S. Pat. No. 7,705,280 further discloses plasmonic crystals useful with the methods and devices described herein. Optionally, the plasmonic crystal is assembled by transfer printing. In a specific embodiment, the plasmonic crystal is in physical contact with the flowing fluid. In one embodiment, the second flexible or stretchable substrate and the plasmonic crystal comprise a unitary structure. Optionally, the photonic crystal comprises the substrate having a nanoimprinted or replica-molded structure.

In embodiments, the tube for flowing the fluid is flexible or stretchable. Optionally the tube has a circular cross section. Optionally the tube has a non-circular cross section, such as a rectangular cross section or polygonal cross section. In embodiments, the tube has an outer diameter selected over the range of 100 µm to 10 mm. In embodiments, the tube has an inner diameter selected over the range of 100 µm to 10 mm. Optionally the tube has a nanostructured or patterned surface, for example for accommodating the flexible LED array or a component thereof or the plasmonic crystal. In one embodiment, the plasmonic crystal is molded into the tube, for example by replica molding or nano-imprint lithography. Optionally the plasmonic crystal comprises a nanostructured or microstructured surface of the tube and the tube comprises the second flexible or stretchable substrate. In one embodiment, the tube is positioned in fluid communication with a patient or subject, for example such that the fluid is delivered to or withdrawn from the patient or subject. Optionally, the fluid flowing through the tube is fluid for intravenous delivery. Optionally, the tube is an intravenous delivery tube. In one embodiment, the tube comprises a biocompatible material. Optionally the tube has a non-circular cross section. In embodiments, the tube has an outer lateral dimension selected over the range of 100 µm to 10 mm. In embodiments, the tube has an inner lateral dimension selected over the range of 100 µm to 10 mm. In specific embodiments, the tube is at least partially transparent to electromagnetic radiation having a wavelength or wavelength distribution selected over 100 nm to 5000 nm.

In a specific embodiment, a plasmonic crystal comprises a substrate having a first surface with a plurality of features provided in a first array, where the substrate comprises a dielectric material; and one or more films comprising an electrically conductive material, wherein at least a portion of the one or more films is supported by the first surface, and wherein at least a portion of the one or more films comprising the electrically conducting material is spatially aligned with each of the features of the first surface; wherein the spatial distribution, physical dimensions or both of the features of the first array are selected such that at least a portion of electromagnetic radiation incident to the plasmonic crystal excites plasmonic responses in the one or more films comprising the electrically conducting material. In embodiments, the electrically conducting material is positioned in physical contact with the fluid. In embodiments, the dielectric material receives electromagnetic radiation produced by the flexible or stretchable array of LEDs.

Features of the first array of the first surface of the substrate useful in the described embodiments include apertures, recessed features, relief features or any combination of these. In an embodiment, for example, features of the first array comprise apertures extending through the entire thickness of the substrate, and optionally comprise a nanohole array. In other embodiments, features of the first array comprise relief features extending from the substrate, including but not limited to, arrays of cubes, columns, ribbons, posts and prisms or any combination of these relief features. In other embodiments, features of the first array comprise recessed features extending into the substrate including, but not limited to, depressions, channels, grooves, bores, openings, slits or any combination of these.

Optionally, the substrate of such a plasmonic crystal comprises a polymer material. Optionally, the substrate comprises a nanoimprinted structure or a replica-molded structure. Optionally, the plasmonic crystal comprises a three dimensional plasmonic crystal. Optionally, the one or more films comprising the electrically conducting material comprise a metallic or semiconducting optical grating structure. Optionally, the one or more films comprising an electrically conducting material comprise one or more metal or semiconductor films having thicknesses selected from the range of about 5 nm to about 5 µm. Optionally, a portion of the one or more films of the electrically conductive material have the same cross sectional shapes as at least a portion of the features of the first array.

In embodiments, the features of a first array in the above described plasmonic crystal are selected from the group consisting of: apertures extending entirely through the substrate; relief features extending from the substrate; and recessed features extending into the substrate. Optionally at least a portion of features of a first array of a plasmonic crystal are nanosized features or nanostructured features. For example, in some embodiments, the features extend heights into the substrate or extend heights away from the substrate selected from the range of 5 nm to 5 µm. In specific embodiments, the features of have cross sectional shapes selected from the group consisting of circular, square, rectangular, trapezoidal, ellipsoid, triangular or any combination of these. Optionally, the features of have submicron cross sectional dimensions. In a specific embodiment, the features are provided in a periodic array. Optionally, the periodic array further comprises at least one defect.

In embodiments, the features of the first array are recessed features, relief features, apertures or any combination of these, wherein one or more films comprising the electrically conductive material comprises a continuous or discontinuous film supported by the first surface and covering at least a portion of the features provided in the first array. Optionally, the continuous film is a unitary film. In one embodiment, the continuous or discontinuous film is provided in physical contact with the first surface. In one embodiment, the continuous or discontinuous film is provided in conformal contact with the first surface. In an embodiment, each of the features have side surfaces and a top surface or a bottom surface; wherein the continuous film covers the side surfaces and the top surface or the bottom surface of at least a portion of the features.

In some embodiments, a plasmonic crystal further comprises an additional substrate in contact with the substrate having the first surface, wherein at least a portion of the features of the first array are apertures extending through the substrate having the first surface, wherein the additional substrate is positioned such that the apertures in the substrate having the first surface expose exposed regions of the additional substrate, and wherein the continuous film covers at least a portion of the exposed regions of the additional substrate.

In specific embodiments, the one or more films comprise: a first film supported by a portion of the first surface, and a plurality of films provided in a second array, wherein at least one of the films of the second array is spatially aligned with each of the features of the first surface; and wherein at least a portion of the films of the second array are physically displaced from the first film. Optionally, the first film is provided in a first layer and the films of the second array are provided in a second layer, wherein the plasmonic crystal has a multilayered geometry. In an embodiment the first layer having the first film is separated from the second layer having the array of second films by distances selected over the range of about 5 nm to about 5 µm.

In embodiments, the first array of features comprises an array of recessed features having bottom surfaces or relief features having top surfaces; wherein at least a portion of the films of the second array are positioned on the bottom surfaces or the top surface of the features. In embodiments, the first array of features comprises recessed features, relief features or apertures having side surfaces, wherein the one or more films comprising the electrically conducting material further comprise films covering a portion of the side surfaces of the features.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIGS. 4A, 4B, 4C, 4D, and 4E provide a schematic showing various approaches for creating layers of flexible or stretchable electronic circuits. FIG. 4A provides a side plan view of a flexible or stretchable electronic circuit comprising an array of electronically interconnected island and bridge structures. FIGS. 4B, 4C, 4D, and 4E provide side plan views of stacked configurations of stretchable or flexible electronic circuits wherein the layers are connected by an adhesive (FIG. 4B), directly connected (FIG. 4C), connected by a substrate (FIG. 4D), and connected by substrates and adhesive (FIG. 4E).

FIGS. 4F, 4G, and 4H provide a schematic showing various approaches for creating layers of flexible or stretchable electronic circuits. FIGS. 4F, 4G, and 4H provide side plan views of stacked configurations of stretchable or flexible electronic circuits wherein the layers are connected by encapsulation (FIG. 4F), lamination (FIG. 4G), and printing on a laminated layer (FIG. 4H).

FIG. 11E provides a magnified view of FIG. 11D from the top. FIG. 11F provides data showing I-V characteristics of the array in its flat and inflated state. FIG. 11G provides data showing 3D-FEM results.

FIG. 12C provides data showing 3D-FEM modeling results.

FIGS. 18A, 18B and 18C provide schematic illustrations (left frames) and corresponding microscope images (top right frames) and SEM images (bottom right frames) of devices during transfer printing.

FIGS. 21A and 21B provide optical microscope images of two pixels in a μ-ILED array with a serpentine bridge design before (left frame) and after (right frame) external stretching along the horizontal direction. FIG. 21C provides data showing the results of a FEM simulation.

FIGS. 23A and 23B provide optical images of an 8×8 μ-ILED array on a thin PDMS substrate. FIG. 23C provides data showing the results of a FEM calculation.

FIG. 24A provides schematic illustrations of a 3×8 μ-ILED array integrated on a thin PDMS substrate; the inset represents an optical microscope image of this μ-ILED array on a handle glass substrate before transfer printing. FIG. 24B shows a magnified view of the SEM image in FIG. 12B. FIG. 24C provides data showing voltage at 20 μA current for each twisting cycle of 360° during a fatigue test.

FIG. 29A provides an optical image of a 6×6 μ-ILED array integrated on fabric in its bent and on state; the inset shows the device in its flat and off state. FIG. 29B provides data showing I-V characteristics of this array in its bent state; the inset provides a graph of the voltage needed to generate a current of 20 μA during a fatigue test.

FIG. 31A provides SEM images of a fabric before (left frame) and after (right frame) coating with a thin layer of PDMS. FIG. 31B provides SEM images of Al foil before (left frame) and after (right frame) coating with a thin layer of PDMS.

FIG. 33 provides a schematic illustration of the encapsulation of an implantable array of μ-ILEDs.

DETAILED DESCRIPTION

Figure 1A:
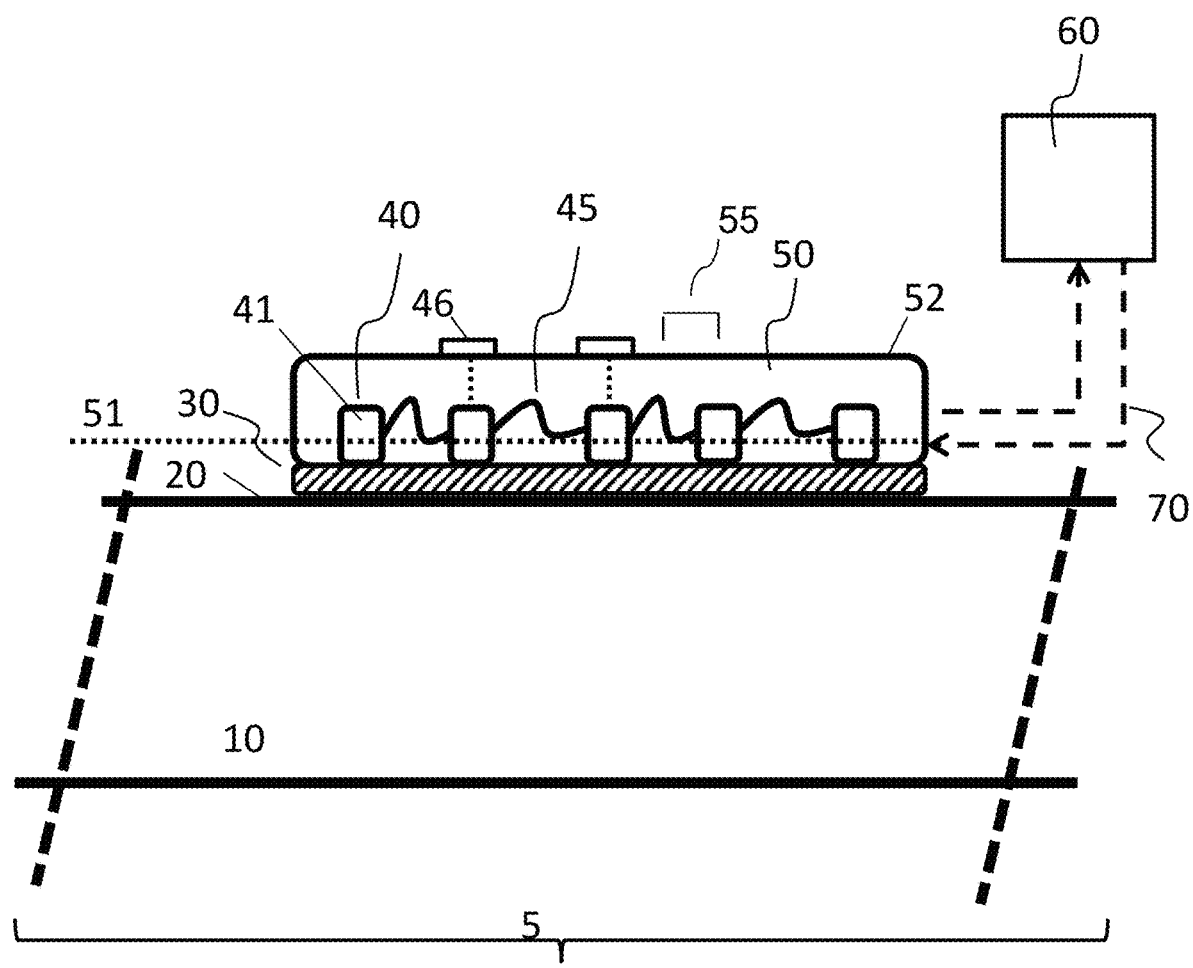
FIG. 1A provides a side plan view of a biomedical device comprising a suture-mounted stretchable or flexible electronic circuit.

In general the terms and phrases used herein have their art-recognized meaning, which can be found by reference to standard texts, journal references and contexts known to those skilled in the art. The following definitions are provided to clarify their specific use in the context of the invention.

"Transferable" or "printable" are used interchangeably and relates to materials, structures, device components and/or integrated functional devices that are capable of transfer, assembly, patterning, organizing and/or integrating onto or into substrates. In an embodiment, transferring or printing refers to the direct transfer of a structure or element from one substrate to another substrate, such as from a multilayer structure to a device substrate or a device or component supported by a device substrate. Alternatively, transferable refers to a structure or element that is printed via an intermediate substrate, such as a stamp that lifts-off the structure or element and then subsequently transfers the structure or element to a device substrate or a component that is on a device substrate. In an embodiment, the printing occurs without exposure of the substrate to high temperatures (i.e. at temperatures less than or equal to about 400 degrees Celsius). In one embodiment, printable or transferable materials, elements, device components and devices are capable of transfer, assembly, patterning, organizing and/or integrating onto or into substrates via solution printing or dry transfer contact printing. Similarly, "printing" is used broadly to refer to the transfer, assembly, patterning, organizing and/or integrating onto or into substrates, such as a substrate that functions as a stamp or a substrate that is itself a target (e.g., device) substrate. Such a direct transfer printing provides low-cost and relatively simple repeated transfer of a functional top-layer of a multilayer structure to a device substrate. This achieves blanket transfer from, for example, a wafer to a target substrate without the need for a separate stamp substrate.

"Substrate" refers to a material having a surface that is capable of supporting a component, including a device, component or an interconnect. An interconnect that is "bonded" to the substrate refers to a portion of the interconnect in physical contact with the substrate and unable to substantially move relative to the substrate surface to which it is bonded. Unbonded portions, in contrast, are capable of substantial movement relative to the substrate. The unbonded portion of an interconnect generally corresponds to that portion having a "bent configuration," such as by strain-induced interconnect bending.

The term "surface" as used herein is intended to be consistent with its plain meaning which refers to an outer boundary of an object. In embodiments, surfaces may be given specific names, such as "receiving surface", "contact surface", "external surface". In some embodiments, named surfaces can refer to their target use and/or identify subregions of a surface. In some embodiments, named surfaces can refer to their orientation, for example relative to other nearby or adjacent components.

"Functional layer" or "device layer" refers to a layer that imparts at least partial functionality to that device or device component. Depending on the particular device or device component, a functional layer can include a broad range of compositions. In contrast, a functional layer for incorporation into electronics (MESFETs), LEDs, or optical systems may have a different layering configuration and/or compositions. Accordingly, the specific functional layer incorporated into a multilayer structure depends on the final device or device component in which the functional layer will be incorporated. For example, the functional layer may contain semiconductor components. Alternatively, the functional layer may comprise multiple layers, such as multiple layers including a semiconductor separated by support layers. The functional layer may comprise a plurality of patterned elements, such as interconnects running between electrodes or islands. The functional layer may be heterogeneous or may have one or more properties that are inhomogeneous. "Inhomogeneous property" refers to a physical parameter that can spatially vary, thereby effecting the position of the neutral mechanical plane within a multilayer device.

"Structural layer" refers to a layer that imparts structural functionality, for example by supporting and/or encapsulating device components.

"Buffer layer" refers to a layer of a device or device component which is useful for protecting other layers of the device component. In one embodiment, a buffer layer protects another device layer from etching. In an embodiment, a buffer layer does not impact or has a minimal impact on the function of the device. In one embodiment, an etch block layer is a buffer layer.

"Release" and "releasing" refer to at least partially separating two layers, devices or device components from one another, for example by mechanical or physical separation, or by removal of at least a portion of one layer, device or device component. In some embodiments, removal of a sacrificial layer results in the release of a layer, device or device component. In some embodiments, layers, devices or device components are released by etching away a portion of the layer, device or device component. In certain embodiments, released components remain attached to the object with they are released from by one or more anchors. In some embodiments, released components are subsequently attached to the object they are released from by one or more anchors.

The term "patterning" is used herein as in the art of microfabrication to broadly refer to a process by which portions of a layer, device or device component are selectively removed or deposited to create a specified structure.

"Supported by a substrate" refers to a structure that is present at least partially on a substrate surface or present at least partially on one or more intermediate structures positioned between the structure and the substrate surface. The term "supported by a substrate" may also refer to structures partially or fully embedded in a substrate.

"Printable electronic device" or "printable electronic device component" refer to devices and structures that are configured for assembly and/or integration onto substrate surfaces, for example by using dry transfer contact printing and/or solution printing methods. In embodiments, a printable electronic device component is a printable semiconductor element. In embodiments, printable semiconductor elements are unitary single crystalline, polycrystalline or microcrystalline inorganic semiconductor structures. In various embodiments, printable semiconductor elements are connected to a substrate, such as a mother wafer, via one or more bridge or anchor elements. In this context of this description, a unitary structure is a monolithic element having features that are mechanically connected. Semiconductor elements of various embodiments may be undoped or doped, may have a selected spatial distribution of dopants and may be doped with a plurality of different dopant materials, including p- and n-type dopants. Certain microstructured printable semiconductor elements include those having at least one cross sectional dimension greater than or equal to about 1 μm and nanostructured printable semiconductor elements having at least one cross sectional dimension less than or equal to about 1 μm.

Printable semiconductor elements useful for a variety of applications comprise elements derived from "top down" processing of high purity bulk materials, such as high purity crystalline semiconductor wafers generated using conventional high temperature processing techniques. In an embodiment, a printable semiconductor element comprises a composite heterogeneous structure having a semiconductor operationally connected to or otherwise integrated with at least one additional device component or structure, such as a conducting layer, dielectric layer, electrode, additional semiconductor structure or any combination of these. In some methods and systems, the printable semiconductor element(s) comprises a semiconductor structure integrated with at least one additional structure selected from the group consisting of: another semiconductor structure; a dielectric structure; conductive structure, and an optical structure (e.g., optical coatings, reflectors, windows, optical filter, collecting, diffusing or concentration optic etc.). In some embodiments a printable semiconductor element comprises a semiconductor structure integrated with at least one electronic device component selected from the group consisting of: an electrode, a dielectric layer, an optical coating, a metal contact pad and a semiconductor channel. In some embodiments, printable semiconductor elements comprise stretchable semiconductor elements, bendable semiconductor elements and/or heterogeneous semiconductor elements (e.g., semiconductor structures integrated with one or more additional materials such as dielectrics, other semiconductors, conductors, ceramics etc.). Printable semiconductor elements include printable semiconductor devices and components thereof, including but not limited to printable LEDs, lasers, solar cells, p-n junctions, photovoltaics, photodiodes, diodes, transistors, integrated circuits, and sensors.

"Electronic device component" refers to a printable semiconductor or electrical device. Exemplary electronic device component embodiments are configured for performing a function, for example emitting electromagnetic radiation or converting electromagnetic radiation into electrical energy. In specific embodiments, multiple electronic device components are electrically interconnected and perform a more complex task or function than the individual device components perform alone. Useful electronic device components include, but are not limited to P-N junctions, thin film transistors, single junction solar cells, multi-junction solar cells, photodiodes, light emitting diodes, lasers, CMOS devices, MOSFET devices, MESFET devices, photovoltaic cells, microelectricalmechanical devices and HEMT devices.

"Vertical type LED" refers to a light emitting diode device in which the functional components or layers of the device are arranged in a stacked configuration and the electrical contacts are made at the top and bottom of the stack. In some embodiments, a vertical type LED incorporates one or more phosphor layers which absorb electromagnetic radiation of one wavelength or wavelength region and emit electromagnetic radiation of a second wavelength or wavelength region.

"ON/OFF state" refers to a configuration of a device component capable of and/or configured for generation of electromagnetic radiation, such as a light emitting diode or a laser. In one embodiment, an ON/OFF state distinguishes between moments when a device component is generating electromagnetic radiation and when a device component is not generating electromagnetic radiation. In an embodiment, an ON/OFF state distinguishes between moments when a device component is generating electromagnetic radiation having an intensity above a threshold value and when a device component is generating electromagnetic radiation having an intensity below a threshold value.

"Solution printing" is intended to refer to processes whereby one or more structures, such as transferable or printable elements, are dispersed into a carrier medium and delivered in a concerted manner to selected regions of a substrate surface. In an exemplary solution printing method, delivery of structures to selected regions of a substrate surface is achieved by methods that are independent of the morphology and/or physical characteristics of the substrate surface undergoing patterning. Solution printing methods include, but are not limited to, ink jet printing, thermal transfer printing, and capillary action printing.

"Contact printing" refers broadly to a dry transfer contact printing method such as with a stamp that facilitates transfer of features from a stamp surface to a substrate surface. In an embodiment, the stamp is an elastomeric stamp. Alternatively, the transfer can be directly to a target (e.g., device) substrate or host substrate. The following references relate to self-assembly techniques which may be used in methods described herein to transfer, assembly and interconnect transferable semiconductor elements via contact printing and/or solution printing techniques and are incorporated by reference in their entireties herein: (1) "Guided molecular self-assembly: a review of recent efforts", Jiyun C Huie Smart Mater. Struct. (2003) 12, 264-271; (2) "Large-Scale Hierarchical Organization of Nanowire Arrays for Integrated Nanosystems", Whang, D.; Jin, S.; Wu, Y.; Lieber, C. M. Nano Lett. (2003) 3(9), 1255-1259; (3) "Directed Assembly of One-Dimensional Nanostructures into Functional Networks", Yu Huang, Xiangfeng Duan, Qingqiao Wei, and Charles M. Lieber, Science (2001) 291, 630-633; and (4) "Electric-field assisted assembly and alignment of metallic nanowires", Peter A. Smith et al., Appl. Phys. Lett. (2000) 77(9), 1399-1401.

Useful contact printing methods for assembling, organizing and/or integrating transferable elements include dry transfer contact printing, microcontact or nanocontact printing, microtransfer or nanotransfer printing and self-assembly assisted printing. Use of contact printing is beneficial because it allows assembly and integration of a plurality of transferable semiconductors in selected orientations and positions relative to each other. Contact printing also enables effective transfer, assembly and integration of diverse classes of materials and structures, including semiconductors (e.g., inorganic semiconductors, single crystalline semiconductors, organic semiconductors, carbon nanomaterials etc.), dielectrics, and conductors. Contact printing methods optionally provide high precision registered transfer and assembly of transferable semiconductor elements in preselected positions and spatial orientations relative to one or more device components prepatterned on a device substrate. Contact printing is also compatible with a wide range of substrate types, including conventional rigid or semi-rigid substrates such as glasses, ceramics and metals, and substrates having physical and mechanical properties attractive for specific applications, such as flexible substrates, bendable substrates, shapeable substrates, conformable substrates and/or stretchable substrates. Contact printing assembly of transferable structures is compatible, for example, with low temperature processing (e.g., less than or equal to 298K). This attribute allows optical systems to be implemented using a range of substrate materials including those that decompose or degrade at high temperatures, such as polymer and plastic substrates. Contact printing transfer, assembly and integration of device elements is also beneficial because it can be implemented via low cost and high-throughput printing techniques and systems, such as roll-to-roll printing and flexographic printing methods and systems.

"Stretchable" refers to the ability of a material, structure, device or device component to be strained without undergoing fracture. In an exemplary embodiment, a stretchable material, structure, device or device component may undergo strain larger than about 0.5% without fracturing, preferably for some applications strain larger than about 1% without fracturing and more preferably for some applications strain larger than about 3% without fracturing.

The terms "foldable," "flexible" and "bendable" are used synonymously in the present description and refer to the ability of a material, structure, device or device component to be deformed into a curved shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to about 5%, preferably for some applications larger than or equal to about 1%, and more preferably for some applications larger than or equal to about 0.5%. A used herein, some, but not necessarily all, flexible structures are also stretchable. A variety of properties provide flexible structures (e.g., device components), including materials properties such as a low modulus, bending stiffness and flexural rigidity; physical dimensions such as small average thickness (e.g., less than 100 µm, optionally less than 10 µm and optionally less than 1 µm) and device geometries such as thin film and mesh geometries.

"Semiconductor" refers to any material that is an insulator at very low temperatures, but which has an appreciable electrical conductivity at temperatures of about 300 Kelvin. In the present description, use of the term semiconductor is intended to be consistent with use of this term in the art of microelectronics and electrical devices. Useful semiconductors include element semiconductors, such as silicon, germanium and diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors CuCl, group IV-VI semiconductors such as PbS, PbTe and SnS, layer semiconductors such as $PbI_2$, $MoS_2$ and GaSe, oxide semiconductors such as CuO and $Cu_2O$. The term semiconductor includes intrinsic semiconductors and extrinsic semiconductors that are doped with one or more selected materials, including semiconductor having p-type doping materials (also known as P-type or p-doped semiconductor) and/or n-type doping materials (also known as N-type or n-doped semiconductor), to provide beneficial electrical properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, SnO$_2$, TiO, TiO$_2$, Bi$_2$S$_3$, Bi$_2$O$_3$, Bi$_2$Te$_3$, BiI$_3$, UO$_2$, UO$_3$, AgGaS$_2$, PbMnTe, BaTiO$_3$, SrTiO$_3$, LiNbO$_3$, La$_2$CuO$_4$, La$_{0.7}$Ca$_{0.3}$MnO$_3$, CdZnTe, CdMnTe, CuInSe$_2$, copper indium gallium selenide (CIGS), HgCdTe, HgZnTe, HgZnSe, PbSnTe, Tl$_2$SnTe$_5$, Tl$_2$GeTe$_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful in the field of sensors and light emitting materials, such as light emitting diodes (LEDs) and solid state lasers. Impurities of semiconductor materials are atoms, elements, ions and/or molecules other than the semiconductor material(s) themselves or any dopants provided to the semiconductor material. Impurities are undesirable materials present in semiconductor materials which may negatively impact the electrical properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

"Semiconductor element", "semiconductor structure" and "semiconductor circuit element" are used synonymously in the present description and broadly refer to any semiconductor material, composition, structure, device or device component, and expressly includes high quality, single crystalline and polycrystalline semiconductors, semiconductor materials fabricated via high temperature processing, doped semiconductor materials, inorganic semiconductors and composite semiconductor materials and structures having one or more additional semiconductor components and/or non-semiconductor components, such as dielectric layers or materials and/or conducting layers or materials. In some embodiments, for example, semiconductor element refers to a semiconductor-containing device or component thereof, such as LEDs, lasers, solar cells, semiconductor junctions, p-n junctions, photovoltaics, photodiodes, diodes, transistors, integrated circuits, logic circuits, sensors, heaters, temperature sensors, thermistors and resistive heating elements. Semiconductor elements expressly include structures having an average thickness selected over the range of 250 nm to 100 µm, one or more lateral dimensions selected over the range of 250 nm to 100000 µm, and any combinations of these. Optionally semiconductor elements are provided in physical contact with other dielectric or insulating materials and structures. Optionally, semiconductor elements are provided in physical contact or electrical communication with other metallic, doped or conducting materials and structures. Optionally, semiconductor structures are provided in physical contact or electrical communication with other semiconductor devices, including, but not limited to LEDs, lasers, transistors, integrated circuits, logic circuits, photodiodes, multiplexer circuitry and amplifier circuitry. Optionally, a plurality of semiconductor structures are provided in array configurations, including arrays with a fixed element pitch or a variable element pitch. Semiconductor structures may optionally be provided in a plurality of individually encapsulated stacked layers, including stacked layers of array structures. Semiconductor elements utilized in the devices and methods described herein include high purity semiconductor elements having oxygen impurities less than about 5 to 25 parts per million atoms, carbon impurities less than about 1 to 5 parts per million atoms, and heavy metal impurities less than or equal to about 1 part per million atoms (ppma), preferably less than or equal to about 100 parts per billion atoms (ppba) for some applications, and more preferably less than or equal to about 1 part per billion atoms (ppba) for some applications. Semiconductor elements having low levels of heavy metal impurities (e.g. less than about 1 parts per million atoms) are beneficial for applications and devices requiring good electronic performance, as the presence of heavy metals in semiconductor materials can severely degrade their electrical properties.

In certain embodiments, the term "orientation" refers to a specific plane of a crystal structure, for example a semiconductor crystal. In certain embodiments, the term "direction" refers to a specific axis, or equivalent axes, of a crystal structure. In embodiments, use of the terms orientation and direction with a specific numeric indicator is intended to be consistent with use in the fields of crystallography and microfabrication.

"Quantum well" refers to an active layer of a light emitting diode device. In one embodiment, a quantum well is a layer of an LED device having a relatively narrow bandgap, surrounded on two sides by layers having a relatively wider bandgap. A "quantum well barrier layer" in the context of a subcomponent of a light emitting diode refers to a layer of a light emitting diode device which is positioned adjacent to a quantum well layer and has a larger bandgap than the quantum well material. In one embodiment, a quantum well layer is sandwiched between two quantum well barrier layers. In another embodiment, multiple quantum well layers are sandwiched between multiple quantum well barrier layers.

"Good electronic performance" and "high performance" are used synonymously in the present description and refer to devices and device components have electronic characteristics, such as field effect mobilities, threshold voltages and on—off ratios, providing a desired functionality, such as electronic signal switching and/or amplification. Exemplary printable elements exhibiting good electronic performance may have intrinsic field effect mobilities greater than or equal 100 cm$^2$ V$^{-1}$ s$^{-1}$, and for some applications, greater than or equal to about 300 cm$^2$ V$^{-1}$ s$^{-1}$. Exemplary transistors exhibiting good electronic performance may have device field effect mobilities great than or equal to about 100 cm$^2$ V$^{-1}$ s$^{-1}$, for some applications, greater than or equal to about 300 cm$^2$ V$^{-1}$ s$^{-1}$, and for other applications, greater than or equal to about 800 cm$^2$ V$^{-1}$ s$^{-1}$. Exemplary transistors of exhibiting good electronic performance may have threshold voltages less than about 5 volts and/or on—off ratios greater than about $1 \times 10^4$.

"Plastic" refers to any synthetic or naturally occurring material or combination of materials that can be molded or shaped, generally when heated, and hardened into a desired shape. Useful plastics include, but are not limited to, polymers, resins and cellulose derivatives. In the present description, the term plastic is intended to include composite plastic materials comprising one or more plastics with one or more additives, such as structural enhancers, fillers, fibers, plasticizers, stabilizers or additives which may provide desired chemical or physical properties.

"Prepolymer" refers to a material which is a polymer precursor and/or a material which, when cured, is a polymer. A "liquid prepolymer" refers to a prepolymer which exhibits one or more properties of a liquid, for example flow properties. Specific prepolymers include, but are not limited to, photocurable polymers, thermally curable polymers and photocurable polyurethanes.

"Curing" refers to a process by which a material is transformed such that the transformed material exhibits one or more properties different from the original, non-transformed material. In some embodiments, a curing process allows a material to become solid or rigid. In an embodiment, curing transforms a prepolymer material into a polymer material. Useful curing processes include, but are not limited to, exposure to electromagnetic radiation (photocuring processes), for example exposure to electromagnetic radiation of a specific wavelength or wavelength range (e.g., ultraviolet or infrared electromagnetic radiation); thermal curing processes, for example heating to a specific temperature or within a specific temperature range (e.g., 150° C. or between 125 and 175° C.); temporal curing processes, for example waiting for a specified time or time duration (e.g., 5 minutes or between 10 and 20 hours); drying processes, for example removal of all or a percentage of water or other solvent molecules; and any combination of these. For example, one embodiment for curing a silver epoxy comprises heating the silver epoxy to 150° C. for a duration of 5 minutes.

"Polymer" refers to a molecule comprising a plurality of repeating chemical groups, typically referred to as monomers. Polymers are often characterized by high molecular masses. Polymers are typically composed of repeating structural units connected by covalent chemical bonds or the polymerization product of one or more monomers. The term polymer includes homopolymers, or polymers consisting essentially of a single repeating monomer subunit. The term polymer also includes copolymers, or polymers consisting essentially of two or more monomer subunits, such as random, block, alternating, segmented, graft, tapered and other copolymers. Useful polymers include organic polymers and inorganic polymers, both of which may be in amorphous, semi-amorphous, crystalline or partially crystalline states. Polymers may comprise monomers having the same chemical composition or may comprise a plurality of monomers having different chemical compositions, such as a copolymer. Cross linked polymers having linked monomer chains are also useful for some embodiments. Useful polymers include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyimide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulfone based resins, vinyl-based resins, rubber (including natural rubber, styrene-butadiene, polybutadiene, neoprene, ethylene-propylene, butyl, nitrile, silicones), acrylic, polystyrene, polyvinyl chloride, polyolefin or any combinations of these.

"Elastomer" refers to a polymeric material which can be stretched or deformed and return to its original shape without substantial permanent deformation. Elastomers commonly undergo substantially elastic deformations. Useful elastomers may comprise polymers, copolymers, composite materials or mixtures of polymers and copolymers. An elastomeric layer refers to a layer comprising at least one elastomer. Elastomeric layers may also include dopants and other non-elastomeric materials. Useful elastomer embodiments include, but are not limited to, thermoplastic elastomers, styrenic materials, olefenic materials, polyolefin, polyurethane thermoplastic elastomers, polyamides, synthetic rubbers, PDMS, polybutadiene, polyisobutylene, poly (styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefenic materials, polyolefin, polyurethane thermoplastic elastomers, polyam ides, synthetic rubbers, polyisobutylene, poly(styrene-butadiene-styrene), polyurethanes, polychloroprene and silicones. In an embodiment, a flexible polymer is a flexible elastomer.

"Transfer device" or "transfer substrate" refers to a substrate, device or device component capable of and/or configured for receiving and/or relocating an element or array of elements, such as printable elements. Useful transfer devices include conformal transfer devices, such as devices having one or more contact surfaces capable of establishing conformal contact with elements undergoing transfer. An elastomeric stamp and/or transfer device is useful with a variety of the methods and devices described herein. Useful elastomeric transfer devices include, but are not limited to, elastomeric stamps, composite elastomeric stamps, an elastomeric layer, a plurality of elastomeric layers and an elastomeric layer coupled to a substrate such as a glass, ceramic, metal or polymer substrate.

"Elastomeric stamp" or "elastomeric transfer device" are used interchangeably and refer to an elastomeric material having a surface that can receive as well as transfer a feature. Exemplary elastomeric transfer devices include stamps, molds and masks. The transfer device affects and/or facilitates feature transfer from a donor material to a receiver material. Stamps and transfer device may be used for assembling components via transfer printing, such as dry contact transfer printing.

"Target substrate" is used broadly to refer to the desired final substrate that will support the transferred structure. In an embodiment, the target substrate is a device substrate. In an embodiment, the target substrate is a device component or element that is itself supported by a substrate.

"Large area" refers to an area, such as the area of a receiving surface of a substrate used for device fabrication, greater than or equal to about 36 square inches.

"Pre-metalized" refers to a structure which includes metallic layers, components or features.

"Pre-patterned" refers to a structure which includes one or more devices, components or relief features.

"Optical communication" refers to a configuration of two or more elements wherein one or more beams of electromagnetic radiation are capable of propagating from one element to the other element. Elements in optical communication may be in direct optical communication or indirect optical communication. "Direct optical communication" refers to a configuration of two or more elements wherein one or more beams of electromagnetic radiation propagate directly from a first device element to another without use of optical components for steering and/or combining the beams. "Indirect optical communication" refers to a configuration of two or more elements wherein one or more beams of electromagnetic radiation propagate between two elements via one or more device components including, but not limited to, wave guides, fiber optic elements, reflectors, filters, prisms, lenses, gratings and any combination of these device components.

"Electrical contact" and "electrical communication" refers to the arrangement of one or more objects such that an electric current efficiently flows from one object to another. For example, in some embodiments, two objects having an electrical resistance between them less than 100Ω are considered in electrical communication with one another. An electrical contact can also refer to a component of a device or object used for establishing electrical communication with external devices or circuits, for example an electrical interconnection. "Electrical contact" also refers to the ability of two or more materials and/or structures that are capable of transferring charge between them, such as in the form of the transfer of electrons or ions. "Electrical communication" also refers to a configuration of two or more components such that an electronic signal or charge carrier can be directly or indirectly transferred from one component to another. As used herein, electrical communication includes one way and two way electrical communication. In some embodiments, components in electrical communication are in direct electrical communication wherein an electronic signal or charge carrier is directly transferred from one component to another. In some embodiments, components in electrical communication are in indirect electrical communication wherein an electronic signal or charge carrier is indirectly transferred from one component to another via one or more intermediate structures, such as circuit elements, separating the components.

"Electrical resistivity" refers to a property of a material characteristic of the resistance to flow of electrons through the material. In certain embodiments, the resistivity of a material ($\rho$) is related to the resistance (R) of a length of material (L) having a specific cross sectional area (A), e.g., $\rho = R \times A/L$.

"Electrical interconnection" and "electrical interconnect" refers to a component of an electrical device used for providing electrical communication between two or more device components. In some embodiments, an electrical interconnect is used to provide electrical communication between two device components spatially separated from one another, for example spatially separated by a distance greater than 50 nm, for some applications greater than 100 nm, for other applications greater than 1 µm, and for yet other applications greater than 50 µm. "Electrode contact" refers to a component of an electronic device or device component to which an electrical interconnect attaches or provides electrical communication to or from.

"Embed" refers to a process by which one object or device is buried, conformally surrounded or otherwise placed or positioned within or below the surface another object, layer or material.

"Encapsulate" refers to the orientation of one structure such that it is entirely surrounded by one or more other structures. "Partially encapsulated" refers to the orientation of one structure such that it is partially surrounded by one or more other structures. "Completely encapsulated" refers to the orientation of one structure such that it is completely surrounded by one or more other structures. Some embodiments contemplate devices having partially or completely encapsulated electronic devices, device components and/or inorganic semiconductor components and/or electrodes.

"Replicate" refers to a process by which one or more relief features are transferred and/or recreated during casting, molding, embedding, or embossing processes. Replicated features generally resemble the features they originate from except that the replicated features represent the negative of the original features; that is where the original features are raised features, the replicated features are recessed features and where the original features are recessed features, the replicated features are raised features. "Replica molding" and "nano imprint lithography" refer to specific replicating methods known in the art of microfabrication.

"Relief feature" refers to portions of an object or layer exhibiting differences in elevation and slope between the higher and lower parts of the surface of a given area or portion of the object or layer. "Raised features" refer to relief features which extend above the surface or average surface level of an object or layer or relief features which have elevations higher than other portions of the surface of an object or layer. "Recessed feature" refer to relief features which extend below the surface or average surface level of an object or layer or relief features which have elevations lower than other portions of the surface of an object or layer.

"Unitary structure" refers to a structure having one or more components within a single continuous or monolithic body, and includes structures having a uniform or non-uniform composition.

"Conformal contact" refers to contact established between surfaces, coated surfaces, and/or surfaces having materials deposited thereon which may be useful for transferring, assembling, organizing and integrating structures (such as printable elements) on a substrate surface. In one aspect, conformal contact involves a macroscopic adaptation of one or more contact surfaces of a conformal transfer device to the overall shape of a substrate surface or the surface of an object such as a printable element. In another aspect, conformal contact involves a microscopic adaptation of one or more contact surfaces of a conformal transfer device to a substrate surface leading to an intimate contact without voids. The term conformal contact is intended to be consistent with use of this term in the art of soft lithography. Conformal contact may be established between one or more bare contact surfaces of a conformal transfer device and a substrate surface. Alternatively, conformal contact may be established between one or more coated contact surfaces, for example contact surfaces having a transfer material, printable element, device component, and/or device deposited thereon, of a conformal transfer device and a substrate surface. Alternatively, conformal contact may be established between one or more bare or coated contact surfaces of a conformal transfer device and a substrate surface coated with a material such as a transfer material, solid photoresist layer, prepolymer layer, liquid, thin film or fluid.

"Conformable" refers to a device, material or substrate which has a bending stiffness sufficiently low to allow the device, material or substrate to adopt any desired contour profile, for example a contour profile allowing for conformal contact with a surface having a pattern of relief features. In certain embodiments, a desired contour profile is that of a tissue in a biological environment, "Bind" and "bond" refers to the physical attachment of one object to another. Bind and bound can also refer the retention of one object on another. In one embodiment an object can bind to another by establishing a force between the objects. In some embodiments, objects are bound to one another through use of an adhesion layer. In one embodiment, an adhesion layer refers to a layer used for establishing a bonding force between two objects.

"Placement accuracy" refers to the ability of a transfer method or device to transfer a printable element, to a selected position, either relative to the position of other device components, such as electrodes, or relative to a selected region of a receiving surface. "Good placement accuracy" refers to methods and devices capable of transferring a printable element to a selected position relative to another device or device component or relative to a selected region of a receiving surface with spatial deviations from the absolutely correct position less than or equal to 50 µm, more preferably less than or equal to 20 µm for some applications and even more preferably less than or equal to 5 µm for some applications. Methods and devices described herein include those comprising at least one printable element transferred with good placement accuracy.

"Fidelity" refers to a measure of how well a selected pattern of elements, such as a pattern of printable elements, is transferred to a receiving surface of a substrate. Good fidelity refers to transfer of a selected pattern of elements wherein the relative positions and orientations of individual elements are preserved during transfer, for example wherein spatial deviations of individual elements from their positions in the selected pattern are less than or equal to 500 nm, more preferably less than or equal to 100 nm.

"Undercut" refers to a structural configuration wherein the bottom surfaces of an element, such as a printable element, bridge element and/or anchor element, are at least partially detached from or not fixed to another structure, such as a mother wafer or bulk material. Entirely undercut refers to a refers to a structural configuration wherein the bottom surfaces of an element, such as printable element, bridge element and/or anchor element, is completely detached from another structure, such as a mother wafer or bulk material. Undercut structures may be partially or entirely free standing structures. Undercut structures may be partially or fully supported by another structure, such as a mother wafer or bulk material, that they are detached from. Undercut structures may be attached, affixed and/or connected to another structure, such as a wafer or other bulk material, at surfaces other than the bottom surfaces.

"Anchor" refers to a structure useful for connecting or tethering one device or device component to another. "Anchoring" refers to a process resulting in the connection or tethering of one device or device component to another.

"Homogeneous anchoring" refers to an anchor that is an integral part of the functional layer. In general, methods of making transferable elements by homogenous anchoring systems is optionally by providing a wafer, depositing a sacrificial layer on at least a portion of a wafer surface, defining semiconductor elements by any means known in the art, and defining anchor regions. The anchor regions correspond to specific regions of the semiconductor element. The anchor regions can correspond to a geometrical configuration of a semiconductor layer, e.g., anchors defined by relatively large surface areas and are connected to transferable elements by bridge or tether elements. Such geometry provides a means for facilitating lift-off of specific non-anchored regions for either single-layer or multi-layer embodiments. Alternatively, anchors correspond to semiconductor regions that are attached or connected to the underlying wafer. Removing the sacrificial layer provides a means for removing or transferring semiconductor elements while the portion of semiconductor physically connected to the underlying wafer remains.

"Heterogeneous anchoring" refers to an anchor that is not an integral part of the functional layer, such as anchors that are made of a different material than the semiconductor layer or is made of the same material, but that is defined after the transferable semiconductor elements are placed in the system. One advantage of heterogeneous anchoring compared to homogeneous anchoring relates to better transfer defining strategies and further improvement to the effective useable wafer footprint. In the heterogeneous strategy embodiment, a wafer is provided, the wafer is coated with a sacrificial layer, semiconductor elements are defined, and heterogeneous anchor elements are deposited that anchor semiconductor regions. In an aspect, the anchor is a resist material, such as a photoresist or SiN (silicon nitride), or other material that has a degree of rigidity capable of anchoring and resisting a lift-off force that is not similarly resisted by non-anchored regions. The anchor may span from the topmost semiconductor layer through underlying layers to the underlying wafer substrate. Removal of sacrificial layer provides a means for removing unanchored regions while the anchored regions remain connected to the wafer, such as by contact transfer, for example. In another embodiment, for a multi-layer system, the anchor provides anchoring of a top layer to an underlying semiconductor layer. Alternatively, the anchoring system is for single-layer semiconductor layer systems.

"Carrier film" refers to a material that facilitates separation of layers. The carrier film may be a layer of material, such as a metal or metal-containing material positioned adjacent to a layer that is desired to be removed. The carrier film may be a composite of materials, including incorporated or attached to a polymeric material or photoresist material, wherein a lift-off force applied to the material provides release of the composite of materials from the underlying layer (such as a functional layer, for example).

A "NMS adjusting layer" refers to a layer whose primary function is adjusting the position of the NMS in the device. For example, the NMS adjusting layer may be an encapsulating layer or an add layer such as an elastomeric material.

In the context of this description, a "bent configuration" refers to a structure having a curved conformation resulting from the application of a force. Bent structures may have one or more folded regions, convex regions, concave regions, and any combinations thereof. Useful bent structures useful, for example, may be provided in a coiled conformation, a wrinkled conformation, a buckled conformation and/or a wavy (i.e., wave-shaped) configuration.

Bent structures, such as stretchable bent interconnects, may be bonded to a flexible substrate, such as a polymer and/or elastic substrate, in a conformation wherein the bent structure is under strain. In some embodiments, the bent structure, such as a bent ribbon structure, is under a strain equal to or less than about 30%, a strain equal to or less than about 10%, a strain equal to or less than about 5% and a strain equal to or less than about 1% in embodiments preferred for some applications. In some embodiments, the bent structure, such as a bent ribbon structure, is under a strain selected from the range of about 0.5% to about 30%, a strain selected from the range of about 0.5% to about 10%, a strain selected from the range of about 0.5% to about 5%. Alternatively, the stretchable bent interconnects may be bonded to a substrate that is a substrate of a device component, including a substrate that is itself not flexible. The substrate itself may be planar, substantially planar, curved, have sharp edges, or any combination thereof. Stretchable bent interconnects are available for transferring to any one or more of these complex substrate surface shapes.

"Thermal contact" or "thermal communication" refers to the ability of two materials that are capable of substantial heat transfer from the higher temperature material to the lower temperature material, such as by conduction. Bent structures resting on a substrate are of particular use in providing regions that are in thermal contact (e.g., bond regions) with the substrate and other regions that are not in thermal contact (e.g., regions that are insulated and/or physically separated from the substrate).

"Fluid communication" refers to the configuration of two or more components such that a fluid (e.g., a gas or a liquid) is capable of transport, flowing and/or diffusing from one component to another component. Elements may be in fluid communication via one or more additional elements such as tubes, containment structures, channels, valves, pumps or any combinations of these. In some embodiments, components in fluid communication are in direct fluid communication wherein fluid is capable of transport directly from one component to another. In some embodiments, components in fluid communication are in indirect fluid communication wherein fluid is capable of transport indirectly from one component to another via one or more intermediate structures separating the components.

"Ultrathin" refers to devices of thin geometries that exhibit extreme levels of bendability. In an embodiment, ultrathin refers to circuits having a thickness less than 1 µm, less than 600 nm or less than 500 nm. In an embodiment, a multilayer device that is ultrathin has a thickness less than 200 µm, less than 50 µm, or less than 10 µm.

"Thin layer" refers to a material that at least partially covers an underlying substrate, wherein the thickness is less than or equal to 300 µm, less than or equal to 200 µm, or less than or equal to 50 µm. Alternatively, the layer is described in terms of a functional parameter, such as a thickness that is sufficient to isolate or substantially reduce the strain on the electronic device, and more particularly a functional layer in the electronic device that is sensitive to strain.

"Isolate" refers to the presence of an elastomer layer that substantially reduces the strain or stress exerted on a functional layer when the device undergoes a stretching of folding deformation. In an embodiment, strain is said to be "substantially" reduced if the strain is at least a factor of 20, at least a factor of 50 or at least a factor of 100 times reduced compared to the strain in the same system without the elastomer layer.

"Dielectric" and "dielectric material" are used synonymously in the present description and refer to a substance that is highly resistant to flow of electric current. Useful dielectric materials include, but are not limited to, $SiO_2$, $Ta_2O_5$, $TiO_2$, $ZrO_2$, $Y_{203}$, $Si_3N_4$, STO, BST, PLZT, PMN, and PZT. In some embodiments, dielectric materials include non-conducting or insulating materials. In an embodiment, an inorganic dielectric comprises a dielectric material substantially free of carbon "Device field effect mobility" refers to the field effect mobility of an electronic device, such as a transistor, as computed using output current data corresponding to the electronic device. In an embodiment, an inorganic dielectric comprises a dielectric material substantially free of carbon. Specific examples of inorganic dielectric materials include, but are not limited to, silicon nitride and silicon dioxide.

"Fill factor" refers to the percentage of the area between two elements, such as between two electrodes, that is occupied by a material, element and/or device component. In one embodiment, two electrodes are provided in electrical contact with one or more printable semiconductor elements that provide a fill factor between first and second electrodes greater than or equal to 20%, preferably greater than or equal to 50% for some applications and more preferably greater than or equal to 80% for some applications. In some embodiments, high fill factors are provided by stacking functional layers above/below one another.

"Multilayer stacked geometry" refers to a device comprising a plurality of functional layers in a stacked configuration. In some embodiments, stacked multilayers are provided in an offset configuration such that one or more device components in a first functional layer are not provided directly adjacent to one or more device components in a second functional layer, such as a first functional layer positioned adjacent to, above or below a second functional layer.

"Collecting" and "concentrating", as applied to optics and optical components, refers to the characteristic of optical components and device components that collect light from a first area, in some cases a large area, and optionally direct that light to another area, in some cases a relatively smaller area. In the context of some embodiments, collecting and concentrating optical components and/or optical components are useful for light detection or power harvesting by printed solar cells or photodiodes.

"Conductive material" refers to a substance or compound possessing an electrical resistivity which is typical of or equivalent to that of a metal, for example copper, silver or aluminum. In embodiments, the electrical resistivity of a conductive material is selected over the range of $1\times10^{-10}$ to $1\times10^{-2}$ Ω·cm. In the present description, use of the term conductive material is intended to be consistent with use of this term in the art of electronic devices and electric circuits. In embodiments, conductive materials are useful as electrical interconnections and/or for providing electrical communication between two devices. A "conductive paste" refers to a conductive material comprising a mixture which is generally soft and malleable. In some embodiments, cured conductive pastes lose their soft and malleable nature and generally exhibit properties of a solid or a monolithic body. Exemplary conductive pastes comprise metal micro- and/or nano-particles. Silver epoxy refers to a conductive paste comprising micro- and/or nano particles including metallic silver (Ag) and which, when cured, exhibits a low electrical resistivity, for example an electrical resistivity lower than $1\times10^{-5}$ Ω·cm or selected over the range of $1\times10^{-10}$ to $1\times10^{-5}$ Ω·cm.

"Fill" and "filling" refer to a process of depositing a material into a recessed feature. In one embodiment, a recessed region is filled by scraping material across and into the recessed feature. A filling tool generally refers to a device for moving material into a recessed feature. In an embodiment, a filling tool refers to a device for scraping material across and/or into a recessed region. In a specific embodiment, a filling tool comprises a layer or solid body of PDMS. For certain embodiments, a filling process is conceptually similar to a screen printing process where a material is scraped across a recessed feature by a tool or device having dimensions larger than the recessed feature, thereby at least partially filling the recessed feature with the material.

"Align" refers to a process by which two objects are arranged with respect to one another. "Aligned off center" refers to a process by which the centers of two objects or two areas are arranged such that the two centers are not coincident with respect to one or more spatial dimensions. For certain embodiments, the term aligned off center refers to alignment of the center of two objects such that the centers of the objects are spatially separated by a distance greater than 50 nm, for some applications greater than 100 nm, for other applications greater than 1 µm, and for yet other applications greater than 50 µm.

"Neutral mechanical surface," "NMS," "neutral mechanical plane," and "NMP" interchangeably refer to a position within a device or component under strain that experiences an absence of strain. In some embodiments a NMS or NMP is a plane positioned between two regions or layers of a device or component under strain, such as a plane between regions under compressive strain and regions under expansive strain. The NMP is less susceptible to bending stress than other planes of the device that lie at more extreme positions along a vertical axis of the device and/or within more bendable layers of the device. Thus, the position of the NMP is determined by both the thickness of the device and the materials forming the layer(s) of the device.

"Coincident" refers to refers to the relative position of two or more objects, planes or surfaces, for example a surface such as a NMS or NMP that is positioned within or is adjacent to a layer, such as a functional layer, substrate layer, or other layer. In an embodiment, a NMS or NMP is positioned to correspond to the most strain-sensitive layer or material within the layer.

"Proximate" refers to the relative position of two or more objects, planes or surfaces. For example, a NMS or NMP that is proximate to or closely follows the position of a layer, such as a functional layer, substrate layer, or other layer while still providing desired foldability or bendability without an adverse impact on the strain-sensitive material physical properties. "Strain-sensitive" refers to a material that fractures or is otherwise impaired in response to a relatively low level of strain. In general, a layer having a high strain sensitivity, and consequently being prone to being the first layer to fracture, is located in the functional layer, such as a functional layer containing a relatively brittle semiconductor or other strain-sensitive device element. A NMS or NMP that is proximate to a layer need not be constrained within that layer, but may be positioned proximate or sufficiently near to provide a functional benefit of reducing the strain on the strain-sensitive device element when the device is folded.

"Electronic device" is used broadly herein to refer to devices such as integrated circuits, imagers or other optoelectronic devices. Electronic device may also refer to a component of an electronic device such as passive or active components such as a semiconductor, interconnect, contact pad, transistors, diodes, LEDs, circuits, etc. Devices disclosed herein may relate to the following fields: collecting optics, diffusing optics, displays, pick and place assembly, vertical cavity surface-emitting lasers (VCSELS) and arrays thereof, LEDs and arrays thereof, transparent electronics, photovoltaic arrays, solar cells and arrays thereof, flexible electronics, micromanipulation, plastic electronics, displays, pick and place assembly, transfer printing, LEDs, transparent electronics, stretchable electronics, and flexible electronics.

A "component" is used broadly to refer to a material or individual component used in a device. An "interconnect" is one example of a component and refers to an electrically conducting material capable of establishing an electrical connection with a component or between components. In particular, an interconnect may establish electrical contact between components that are separate and/or can move with respect to each other. Depending on the desired device specifications, operation, and application, an interconnect is made from a suitable material. For applications where a high conductivity is required, typical interconnect metals may be used, including but not limited to copper, silver, gold, aluminum and the like, and alloys. Suitable conductive materials further include semiconductors, such as silicon and GaAs and other conducting materials such as indium tin oxide.

Other components include, but are not limited to, thin film transistors (TFTs), transistors, electrodes, integrated circuits, circuit elements, control elements, microprocessors, transducers, islands, bridges and combinations thereof. Components may be connected to one or more contact pads as known in the art, such as by metal evaporation, wire bonding, and application of solids or conductive pastes, for example.

An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component. Accordingly, a stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than about 1%, 10% or about 30% or up to about 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes.

A "device component" is used to broadly refer to an individual component within an electrical, optical, mechanical or thermal device. Components include, but are not limited to, a photodiode, LED, TFT, electrode, semiconductor, other light-collecting/detecting components, transistor, integrated circuit, contact pad capable of receiving a device component, thin film devices, circuit elements, control elements, microprocessors, transducers and combinations thereof. A device component can be connected to one or more contact pads as known in the art, such as metal evaporation, wire bonding, application of solids or conductive pastes, for example. Electrical device generally refers to a device incorporating a plurality of device components, and includes large area electronics, printed wire boards, integrated circuits, device components arrays, biological and/or chemical sensors, physical sensors (e.g., temperature, light, radiation, etc.), solar cell or photovoltaic arrays, display arrays, optical collectors, systems and displays.

"Sensing element" and "sensor" are used synonymously and refers to a device component useful as a sensor and/or useful for detecting the presence, absence, amount, magnitude or intensity of a physical property, object, radiation and/or chemical. Sensors in some embodiments function to transduce a biological signal into an electrical signal, optical signal, wireless signal, acoustic signal, etc. Useful sensing elements include, but are not limited to electrode elements, chemical or biological sensor elements, pH sensors, optical sensors, photodiodes, temperature sensors, capacitive sensors strain sensors, acceleration sensors, movement sensors, displacement sensors, pressure sensors, acoustic sensors or combinations of these.

"Sensing" refers to detecting the presence, absence, amount, magnitude or intensity of a physical and/or chemical property. Useful electronic device components for sensing include, but are not limited to electrode elements, chemical or biological sensor elements, pH sensors, temperature sensors and capacitive sensors.

"Actuating element" and "actuator" are used synonymously and refers to a device component useful for interacting with, stimulating, controlling, or otherwise affecting an external structure, material or fluid, for example a biological tissue. Useful actuating elements include, but are not limited to, electrode elements, electromagnetic radiation emitting elements, light emitting diodes, lasers and heating elements. Actuating elements include electrodes for providing a voltage or current to a tissue. Actuating elements include sources of electromagnetic radiation for providing electromagnetic radiation to a tissue. Actuating elements include ablation sources for ablating tissue. Actuating elements include thermal sources for heating tissue. Actuating elements include displacement sources for displacing or otherwise moving a tissue. In some embodiments, actuating elements are used for interacting with, modifying a property of or otherwise affecting a device component, for example a barrier layer.

"Actuating" refers to stimulating, controlling, or otherwise affecting an external structure, material or fluid, for example a biological tissue. Useful electronic device components for actuating include, but are not limited to, electrode elements, electromagnetic radiation emitting elements, light emitting diodes, lasers, and heating elements.

"Visualizing" refers to a method of observing or otherwise detecting electromagnetic radiation, for example with an eye or a photodetector.

"Island" or "device island" refers to a relatively rigid device element or component of an electronic device comprising multiple semiconductor elements or active semiconductor structures. "Bridge" or "bridge structure" refers to stretchable or flexible structures interconnecting two or more device islands or one device island to another device component. Specific bridge structures include flexible semiconductor interconnects.

"Barrier layer" refers to a device component spatially separating two or more other device components or spatially separating a device component from a structure, material or fluid external to the device. In one embodiment, a barrier layer encapsulates one or more device components. In embodiments, a barrier layer is an encapsulation layer. In embodiments, a barrier layer separates one or more device components from an aqueous solution, a biological tissue or both. In some embodiments, a barrier layer is a passive device component. In some embodiments, a barrier layer is a functional, but non-active, device component. In a specific embodiment, a barrier layer is a moisture barrier. As used herein, the terms "moisture barrier" and "barrier layer preventing water from contacting" refers to a barrier layer which provides protection to other device components from water or other solvents. In one embodiment, a moisture barrier provides protection to an external structure, material or fluid, for example, by preventing leakage current from escaping an encapsulated device component and reaching the external structure, material or fluid. In a specific embodiment, a barrier layer is a thermal barrier. As used herein, the term "thermal barrier" refers to a barrier layer which acts as a thermal insulator, preventing, reducing or otherwise limiting the transfer of heat from one device component to another or from a device component to an external structure, fluid or material. Useful thermal barriers include those comprising materials having a thermal conductivity of 0.3 W/m·K or less, such as selected over the range of 0.001 to 0.3 W/m·K. In some embodiments, a thermal barrier comprises active cooling components, such as components known in the art of thermal management. Thermal barriers also include those barriers comprising thermal management structures, such as structures useful for transporting heat away from a portion of a device or tissue; in these and other embodiments, a thermal barrier comprises thermally conductive material, for example material having a high thermal conductivity, such as a thermal conductivity characteristic of a metal.

A barrier layer, and optionally a sacrificial layer on a substrate, may be etched to produce a "mesh structure", where at least a portion of the barrier layer(s), and optionally the sacrificial layer on a substrate, is removed. For example a portion of the barrier layer(s) disposed approximately 10 nm or more from an inorganic semiconductor component or additional component is removed. Removal of at least a portion of the barrier layer(s), and optionally the sacrificial layer on the substrate, may produce (i) one or more holes within the barrier layer(s) and/or (ii) electrical components, which are physically joined by a barrier layer(s) at a proximal end and physically separated at a distal end. In one embodiment, a mesh structure may be disposed upon a contiguous bioresorbable substrate, which provides structural support for the device during deployment into a biological environment.

"Contiguous" refers to materials or layers that are touching or connected throughout in an unbroken sequence. In one embodiment, a contiguous layer of a biomedical device has not been etched to remove a substantial portion (e.g., 10% or more) of the originally provided material or layer.

"Biocompatible" refers to a material that does not elicit an immunological rejection or detrimental effect when it is disposed within an in-vivo biological environment. For example, a biological marker indicative of an immune response changes less than 10%, or less than 20%, or less than 25%, or less than 40%, or less than 50% from a baseline value when a biocompatible material is implanted into a human or animal.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal.

"Bioresorbable" refers to a material that is susceptible to being chemically broken down into lower molecular weight chemical moieties by reagents that are naturally present in a biological environment. In an in-vivo application, the chemical moieties may be assimilated into human or animal tissue. A bioresorbable material that is "substantially completely" resorbed is highly resorbed (e.g., 95% resorbed, or 98% resorbed, or 99% resorbed, or 99.9% resorbed, or 99.99% resorbed), but not completely (i.e., 100%) resorbed.

"Nanostructured surface" and "microstructured surface" refer to device surfaces having nanometer-sized and micrometer-sized relief features, respectively. Such structured surfaces are useful, for example, for contacting and penetrating a target tissue and improving adhesion between the implantable biomedical device and the target tissue. The relief features extend a length, x, from a substantially contiguous plane of the device surface. Quantitative descriptors of a structured contact surface include surface roughness parameters, such as $R_{max}$, $R_a$, and normalized roughness ($R_a/R_{max}$), all of which may be measured by atomic force microscopy (AFM). Rmax is the maximum height between a highest peak to a lowest valley. Ra is the center-line-mean roughness, which is the average of an absolute value of a deviation from a center line of a roughness curve to the roughness curve. The surface of a substrate or barrier layer is "substantially smooth", for the purposes of this disclosure, if the surface has an $R_a$ value of 100 nm or less. If the surface has an $R_a$ value greater than 100 nm, the surface is considered to be a "structured surface" for purposes of this disclosure. A structured surface may contain at least one feature selected from the group consisting of barbs, spikes, protrusions and any combination of these.

"Accommodate" and "accommodation" refer to the configuration of one surface or device to match the contours or relief features of another surface or device such that the two surfaces/devices are in intimate contact. In one embodiment, a surface which accommodates a device or device component is a microstructured or nanostructured surface having relief features which match the shape, contours and or dimensions of the device or device component.

"Leakage current" or "leakage" refers to electric current which flows from an electronic device along an unintended path. Under certain conditions, leakage of sufficient current from an electronic device can damage the device and/or components thereof. In certain circumstances, leakage current can also or alternatively damage the material into which it flows.

"Active circuit" and "active circuitry" refers to one or more device components configured for performing a specific function. Useful active circuits include, but are not limited to, amplifier circuits, multiplexing circuits, integrated circuits and current limiting circuits. Useful active circuit elements include, but are not limited to, transistor elements and diode elements.

"Permeability" refers to a property of a material such that one or more substances are able to pass through the material. "Selectively permeable" refers to a property of a material to allow certain substances to pass through the material while preventing other substances from being passed through. In one embodiment, a selectively permeable material allows one or more target chemicals, molecules and/or biomolecules to be passed through the material while preventing water, salt and other substances from being passed through the material. In an embodiment, the barrier layer of a device has spatially patterned permeable regions, impermeable regions or a combination of both permeable regions and impermeable regions.

The term "micro-scale" refers devices or device component having a maximum dimension (e.g., length, width, height, thickness, diameter, etc.) of 1000 µm. As used herein, the term micro-scale is intended to distinguish between objects having dimensions of cm to m and those having dimensions of nm to µm. Micro-scale also refers, in some embodiments, to structures that are made using techniques known in the art of microfabrication.

"Plasmonic crystal" refers to an ordered array of micro- or nano-scale elements which interact with electromagnetic radiation in an enhanced way due to the array structure. U.S. Pat. No. 7,705,280, hereby incorporated by reference, discloses useful plasmonic crystals and methods for making plasmonic crystals.

"Suture" refers to a biomedical device used in the field of medical surgery. In embodiments, a suture is used in a medical procedure to close an opening, wound or surgical incision in a tissue.

"Tensile strength" refers to an ability of a material to resist strain without undergoing fracture, damage or inelastic deformation.

"Young's modulus" refers to a mechanical property of a material, device or layer which refers to the ratio of stress to strain for a given substance. Young's modulus may be provided by the expression;

$$E = \frac{(\text{stress})}{(\text{strain})} = \left(\frac{L_0}{\Delta L} \times \frac{F}{A}\right)$$

where E is Young's modulus, $L_0$ is the equilibrium length, $\Delta L$ is the length change under the applied stress, F is the force applied and A is the area over which the force is applied. Young's modulus may also be expressed in terms of Lame constants via the equation:

$$E = \frac{\mu(3\lambda + 2\mu)}{\lambda + \mu}$$

where µ and λ are Lame constants. High Young's modulus (or "high modulus") and low Young's modulus (or "low modulus") are relative descriptors of the magnitude of Young's modulus in a given material, layer or device. In the present description, a High Young's modulus is larger than a low Young's modulus, about 10 times larger for some applications, more preferably about 100 times larger for other applications and even more preferably about 1000 times larger for yet other applications.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Described herein are flexible and stretchable semiconductor element arrays and methods utilizing flexible and stretchable semiconductor element arrays. Co-integration of flexible LED arrays with flexible plasmonic crystals is useful for construction of fluid monitors, permitting sensitive detection of fluid refractive index and composition. Co-integration of flexible LED arrays with flexible photodetector arrays is useful for construction of flexible proximity sensors. Application of stretchable LED arrays onto flexible threads as light emitting sutures provides novel means for performing radiation therapy on wounds. Radiation therapy is also achievable using biocompatible or bioinert encapsulation over stretchable LED arrays for implantation into biological tissues.

FIG. 1A provides a side plan view of a biomedical device 5 in a biological environment comprising a suture-mounted stretchable or flexible electronic circuit. The biomedical device comprises a suture 10 having an external surface 20 and an optional stretchable or flexible substrate 30 provided on at least a portion of the external surface of the suture 10. The suture may comprise any suitable material, such as a fiber or thread, among others, particularly materials having mechanical properties (e.g., tensile strength, Young's modulus, etc.) and chemical properties (e.g., biocompatibility, bioinertness, etc.) useful for a desired application such as connecting tissue, therapy and/or diagnosis. In some embodiments, the suture 10 is a bioresorbable material, such as silk, and/or substrate 30 is a bioresorbable material, such as silk.

The biomedical device also comprises a stretchable or flexible electronic circuit 40 comprising inorganic semiconductor elements 41 connected by stretchable or flexible conducting elements 45. In an embodiment, for example, stretchable or flexible electronic circuit 40 comprises an array of electronic devices (e.g., LED array, electrode array, transistors, multiplexer circuit, etc.), one or more sensors (e.g., optical sensors, chemical sensors, thermal sensors, etc.) and/or a drug delivery system. The flexible or stretchable electronic circuit is at least partially encapsulated in one or more barrier layers 50, which in some embodiments is a moisture barrier that prevents fluids (e.g., water, biological fluid, blood, ionic solution, etc.) from the biological environment from contacting at least a portion of the stretchable or flexible electronic circuit. In some embodiments, the one or more barrier layers 50 are a bioresorbable material, such as silk. In an embodiment, barrier layer 50 has an external surface in contact with the biological environment that is microstructured or nanostructured 55, for example, having one or more channels, vias, trenches, apertures, etc. In an embodiment, the composition, physical dimensions and mechanical properties of substrate 30, stretchable or flexible electronic circuit 40, barrier layer 50 are selected such that stretchable or flexible electronic circuit 40 is provided proximate to the neutral mechanical surface 51 of this combination of components (note: the neutral mechanical surface is shown schematically as dotted line 51).

Optionally, stretchable or flexible electronic circuit 40 further comprises one or more electrodes 46 positioned on the surface of barrier layer 50 for establishing electrical contact with the biological environment and/or tissue. Electrodes may be in electrical contact with inorganic semiconductor elements of the electronic device 40 and may be present on an external surface 52 of barrier layer 50, and optionally present in a micro- or nanostructured feature 55 on external surface 52, such as in a channel, pore or via. The biomedical device can optionally be connected to a controller 60 for controlling the stretchable or flexible electronic circuit. The controller 60 can be in wired or wireless, one-way or two-way communication with the stretchable or flexible electronic circuit using wired or wireless communication line 70. In an embodiment, the controller 60 controls functionality of the stretchable or flexible electronic circuit such as sensing, thermal control, electromagnetic radiation generation and detection, drug delivery, among others.

Figure 1B:
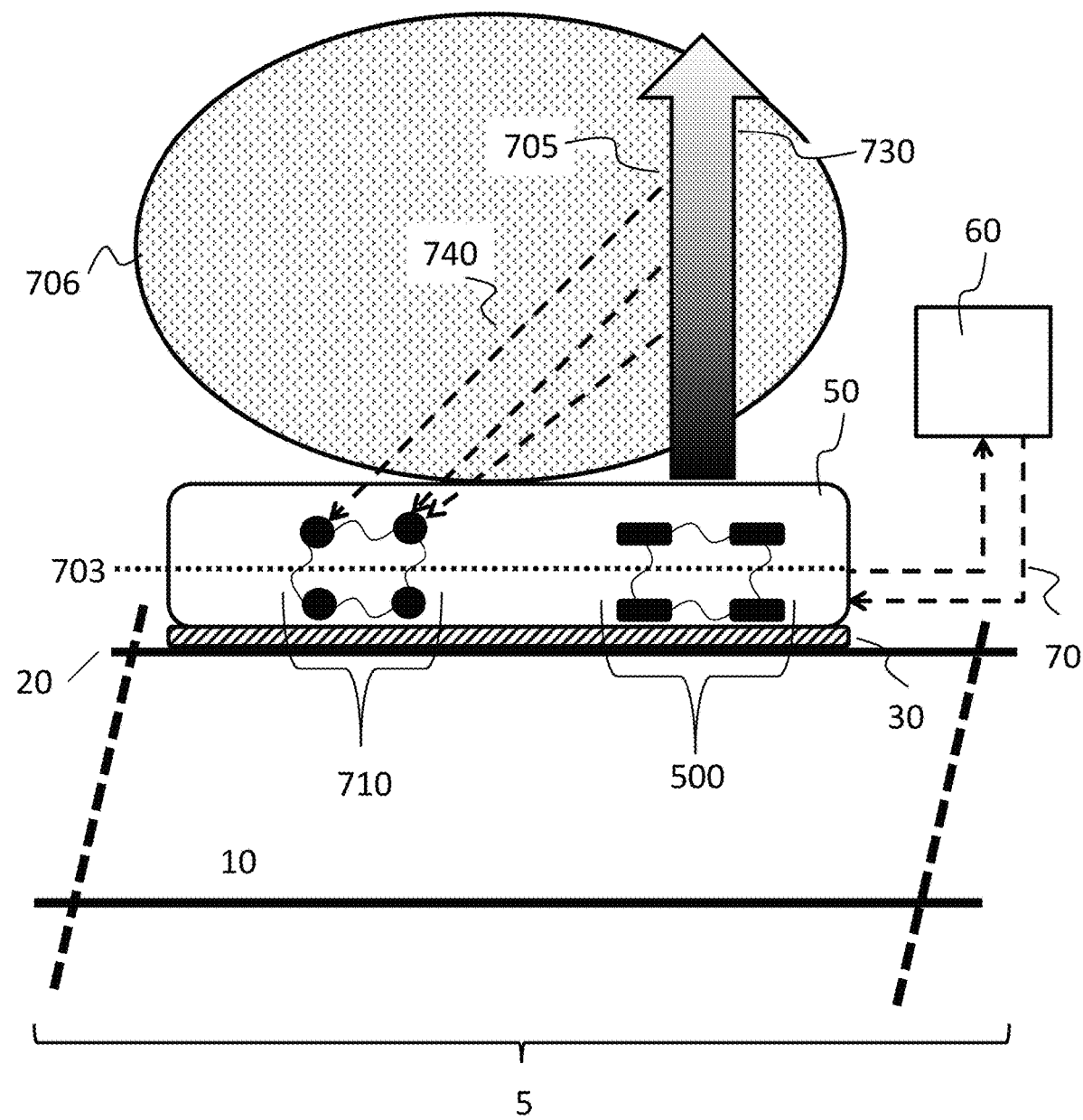
FIG. 1B provides a side plan view of a biomedical device comprising a suture-mounted proximity sensor device having a flexible or stretchable LED array and a flexible or stretchable PD array.

FIG. 1B provides a side plan view of a biomedical device 5 comprising an optical sensor device mounted on the outer surface 20 of a suture 10 having a flexible or stretchable LED array 500 and a flexible or stretchable photodetector (PD) array 710, both of which are encapsulated in one or more barrier layers 50, such as one or more low modulus (e.g., less than or equal to 1 MPa) elastomeric layers. In an embodiment, barrier layer 50 functions as a moisture barrier to prevent transport of water, biological fluids, ionic solutions, soapy water, etc. to the flexible or stretchable LED array 500 and the flexible or stretchable photodetector array 710 components of the optical sensor device 5. The flexible or stretchable LED array 500 is comprised of LED island structures (schematically illustrated in FIG. 1B as rounded rectangles) and electrically conducting bridge structures (schematically illustrated in FIG. 1B as wavy lines). The flexible or stretchable photodetector array 710 is comprised of photodiode island structures (schematically illustrated in FIG. 1B as circles) and electrically conducting bridge structures (schematically illustrated in FIG. 1B as wavy lines). The flexible or stretchable LED array 500 and flexible or stretchable photodetector array 710 are disposed on an optional flexible or stretchable substrate 30 which is disposed on the surface of suture 20.

The optical sensor device comprising a flexible or stretchable LED array 500 and a flexible or stretchable photodetector array 710 is optionally connected to a controller 60 by wired or wireless, one-way or two way communication line 70. In an optical sensing embodiment, the controller activates the LED array 500 to produce electromagnetic radiation 730 within a tissue environment 706. A portion of the electromagnetic radiation reflected, scattered or emitted 740 by the tissue environment 706 is incident on, and detected by, the photodetector array 710, for example to provide a measurement of the chemical or physical properties of the tissue and/or biological environment.

In an embodiment, optical sensor device 5 has a composition, physical dimensions and mechanical properties such that it can establish conformal contact with the nonplanar external surface of the suture 10. In an embodiment, for example, optical sensor device 5 is mounted on the curved external surface 20 of the suture 10. In an embodiment, the composition, physical dimensions and mechanical properties of a flexible or stretchable substrate 30, flexible or stretchable LED array 500, flexible or stretchable photodetector array 710, and barrier layers 50 are selected such that flexible or stretchable LED array 500 and a flexible or stretchable photodetector array 710 are provided proximate to the neutral mechanical surface 703 of this combination of components (note: the neutral mechanical surface is shown schematically as dotted line 703).

In operation, the LED array 500 produces electromagnetic radiation 730, optionally having a selected intensity distribution as a function of wavelength, which propagates away from optical sensor device 701. For some applications, the electromagnetic radiation 730 has wavelengths in the visible or near infrared regions of the electromagnetic spectrum. A portion of the electromagnetic radiation 730 from LED array 500 interacts with objects in the tissue environment 706, resulting in generation of reflected, scattered and/or emitted electromagnetic radiation 740 at various positions 705 within the tissue environment 706. At least a portion of the reflected, scattered and/or emitted electromagnetic radiation 740 is detected by photodetector array 710. By monitoring the intensity, wavelength distribution and/or radiant power of the reflected, scattered and/or emitted electromagnetic radiation 740, certain properties of the objects can be sensed and/or monitored, including composition and physical properties of the tissue in connection with a therapy and/or diagnostic procedure.

Figure 1C:
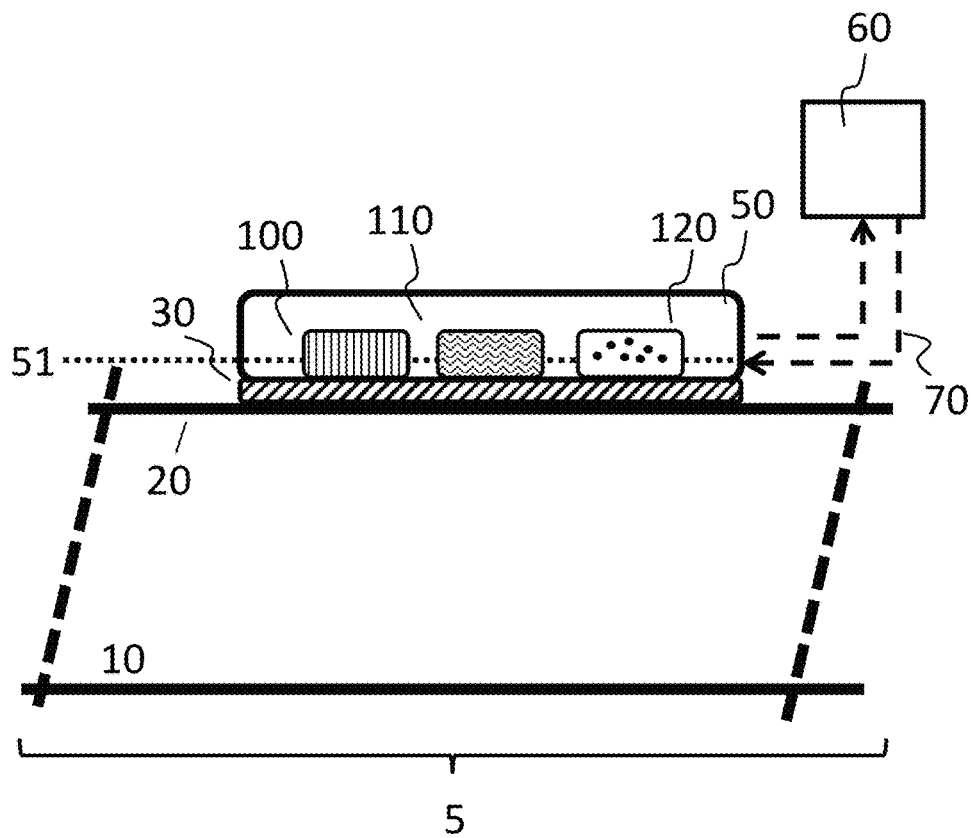
FIG. 1C provides a side plan view of a biomedical device comprising a suture-mounted drug delivery device having a temperature sensor, a heater, and a drug-containing region.
Figure 1D:
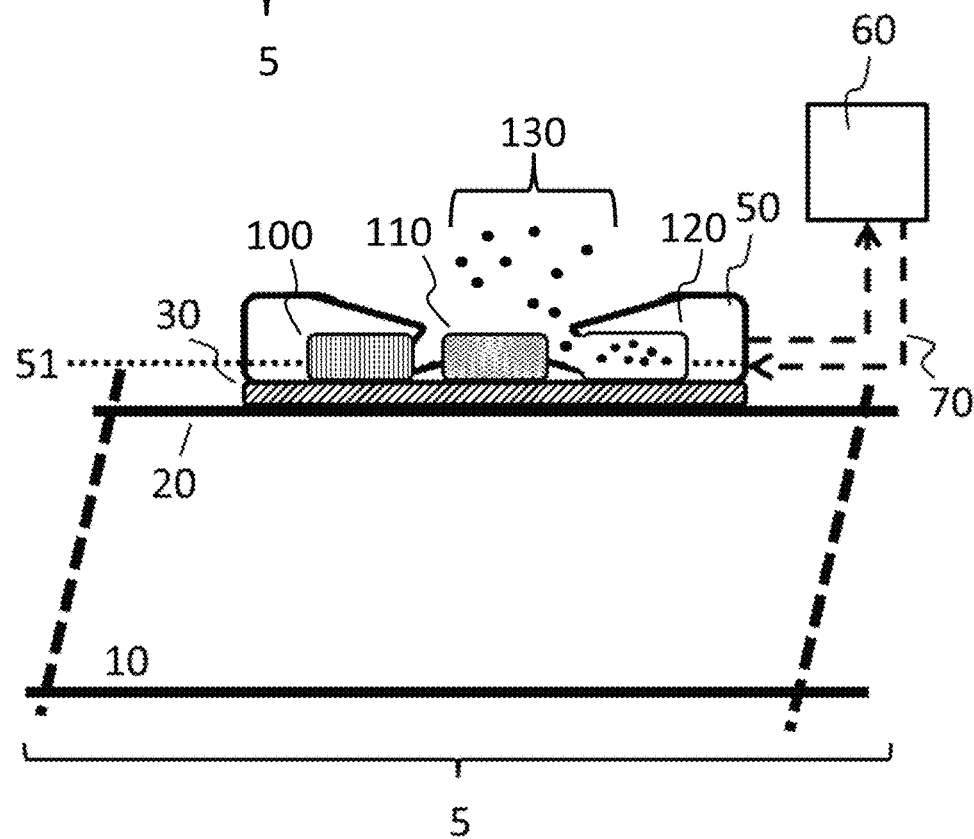
FIG. 1D provides a side plan view of a biomedical device comprising a suture-mounted drug delivery device having a temperature sensor, a heater, and a drug-containing region.

FIGS. 1C and 1D provides a side plan view of a biomedical device 5 comprising a drug delivery device on an optional flexible or stretchable substrate 30 mounted on the outer surface 20 of a suture 10 having an optional temperature sensor 100, a resistive heater 110, such as a semiconductor resistive heater, and a drug-containing region 120, all of which are encapsulated in one or more barrier layers 50, such as one or more low modulus (e.g., less than or equal to 1 MPa) elastomeric layers. In FIGS. 1C and 1D, the pharmaceutical composition initially contained in the drug-containing region 120 is represented schematically as black dots. In an embodiment, barrier layer 50 functions as a moisture barrier to prevent transport of water, biological fluids, ionic solutions, soapy water, etc. to the temperature sensor 100, resistive heater 110, and drug-containing region 120. The resistive heater 110 can be a coil structure, such as a thermistor, which is heated by passing current through the coil region, thereby creating heat. In an embodiment, the composition, physical dimensions and mechanical properties of substrate 30, temperature sensor 100, resistive heater 110, and drug-containing region 120 are selected such that temperature sensor 100, resistive heater 110, and drug-containing region 120 are provided proximate to the neutral mechanical surface 51 of this combination of components (note: the neutral mechanical surface is shown schematically as dotted line 51).

The suture-mounted drug delivery device comprising an optional temperature sensor 100, a resistive heater 110, and a drug-containing region 120 is optionally connected to a controller 60 by wired or wireless, one-way or two way communication line 70. In a drug delivery embodiment, the controller activates the resistive heater 110 to produce heat which melts, degrades or otherwise renders porous, at least a portion of the barrier layer 50. In an embodiment, the controller 60 monitors the output of the temperature sensor 100 and controls the semiconductor heater 110 in order to melt or otherwise degrade the barrier layer 50.

In an embodiment, suture-mounted drug delivery device 5 has a composition, physical dimensions and mechanical properties such that it can establish conformal contact with the nonplanar external surface of the suture 10. In an embodiment, for example, suture-mounted drug delivery device 5 is mounted on the curved external surface 20 of the suture 10. In an embodiment, the composition, physical dimensions and mechanical properties of a flexible or stretchable substrate 30, optional temperature sensor 100, resistive heater 110, drug-containing region 120, and barrier layer 50 are selected such that optional temperature sensor 100, resistive heater 110, and drug-containing region 120 are provided proximate to the neutral mechanical surface 51 of this combination of components (note: the neutral mechanical surface is shown schematically as dotted line 51).

The device before drug delivery is shown in FIG. 1C. As shown in FIG. 1D, in operation the resistive heater 110 produces heat which melts at least a portion of the barrier layer 30 which releases at least a portion of the pharmaceutical composition from the drug containing region 120, resulting in release of the pharmaceutical composition 130 to the tissue and/or biological environment. For some applications, the optional temperature sensor 100 is used to monitor the temperature change produced by the resistive heater 110 to ensure that sufficient heat is created to melt at least a portion of the barrier layer 50 and to ensure that the heat generated does not substantially damage any surrounding tissue or impair the function of the suture 10 or suture-mounted drug delivery device 5.

Figure 1E:
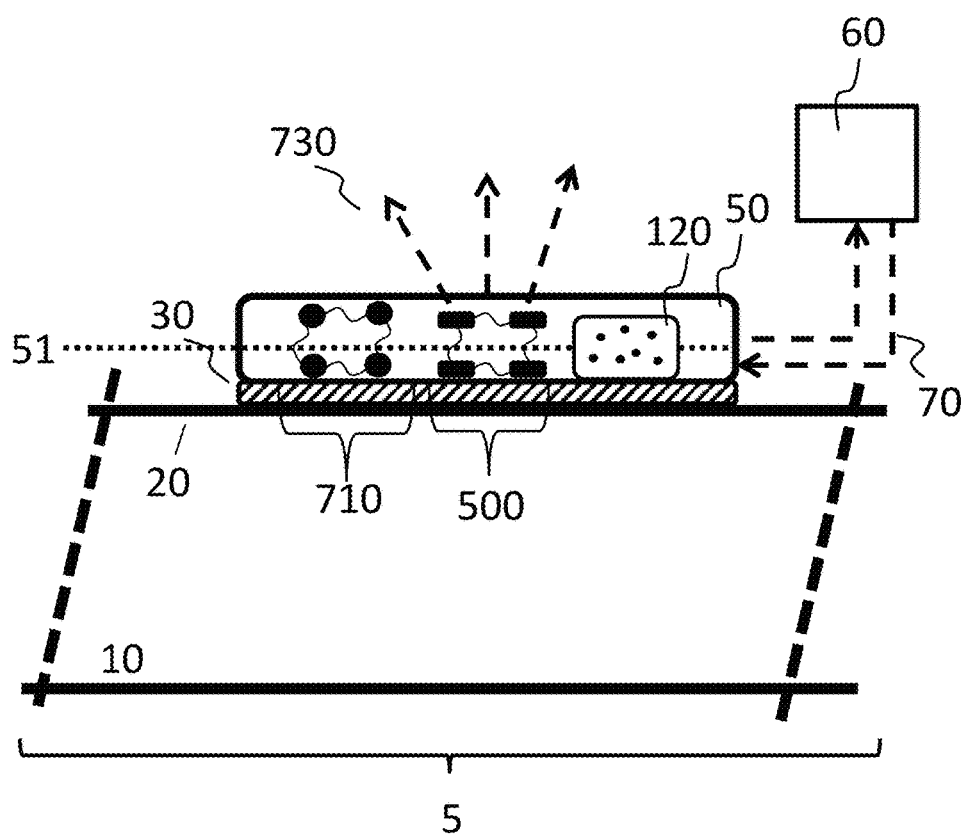
FIG. 1E provides a side plan view of a biomedical device comprising a suture-mounted drug delivery device having an optional photodetector array, an LED array, and a drug-containing region.
Figure 1F:
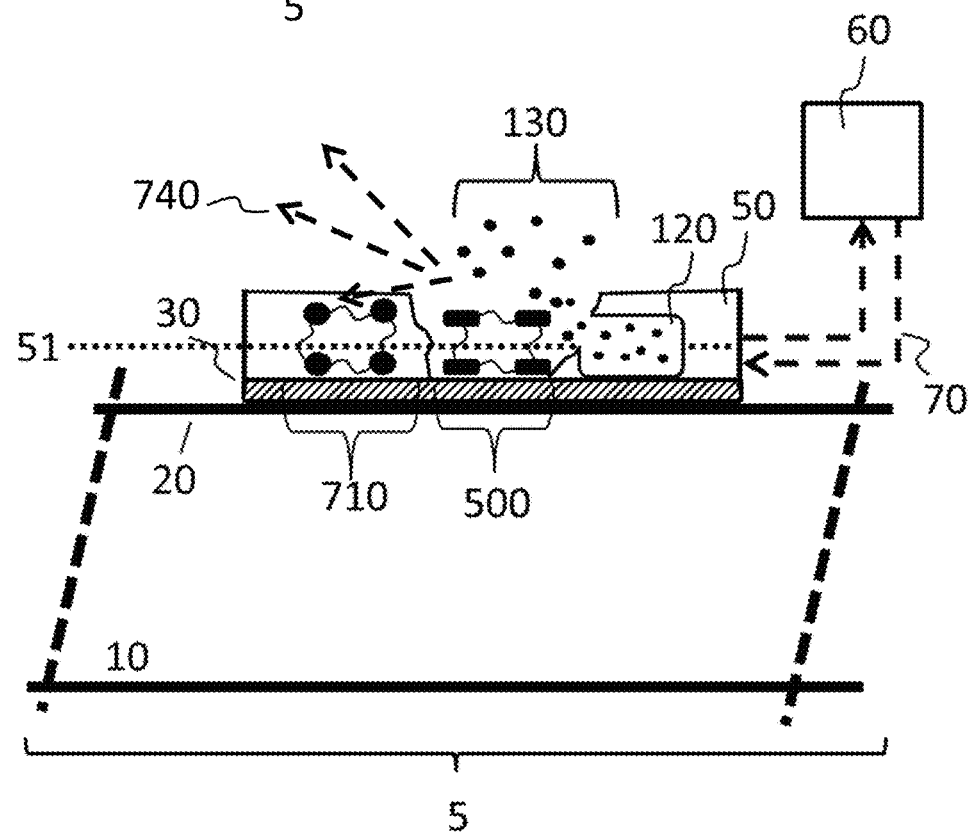
FIG. 1F provides a side plan view of a biomedical device comprising a suture-mounted drug delivery device having an optional photodetector array, an LED array, and a drug-containing region FIG. 2 provides a top plan view of a biomedical device comprising a suture-mounted stretchable or flexible electronic circuit closing a wound in a tissue.

FIG. 1E-F provides a side plan view of a biomedical device 5 comprising a drug delivery device mounted on the outer surface 20 of a suture 10 having a flexible or stretchable LED array 500, a flexible or stretchable photodetector (PD) array 710, and a drug-containing region 120 all of which are encapsulated in one or more barrier layers 50, such as one or more low modulus (e.g., less than or equal to 1 MPa) elastomeric layers. In an embodiment, barrier layer 50 functions as a moisture barrier to prevent transport of water, biological fluids, ionic solutions, soapy water, etc. to the flexible or stretchable LED array 500, the flexible or stretchable photodetector array 710, and drug-containing region 120 components of the suture-mounted drug delivery device 5. The flexible or stretchable LED array 500 is comprised of LED island structures (schematically illustrated in FIG. 1E-F as rounded rectangles) and electrically conducting bridge structures (schematically illustrated in FIG. 1E-F as wavy lines). The flexible or stretchable photodetector array 710 is comprised of photodiode island structures (schematically illustrated in FIG. 1E-F as circles) and electrically conducting bridge structures (schematically illustrated in FIG. 1E-F as wavy lines). The flexible or stretchable LED array 500 and flexible or stretchable photodetector array 710 are disposed on an optional flexible or stretchable substrate 30 which is disposed on the surface of suture 20.

The suture-mounted drug delivery device comprising a flexible or stretchable LED array 500 and a flexible or stretchable photodetector array 710 is optionally connected to a controller 60 by wired or wireless, one-way or two way communication line 70. In a suture delivery embodiment, the controller activates the LED array 500 to produce electromagnetic radiation 730. A portion of the electromagnetic radiation 730 is incident on the photodetector array 710 and is detected by the controller 60.

In an embodiment, suture-mounted drug delivery device 5 has a composition, physical dimensions and mechanical properties such that it can establish conformal contact with the nonplanar external surface of the suture 10. In an embodiment, for example, optical sensor device 5 is mounted on the curved external surface 20 of the suture 10. In an embodiment, the composition, physical dimensions and mechanical properties of a flexible or stretchable substrate 30, flexible or stretchable LED array 500, flexible or stretchable photodetector array 710, and barrier layers 50 are selected such that flexible or stretchable LED array 500 and a flexible or stretchable photodetector array 710 are provided proximate to the neutral mechanical surface 51 of this combination of components (note: the neutral mechanical surface is shown schematically as dotted line 51).

The device before drug delivery is shown in FIG. 1E. As shown in FIG. 1F, in operation, the LED array 500 produces electromagnetic radiation 730, optionally having a selected intensity distribution as a function of wavelength, which photolytically degrades, or otherwise renders porous, the barrier layer 30 sufficient to release at least a portion of the pharmaceutical composition from the drug containing region 120, resulting in release of the pharmaceutical composition 130 to the tissue and/or biological environment. For some applications, the electromagnetic radiation 730 has wavelengths in the visible or near infrared regions of the electromagnetic spectrum. In an embodiment, a portion of the electromagnetic radiation 730 from LED array 500 is detected by photodetector array 710, thereby providing a means for monitoring the drug delivery process. For example, by monitoring the intensity, wavelength distribution and/or radiant power of electromagnetic radiation 730 from LED array 500, certain properties of the released pharmaceutical composition 120 can be determined, including the rate of delivery and relative amount of released pharmaceutical composition 120.

Figure 2:
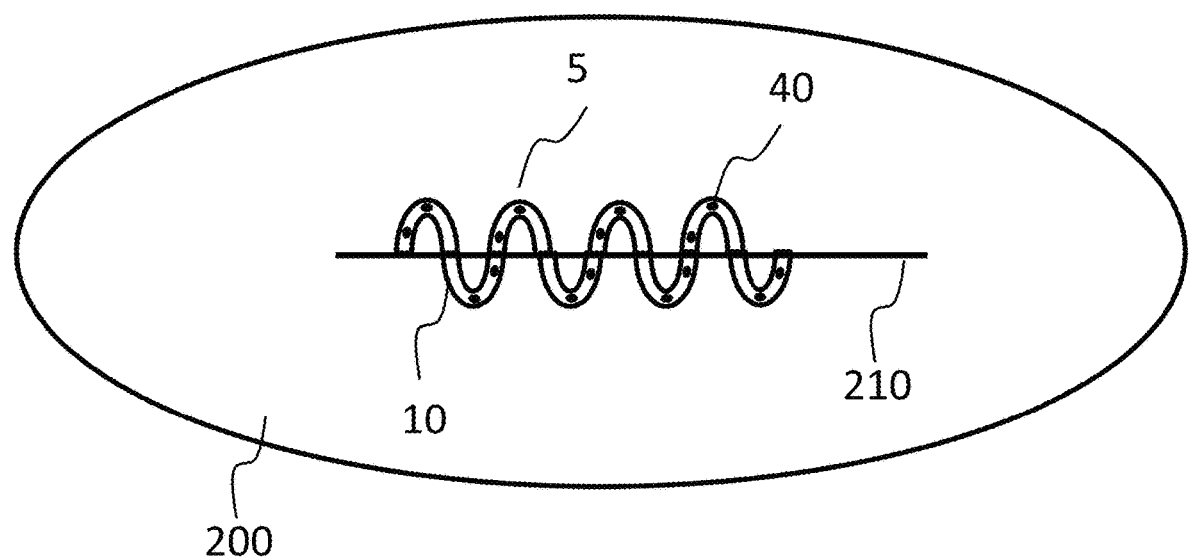

FIG. 2 provides a top plan view of a biomedical device 5 in a biological environment comprising a suture-mounted stretchable or flexible electronic circuit wherein the suture 10 closes a wound 210 in a tissue 200. The elements of the flexible or stretchable electronic circuit 40 are disposed on the surface of the suture 10. In this configuration the suture 10 can be used for closing the wound 210, for example, by sewing or stitching together tissue. In some embodiments, the stretchable or flexible electronic circuit 40 of the biomedical device 5 supports advanced diagnostic and/or therapeutic functionality, such providing optical emission allowing for visualization of suture 10 or enabling drug delivery or delivery of electromagnetic radiation to the wound 210 or tissue 200. In some embodiments, the stretchable or flexible electronic circuit 40 of the biomedical device 5 supports sensing functionality such as measuring the temperature and/or chemical or physical properties of wound 210 or tissue 200, and/or measuring the amount of a therapeutic agent provided to the wound 210 or tissue 200 as a function of time. In some embodiments, biomedical device 5 comprises bioresorbable materials and, thus, is capable of being at least partially resorbed upon making contact with the tissue 200 in the biological environment. In some embodiments, biomedical device 5 has a composition and physical dimensions such that it can be removed from contact with tissue 200 after treatment and/or diagnosis of tissue 200 in the biological environment.

Figure 3:
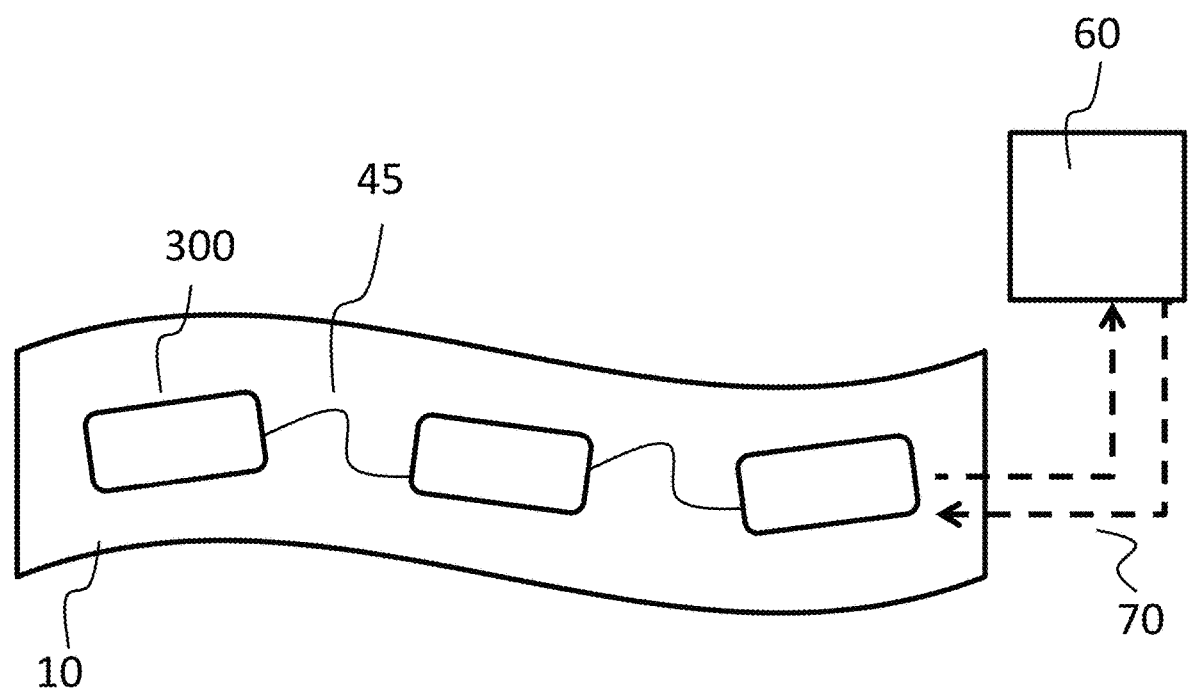
FIG. 3 provides a top plan view of a portion of a biomedical device comprising a suture-mounted stretchable or flexible electronic circuit.

FIG. 3 provides a top plan view of a portion of an example of a biomedical device 5 comprising a suture-mounted stretchable or flexible electronic circuit. Semiconductor elements 41 are disposed on the surface of the suture 10 and are connected by stretchable or flexible conducting elements 45. The biomedical device can optionally be connected to a controller 60 for controlling the stretchable or flexible electronic circuit. The controller 60 can be in wired or wireless, one-way or two-way communication with the stretchable or flexible electronic circuit using wired or wireless communication line 70. The controller 60 can control functions of the stretchable or flexible electronic circuit such as imaging, drug delivery, electromagnetic radiation delivery and detection, among others.

FIG. 4A-E provides a schematic showing various approaches for creating layers of flexible or stretchable electronic circuits 401 optionally provided in a multilayer laminated geometry. FIG. 4A provides a side plan view of a flexible or stretchable electronic circuit 401 comprising an array of electronically interconnected island 400 and bridge 410 structures. The island structures 400 may comprise inorganic semiconductor elements, such as semiconductor-based devices and device arrays, such as LEDs, transistors, lasers, photodetectors, multiplex circuitry, logic circuitry, etc. The bridge structures 410 may be comprised of conductive material, such as a metal, and optionally are provided in a serpentine configuration between the island 400 structures, and optionally encapsulated by a low modulus elastomer layer. In some embodiments, the length and configuration (e.g., serpentine, bent, wavy, buckled, etc.) of bridge structures 410 provides overall device flexibility and/or stretchability for a range of applications. The array 401 of electronically interconnected island 400 and bridge 410 structures may be at least partially encapsulated in a barrier layer, and in some embodiments are completely encapsulated in a barrier layer. FIG. 4B-E provide side plan views of stacked configurations 402 of stretchable or flexible electronic circuits provided in a multilayer geometry wherein the layers are connected by an adhesive 420 (FIG. 4B), directly connected (FIG. 4C), connected by a flexible or stretchable substrate 30 (FIG. 4D), and connected by flexible or stretchable substrates 30 and adhesive 420 (FIG. 4E). As shown in FIG. 4B, an array of electronically interconnected island 400 and bridge 410 structures is provided in a multilayered geometry connected by an adhesive layer 420 and is optionally provided on a flexible or stretchable substrate 35. As shown in FIG. 4C, an array of electronically interconnected island 400 and bridge 410 structures is provided in a multilayered geometry wherein the stacked arrays are provided in direct contact and are optionally provided on a flexible or stretchable substrate 35. As shown in FIG. 4D, an array of electronically interconnected island 400 and bridge 410 structures is provided in a multilayered geometry connected by a flexible and stretchable substrate 30 and is optionally provided on a flexible or stretchable substrate 35. As shown in FIG. 4E, an array of electronically interconnected island 400 and bridge 410 structures is provided in a multilayered geometry connected by flexible or stretchable substrates 30 and an adhesive layer 420, and is optionally provided on a flexible or stretchable substrate 35.

A device as described herein can contain many arrays 401 of electronically interconnected island 400 and bridge 410 structures provided in stacked configurations 402 as set forth in FIG. 4A-E, or any combination of the stacked configurations 402 as set forth in FIG. 4A-E. In an embodiment, for example, a device as described herein comprises a plurality of arrays 401 of electronically interconnected island 400 and bridge 410 structures provided in stacked configurations 402 connected by adhesive 420 and a plurality of arrays 401 of electronically interconnected island 400 and bridge 410 structures provided in stacked configurations 402 connected by a flexible or stretchable substrate 30.

The multilayered stacked geometries of the arrays 401 of electronically interconnected island 400 and bridge 410 structures shown in FIG. 4A-E can be encapsulated in various configurations, for example in a multilayer laminated geometry. FIG. 4F-H provides a schematic showing various approaches for creating stacked layers of flexible or stretchable electronic circuits 402. FIGS. 4F-H provide side plan views of stacked configurations of stretchable or flexible electronic circuits 402 wherein the individual layers are connected by an encapsulation layer 405 (FIG. 4F), lamination of encapsulated layers 405 (FIG. 4H), and printing of electronically interconnected island 400 and bridge 410 structures on a laminated layer 405 (FIG. 4H). The encapsulation layer 405 can serve as a surface for lamination (as shown in FIG. 4G) or a surface for molding one or more additional components, such as optical components (e.g., lens arrays, filters, diffusers, etc.) or drug delivery components (e.g., encapsulated pharmaceutical compositions). Additionally, the encapsulation layer 405 may provide for electronic isolation for a least a portion of the arrays 401 of electronically interconnected island 400 and bridge 410 structures from a biological environment and/or may additionally serve as a moister barrier from a biological environment. In addition to serving as an electronic and/or moisture barrier layer, the encapsulation layer 405 can also serve to provide mechanical stability to the arrays 401 of electronically interconnected island 400 and bridge 410 structures. In an embodiment of that shown in FIG. 4F, the encapsulation layer 405 is a laminate layer. In a further embodiment of that shown in FIG. 4F, the encapsulation layer 405 has mechanical properties chosen so as to allow for stretching or flexing of the stretchable or flexible electronic circuit without causing damage to the circuit or encapsulation layer 405. In an embodiment of that shown in FIG. 4H, the electronically interconnected island 400 and bridge 410 structures are provided on the encapsulation layer 405, for example, by a printing process, such as a dry transfer contact printing technique.

Figure 4I:
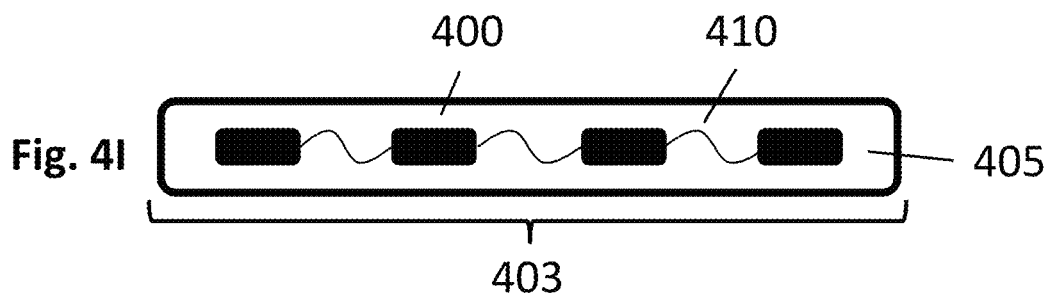
FIGS. 4I, 4J, 4K, 4L, 4M, 4N, 4O, 4P, 4Q, 4R, 4S, 4T, and 4U provide schematic diagrams of strategies to create optical elements on a laminated flexible or stretchable electronic circuit, including lenses (FIGS. 4I, 4J, 4K), diffusers (FIGS. 4L, 4M,4N), a reflective coating (FIGS. 4O-4P), a reflective coating having a transparent section (FIGS. 4Q-4R), and a grating (FIGS. 4S, 4T, 4U).
Figure 4J:
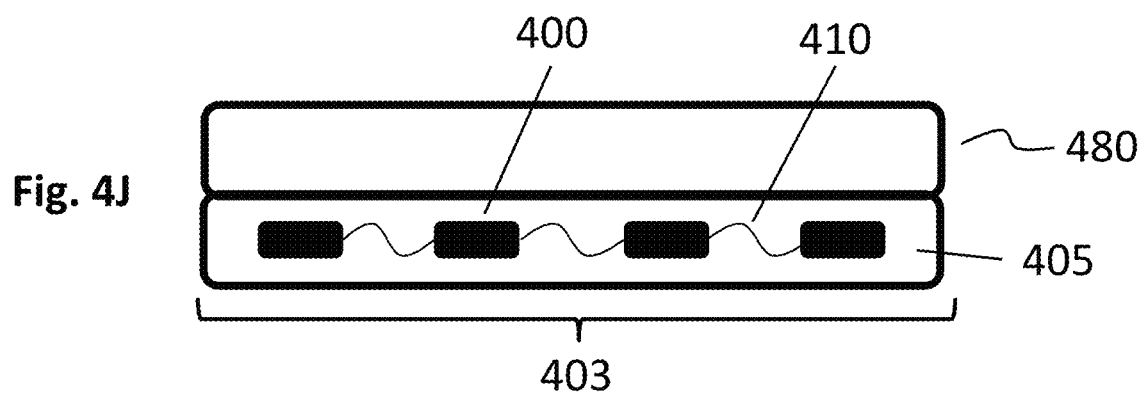
Figure 4K:
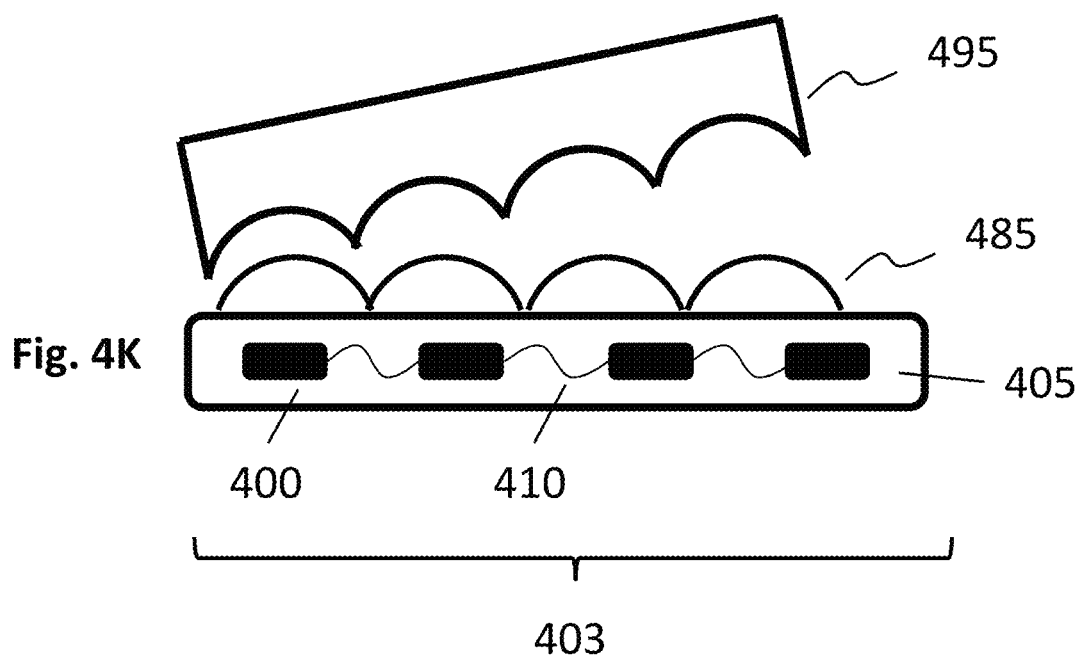
Figure 4L:
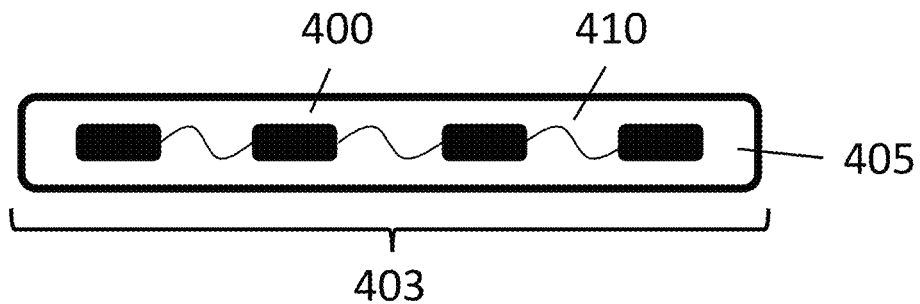
Figure 4M:
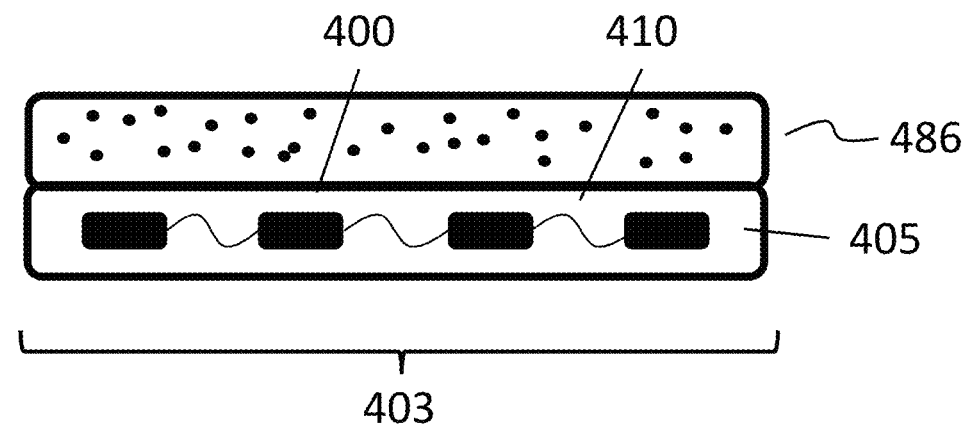
Figure 4N:
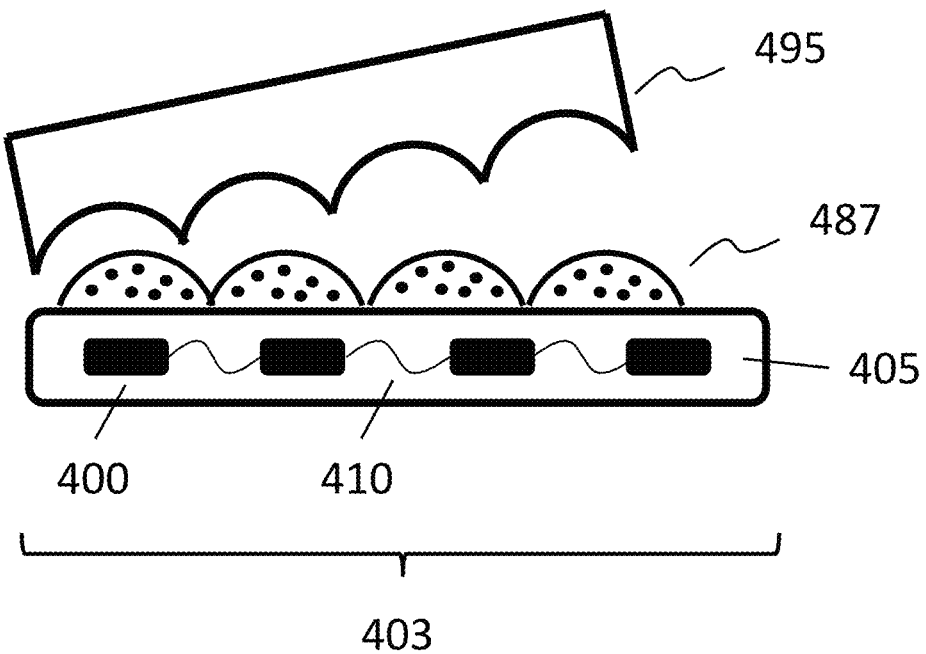
Figure 4O:
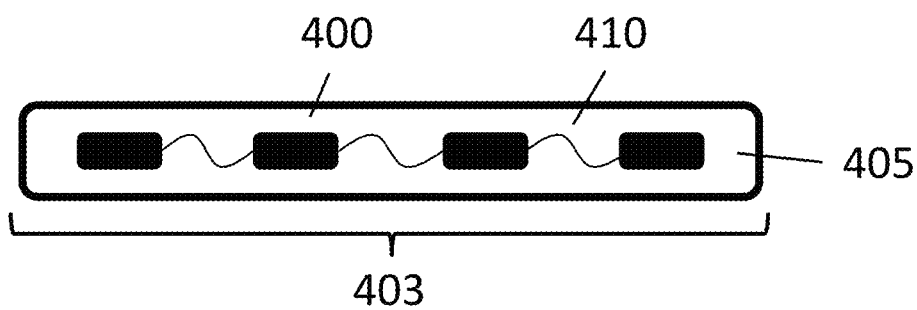
Figure 4P:
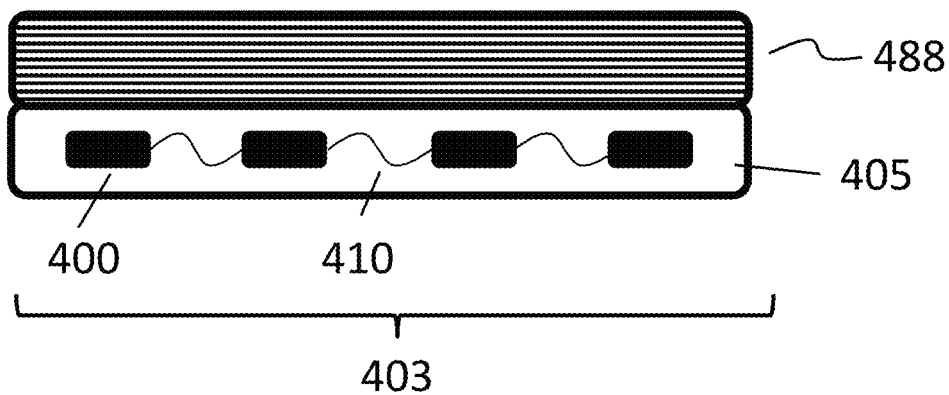
Figure 4Q:
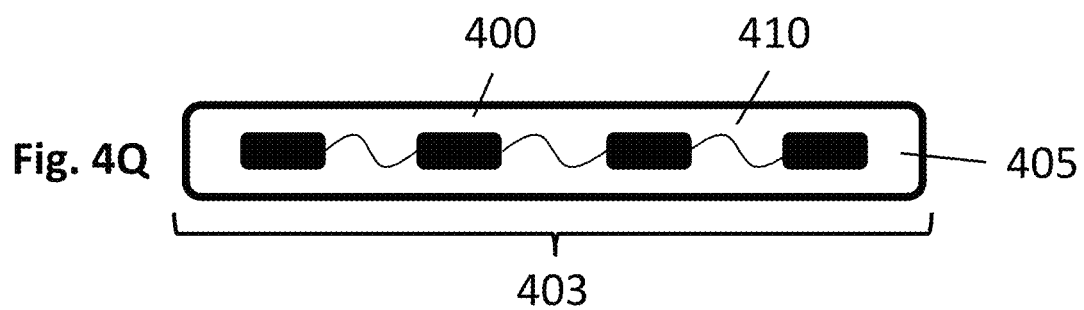
Figure 4R:
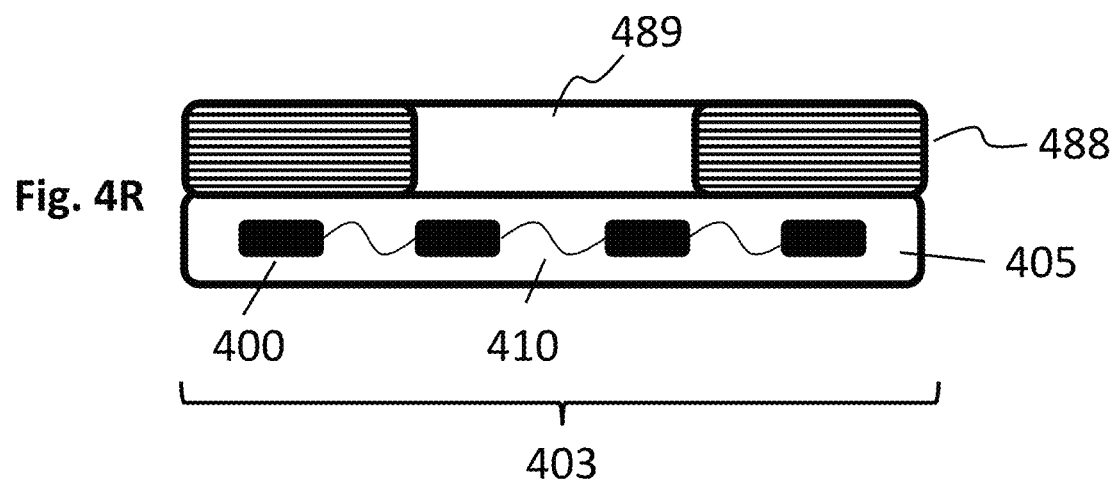
Figure 4S:
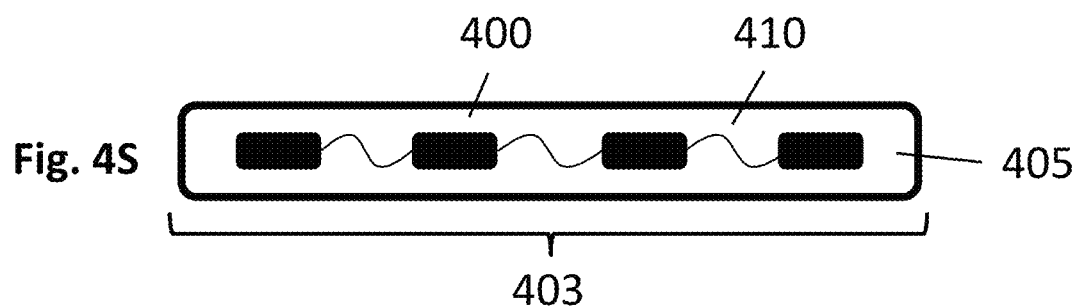
Figure 4T:
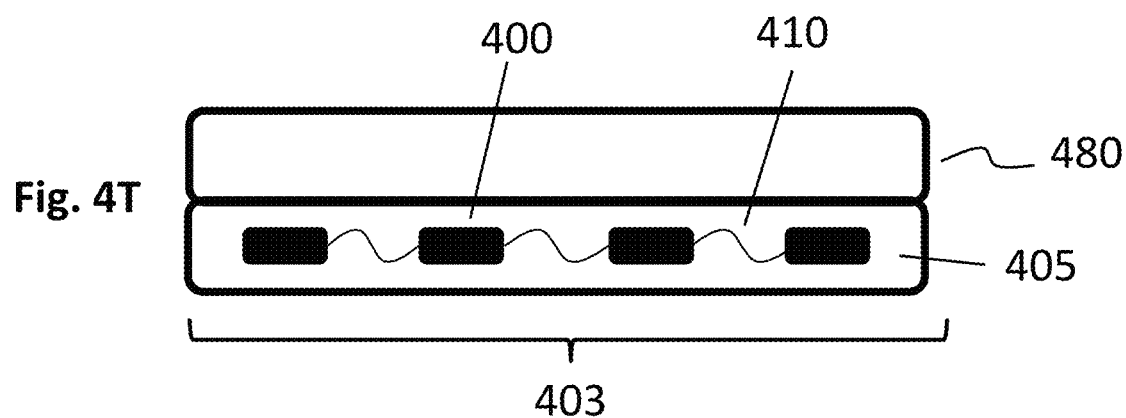
Figure 4U:
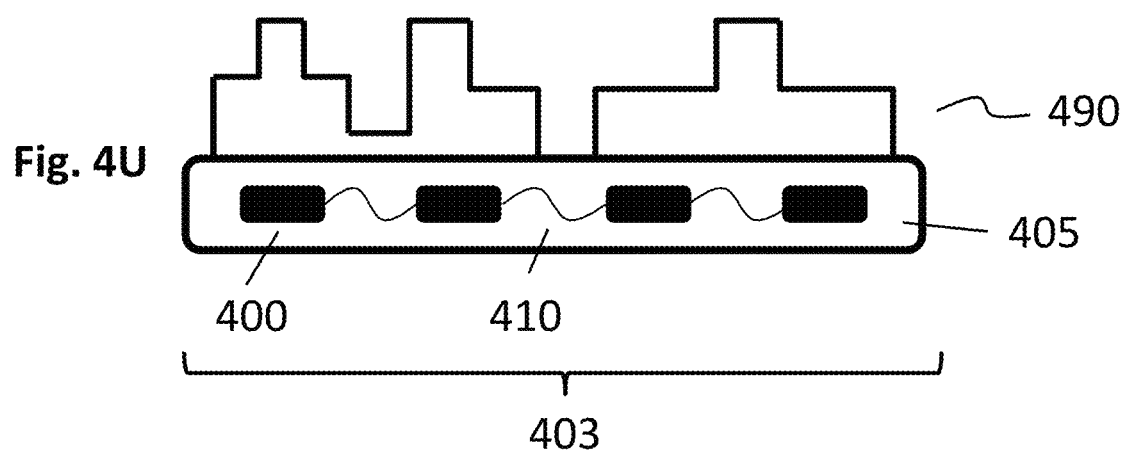

FIGS. 4I-4U provide schematic diagrams of strategies to create optical elements on a laminated flexible or stretchable electronic circuit 455, including lenses 485 (FIG. 4I-4K), diffusers 486 (4L-4N), reflective coatings 487 (40-4P), reflective coatings 487 having a transparent section 489 (4Q-4R), and a micro- or nanostructured grating 490 (4S-4U). In FIG. 4I-4K, the strategy includes providing an array 403 of island 400 and bridge 410 structures contained in an encapsulation layer 405, as shown in FIG. 4I. The array 403 is then coated with a moldable layer 480, such as a prepolymer, as shown in FIG. 4J. The moldable layer 480 is then contacted by a pattern transfer device 495, such as a mold or stamp, to form lenses 485 on the encapsulation layer 405, as shown in FIG. 4K. In FIG. 4L-4N, the strategy includes providing an array 403 of island 400 and bridge 410 structures contained in an encapsulation layer 405, as shown in FIG. 4L. The array 403 is then coated with a moldable layer 486 comprising diffusive elements shown as black dots, such as a prepolymer, as shown in FIG. 4M. The moldable layer 486 is then contacted by a pattern transfer device 495, such as a mold or stamp, to form diffusive lenses 487 on the encapsulation layer 405, as shown in FIG. 4N. In FIG. 4O-P, the strategy includes providing an array 403 of island 400 and bridge 410 structures contained in encapsulation layer 405, as shown in FIG. 4O. The array 403 is then coated with a reflective coating layer 488, as shown in FIG. 4P. The reflective coating layer 488 can be, for example, an antireflective coating layer, a partially reflecting layer, or an optical filter layer. In FIG. 4Q-4R, the strategy includes providing an array 403 of island 400 and bridge 410 structures contained in an encapsulation layer 405, as shown in FIG. 4Q. The array 403 is then coated with a reflective coating layer 488 having a window region 489, as shown in FIG. 4R. The reflective coating layer 488 can be, for example, an antireflective coating layer, a partially reflecting layer, or an optical filter layer. In FIG. 4S-T, the strategy includes providing an array 403 of island 400 and bridge 410 structures contained in an encapsulation layer 405, as shown in FIG. 4S. The array 403 is then coated with a moldable layer 480, such as a prepolymer, as shown in FIG. 4T. The moldable layer 480 is then processed to form a micro- or nanostructure 490 on the barrier layer laminate 405, as shown in FIG. 4U. The micro- or nanostructure 490 can be, for example, a grating or photonic crystal.

Figure 5A:
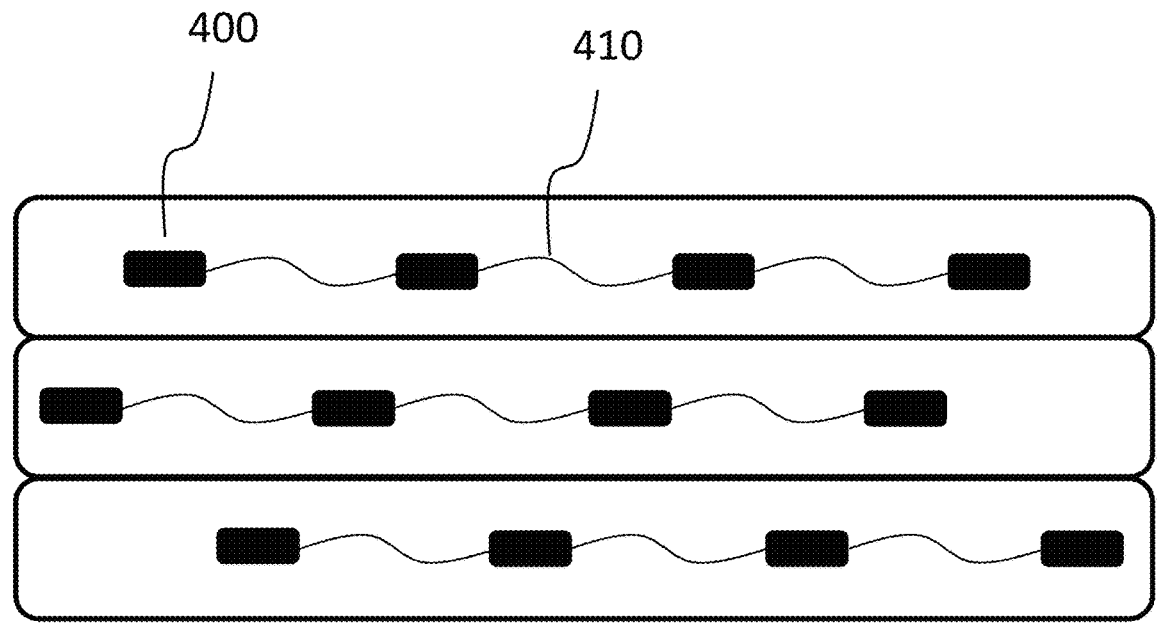
FIG. 5A provides a side plan view of offset and stacked arrays of flexible or stretchable electronic circuits and FIG. 5B provides a top plan view of the same offset and stacked arrays of flexible or stretchable electronic circuits.
Figure 5B:
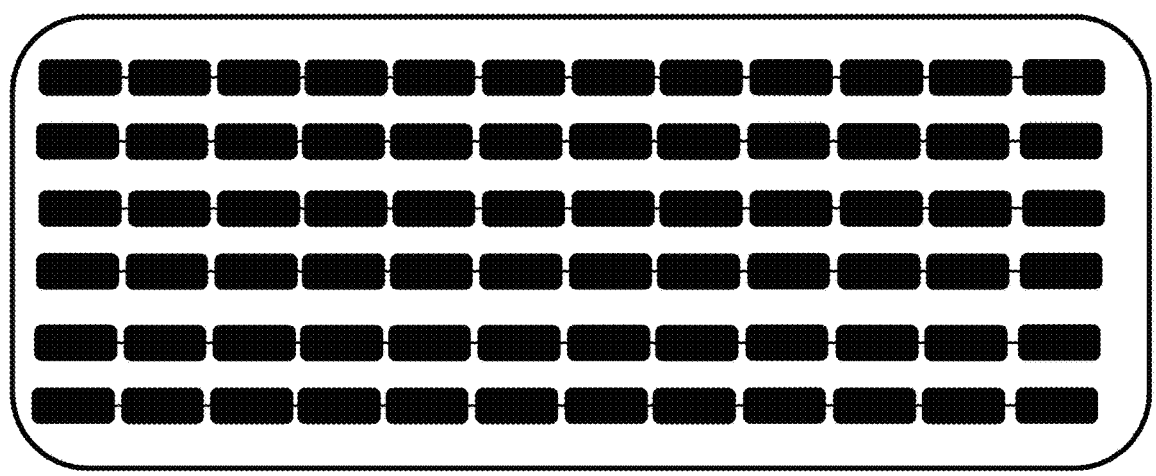

In some embodiments, individually encapsulated arrays of electronically interconnected island 400 and bridge 410 structures, such as individually encapsulated LED arrays, are provided in a multilayer stacked device geometry to form three dimensional arrays of electronically interconnected island 400 and bridge 410 structures. Such multilayer device geometries are particularly beneficial for providing high density arrays of inorganic light emitting diodes (ILEDS) capable of providing radiant intensities and powers useful for biomedical applications. An example, of a three dimensional array of ILEDS is exemplified in FIG. 5A which provides a side plan view of offset and stacked arrays of flexible or stretchable ILED arrays while FIG. 5B provides a top plan view of the same offset and stacked arrays of flexible or stretchable ILED arrays. As shown in FIG. 5B, offset stacks of individual 2D arrays of electronically interconnected island 400 and bridge 410 structures provides very high two dimensional density of electronically interconnected island 400 and bridge 410 structures, while at the same time maintaining a high degree of flexibility and/or stretchability. This configuration is especially useful in imaging, sensing, and phototherapy applications wherein at least a portion of the three dimensional stacked arrays of electronically interconnected island 400 and bridge 410 structures comprise ILEDs for generation electromagnetic radiation and/or wherein at least a portion of the three dimensional stacked arrays of electronically interconnected island 400 and bridge 410 structures comprise photodiodes for detecting electromagnetic radiation. LED arrays useful in this aspect include multilayer structures comprising a plurality of individually encapsulated LED arrays provided in a laminated device configuration.

Figure 6:
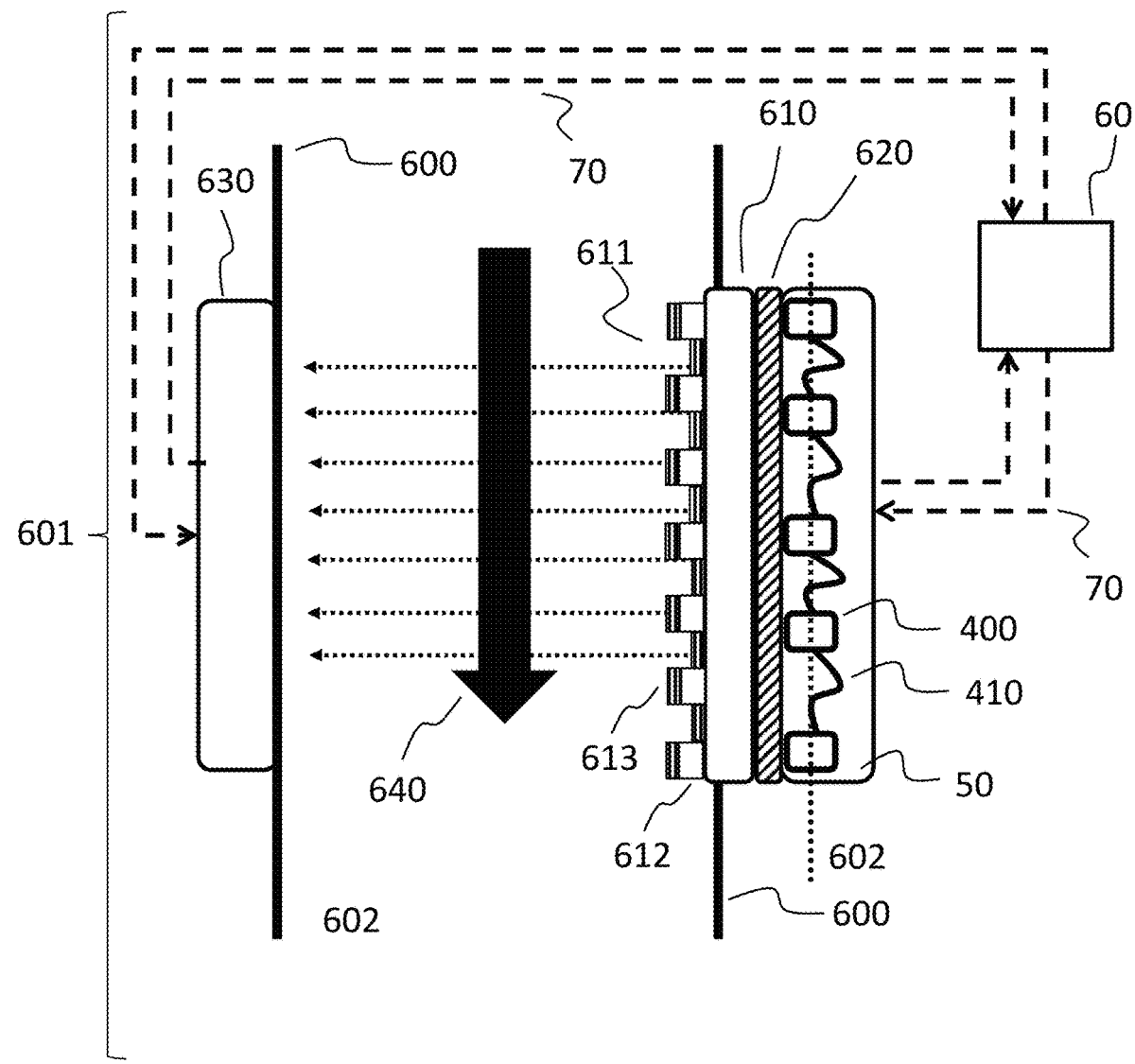
FIG. 6 provides a side plan view of a fluid delivery monitor device comprising a flexible or stretchable electronic circuit.

FIG. 6 provides a side plan view of a fluid delivery monitor device 601 comprising a flexible or stretchable electronic circuit. The fluid delivery monitor device 601 comprises a tube 602 for delivery of fluid having an outer wall 600 for containing a fluid having a flow direction indicated by arrow 640. The fluid delivery monitor device further comprises a plasmonic crystal 610 disposed within or on the tube wall 600 and in fluid communication with the fluid in the tube 602. Photonic crystal has sensing surface 611 provided in physical contact with fluid in tube 602. In an embodiment, sensing surface comprises: (1) a substrate having a first surface with a plurality of features 612 provided in a first array and (2) one or more films 613 comprising an electrically conductive material, wherein at least a portion of the one or more films 613 is supported by the first surface, and wherein at least a portion of the one or more of the films 613 comprise the electrically conducting material is spatially aligned with each of the features 612 of the first surface. In an embodiment, the substrate having the first surface with a plurality of features 612 comprises a nanoimprinted or replica-molded structure.

In some embodiments, plasmonic crystal 610 is a molded or embossed structure, and optionally is molded or embossed on the inner surface of the tube 602 to provide access of the sensing surface to the fluid in the tube 602. Alternatively, plasmonic crystal 610 is disposed in an aperture in tube 602 to provide access of the sensing surface to the fluid in the tube 602. In optical communication with the plasmonic crystal 610 and tube 602 is an array of electronically interconnected island 400 and bridge 410 structures encapsulated in a barrier layer 50, wherein the island structures are LEDs, for example provided in a 2D LED array or 3D LED array. In an embodiment, for example, array of electronically interconnected island 400 and bridge 410 structures is a multilayer structure comprising a plurality of individually encapsulated LED arrays. In the configuration shown in FIG. 6, an optional flexible or stretchable substrate 620 is disposed between the plasmonic crystal 610 and the array of electronically interconnected island 400 and bridge 410 structures. In some embodiments, plasmonic crystal 610 is in physical contact with the LED array or alternatively is in physical contact with optional substrate 610 provided between the plasmonic crystal and the LED array. Alternatively, the plasmonic crystal 610 is molded on a surface of a LED array. In an embodiment, the composition, physical dimensions and mechanical properties of flexible or stretchable substrate 620, array of electronically interconnected island 400 and bridge 410 structures and barrier layer 50 are selected such that array of electronically interconnected island 400 and bridge 410 structures is provided proximate to the neutral mechanical surface 602 of this combination of components (note: the neutral mechanical surface is show schematically as dotted line 602).

In some embodiments, plasmonic crystal 610, LED array and optional substrate 610 are provided in a laminated device geometry. In some embodiments, plasmonic crystal 610, LED array and optional substrate 620 are each flexible device components capable of efficient integration with tube 602, e.g., able to assume a nonplanar (e.g., curved configuration or bent configuration).

The fluid delivery monitoring device 601 of FIG. 6 also comprises a detector 630 positioned on an outer wall 600 of the tube. Detector 630 is in optical communication with plasmonic crystal 610, and is positioned for detecting electromagnetic radiation produced by the LED island structures 400 and transmitted by plasmonic crystal 610. In an embodiment, for example, detector 630 is a flexible and/or stretchable photodetector or array of photodetectors, such as an array of inorganic semiconductor-based photodetectors. As shown in FIG. 6, the detector 630 is in optical communication with plasmonic crystal 610 and the LED array. An optional controller 60 is also shown which is provided in wired or wireless communication with both the array of electronically interconnected island 400 and bridge 410 structures and the detector 630. The controller 60 is in one-way or two-way communication with the detector 630 and the array of electronically interconnected island 400 and bridge 410 structures by wired or wireless communication line 70. The controller 60 can control functions of the fluid delivery monitor such as imaging, drug delivery, and electromagnetic radiation delivery and detection, among others.

In operation, the array of LEDs of the fluid delivery monitoring device 601 generates electromagnetic radiation, at least a portion of which is transmitted through the plasmonic crystal 610 and detected by detector 630. Interaction of the fluid in tube 602 and one or more exposed sensing surfaces of plasmonic crystal 610 establishes, in part, the optical transmission properties of the plasmonic crystal 610, such as the wavelengths of electromagnetic radiation transmitted by the plasmonic crystal and the percentage transmission of the plasmonic crystal as function of wavelength. For example, the composition of the fluid determines the refractive index proximate to the external surface of the plasmonic crystal which significantly impacts the transmission properties. Therefore, by monitoring the intensity and/or wavelength of light transmitted by plasmonic crystal 610, the composition of the fluid may be monitored, for example, monitored as a function of time. In an embodiment, fluid delivery monitoring device 601 is a component of an intravenous delivery system and is useful for monitoring the amount of a fluid component, such as a drug, biological materials (e.g., proteins, blood or a component thereof) or nutrient, administered to a patient undergoing treatment.

Figure 7:
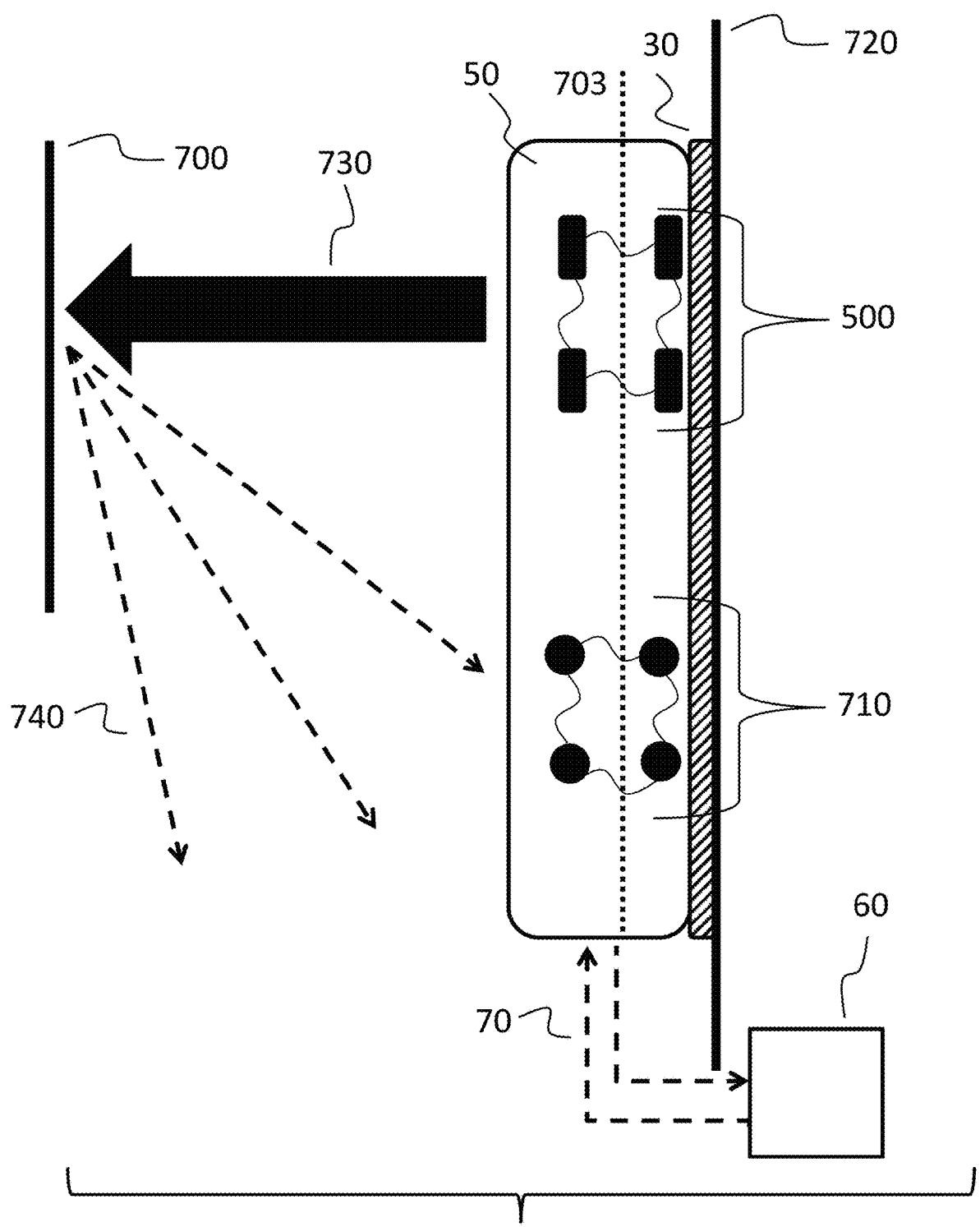
FIG. 7 provides a side plan view of a proximity sensor device comprising a flexible or stretchable LED array and a flexible or stretchable PD array.

FIG. 7 provides a side plan view of an optical sensor device 701 comprising a flexible or stretchable LED array 500 and a flexible or stretchable photodetector array 710, both of which are encapsulated in one or more barrier layers 50, such as one or more low modulus (e.g., less than or equal to 1 MPa) elastomeric layers. In an embodiment, barrier layer 50 functions as a moisture barrier for prevent transport of water, biological fluids, ionic solutions, soapy water, etc. to the flexible or stretchable LED array 500 and the flexible or stretchable photodetector array 710 components of the proximity sensor device 701. The flexible or stretchable LED array 500 comprises LED island structures (schematically illustrated in FIG. 7 as rounded rectangles) and electrically conducting bridge structures (schematically illustrated in FIG. 7 as wavy lines). The flexible or stretchable photodetector array 710 also comprises of photodiode island structures (schematically illustrated in FIG. 7 as circles) and electrically conducting bridge structures (schematically illustrated in FIG. 7 as wavy lines). The flexible or stretchable LED array 500 and flexible or stretchable photodetector array 710 are disposed on an optional flexible or stretchable substrate 30 which is disposed on the surface of device 720, such as a surgical glove, a tools, a robotic device, among others.

The proximity sensor device comprising a flexible or stretchable LED array 500 and a flexible or stretchable photodetector array 710 is optionally connected to a controller 60 by wired or wireless, one-way or two way communication line 70. In a proximity sensing embodiment, the controller activates the LED array 500 to produce electromagnetic radiation 730 in the direction of the surface of an object 700, optionally in a biological environment. A portion of the electromagnetic radiation reflected, scattered or emitted 740 by the object 700 is incident on the photodetector array 710 and is detected by the controller 60.

In an embodiment, proximity sensor device 701 has a composition, physical dimensions and mechanical properties such that it can establish conformal contact with the nonplanar external surface of a surgical device. In an embodiment, for example, proximity sensor device 701 is mounted on the curved external surface of a surgical glove or surgical tool. In an embodiment, for example, proximity sensor device 701 is mounted on the curved or planar external surface of a robotic manipulator or a machine part. In an embodiment, the composition, physical dimensions and mechanical properties of a flexible or stretchable substrate, flexible or stretchable LED array 500, flexible or stretchable photodetector array 710, and barrier layers 50 are selected such that flexible or stretchable LED array 500 and a flexible or stretchable photodetector array 710 are provided proximate to the neutral mechanical surface 703 of this combination of components (note: the neutral mechanical surface is show schematically as dotted line 703).

In operation, the LED array 500 produces electromagnetic radiation 730, optionally having a selected intensity distribution as a function of wavelength, which propagates away from proximity sensor device 701. For some applications, the electromagnetic radiation 730 has wavelengths in the visible or near infrared regions of the electromagnetic spectrum. A portion of the electromagnetic radiation 730 from LED array 500 interacts with an object 700, resulting in generation of reflected, scattered and/or emitted electromagnetic radiation 740. At least a portion of the reflected, scattered and/or emitted electromagnetic radiation 740 is detected by photodetector array 710. By monitoring the intensity, wavelength distribution and/or radiant power of the reflected, scattered and/or emitted electromagnetic radiation 740, certain properties of the object can be sensed and/or monitored, including position and/or distance from the proximity sensor.

Figure 8:
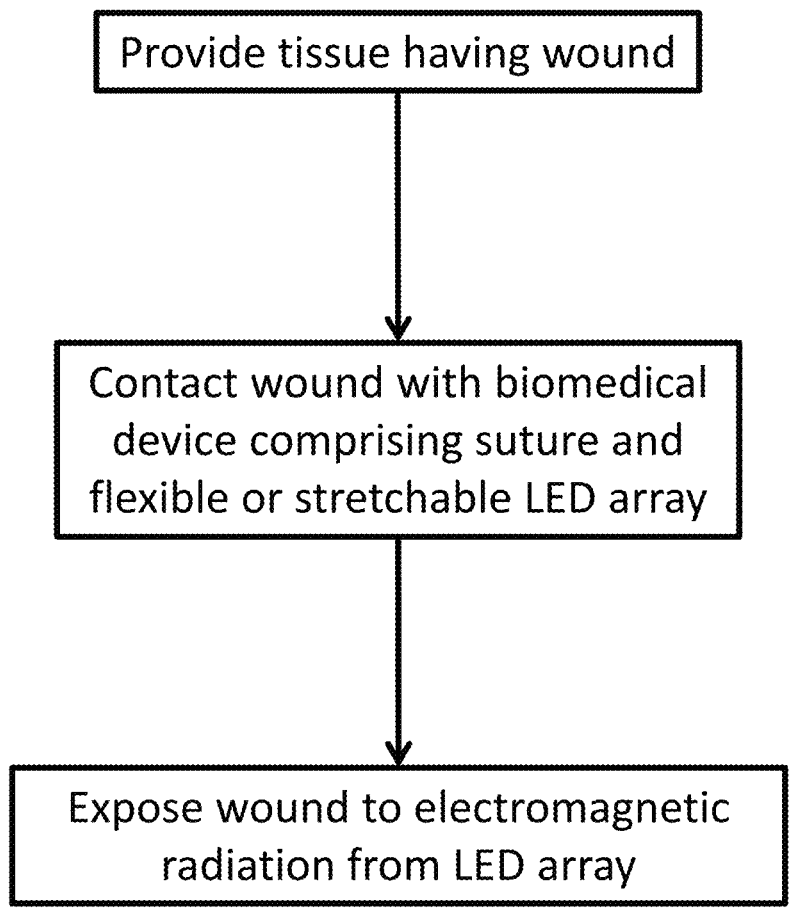
FIG. 8 provides a flow diagram of a method employing a biomedical device comprising a suture having a flexible or stretchable LED array for exposing a wound to electromagnetic radiation.
Figure 9:
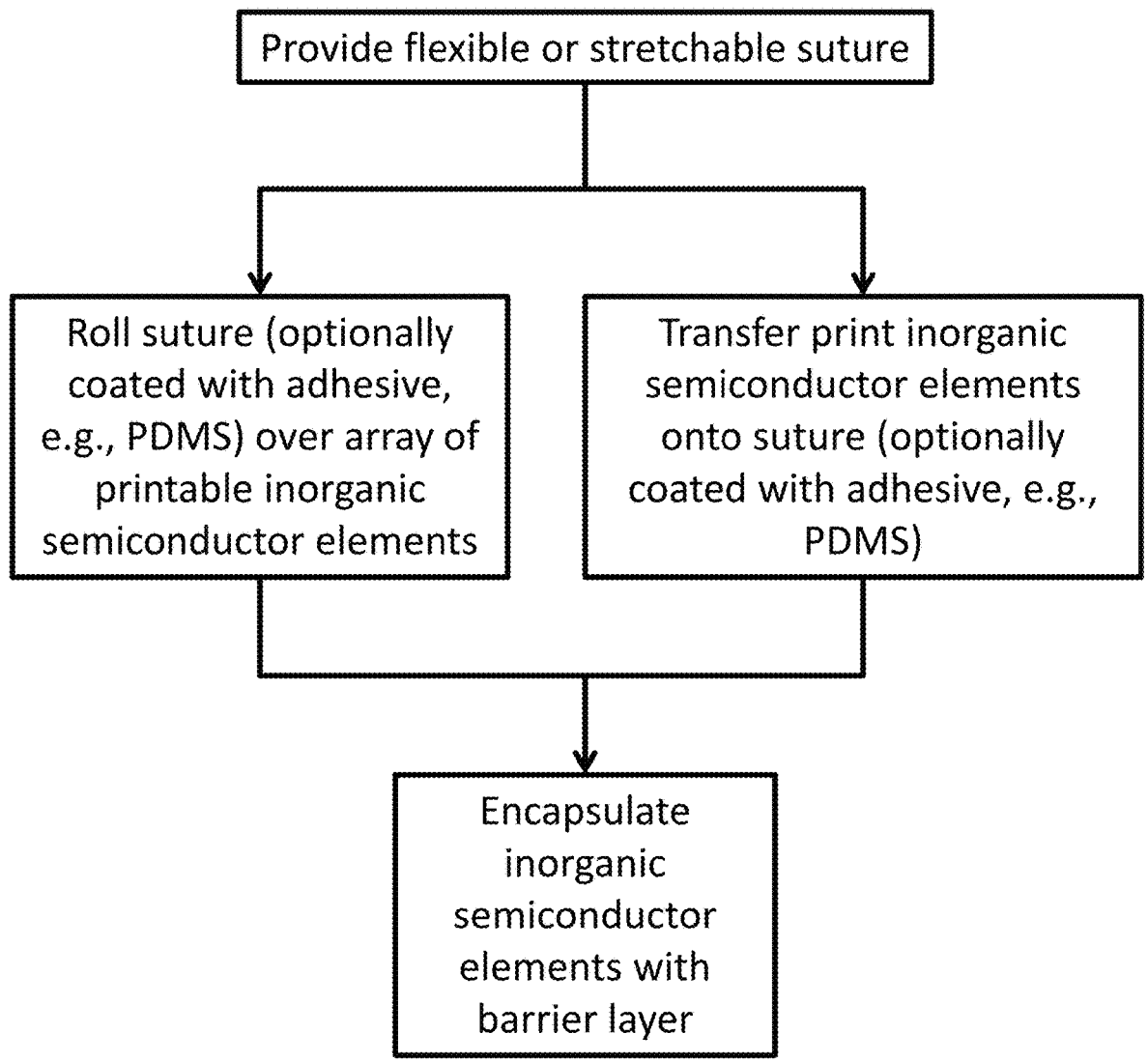
FIG. 9 provides a flow diagram of methods of making a biomedical device.
Figure 10:
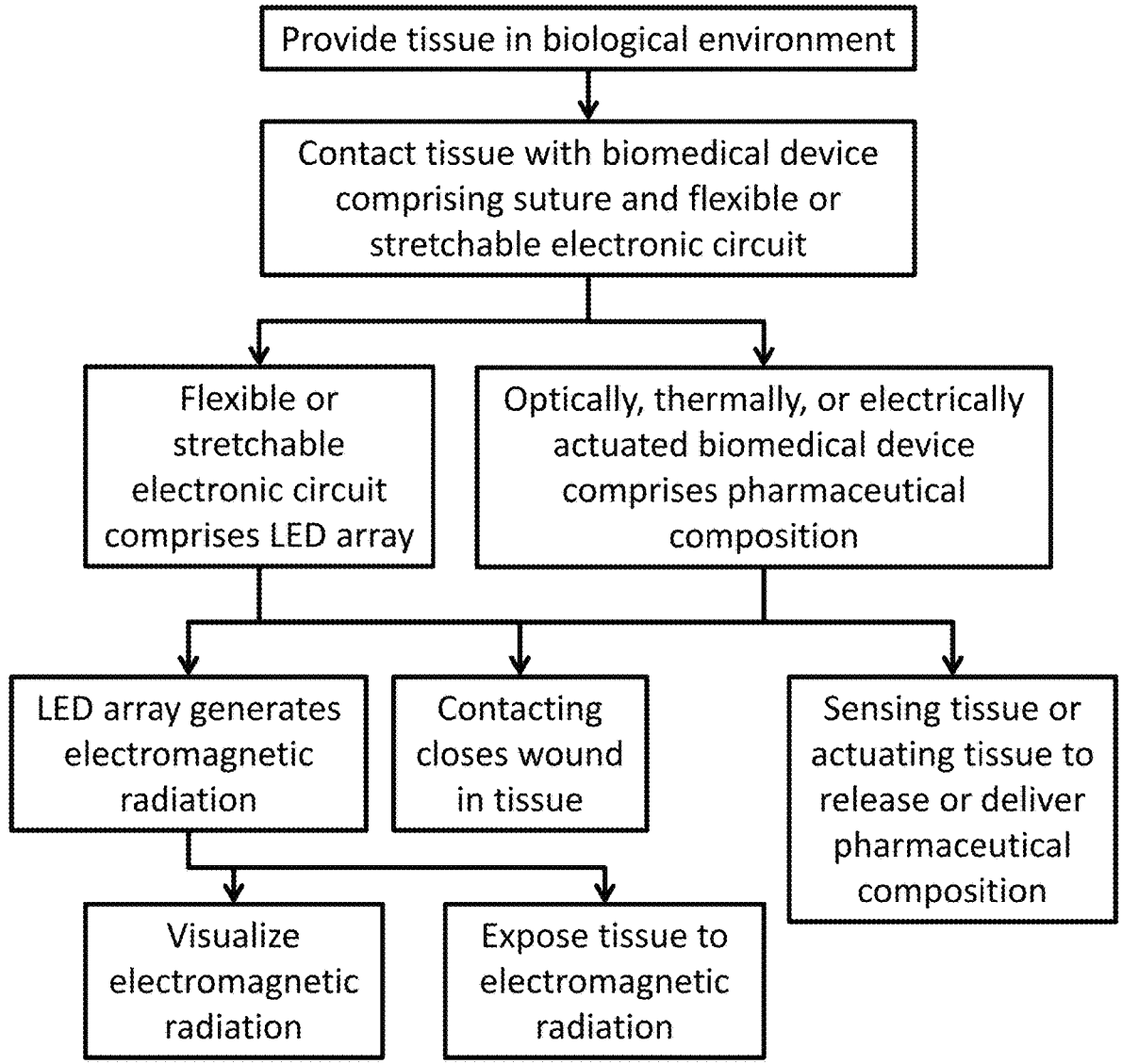
FIG. 10 provides a flow diagram of a method of treating a tissue in a biological environment.

The flexible or stretchable waterproof electronics described herein are useful in a diverse array of methods. FIG. 8 provides a flow diagram of a wound treatment method employing a biomedical device comprising a suture having a flexible or stretchable LED array for exposing the wound to electromagnetic radiation. FIG. 9 provides a flow diagram of a method of making a suture comprising roll printing or transfer printing inorganic semiconductor elements onto a flexible or stretchable thread and encapsulating the inorganic semiconductor elements with a barrier layer. FIG. 10 provides a flow diagram of a method of treating a tissue in a biological environment comprising contacting the tissue with a biomedical device comprising a suture and a flexible or stretchable electronic circuit. The tissue can be treated using many methods, such as methods comprising exposure to electromagnetic radiation, closing a wound in the tissue with a suture as described herein, actuating or sensing the tissue and/or wound, and release of a pharmaceutical composition to the wound and/or tissue from the biomedical device, among others.

The invention may be further understood by the following non-limiting examples.

EXAMPLE 1

Waterproof AlInGaP Optoelectronics on Flexible Tubing, Sutures, Gloves and Other Unusual Substrates, with Application Examples in Biomedicine and Robotics This example explores new areas and implements mechanically optimized layouts to achieve arrays of inorganic LEDs and PDs in systems that can accommodate extreme modes of mechanical deformation, for integration on substrates of diverse materials and formats. Additionally, materials and design strategies allow operation even upon complete immersion in saline solutions, biofluids, solutions of relevance to clinical medicine and soapy water, thereby opening new and unconventional opportunities for seamless integration of optoelectronics with biomedical and robotic systems. Light emitting sutures, thin implantable sheets (i.e. LED tattoos) and balloon catheters, and flexible, optical proximity and refractive index sensors provide some examples. Specifically, this example describes seven advances, in the following order: (1) experimental and theoretical aspects of mechanical designs that enable freely deformable, interconnected collections of LEDs and PDs on soft, elastomeric membranes, bands and coatings, (2) strategies for achieving high effective fill factors in these systems, using laminated multilayer constructs, (3) device examples on diverse substrates and in varied geometrical forms, (4) low modulus, biocompatible encapsulation materials that preserve key mechanical properties and, at the same time, enable robust operation when integrated on or implanted in living systems, (5) flexible optoelectronic components for biomedicine, with in vivo demonstrations on animal models, (6) illuminated plasmonic crystal devices, as high performance refractive index monitors for intravenous delivery systems and (7) waterproof optical proximity sensors that mount on the curved fingertips of vinyl gloves, for possible use in robotics or advanced surgical devices.

Figure 17A:
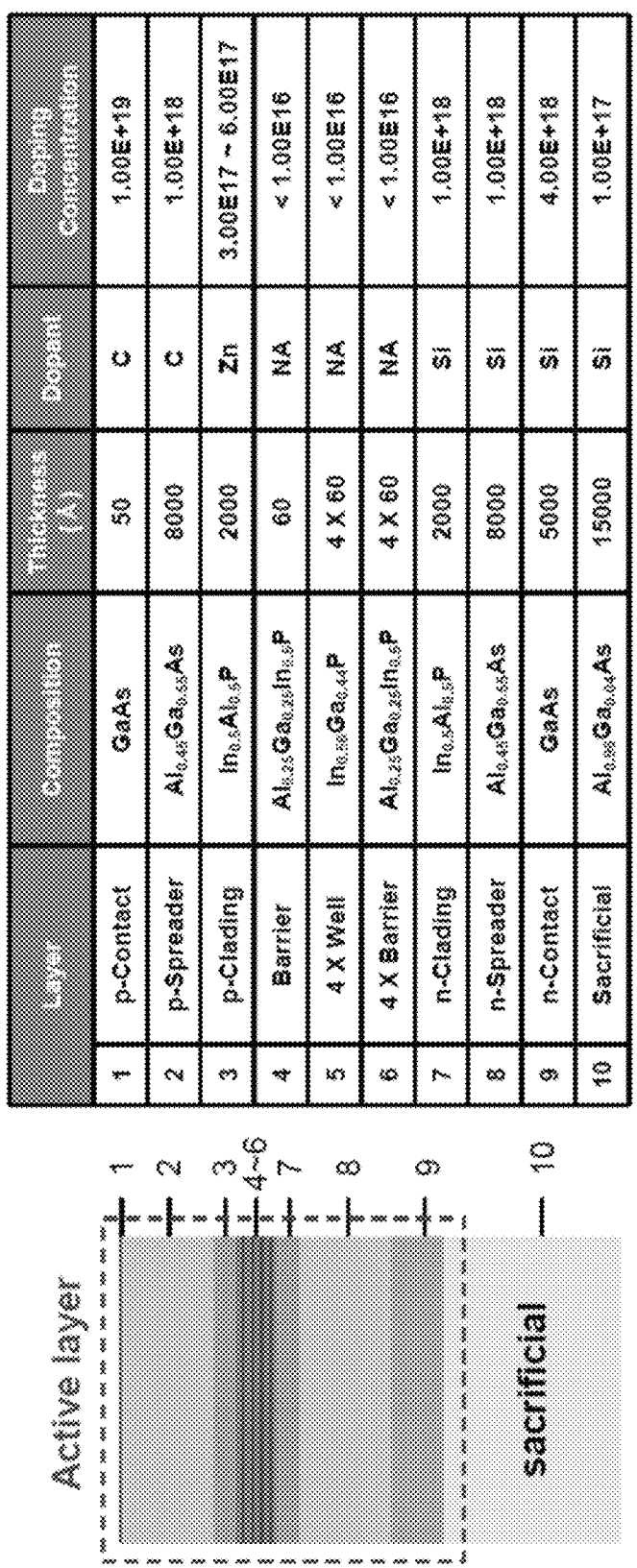
FIG. 17A provides a schematic illustration and composition of a μ-ILED element.

For active materials, thin epitaxial semiconductor layers grown on GaAs wafers are prepared, and then vertically etched to define lateral dimensions of devices built with them. Release from the wafer via selective elimination of an underlying layer of AlAs, followed by transfer printing accomplishes integration on substrates of interest. The fabrication scheme described here uses a dual transfer process that involves first printing the semiconductor materials to a temporary substrate (glass plate coated with a trilayer of epoxy/polyimide (P1)/poly(methylmethacrylate) (PMMA)) for forming contacts, interconnections and structural bridges, and encapsulation layers. Dissolving the PMMA releases fully formed, interconnected collections of devices. A second transfer printing step achieves integration on elastomeric sheets (e.g. poly(dimethylsiloxane), PDMS) or other substrates coated with thin layers of PDMS, with strong bonding only at the locations of the devices. For all examples described in this example, the LEDs (referred to herein as μ-ILEDs to highlight the small sizes and the distinction over organic devices), and the PDs (i.e. μ-IPDs) have lateral dimensions of 100×100 μm and thicknesses of 2.5 μm, corresponding to volumes that are orders of magnitude smaller than those of commercially available devices. The thin geometries are important because they allow the use of thin film metallization for interconnect and optimized mechanical designs, described next. Details of the processing and layouts appear in FIGS. 17-19.

Figure 11A:
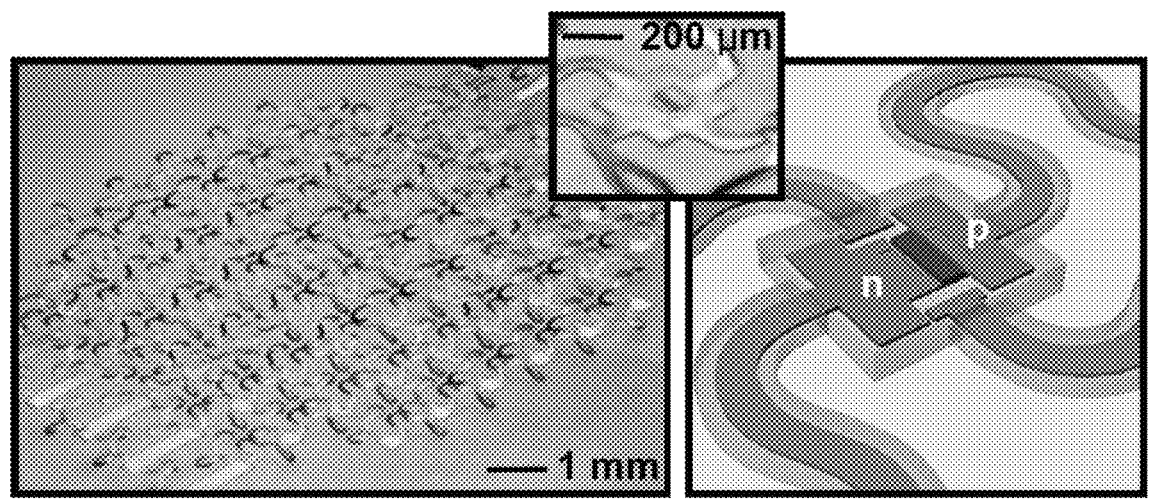
FIG. 11A provides an optical image of an array of µ-ILEDs (left) and a schematic illustration (right) and corresponding photograph (inset) of a single µ-ILED element.

FIGS. 11A and 20 present optical images, schematic illustrations, scanning electron microscope (SEM) images, and finite element modeling of the mechanics of arrays of μ-ILEDs connected by serpentine shaped ribbons that serve as either structural bridges or electrical interconnects, transferred to a thin, pre-strained sheet of PDMS (~400 μm thick). Here, and as described below, the devices are connected in series (FIG. 18A), such that all of them turn on and off together; a single failed device leads to failure of the entire array. The interconnects consist of thin films of metal with photodefined layers of epoxy on top and bottom to locate the metal at the neutral mechanical plane. The bridges are similar, but without the metal. Detailed geometries appear in FIG. 19. Releasing the pre-strain yields non-coplanar layouts in the serpentines via a controlled, non-linear buckling response, as shown in the left frame of FIG. 11A (~20% pre-strain). The right frame and inset of FIG. 11A present a schematic illustration and magnified optical image of a representative μ-ILED, respectively. These design choices are informed by careful studies of the mechanics through three dimensional finite element modeling (3D-FEM) of the complete systems; they represent highly optimized versions of those used for silicon circuits and μ-ILEDs. The results enable stable and robust operation during large scale uniaxial, biaxial, shear and other mixed modes of deformation, as described in the following.

Figure 11B:
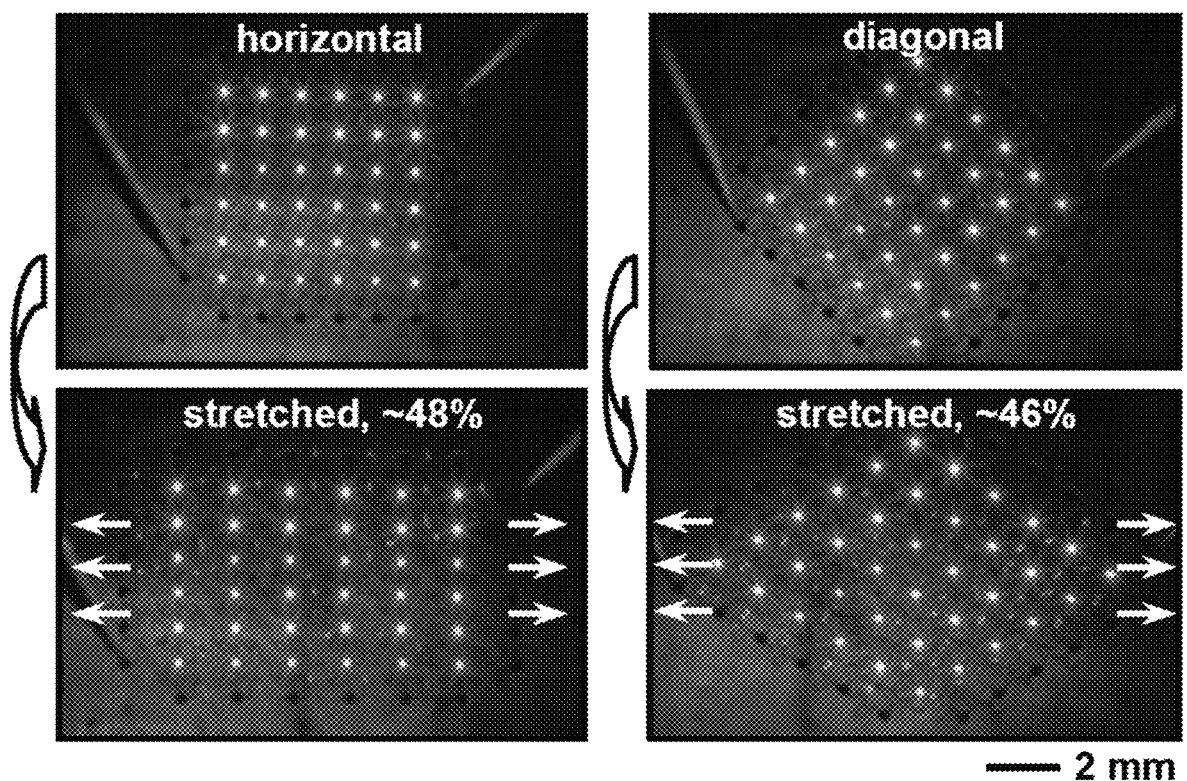
FIG. 11B provides optical images of a stretchable array of µ-ILEDs.
Figure 20A:
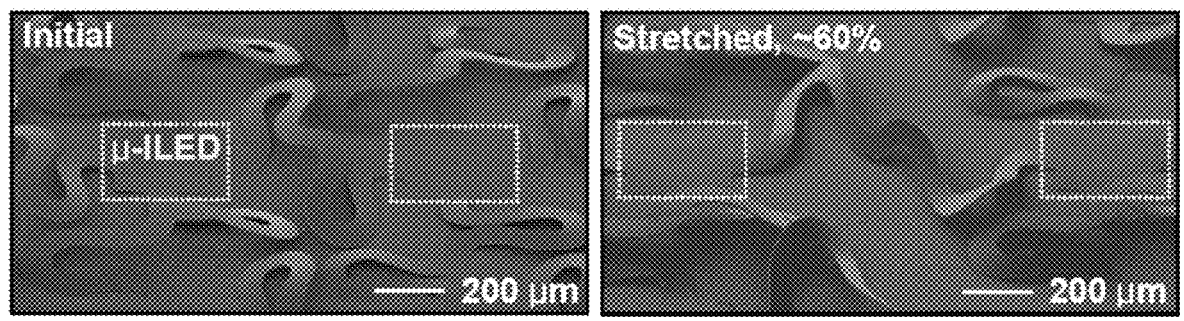
FIG. 20A provides SEM images of adjacent μ-ILEDs before (left) and after (right) stretching along the horizontal direction.
Figure 22:
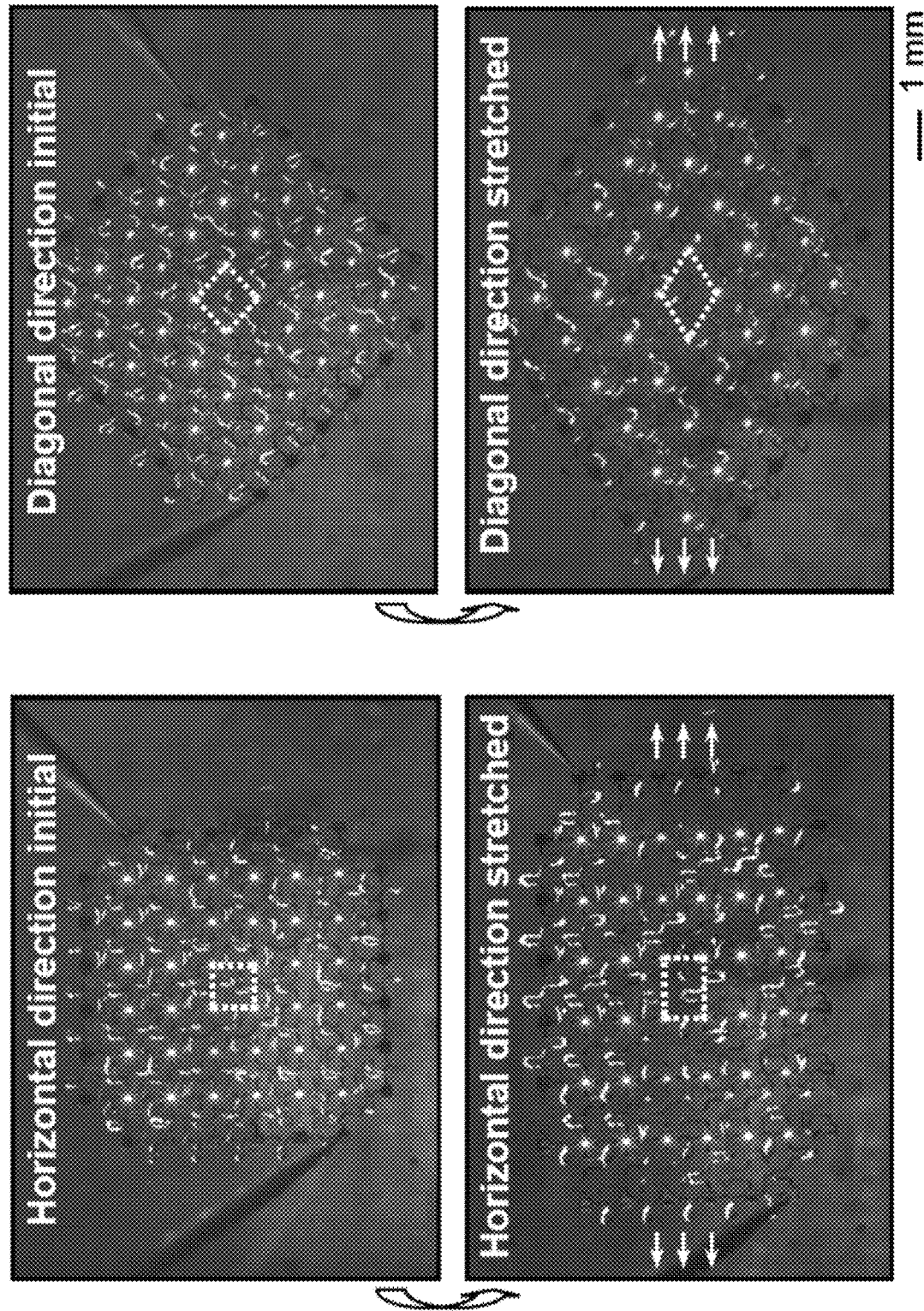
FIG. 22 provides optical images of a 6×6 μ-ILED array.

FIGS. 20A and 21A show tilted view scanning electron microscope (SEM) images and corresponding optical microscope images of adjacent μ-ILEDs and non-coplanar serpentine interconnects formed with ~20% biaxial pre-strain before (left) and after (right) uniaxial stretching (~60%), respectively. The separations between adjacent pixels change by an amount expected from the pre-strain and the applied strain, where a combination of in- and out-of-plane conformational changes in the serpentines accommodate the resulting deformations in a way that avoids any significant strains at the positions of the μ-ILEDs. In particular, 3D-FEM modeling results (FIG. 20B) reveal peak strains in the metal interconnect and the μ-ILEDs that are >300 times smaller than the applied strain (FIG. 21C shows similar results for ~59% stretching along the diagonal direction, corresponding to FIG. 21B). FIGS. 11B and 22 present two dimensional, in-plane stretching of a 6×6 array of μ-ILEDs along horizontal (left) and diagonal (right) directions. The uniform and constant operating characteristics of all devices are clearly apparent in the dark and bright (without and with external illumination) images of FIG. 11B and FIG. 22 as well as in the current-voltage (I-V) characteristics (left frame of FIG. 11C). The applied strains, calculated from the separations of inner edges of adjacent pixels before and after stretching, reach ~48% and ~46% along the horizontal and diagonal directions, respectively. The I-V characteristics are invariant even after 100000 cycles of 75% stretching along the horizontal direction (right frame of FIG. 11C).

Uniaxial stretching and compressing are among the simplest modes of deformation. Others of interest include biaxial, shear and related. The results of FIGS. 11D-G, and 23 demonstrate the ability of the reported designs to allow these sorts of motions, through large strains induced by pneumatic pressure, achieved by inflation of a thin (500 μm) membrane of PDMS that supports an array similar to that of FIG. 11B. Injecting air through a syringe in a specially designed cylinder that serves as a mount for the device deforms the initially flat array (top frame of FIG. 11D) into a balloon shape (bottom frame of FIG. 11D). FIG. 11E shows four pixels in the 'flat' (top) and 'inflated' states (bottom) during operation, with external illumination. The area expansion induced in this manner can reach ~85% without any device failures. The I-V characteristics also show no appreciable differences between the flat and inflated states (FIG. 11F). 3D-FEM is used to model the inflation induced deformation of a circular elastomeric membrane, with the same thickness (500 μm) and diameter (20 mm) as in experiment, but without a mounted μ-ILED array. As illustrated in FIGS. 11G and 23C, both the circumferential and meridional strains reach ~37.3% when inflated to a height of 8.3 mm, the same as in the bottom frame of FIG. 11D. Measured displacements of devices in the system of the bottom frame of FIG. 11E indicate strains of ~36%, which are comparable to values calculated by 3D-FEM. This observation suggests an important conclusion: with the designs reported here, the arrays provide negligible mechanical loading of the soft, elastomeric membrane support, consistent with the very low effective modulus provided by the optimized, non-coplanar serpentines.

Figure 11D:
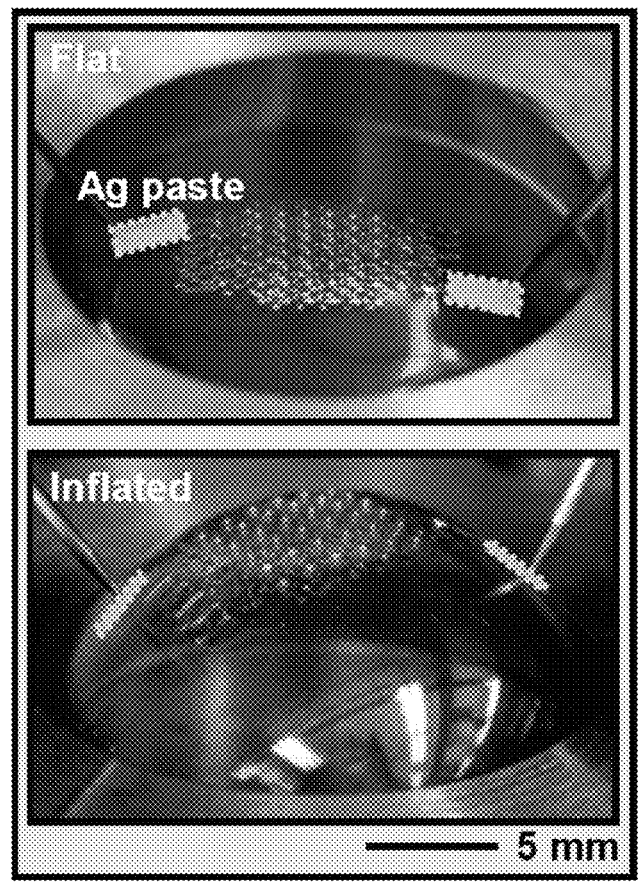
FIG. 11D provides optical images of a stretchable array of µ-ILEDs on a thin PDMS membrane in a flat configuration (top) and in a hemispherical, balloon state (bottom) induced by pneumatic pressure.
Figure 12A:
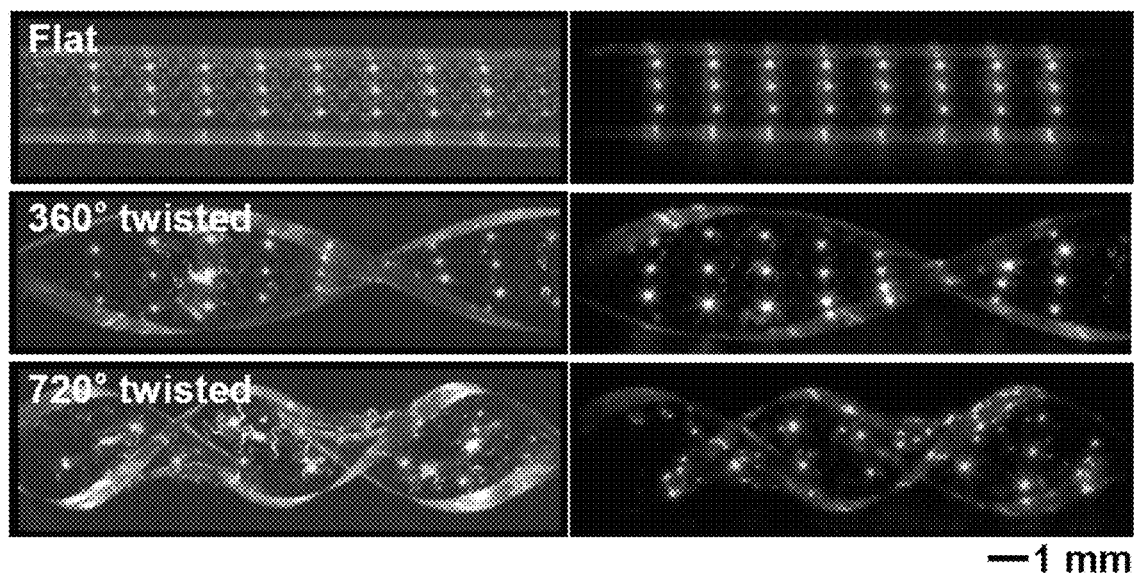
FIG. 12A provides optical images of an array of µ-ILEDs on a band of PDMS twisted to different angles, collected with (left) and without (right) external illumination.
Figure 12B:
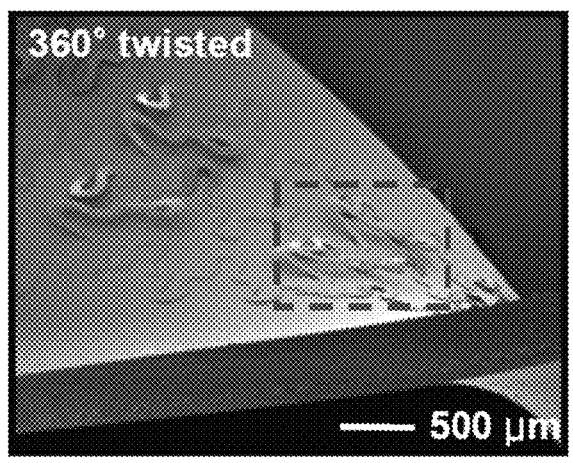
FIG. 12B provides an SEM image of the array when twisted to 360°.
Figure 12C:
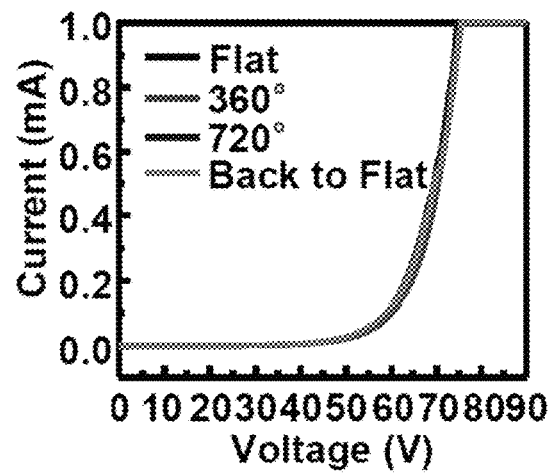
FIG. 12C provides data showing I-V characteristics of the array twisted by various amounts.
Figure 12D:
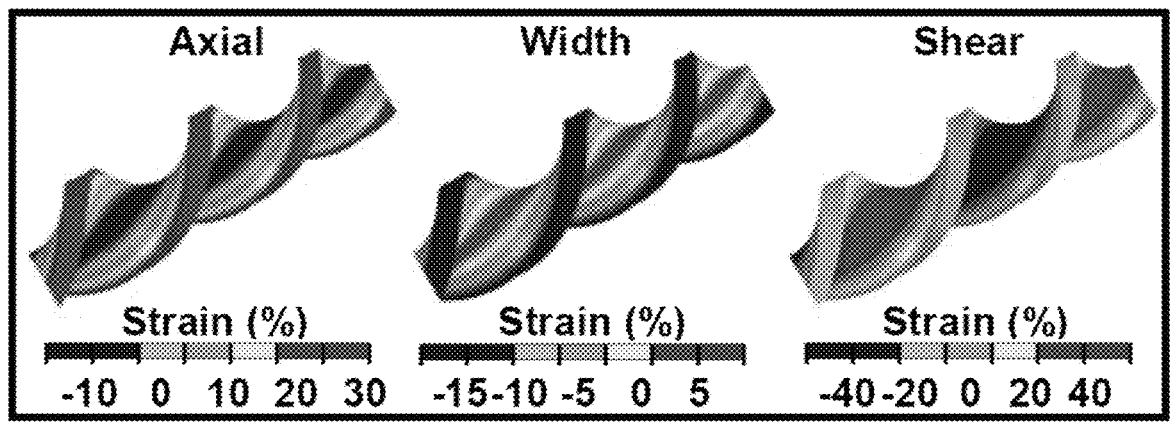
FIG. 12D shows axial strain, width strain, and shear strain.
Figure 12E:
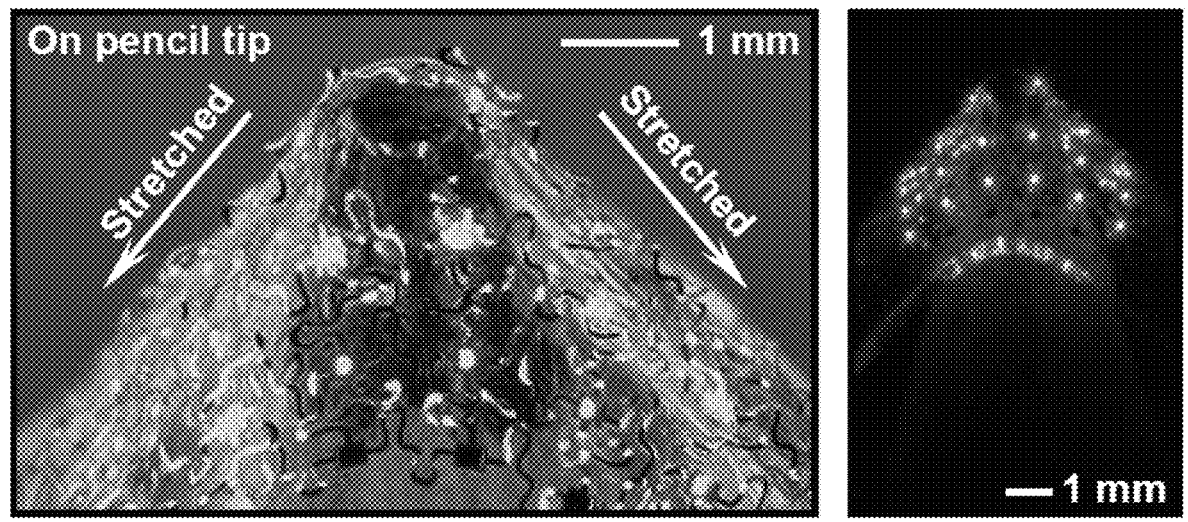
FIG. 12E provides optical images of an array of p-ILEDs stretched on the sharp tip of a pencil, collected with (left) and without (right) external illumination. The white arrows indicate the direction of stretching.
Figure 12F:
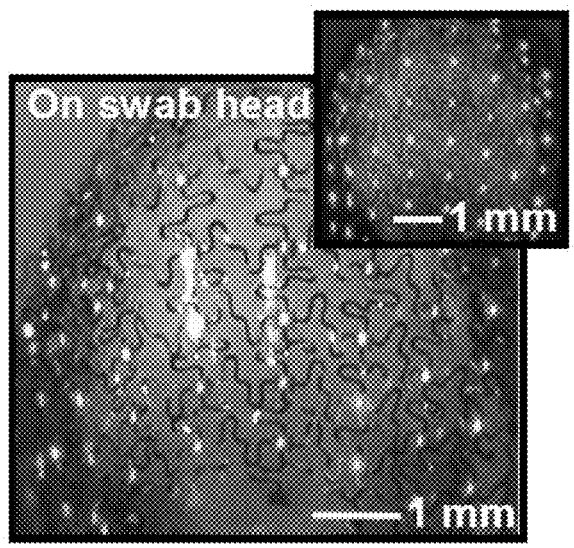
FIG. 12F provides optical images of a stretchable µ-ILED array wrapped and stretched downward on the head of a cotton swab; the inset image was obtained without external illumination.
Figure 12G:
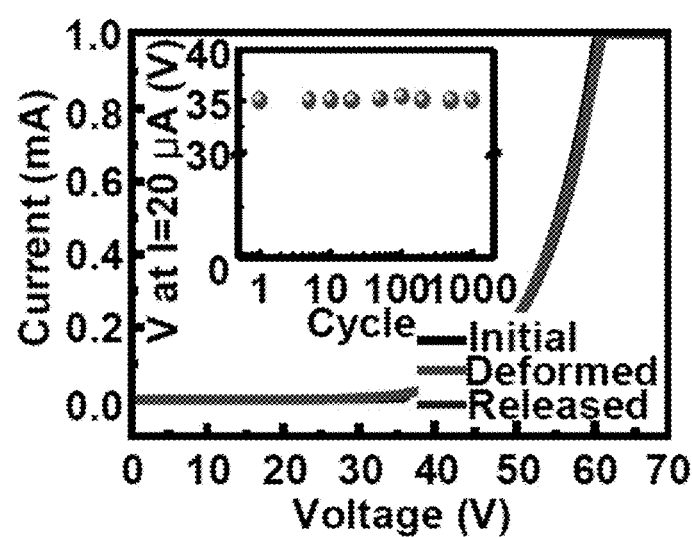
FIG. 12G provides data showing I-V characteristics of the array in FIG. 12E, before (initial), during (deformed) and after (released) deformation; the inset provides a graph of the voltage needed to generate a current of 20 µA, measured after different numbers of cycles of deformation.

Corkscrew twisting (FIG. 12A) provides another well-defined mode of deformation that is of interest. Here, large shear strains occur in addition to stretching/compressing in the axial and width directions. The device test structure in this case consists of a 3×8 array of μ-ILEDs transferred to a band of PDMS without pre-strain (see FIG. 24A for details). Optical images of flat, 360°, and 720° twisting deformations with (left) and without (right) external illumination (FIG. 12A) reveal uniform and invariant emission. These strains lead to out-of-plane motions of the serpentines, as shown in FIGS. 12B and 24B. The μ-ILEDs remain attached to the PDMS substrate due to their strong bonding. Electrical measurements indicate similar I-V characteristics with different twisting angles (FIG. 12C) and at different stages of fatigue tests, as shown in FIG. 24C. FIG. 12D presents distributions of various strain components, evaluated at the surface of a band of PDMS with thickness 0.7 mm by 3D-FEM: axial stretching (left frame), width stretching (middle frame) and shear (right frame). (For 360° twisting, see FIG. 25). The results demonstrate that the PDMS surface undergoes both extreme axial/width stretching and shear deformations, with shear dominating, and reaching values of ~40% for the 720° twist. As for the case of FIGS. 11D and 11G, the distributions of strain for the bare PDMS substrate can provide reasonably good estimates for the system. These controlled uniaxial (FIG. 11B), biaxial (FIG. 11D) and twisting (FIG. 12A) modes suggest an ability to accommodate arbitrary deformations. As two examples, FIGS. 12E and 12F show cases of stretching onto the sharp tip of a pencil and wrapped onto a cotton swab. The array of 6×6 μ-ILEDs pulled onto the pencil (red arrows indicate stretching directions) experiences local, peak strains of up to ~100%, estimated from distances between adjacent devices in this region. Similar but milder and more spatially distributed deformations occur on the cotton swab, with an 8×8 array. In both cases, observation and measurement indicate invariant characteristics, without failures, even in fatigue tests (FIGS. 12G and 26).

Figure 13A:
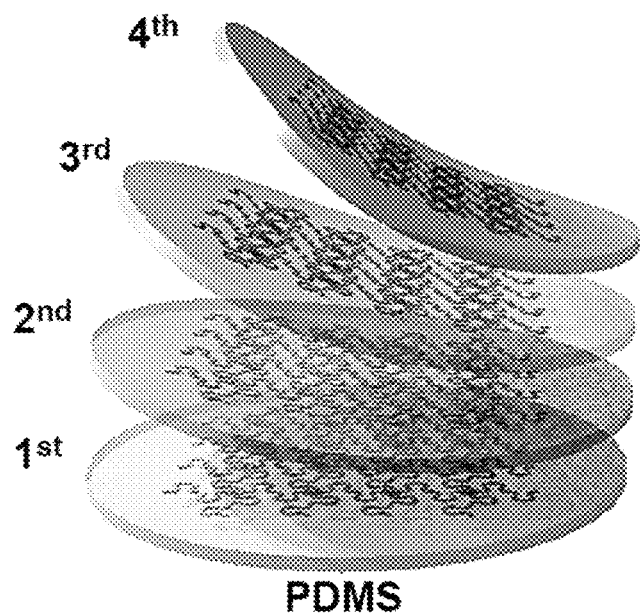
FIG. 13A provides a schematic, exploded view illustration for a stacked device formed by multilayer lamination.
Figure 13B:
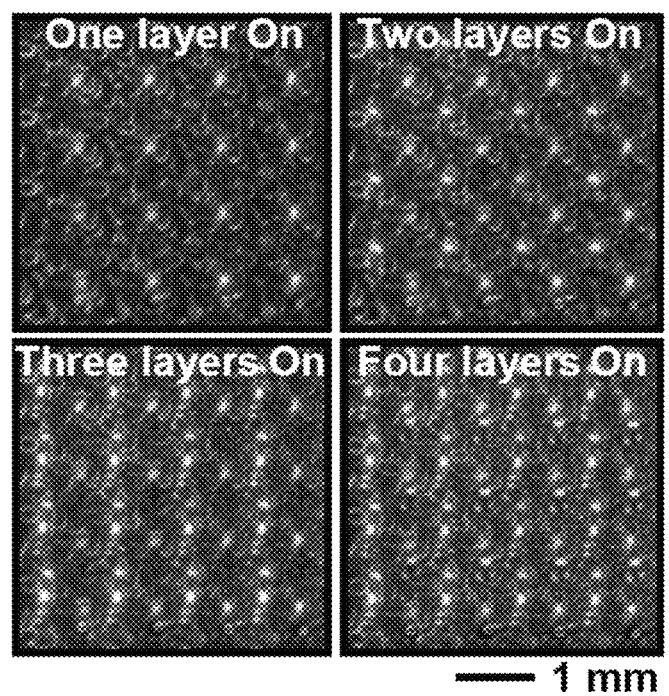
FIG. 13B provides optical images of a four layer stack of µ-ILEDs.
Figure 13C:
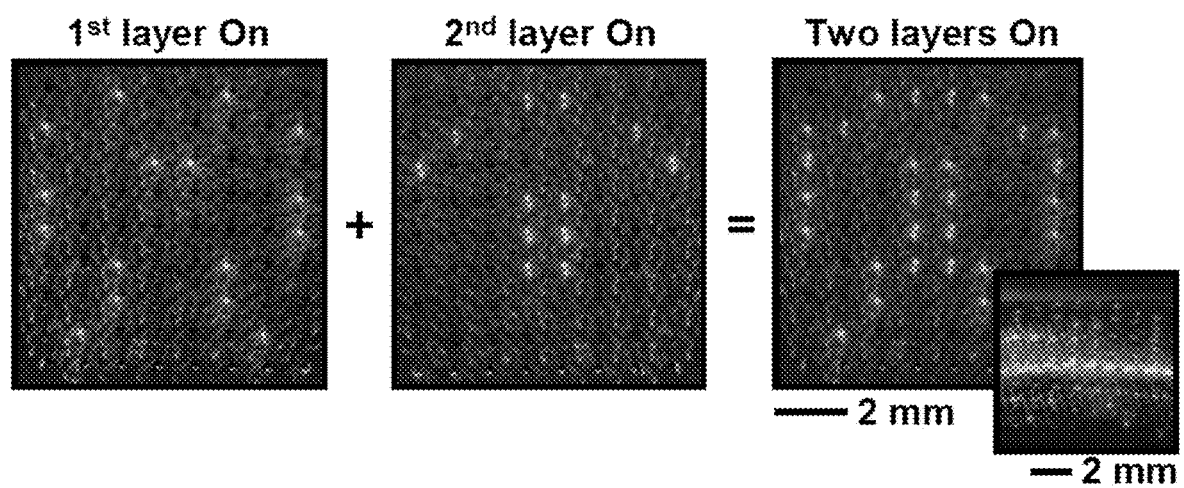
FIG. 13C provides optical images of a two layer stack of μ-ILEDs.
Figure 27A:
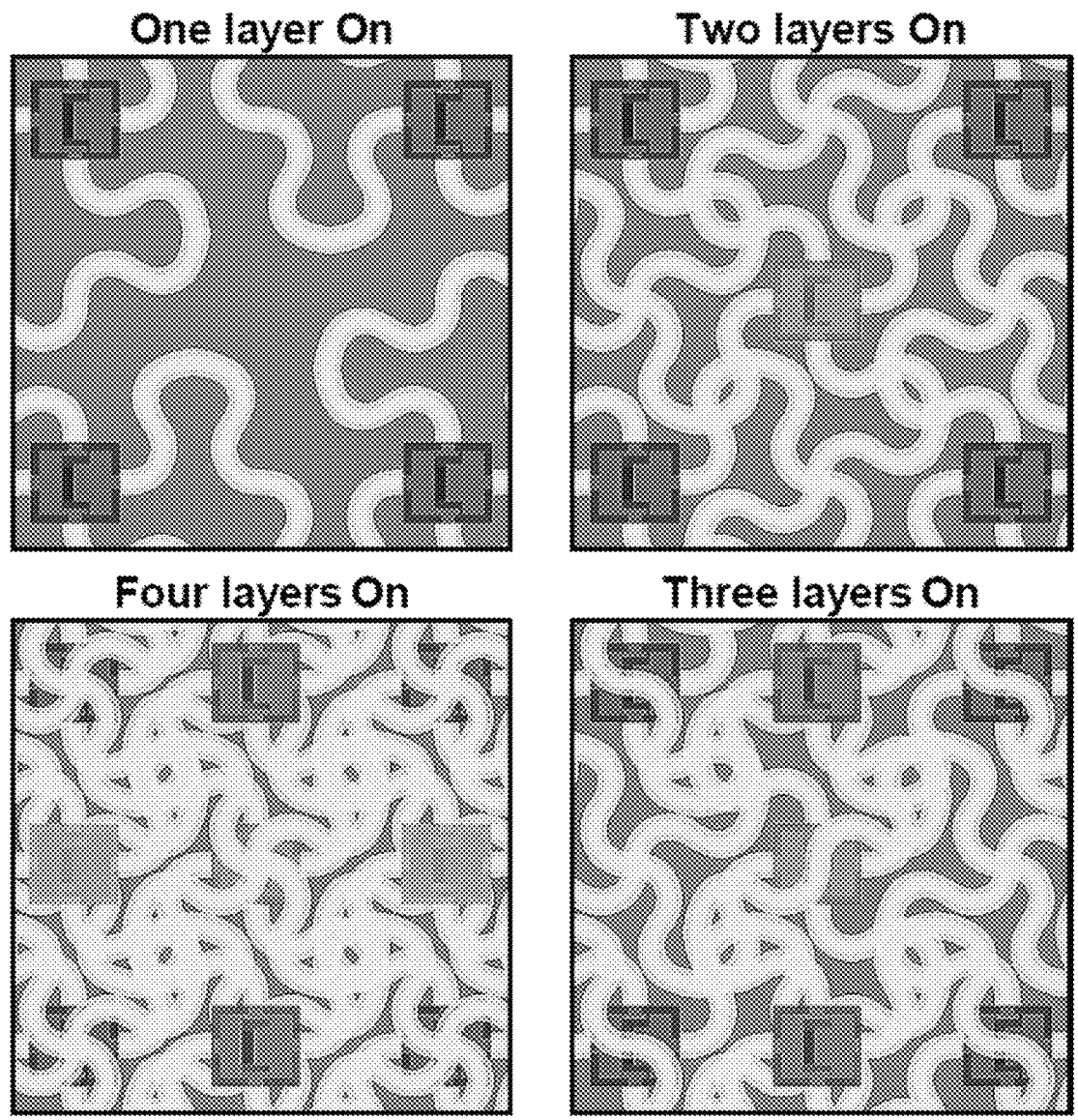
FIG. 27A provides a schematic illustration of stacked devices.
Figure 27B:
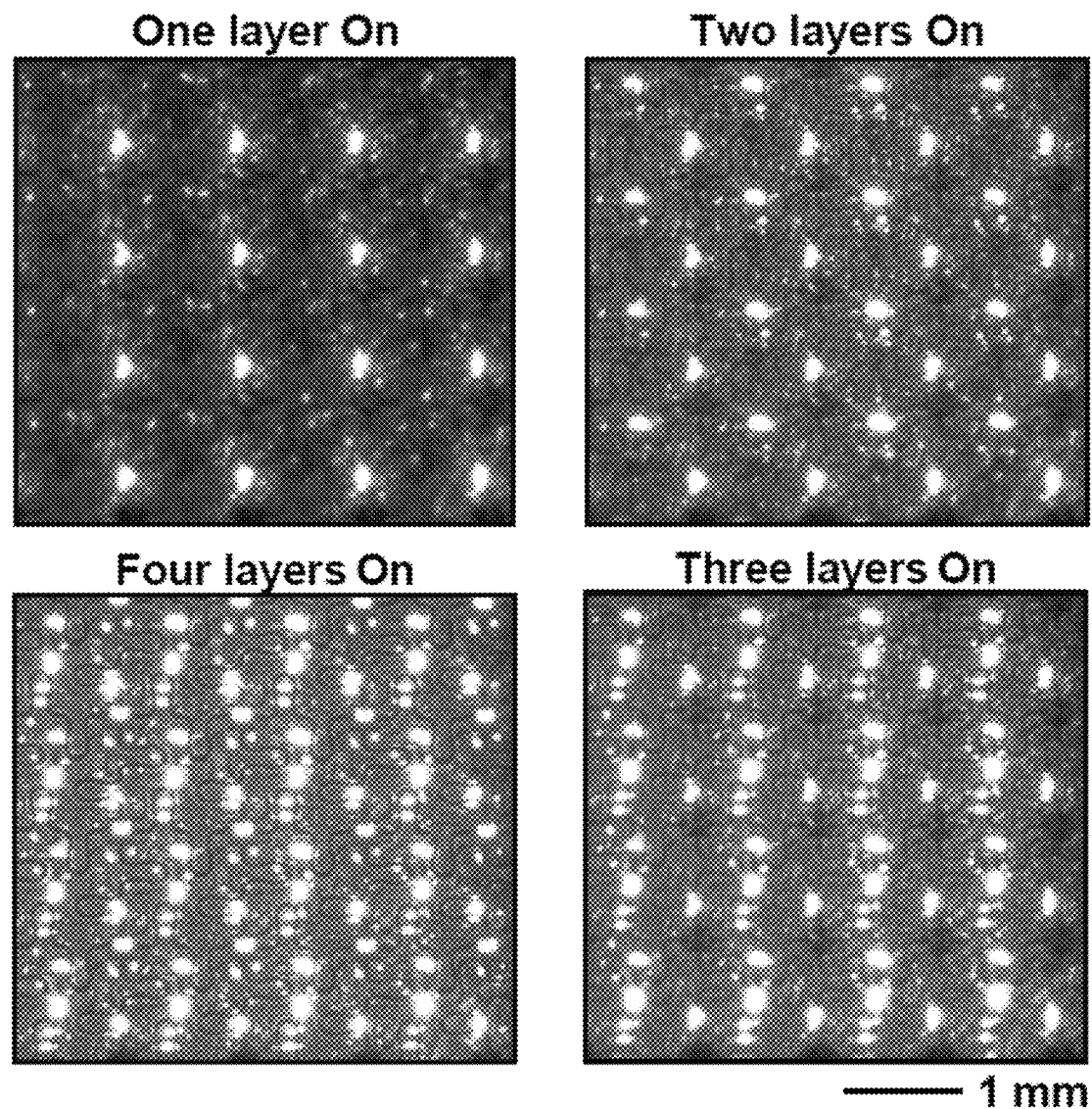
FIG. 27B provides optical images of stacked devices collected without external illumination.
Figure 28A:
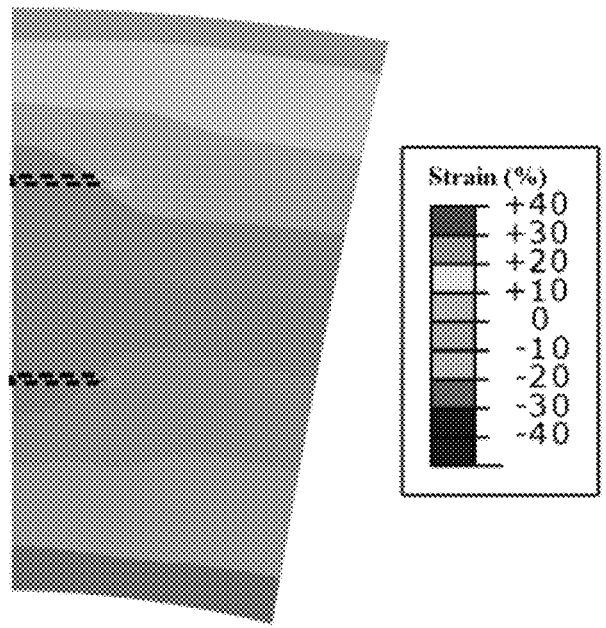
FIG. 28A provides data showing the strain distribution of a two-layer system in a stacked array bent to a radius of curvature 2 mm.
Figure 28B:
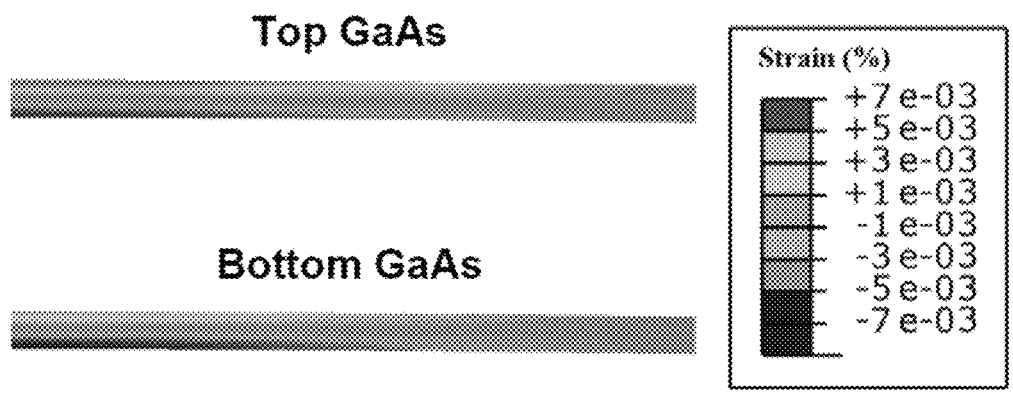
FIG. 28B provides data showing the strain distribution in layers of a μ-ILED island.

A feature of the layouts that enable these responses is the relatively small area coverage of active devices, such that the serpentine structures can absorb most of the motions associated with applied strain. An associated disadvantage, for certain applications, is that only a small part of the overall system emits light. This limitation can be circumvented with layouts that consist of multilayer stacks of devices, in laminated configurations, with suitable spatial offsets between layers. The exploded view schematic illustration in FIG. 13A shows this concept with four layers. FIG. 27 provides details. Integration is accomplished with thin coatings of PDMS (~300 μm) that serve simultaneously as elastomeric interlayer dielectrics, encapsulants and adhesives. Here, each layer consists of a substrate of PDMS (300 μm thick) and an array of LEDs (total thickness with interconnect, ~8 μm). The total thickness of the four layer system, including interlayers of PDMS, is ~1.3 mm. Optical images of emission from a four layer system appear in FIG. 13B (with external illumination) and FIG. 27B (without external illumination). FIG. 13C shows a two layer case, where each layer lights up in a different pattern. The inset on the right illustrates the same system in a bent state (bending radius=2 mm), where the maximum strain in top and bottom GaAs layers is only 0.006% and 0.007%, respectively as shown by 3D-FEM simulation (FIG. 28). The PDMS interlayers restrict the motion of the serpentines, but by an amount that reduces only slightly the overall deformability. The extent of free movement can be maximized by minimizing the modulus of the encapsulant. Here, PDMS was mixed in a ratio to yield a Young's modulus of ~0.1 MPa, to retain nearly ~90% of the stretchability of the unencapsulated case.

Figure 13D:
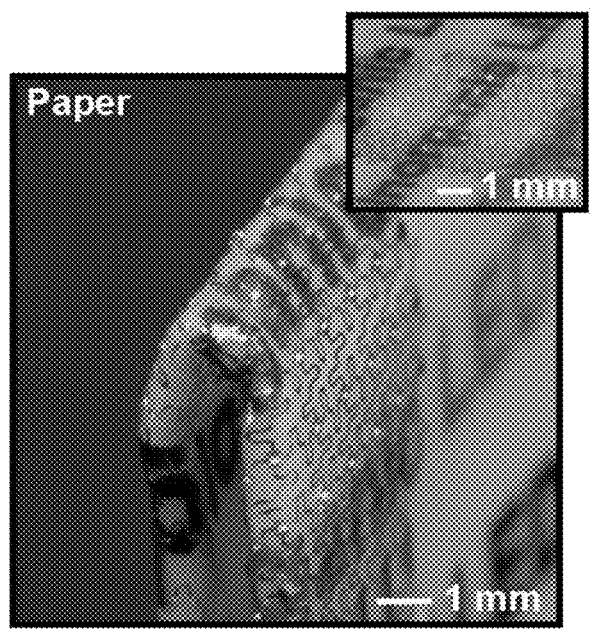
FIG. 13D provides an optical image of an array of μ-ILEDs on a piece of paper, in a folded state; the inset shows the device in its flat state.
Figure 13E:
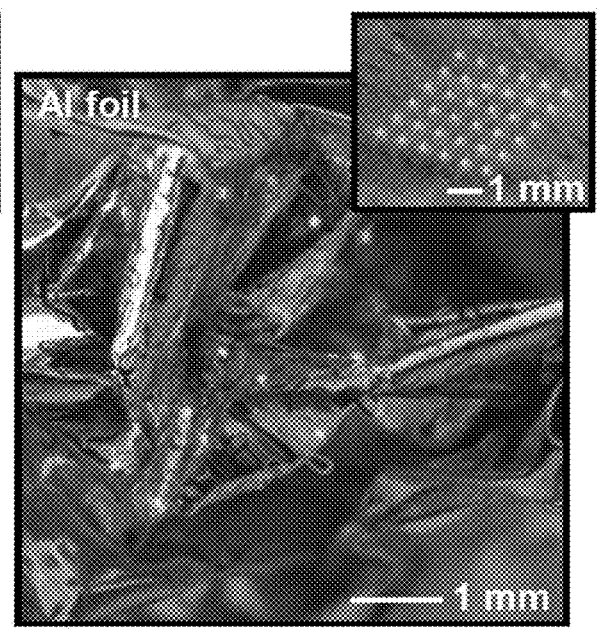
FIG. 13E provides an optical image of an array of μ-ILEDs on a sheet of aluminum foil in a crumpled state; the inset shows the device in its flat state.
Figure 13F:
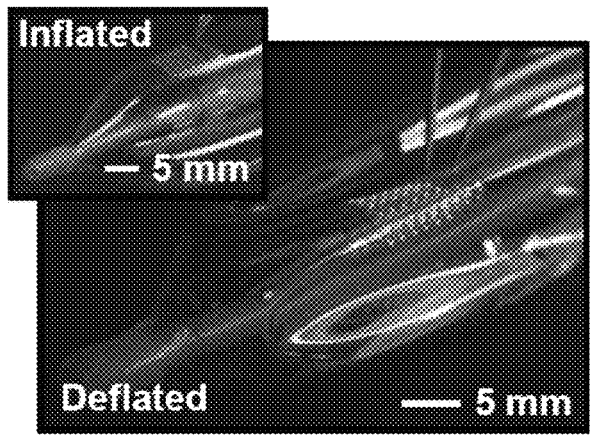
FIG. 13F provides optical images of an array of μ-ILEDs on a catheter balloon in its inflated (inset) and deflated states.
Figure 29D:
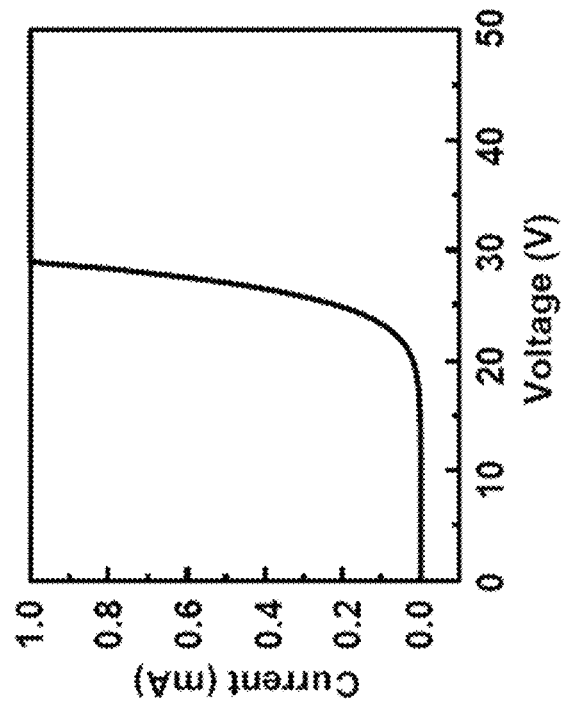
FIG. 29D provides data showing I-V characteristics in the bent state as shown in FIG. 29C.
Figure 29C:
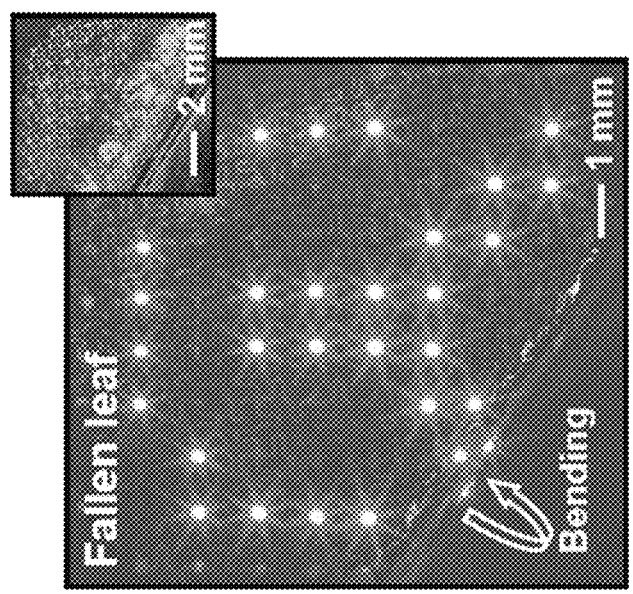
FIG. 29C provides and optical image of an 8×8 μ-ILED array integrated on a fallen leaf in its bent and on state; the inset image was collected with external illumination.

The favorable mechanical characteristics enable integration onto a variety of substrates that are incompatible with conventional optoelectronics. As demonstrations, μ-ILED devices were built on swatches of fabric (FIG. 29A), tree leaves (FIG. 29C), sheets of paper (FIG. 13D), pieces of aluminum foil (FIG. 13E) and balloon catheters (FIG. 13F). In all cases, transfer printing successfully delivers the devices to these substrates with thin (~50 μm) coatings of PDMS that serve as planarizing and strain isolating layers, and as adhesives. Bending and folding tests for each case indicate robust operation under deformed states. The smallest bending radii explored experimentally were 4 mm, 2.5 mm, and 400 μm for the fabric, leaf, and paper, respectively. Theoretical modeling, using Young's moduli and thicknesses 1.2 MPa, 800 μm, 23.5 MPa, 500 μm, 600 MPa and 200 μm for the fabric, leaf and paper, respectively, shows that the fabric, leaf and paper can be completely folded, in the sense that the strain in the GaAs remains much smaller than its failure strain (~1%) even when the bend radius equals the substrate thickness. Without the strain isolation provided by the PDMS, the fabric can still be folded, but the leaf and paper can only be bent to minimal radii of 1.3 mm and 3.5 mm, respectively. This result occurs because the Young's modulus of PDMS (0.4 MPa) is much smaller than those of leaf and paper (i.e., strain isolation), while the Young's moduli of PDMS and fabric are more similar. Random wrinkling, including multi-directional folding with inward and outward bending can be accommodated, as is apparent in the devices on paper and aluminum foil (~30 μm). In images of the latter case (FIG. 13E), the number density of wrinkles reaches ~200 per $cm^2$ with approximate radii of curvature as small as 150 μm (See FIGS. 29-34 for additional images, plots of I-V characteristics, results of fatigue tests, and surface topography of these substrates).

Figure 13G:
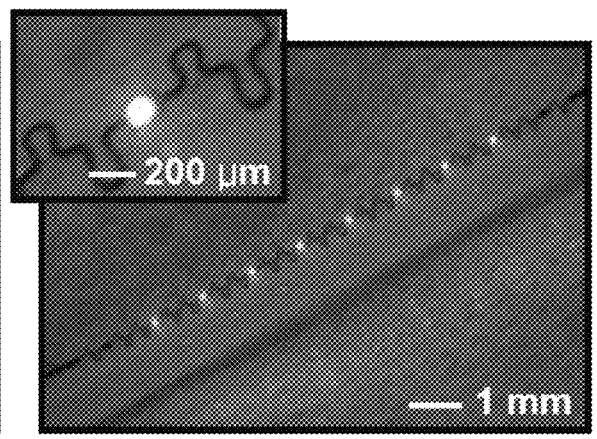
FIG. 13G provides optical images of an array of μ-ILEDs on a rigid plastic tube; the inset shows a magnified view of a single ILED.
Figure 13H:
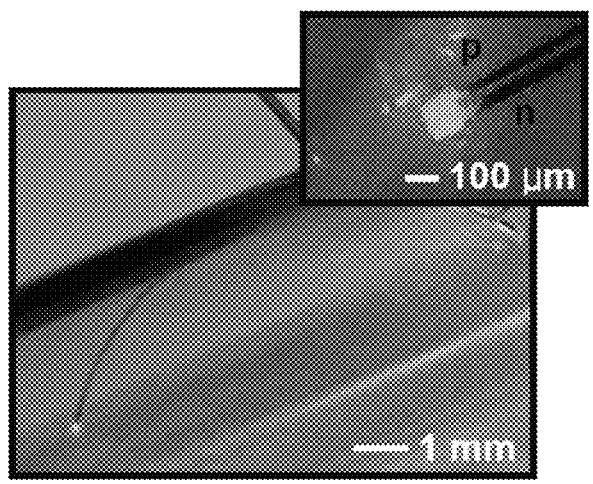
FIG. 13H provides an optical image of an isolated μ-ILED with straight interconnects wrapped around a glass tube; the inset provides a magnified view.
Figure 13I:
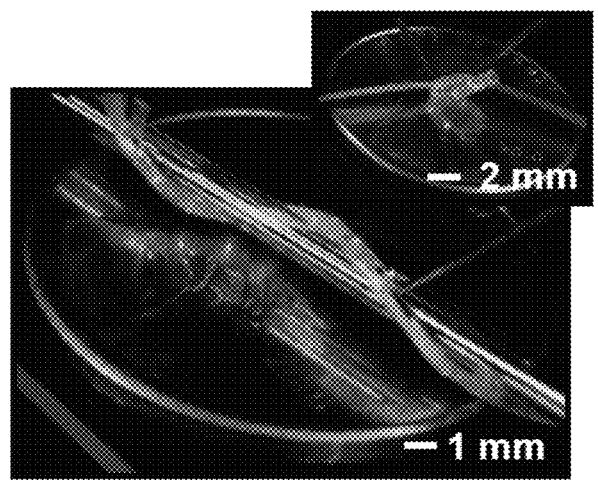
FIG. 13I provides an optical image of an array of μ-ILEDs on a fiber, wrapped around a glass tube; the inset shows an image of an array of μ-ILEDs on a fiber in a knotted state.
Figure 32A:
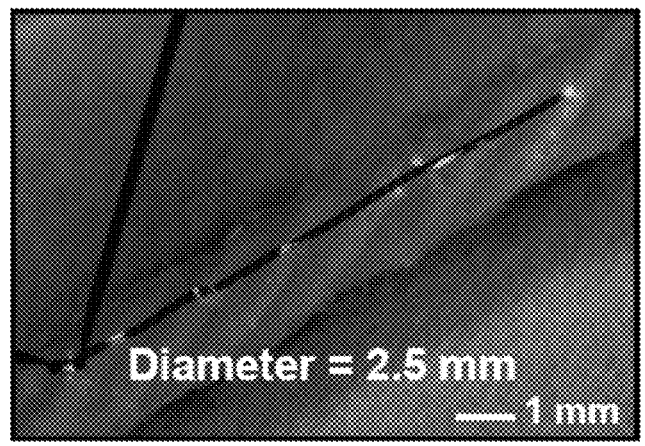
FIGS. 32A, 32B and 32C provide optical images of μ-ILEDs integrated on flexible threads.
Figure 32B:
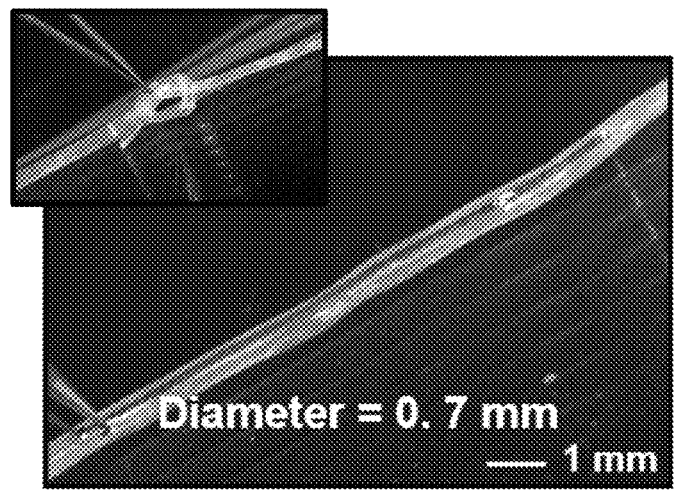
Figure 32C:
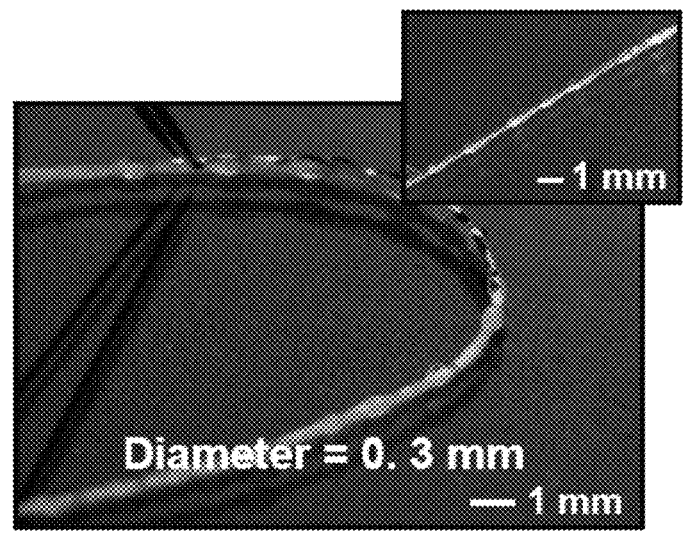
Figure 32D:
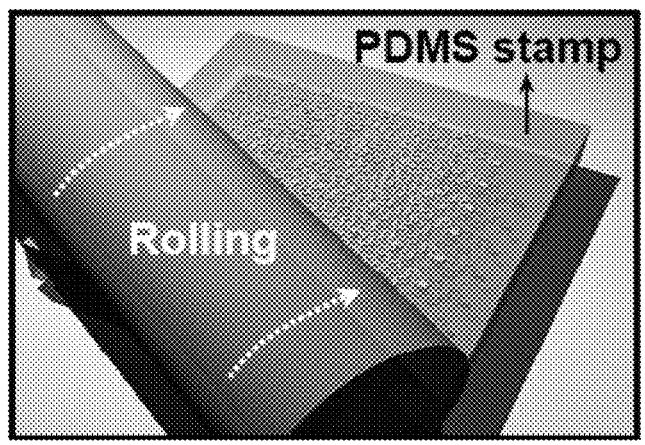
FIG. 32D provides a schematic illustration describing a 'rolling method' for transfer printing.
Figure 32E:
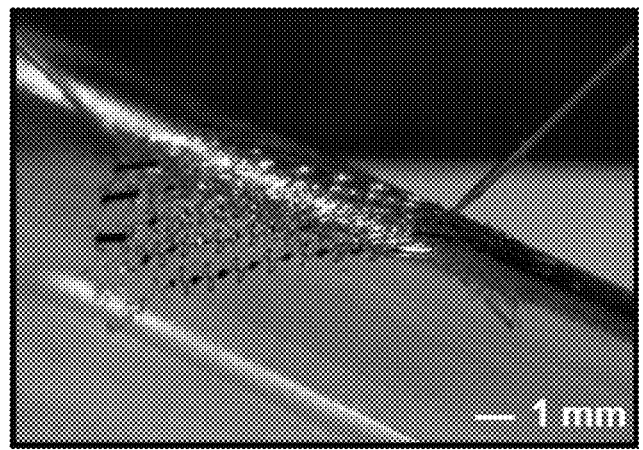
FIG. 32E provides an optical image of a 4×6 μ-ILED array on a glass tube using a rolling method for printing.

The arrays of μ-ILEDs mounted on the surface of an otherwise conventional catheter balloon (FIG. 13F) enables highly localized photodynamic drug delivery to selectively treat a variety of intraluminal tumors and cardiovascular disorders, including atherosclerotic plaque lesions. Phototherapy (e.g., stabilization of plaque) and spectroscopic characterization of arterial tissue represent other uses. Thin threads and fibers represent other substrates of biomedical interest, due to their use as sutures and implants, as described next. FIGS. 13G and 13H present images of an array of μ-ILEDs (1×8) with serpentine metal bridges and a single μ-ILED device with long (1.25 cm×185 μm) metal interconnects, both on flexible, thin (~8 μm) ribbons mounted onto cylindrical supports. FIG. 13I shows related systems, consisting of μ-ILED arrays on pieces of thread, and wrapped around a rod and tied in a knot (inset). FIGS. 32A-C provide additional images with different thicknesses of conventional threads. Threads of nylon (FIG. 13I) and cotton (FIGS. 32A-C) were explored, with diameters of ~0.7 mm, ~2.5 mm, and ~0.7 mm, ~0.3 mm, respectively. Integration on these and other small substrates is challenging with the usual techniques for transfer printing. Instead, threads were rolled over the glass carrier substrate in a manner that avoided the use of a separate transfer stamp and the associated difficulties in alignment and contact (see FIGS. 32D-E). As clearly illustrated in FIG. 13I, the optimized mechanical designs described previously enable these systems to be twisted, bent and tied into knots without affecting the operation, even when encapsulated with PDMS. The approximate minimum bending radii for main and inset frame of FIG. 13I is ~3 mm and ~0.7 mm, respectively.

Figure 14A:
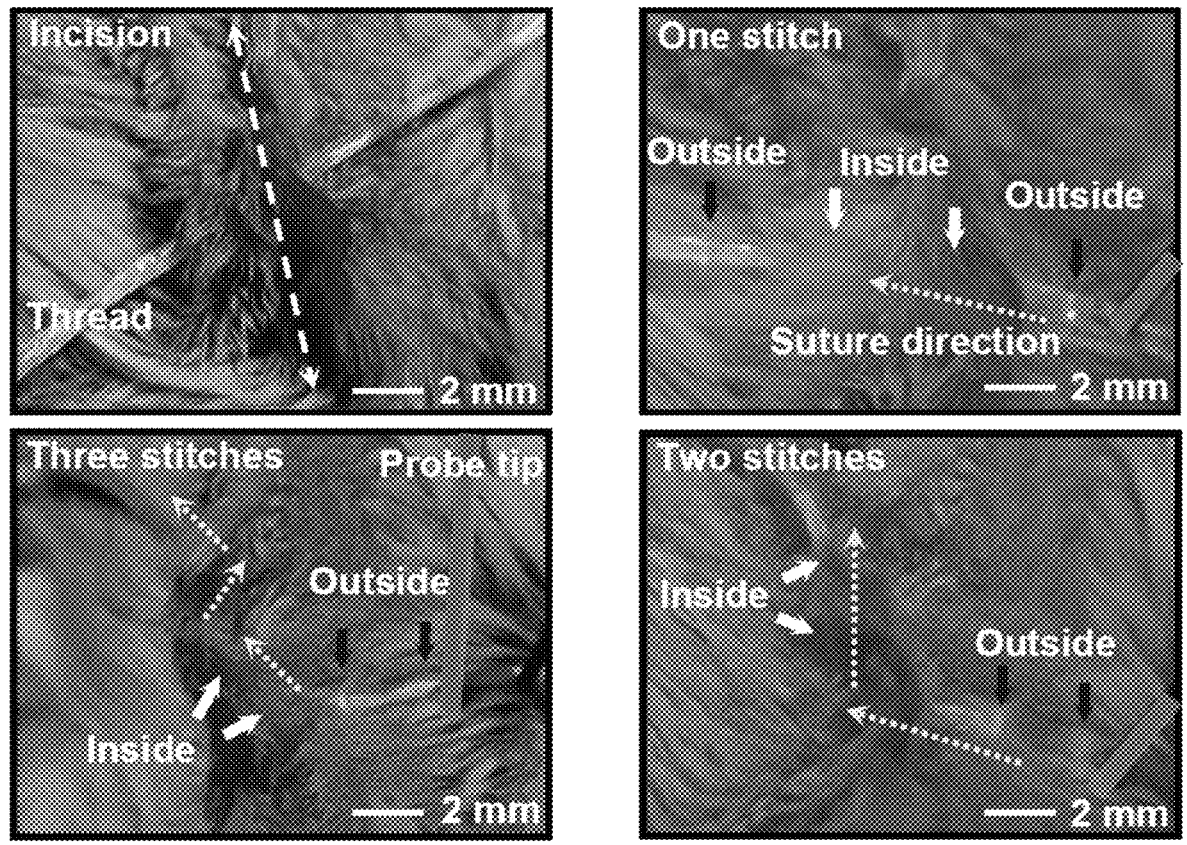
FIG. 14A provides optical images of a light emitting suture in an animal model with a conventional suture needle.
Figure 32F:
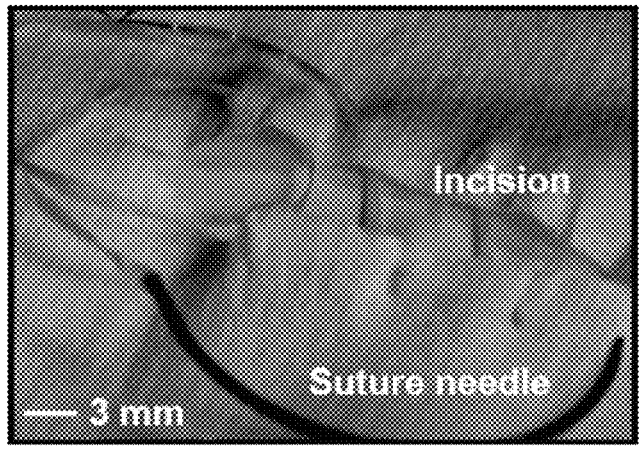
FIG. 32F provides an optical image showing a suture demonstration using a μ-ILED array mounted on a thread at an incision in paper.

FIG. 14A demonstrates the use of a device like those in FIG. 13I as a light emitting suture in an animal model, manipulated with a conventional suture needle starting from the initial incision (upper left) to the completion of three stitches (lower left; FIG. 32F shows an incised paper sheet sutured with a similar device, in a similar manner). The 1×4 array of μ-ILEDs in this case operates without any failures, due partly to favorable mechanics as described previously but also to a fully encapsulating layer of PDMS as a soft, elastomeric and biocompatible barrier to the surrounding tissue and associated biofluids. This layer prevents device degradation and electrical shorting through the surrounding biofluid or to the tissue; its low modulus avoids any significant alteration in the overall mechanics, as described above. The frames in FIG. 14A show a few of the μ-ILEDs in the array deployed subcutaneously, and others on the outer epidermis layer of skin (The white and blue arrows in the images correspond to pixels located on the subdermal and epidermal, respectively. The yellow dotted arrows highlight the stitch directions.). Such light emitting, 'photonic', or 'light-emitting', sutures are useful for accelerated healing and for transducers of vital signs or physiological parameters such as blood oxygenation and perfusion. Alternatively, for longer term implantable applications, subdermal μ-ILEDs can overcome scattering limitations and bring in-vivo illumination to deep layers of tissue. This approach could yield capabilities complementary to those of fiber-optic probe-based medical spectroscopic methods, by enabling real-time evaluation of deep-tissue pathology while allowing precise delivery of radiation in programmable arrays. Such devices can be formed in geometries of strips or threads, or of sheets. As an example of the latter, the left frame of FIGS. 14B and S17 show a schematic exploded view and an illustration of fabrication procedures, respectively, for a 5×5 array of μ-ILEDs on a thin sheet of polyethylene terephthalate (PET; Grafix DURA-RAR, 50 μm thickness) film coated with an adhesive layer (epoxy) and encapsulated on top and bottom with PDMS. Thin (~500 μm) ceramic insulated gold wires that connect to metal pads at the periphery of the array provide access to external power supplies. FIG. 14C presents a picture of an animal model with the device implanted subdermally in direct contact with the underlying musculature (See methods section for details). The inset shows the same device before implantation. For continuous operation at the current levels reported here, peak increases in temperature at the tissue of a couple of degrees C. are estimated. Short pulsed mode operation could further minimize the possibility of adverse thermal effects and also, at the same time, allow the use of phase-sensitive detection techniques for increasingly sophisticated diagnostics, imaging and physiological monitoring.

Figure 15A:
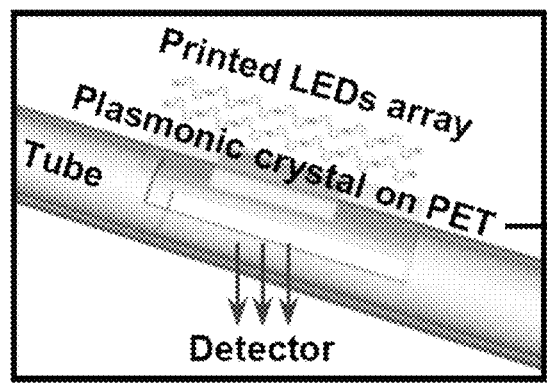
FIG. 15A provides a schematic illustration of a flexible plasmonic crystal device.
Figure 15B:
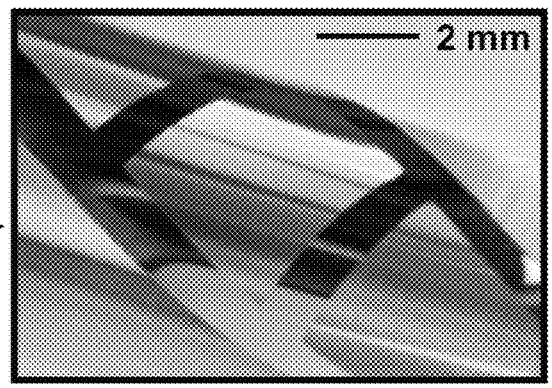
FIG. 15B shows an optical image of a thin, molded plasmonic crystal on a plastic substrate wrapped around a cylindrical support.
Figure 15C:
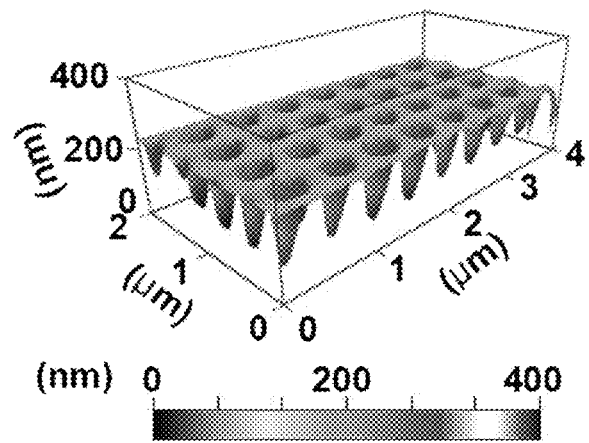
FIG. 15C provides an atomic force microscope image of the surface of a plasmonic crystal.
Figure 15D:
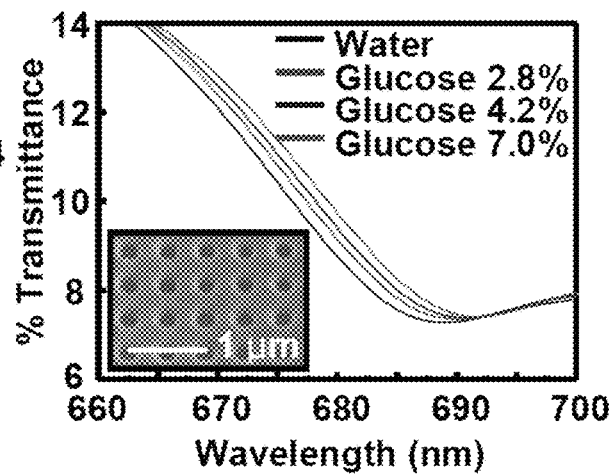
FIG. 15D provides data showing transmission spectra collected over a range of wavelengths relevant for illumination of a plasmonic crystal by μ-LEDs.
Figure 15E:
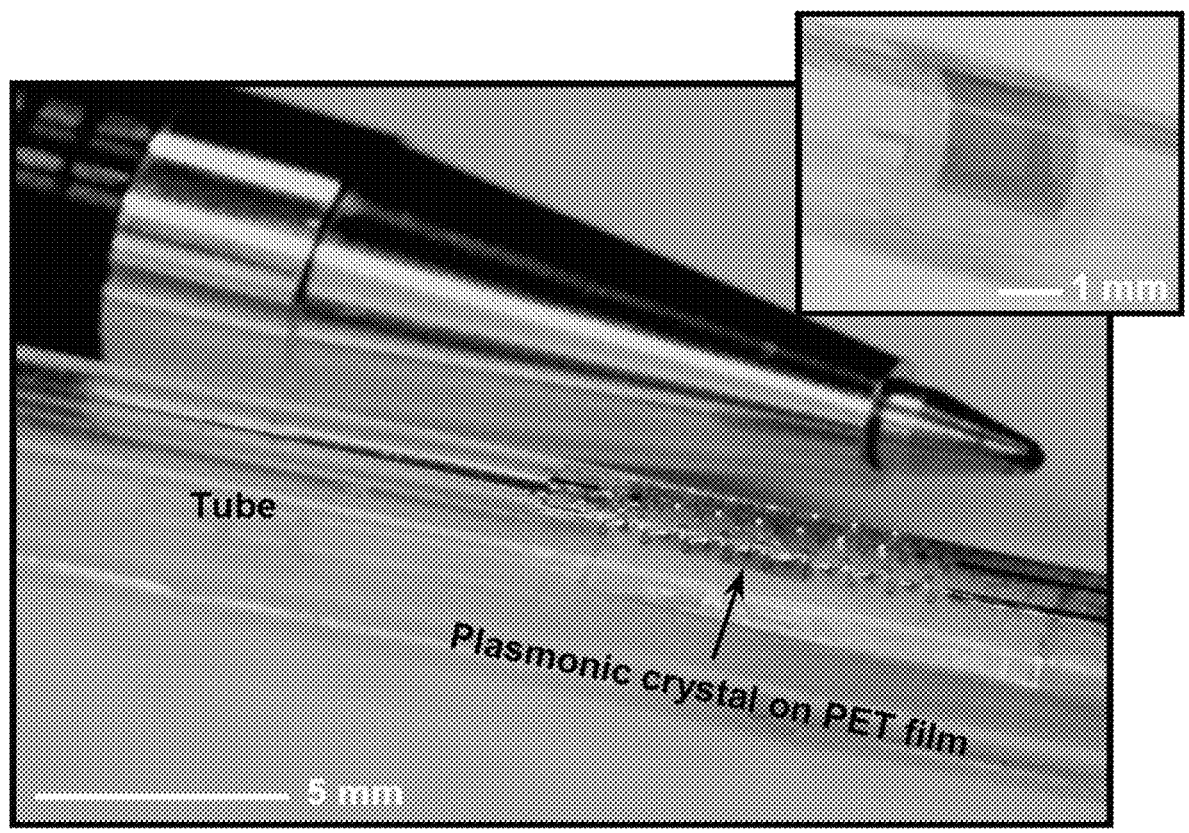
FIG. 15E provides an optical image of a sensor integrated on a flexible tube, next to the tip of a pen; the inset shows the backside of a plasmonic crystal before integration of μ-ILEDs.
Figure 15F:
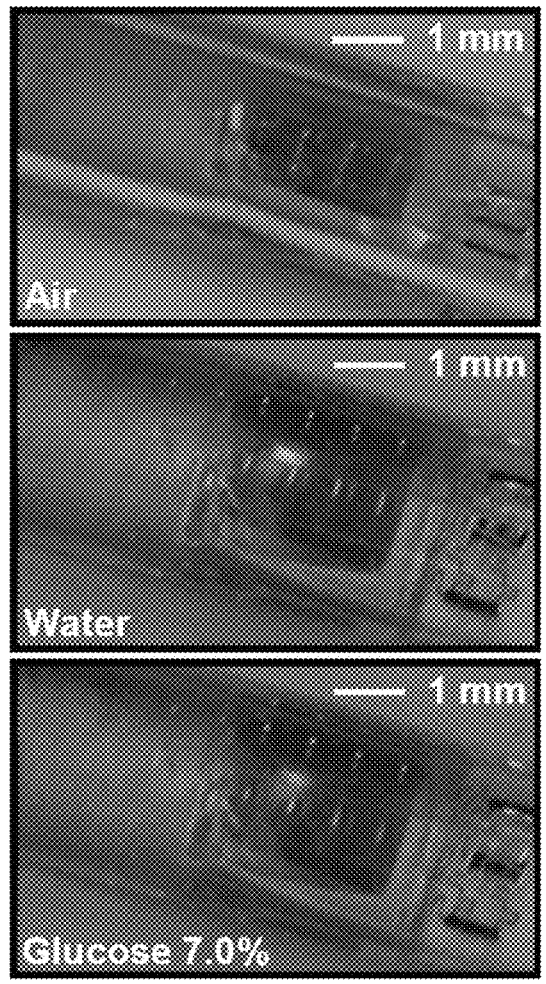
FIG. 15F provides optical images of a flexible plasmonic crystal device with different fluids in the tube.
Figure 15G:
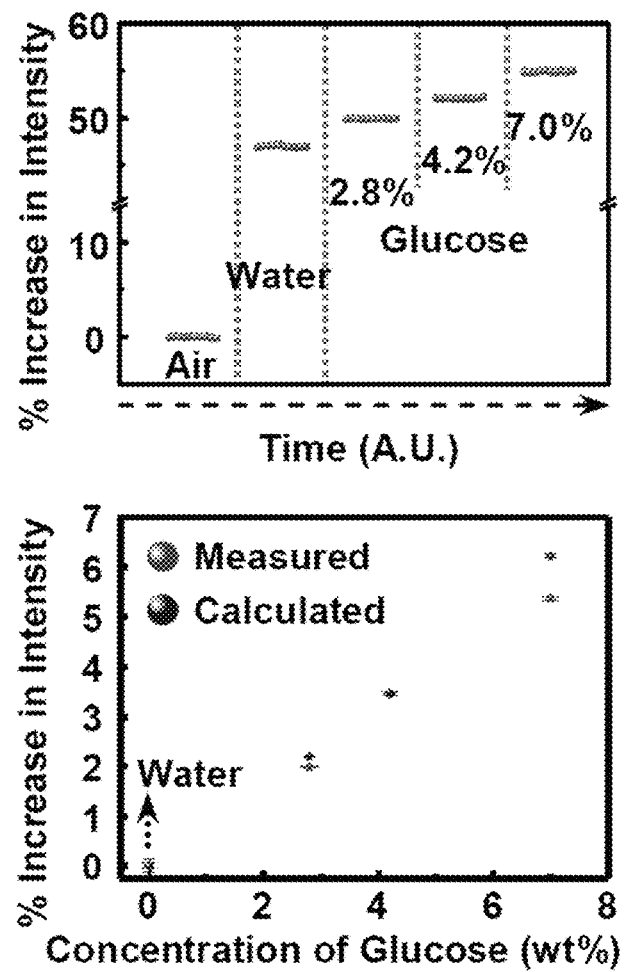
FIG. 15G provides data showing measurement results from a sensor (top), as a sequence of fluids pass through; the bottom frame shows the percentage increase in light transmitted from the μ-ILED through the plasmonic crystal.
Figure 34A:
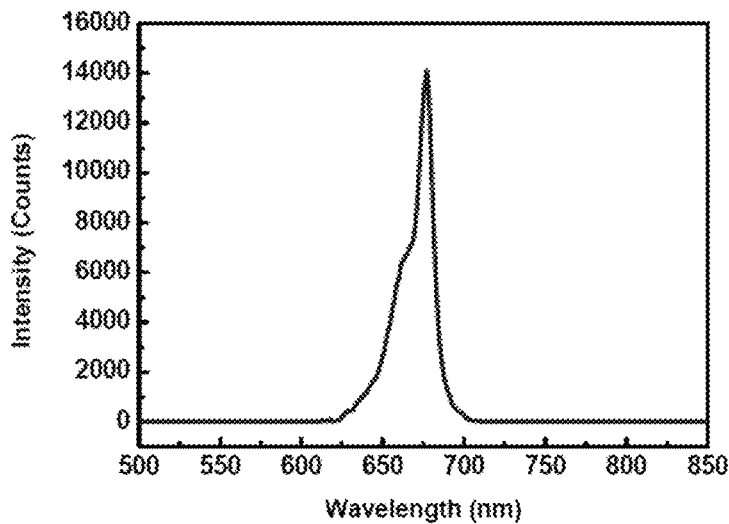
FIG. 34A provides data showing the light intensity spectrum of a single μ-ILED.
Figure 34B:
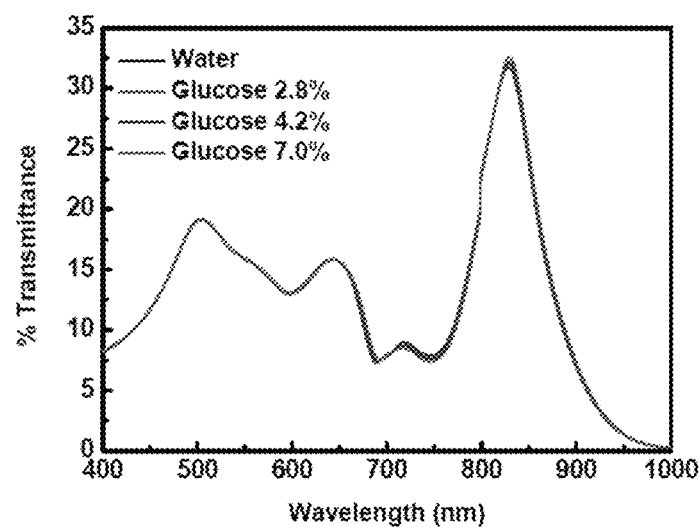
FIGS. 34B and 34C provide data showing percent transmittance and transmitted light intensity through a plasmonic crystal device as a function of composition of fluid in contact with the plasmonic crystal.
Figure 34C:
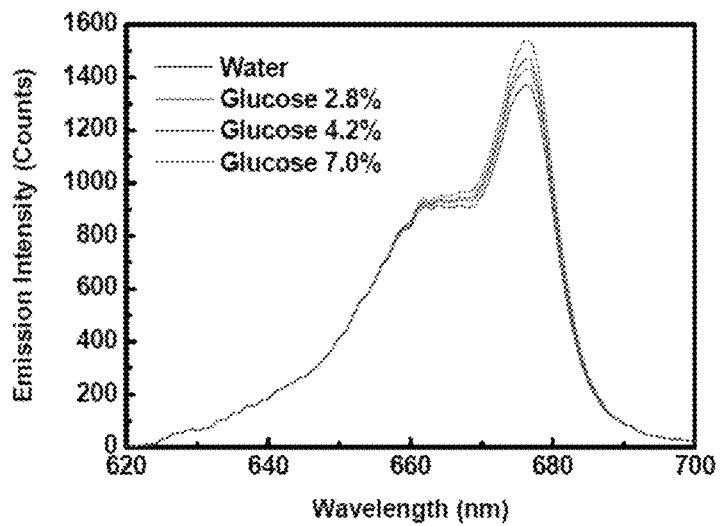
Figure 35A:
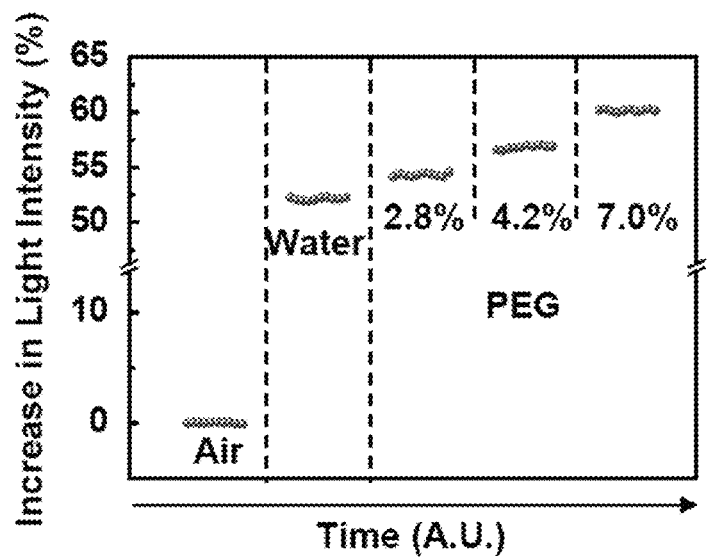
FIGS. 35A, 35B and 35C provide data from a flexible plasmonic sensor device, showing changes in detected intensity and refractive index as functions of composition of fluid in contact with the plasmonic crystal.
Figure 35B:
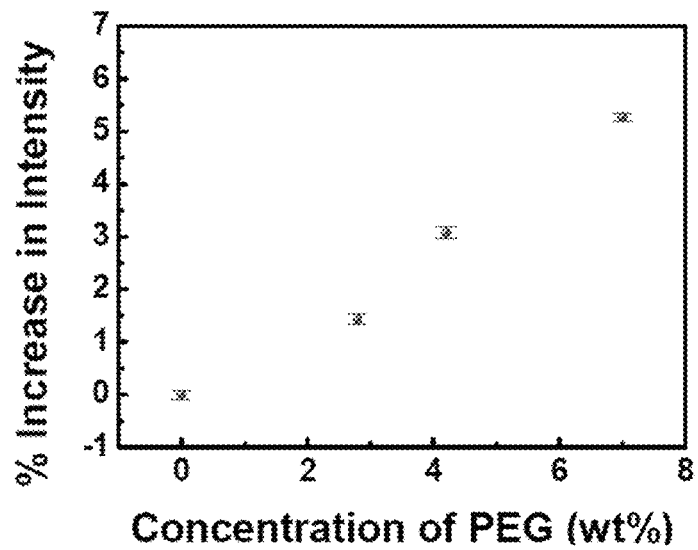
Figure 35C:
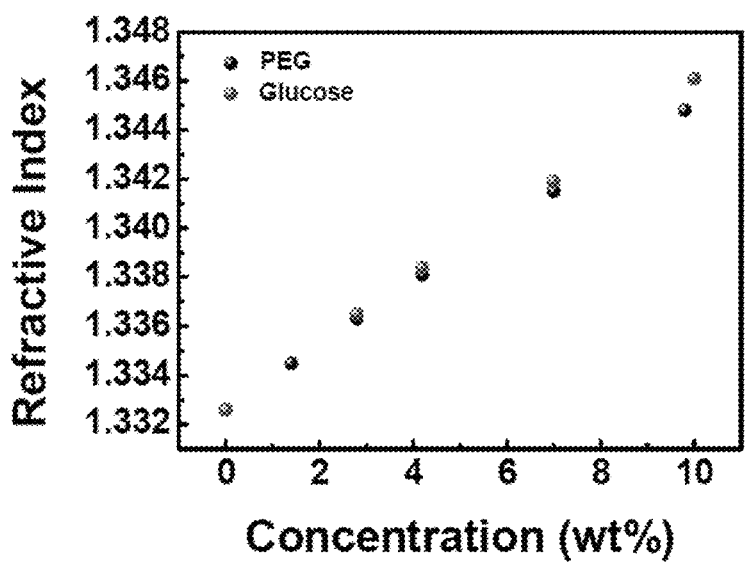

Use of μ-LED technologies in such applications requires integrated photonic structures for transmission/collection of light and/or for optical sensing of surface binding events or changes in local index of refraction. In this context, plasmonic crystals represent a useful class of component, particularly for latter purposes. FIG. 15 summarizes an illuminated sensor device that combines thin, molded plasmonic crystals with arrays of μ-LEDs, in a tape-like format that can be integrated directly on flexible tubing suitable for use in intravenous (IV) delivery systems, for monitoring purposes. FIG. 15A provides an exploded view schematic illustration of the system. The plasmonic structure consists of a uniform layer of Au (50 nm) sputter deposited onto a thin polymer film embossed with a square array of cylindrical holes (i.e. depressions) using the techniques of soft lithography, as illustrated in FIGS. 15B and 15c. The relief geometry (depth ~200 nm; hole diameter ~260 nm; pitch ~520 nm; see FIG. 15C, and inset of FIG. 15D) and thickness of the Au were optimized to yield measurable changes in transmission associated with surface binding events or variations in the surrounding index of refraction at the emission wavelength of the μ-LEDs. The full spectral responses appear in FIG. 34. FIG. 15D provides transmittance data measured using a spectrometer over a relevant range of wavelengths, for different surrounding fluids (see below for details). The completed microsensor devices appear in FIGS. 15E and 15F. As different fluids flow through the tubing, the amount of light that passes from the μ-LEDs and through the integrated plasmonic crystal changes, to provide highly sensitive, quantitative measurements of the index of refraction. The data of FIG. 15G show the response of a representative tube-integrated device, with comparison to calculations based on data from corresponding plasmonic structures on rigid substrates, immersed in bulk fluids and probed with a conventional, bench-scale spectrometer (FIGS. 34 and 35). This kind of system can be used for continuous monitoring of the dosage of nutrients, such as glucose illustrated here, or of polyethylene glycol (PEG) as illustrated below, or other biomaterials of relevance for clinical medicine.

Figure 16A:
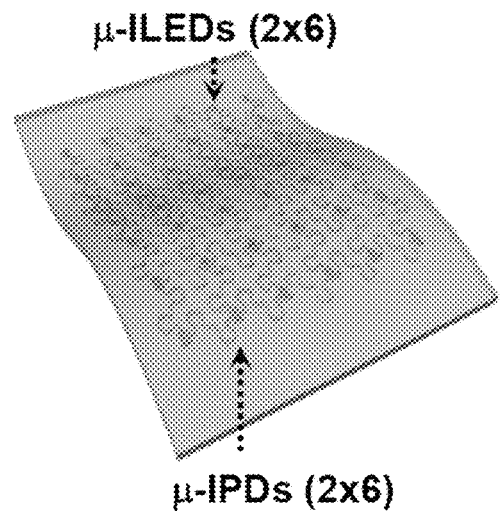
FIG. 16A provides a schematic illustration of a stretchable optical proximity sensor based on an array of μ-ILEDs and μ-IPDs.
Figure 16B:
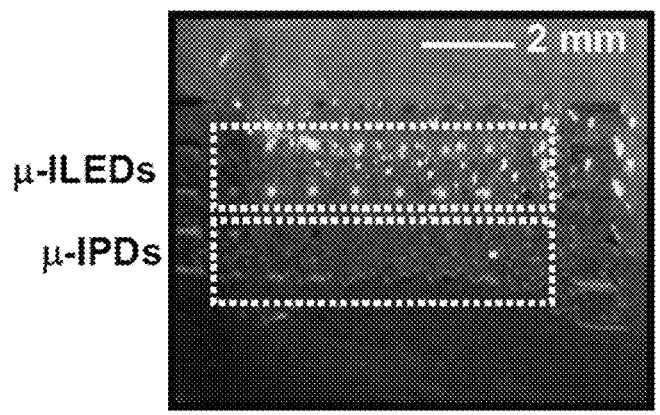
FIG. 16B provides an optical image of a stretchable optical proximity sensor mounted on the fingertip region of a vinyl glove.
Figure 16C:
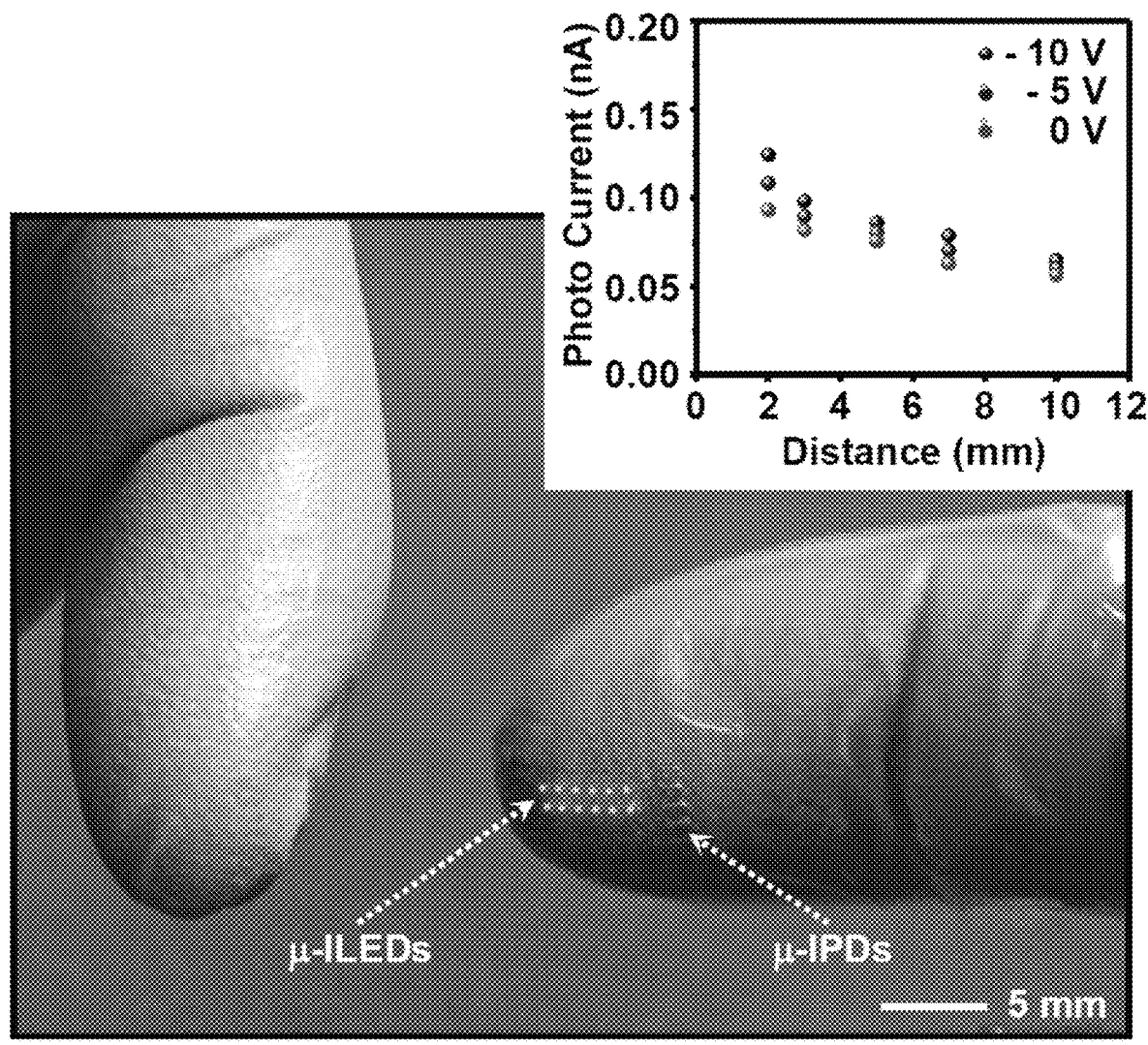
FIG. 16C provides an optical image of an array of μ-ILEDs transfer-printed on the fingertip region of a vinyl glove; the inset shows a plot of photocurrent as a function of distance between the sensor and an object.
Figure 16D:
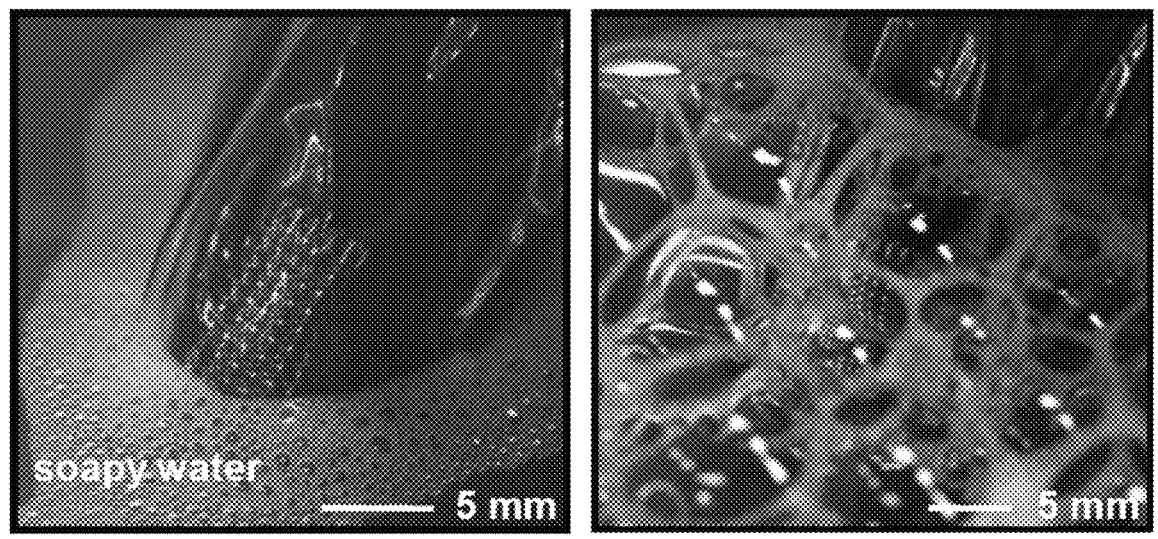
FIG. 16D provide optical images of a stretchable optical proximity sensor mounted on the fingertip region of a vinyl glove before (left) and after (right) immersion into soapy water.
Figure 16E:
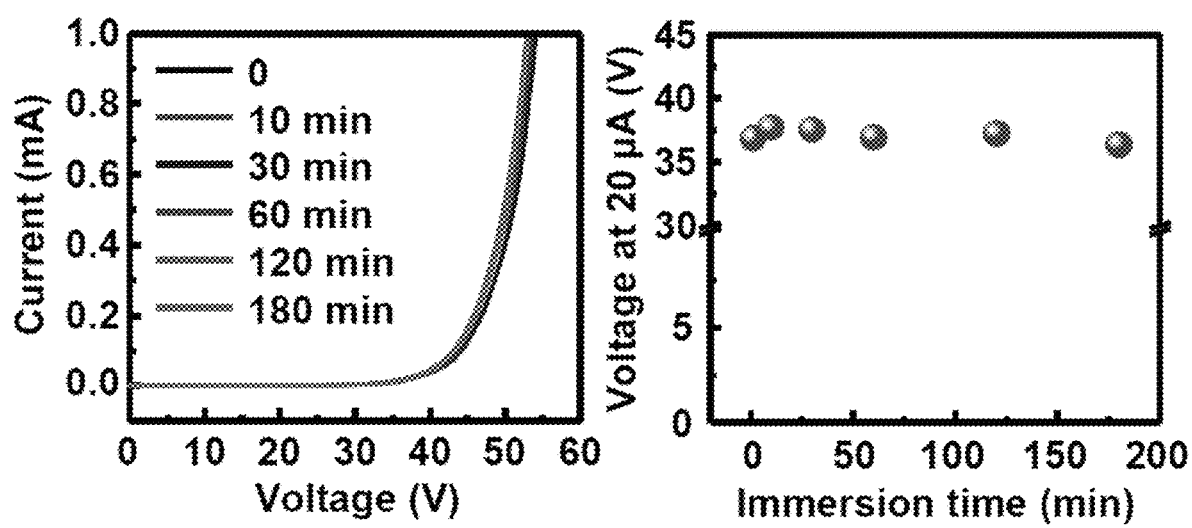
FIG. 16E provides data showing I-V characteristics of a μ-ILED array after operation in saline solution for different immersion times.
Figure 36A:
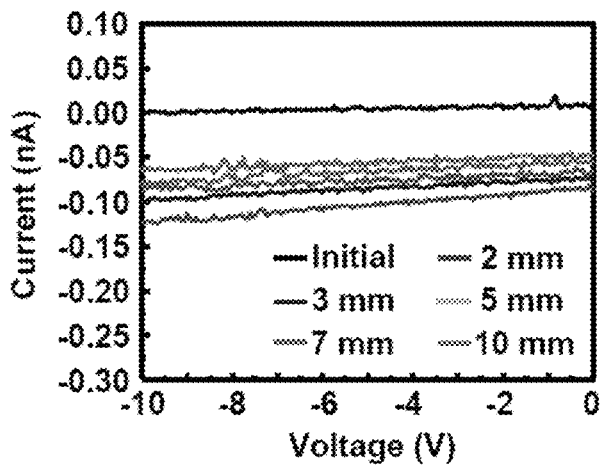
FIG. 36A provides data showing I-V characteristics of photodiodes at different distances between an optical proximity sensor and an approaching object.
Figure 36B:
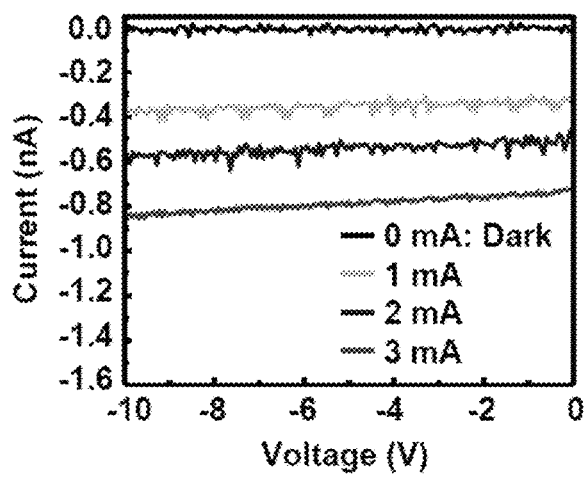
FIG. 36B provides data showing I-V characteristics of a 2nd layer (an array of μ-IPDs).
Figure 36C:
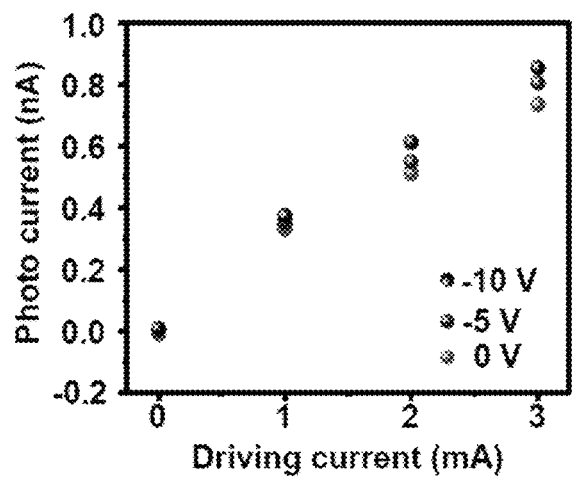
FIG. 36C provides data showing photocurrent of an array of 6×6 p-IPDs that is stacked on the layer of a 6×6 μ-ILEDs array as a function of operation current of μ-ILEDs in the stacked device.
Figure 36D:
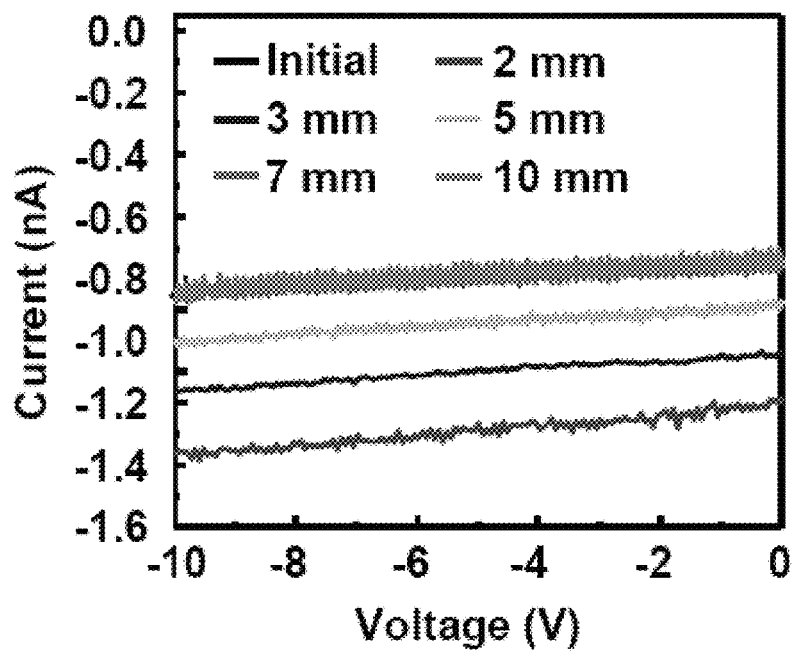
FIG. 36D provides data showing current-voltage characteristics of an array of 6×6 photodiodes as a function of distance between the device and the approaching object in the stacked device.
Figure 36E:
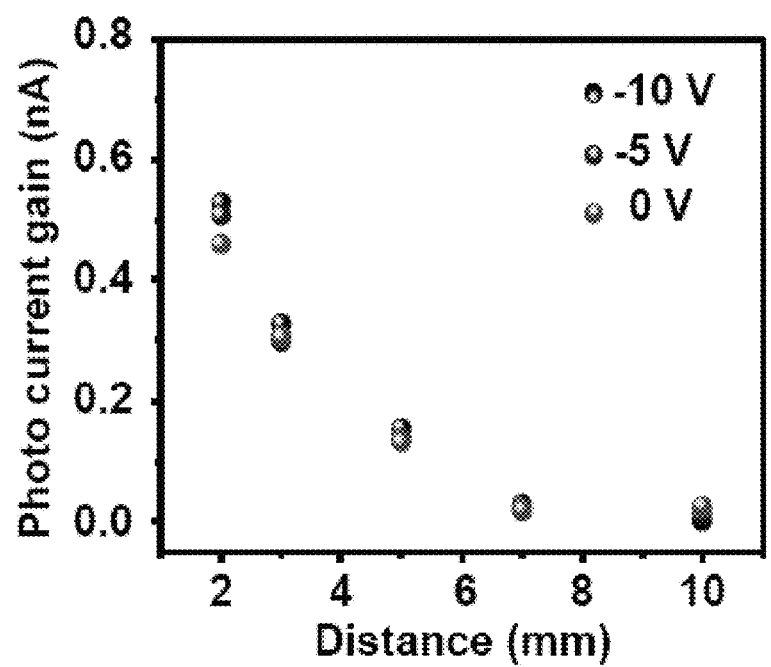
FIG. 36E provides a re-plotting of FIG. 36D as a function of distance between approaching object and μ-IPDs.

Integration of μ-IPDs with such sensors can yield complete, functional systems. To demonstrate this type of capability and also another application example, a flexible, short range proximity sensor was built that could be mounted on machine parts, or robotic manipulators, or for use in instrumented surgical gloves. This device exploits co-integration of μ-ILEDs and μ-IPDs in a stretchable format that provides both a source of light and an ability to measure backscatter from a proximal object. The intensity of this backscatter can be correlated to the distance to the object. The μ-IPDs use reversed biased GaAs diodes, as functional, although inefficient, detectors of light emitted from the μ-ILEDs. A schematic diagram of the integrated system appears in FIG. 16A. FIGS. 16B and 16C show this type of system, with 4×6 arrays of μ-ILEDs and μ-IPDs, integrated onto the fingertip region of a vinyl glove. As expected, the photocurrent measured at the μ-IPDs increases monotonically with decreasing distance to the object, as shown in the inset of FIG. 16C for different reverse bias voltages (−10, −5, and 0 V). FIG. 36A provides I-V characteristics of μ-IPDs. Stacked geometries, such as those presented in FIG. 13D, can also be used, as shown in FIGS. 36B-E. Similar to other devices described here, encapsulation with PDMS renders the systems waterproof. The left and right frames of FIG. 16D show images of 4×6 array of μ-ILEDs on a vinyl glove, before and after immersion in soapy water. The uniform light emission characteristics of all devices in the array are clearly apparent. I-V characteristics are invariant even after operation in saline solution (~9%) for 3 hours (FIG. 16E) and 1000 cycles of immersion (FIG. 37) in this solution, proving the sustainability of this device inside the body or during use in a surgical procedure.

In summary, the advances described here in mechanics, high fill factor multilayer layouts and biocompatible designs provide important, unusual capabilities in inorganic opto-electronics, as demonstrated by successful integration onto various classes of substrate and by use in representative devices for biomedical and robotics applications.

Methods. Delineating Epitaxial Semiconductor Material for μ-ILEDs and μ-IPDs. For fabrication of the μ-ILEDs and μ-IPDs, the process began with epitaxial films that included a quantum well structure (4×(6-nm-thick $Al_{0.25}Ga_{0.25}In_{0.5}P$ barriers/6-nm-thick $In_{0.56}Ga_{0.44}P$ wells)/6-nm-thick $Al_{0.25}Ga_{0.25}In_{0.5}P$ barriers) and an underlying sacrificial layer of $Al_{0.96}G_{0.04}As$ on a GaAs wafer. Details appear in FIG. 17A. Inductively coupled plasma reactive ion etching (ICP-RIE; Unaxis SLR 770 system) with $Cl_2/H_2$ through a hard mask of $SiO_2$ formed trenches down to the $Al_{0.96}G_{0.04}As$, to delineate active materials in 6×6 or 8×8 or 3×8 or 1×4 arrays of squares with sizes of 100 μm×100 μm. Next, photolithography defined photoresist structures at the four corners of each square to hold the epitaxial layers to the underlying GaAs wafer during removal of the $Al_{0.96}G_{0.04}As$ with diluted hydrofluoric (HF, Transene, USA) acid (deionized water (DI): 49% HF acid=1:100).

Fabricating Arrays of μ-ILEDs and μ-IPDs in Mesh Designs with Serpentine Interconnects on Glass Substrates. The released squares of epitaxial material formed according to procedures described above were transfer printed onto a glass substrate coated with layers of a photodefinable epoxy (SU8-2; Microchem.; 1.2 μm thick), polyimide (PI; Sigma-Aldrich; 1.2 μm thick), and poly(methylmethacrylate) (PMMA A2; Microchem.; 100 nm thick) from top to bottom. Next, another layer of epoxy (SU8-2, 2.0 μm) was spin-cast and then removed everywhere except from the sidewalls of the squares by reactive ion etching (RIE; PlasmaTherm 790 Series) to reduce the possibility of partial removal of the bottom n-GaAs layer during the 1st step of an etching process (1st step: $H_3PO_4:H_2O_2:DI=1:13:12$ for 25 seconds/2nd step: HCl:DI=2:1 for 15 seconds/3rd step: $H_3PO_4:H_2O_2:DI=1:13:12$ for 24 seconds) that exposed the bottom n-GaAs layer for n-contacts. Next, another layer of epoxy (1.2 μm thick) spin-cast and photopatterned to expose only certain regions of the top p-GaAs and bottom n-GaAs, provided access for metal contacts (non-Ohmic contacts) and interconnect lines (Cr/Au, 30 nm/300 nm) deposited by electron beam evaporation and patterned by photolithography and etching. These lines connected devices in a given row in series, and adjacent rows in parallel. A final layer of spin cast epoxy (2.5 μm) placed the devices and metal interconnects near the neutral mechanical plane. Next, the underlying polymer layers (epoxy/PI/PMMA) were removed in regions not protected by a masking layer of $SiO_2$ (150 nm thick) by RIE (oxygen plasma, 20 sccm, 150 mtorr, 150 W, 40 min). Wet etching the remaining $SiO_2$ with buffered oxide etchant exposed the metal pads for electrical probing, thereby completing the processing of arrays of μ-ILEDs (and/or μ-IPDs) with serpentine interconnects.

Transfer Printing of Stretchable Arrays of Devices to Substrates of Interest. Dissolving the PMMA layer of the structure described above with acetone at 75° C. for 10 minutes released the interconnected array of devices from the glass substrate. Lifting the array onto a flat elastomeric stamp and then evaporating layers of $Cr/SiO_2$ (3 nm/30 nm) selectively onto the backsides of the devices enabled strong adhesion to sheets or strips of PDMS or to other substrates coated with PDMS. For the PDMS balloon of FIG. 11D, prestrain was applied by partially inflating the balloon, followed by transfer printing the μ-ILEDs and then releasing (deflating) the balloon. For small substrates, roller printing techniques were used. See below for details.

Stretching Tests and Electrical Characterization. Stretching tests were performed using custom assemblies of manually controlled mechanical stages, capable of applying strains along x, y, and diagonal directions. For fatigue testing, one cycle corresponds to deformation to a certain level and then return to the undeformed state. Each fatigue test was performed up to 1000 cycles to levels of strains similar to those shown in the various figures. Electrical measurements were conducted using a probe station (4155C; Agilent), by directly contacting metal pads while stretched, bent, or twisted. For FIG. 12D, the measurement was performed using a lead-out conductor line, bonded to metal pads of the arrays of μ-ILEDs. Typical voltage scan ranges for measurement of the 6×6, 8×8, and 3×8 arrays was 0~60 V, 0~80V, and 0~90V, respectively.

Animal Experiments. All procedures were performed under approved animal protocols. A female Balb/c mouse was anesthetized with an intraperitoneal injection of a mix of ketamine/xylazine. The depth of anesthesia was monitored by palpebral and withdrawal reflexes to confirm that the animal had reached "stage 3" of anesthesia. Once the animal was lightly anesthetized, the back was shaved and cleaned at the incision site with 70% ethanol, followed by a betadine surgical scrub. Previous implants were removed from the mouse and the animal was euthanized according to approved protocols. To validate the performance of sutures in real conditions, the incision opened during surgery was closed with a customized 16-gauge needle and three passes with the light emitting suture were performed to seal the wound. The suture was then tested by verifying the proper operation of the μ-ILEDs. For the implants, the incision was performed on the dorsal side of the mouse and the suturing was carried out across the dermal layers (outer layers and subcutaneous tissues) above the muscle tissue.

Fabrication of Thin Plasmonic Crystals on Plastic. Soft lithography techniques were used to form structures of surface relief on thin layers of a photocurable polyurethane (PU, NOA 73, Norland Products) cast onto sheets of poly (ethylene terephthalate). Sputter deposition (5 mTorr Ar environment; AJA sputtering system) of uniform, thin (~50 nm) layers of gold completed the fabrication. The geometry of the relief and the thickness of the gold were selected to optimize the performance of the plasmonic crystals at the emission wavelength of the μ-ILEDs.

Spectroscopic Measurement of Transmission Properties of the Plasmonic Crystals. Transmission spectra were measured using a Varian 5G UV-Vis-NIR spectrophotometer operating in normal incidence transmission mode, without temperature control. A flow cell was mounted on top of the plasmonic crystal and aqueous solutions of glucose with different concentrations/refractive indexes were injected with a syringe pump (Harvard Apparatus) at a flow rate of 0.2 mL/min. Transmission spectra over a wavelength range of 355-1400 nm were collected during the process to monitor changes in multiple plasmonic responses. Such data were used in the process of optimizing the layouts of the crystals, and for interpreting measurements collected with the flexible, illuminated and tube-integrated sensors.

Fabrication and Testing of Flexible, Illuminated Plasmonic Crystal Sensors. The procedure for integrating a plasmonic crystal with μ-ILED light sources on a tube (Tygon R-3603, inner and outer diameter: 0.318 mm and 0.476 mm, respectively), began with formation of a contact window by cutting an opening in the tube, to enable direct contact of fluid in the tube with the plasmonic crystal. The embossed side of the crystal was placed face down against the window and then sealed with a transparent adhesive tape. Next, a thin layer of PDMS was coated on the tape and adjacent regions of the tubing as a bonding layer for a transfer printed, stretchable array of μ-ILEDs aligned to the plasmonic crystal. This step completed the integration process. Light from the device was collected with a separate, commercial Si photodetector (ThorLabs, Model DET110) placed on the opposite side of the tubing. Output from the detector was sampled digitally at a rate of 10 kHz. Averaging times of 6 seconds were used for each recorded data point.

Photographs. Images in FIGS. 11A and 13E were combined images to eliminate out-focused regions. Tens of pictures were captured at different focal depths using a Canon 1Ds Mark III with a Canon MP-E 1-5x Macro lens, and those captured pictures are merged in the software "helicon focus" to create completely focused image from several partially focused images.

Figure 11C:
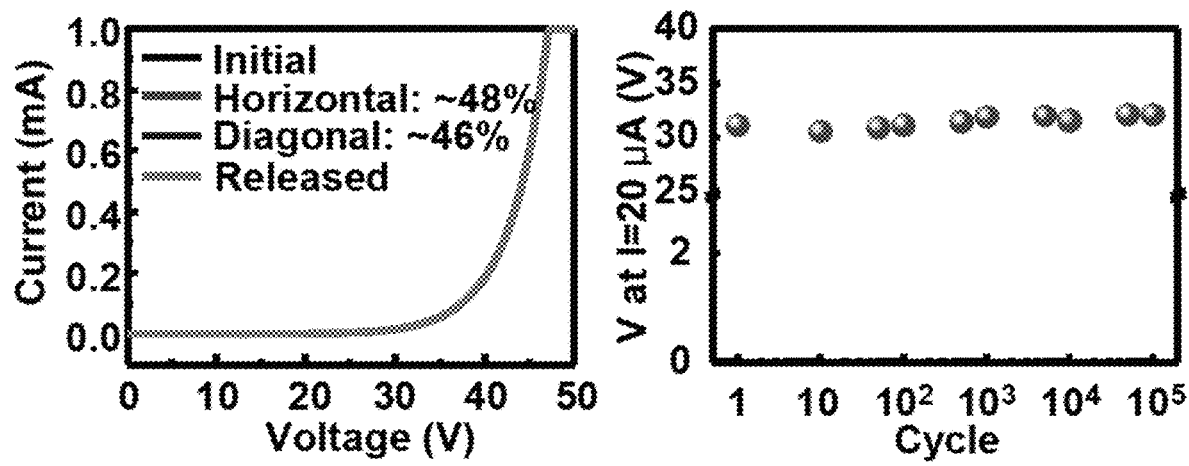
FIG. 11C provides data showing current-voltage (I-V) characteristics of a µ-ILED array under different strain configurations (left) and voltage at 20 µA current for different cycles of stretching (right).

Figure Captions. FIG. 11. Device layouts of µ-ILED arrays and their responses to uniaxial and balloon-shape biaxial stretching. FIG. 11A, Optical image of a 6×6 array of µ-ILEDs (100 µm×100 µm, and 2.5 µm thick, in an interconnected array with a pitch of ~830 µm) with non-coplanar serpentine bridges on a thin (~400 µm) PDMS substrate (left frame). Schematic illustration (right) and corresponding photograph (inset) of a representative device, with encapsulation. FIG. 11B, Optical images of a stretchable 6×6 array of µ-ILEDs, showing uniform emission characteristics under different uniaxial applied strains (top left: 0%, bottom left: 48% along horizontal direction, top right: 0%, bottom right: 46% along diagonal direction). FIG. 11C, Current-voltage (I-V) characteristics of this array measured in the strained configurations shown in b (left) and voltage at 20 µA current for different cycles of stretching to 75% along the horizontal direction (right). FIG. 11D, Tilted (left) view optical images of a stretchable array (6×6) of µ-ILEDs on a thin (~500 µm) PDMS membrane in a flat configuration (top) and in a hemispherical, balloon state (bottom) induced by pneumatic pressure. FIG. 11E, the magnified view of FIG. 11D from the top. The yellow dashed boxes highlight the dimensional changes associated with the biaxial strain. FIG. 11F, I-V characteristics of the array in its flat and inflated state. FIG. 11G, Distribution of meridional and circumferential strains determined by 3D-FEM.

FIG. 12. Responses of µ-ILED arrays to twisting and stretching on sharp tips. FIG. 12A, Optical images of an array of µ-ILEDs (3×8) on a band of PDMS twisted to different angles (0° (flat), 360°, and 720° from top to bottom), collected with (left) and without (right) external illumination. FIG. 12B, SEM image of the array when twisted to 360°. The serpentine interconnects move out of the plane (red box) to accommodate the induced strains. FIG. 12 , I-V characteristics of the array twisted by various amounts (0 (flat), 360 and)720°. FIG. 12C, Distributions of axial (left), width (center) and shear (right) strain determined by 3D-FEM for twisting to 720°. FIG. 12E, Optical images of an array of µ-ILEDs (6×6), tightly stretched on the sharp tip of a pencil, collected with (left) and without (right) external illumination. The white arrows indicate the direction of stretching. FIG. 12F, Optical images of a stretchable 8×8 array wrapped and stretched downward on the head of a cotton swab. The inset image was obtained without external illumination. FIG. 12G, I-V characteristics of the array in FIG. 12E, before (initial), during (deformed) and after (released) deformation. The inset provides a graph of the voltage needed to generate a current of 20 µA, measured after different numbers of cycles of deformation.

FIG. 13. Multilayer laminated configurations of arrays of µ-ILEDs for high effective area coverage and integration on various unusual substrates. FIG. 13A, Schematic, exploded view illustration for a stacked device formed by multilayer lamination. FIG. 13B, Optical images of a four layer stack of 4×4 arrays with layer-to-layer offsets designed to minimize overlap of interconnect lines with positions of the µ-ILEDs. The images show emission with different numbers of layers in operation (1st layer on, 1st and 2nd layers on, 1st, 2nd and 3rd layers on, and 1st, 2nd, 3rd and 4th layers on). FIG. 13C, Optical images of a two layer stack of 8×8 arrays, with different layers in operation. The inset shows the device in a bent state (bending radius ~2 mm) with both layers on. FIG. 13D, Optical image of an array of µ-ILEDs (8×8) on a piece of paper, in a folded state (bending radius ~400 µm) during operation. The inset shows the device in its flat state. FIG. 13E, Image of a 6×6 array on a sheet of aluminum foil under crumpled state. The inset shows the device in its flat state. FIG. 13F, Images of a 6×6 array on a catheter balloon in its inflated (inset) and deflated states. FIG. 13G, Images of a thin (~8 µm), narrow (820 µm) strip of µ-ILEDs (1×8) with serpentine interconnects on a rigid plastic tube (diameter ~2.0 mm, left). Inset shows the magnified view of a single pixel. FIG. 13H, a thin strip LED device consisting of an isolated µ-ILED with straight interconnects wrapped around a glass tube (diameter ~5.0 mm, right). The insets provide a magnified view. FIG. 13I, Image of a 1×8 array with serpentine metal bridges on a ~700 µm diameter fiber, wrapped around a glass tube (diameter ~1.4 mm, left frame) and, in a knotted state (inset), respectively, resting on coins (pennies) to set the scale.

Figure 14B:
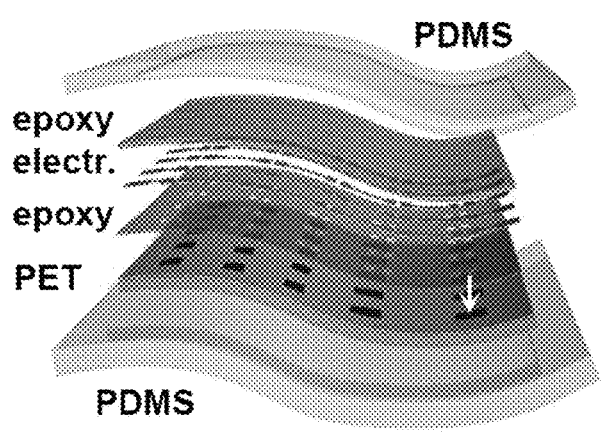
FIG. 14B provides a schematic exploded view illustration of an array of μ-ILEDs on a thin film coated with an adhesive.
Figure 14C:
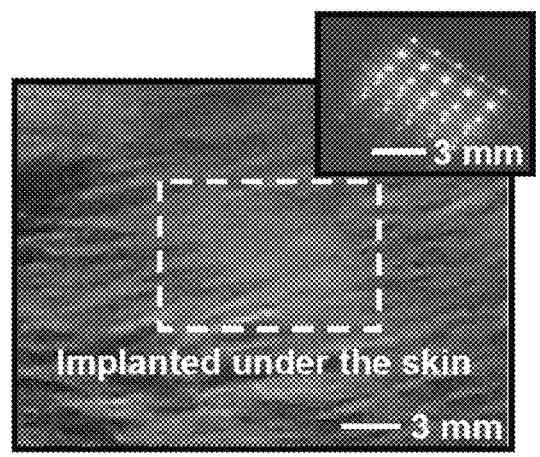
FIG. 14C provides an optical image of an animal model with a μ-ILED array implanted under the skin and on top of the muscle tissue; the inset shows the device before implantation.

FIG. 14. Demonstrations of application possibilities for systems of µ-ILEDs in biomedicine. FIG. 14A, Light emitting suture consisting of a 1×4 array of µ-ILEDs on a thread (diameter ~700 µm), demonstrated in an animal model with a conventional suture needle. The images correspond to one stitch in its off state, after one stitch, two stitches, and three stitches in the on state, in the clockwise direction from the top left frame, respectively. The yellow arrows indicate the suturing directions. FIG. 14B, Schematic exploded view illustration of an array of µ-ILEDs (5×5) on a thin PET film (50 µm thick) coated with an adhesive. Layers of PDMS on the top and bottom provide a soft, elastomeric encapsulation that offers biocompatibility and an excellent barrier to biofluids and surrounding tissue. FIG. 14C, Image of an animal model with this array implanted under the skin, and on top of the muscle tissue. The inset shows the device before implantation.

FIG. 15. Refractive index microsensors based on thin, molded plasmonic crystals integrated with arrays of µ-LEDs, in tape-like formats integrated directly on flexible tubing suitable for use in intravenous (IV) delivery systems. FIG. 15A, Schematic exploded view of the sensor/tube system. FIG. 15B, Thin, molded plasmonic crystal on a plastic substrate wrapped around a cylindrical support, showing colors due to diffraction. FIG. 15C, Atomic force microscope image of the surface of such a crystal. FIG. 15D, Normal incidence transmission spectra collected with a commercial spectrometer over a range of wavelengths relevant for illumination with red µ-LEDs. FIG. 15E, Image of a sensor integrated on an flexible plastic tube (Tygon), next to the tip of a pen. The inset shows the backside of the plasmonic crystal before integration of the µ-ILEDs. FIG. 15F, Images of the tube-integrated sensor viewed from the µ-ILED side of the device, with different fluids in the tube. FIG. 15G, Measurement results from a representative sensor (top), operated while integrated with a tube, as a sequence of aqueous solutions of glucose pass through. The bottom frame shows the percentage increase in light transmitted from the µ-ILED, through the plasmonic crystal and measured on the opposite side of the tube with a silicon photodiode, as a function of glucose concentration. The calculations are based on the response of a separate, conventional plasmonic crystal evaluated using bulk solutions and a commercial spectrometer.

FIG. 16. Stretchable optical proximity sensor based on an array of μ-ILEDs and μ-IPDs mounted on the fingertip of a vinyl glove. FIG. 16A, Schematic illustration of co-integrated 2×6 arrays of μ-ILEDs and μ-IPDs to yield a thin, stretchable optical proximity sensor. FIG. 16B, Image of the sensor, mounted on the fingertip region of a vinyl glove. FIG. 16C, Optical images of an array of μ-ILEDs (4×6) with serpentine metal bridges, transfer-printed on the fingertip region of a vinyl glove. The inset shows a plot of photocurrent as a function of distance between the sensor and an object (white filter paper) for different reverse bias and different voltages. FIG. 16C, Left and right frames correspond to images before and after immersion into soapy water. FIG. 16D, IV characteristics of the same μ-ILEDs array as shown in FIG. 16C after operation in saline solution (~9%) for different immersion time.

Figure 38A:
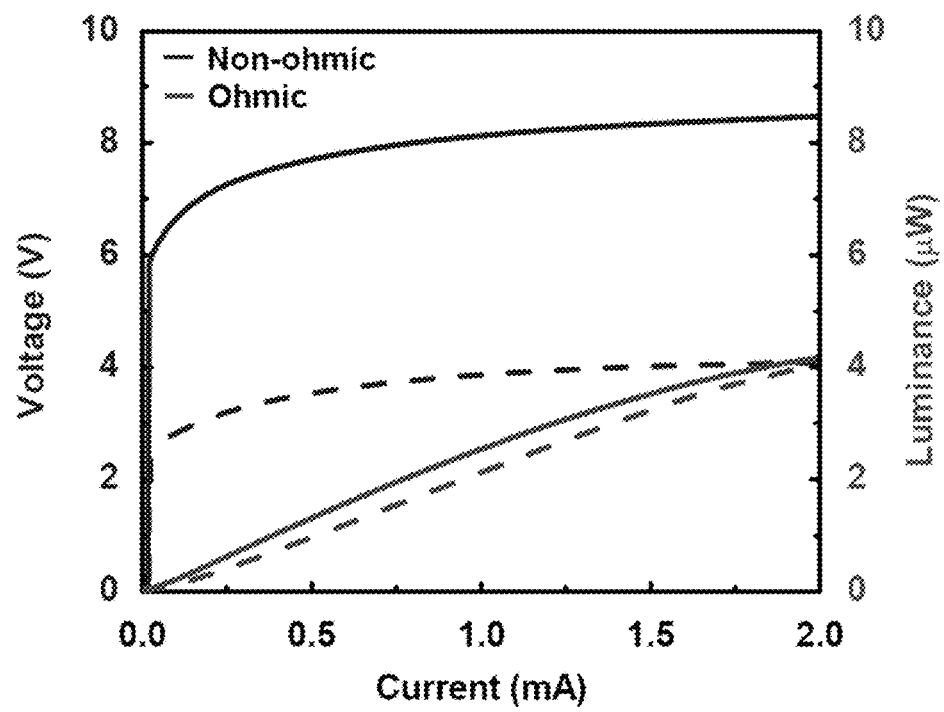
FIG. 38A provides data showing the result of Luminance (L)—Current (I)—Voltage (V) measurement of an individual pixel with and without applied ohmic contacts.

Contact Scheme. Here, simple metal (Cr/Au) to doped GaAs contacts are used instead of ohmic contacts. For improved electrical characteristics, conventional ohmic contacts of metal interconnects to GaAs can be implemented. To form the ohmic contact, a series of metal stacks followed by appropriate annealing (n ohmic contact metals: Pd/Ge/Au followed by anneal at 175° C. for 1 hour, p ohmic contact metal: Pt/Ti/Pt/Au in this paper) can be used, which results in lower take-off voltage can be obtained as shown in FIG. 38A.

Figure 38B:
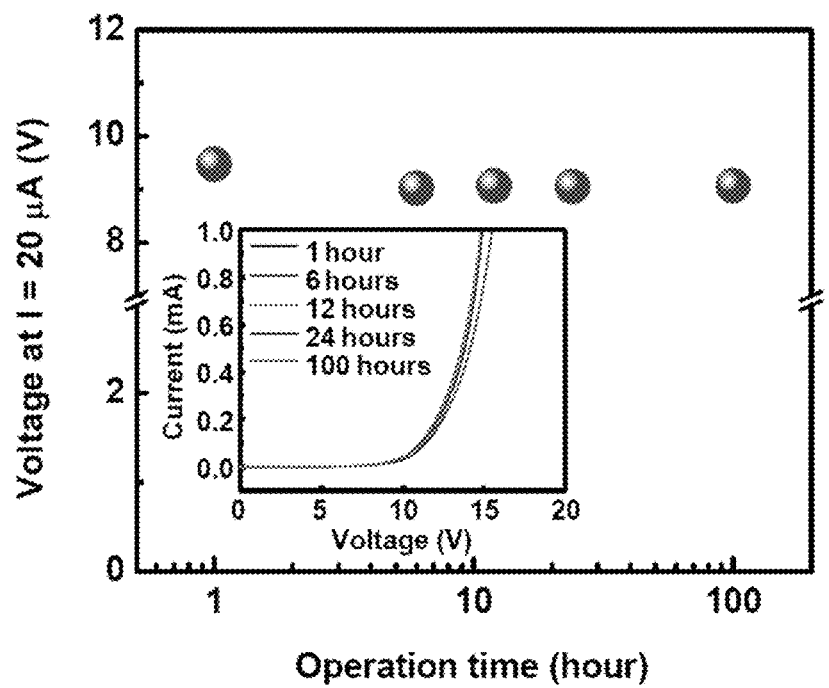
FIG. 38B provides data showing applied voltage to generate a current of 20 μA, measured after different operation times.

Long-term operation. Long-term operation was tested using two LED devices, connected in series, on a thin slab of PDMS was performed under the constant current mode (0.75 mA). Both devices showed robust and reliable performance during the continuous operation for 100 hours without affecting I-V characteristics as shown in FIG. 38B.

Figure 39A:
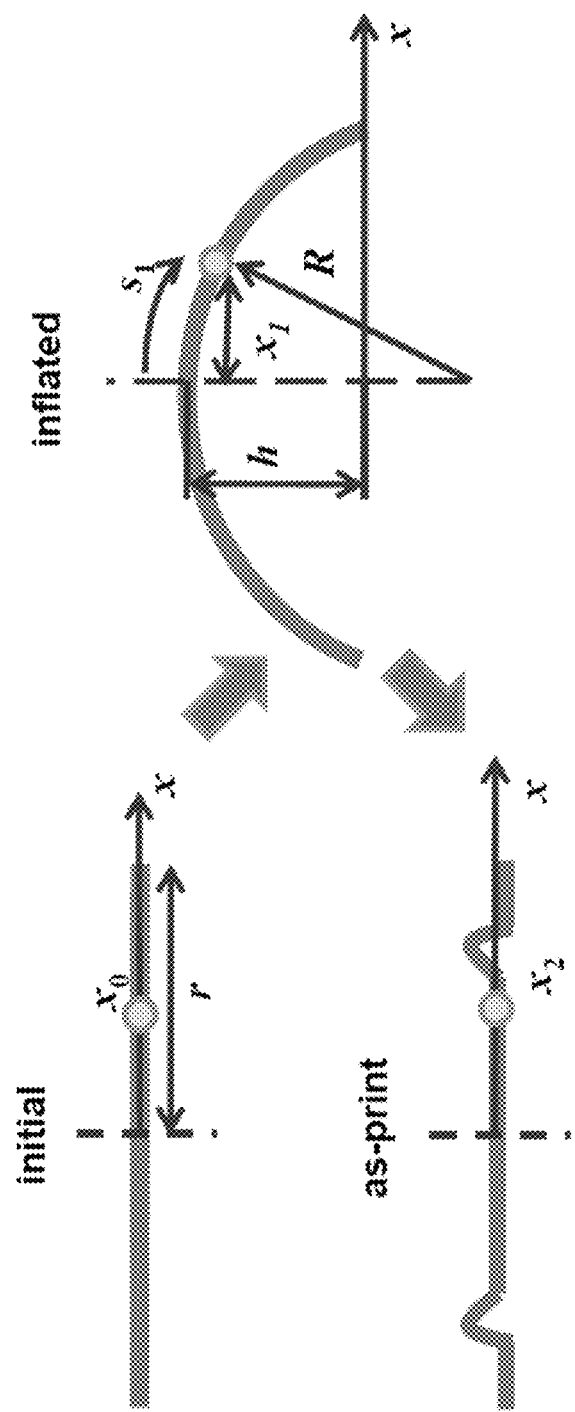
FIG. 39A provides a schematic illustration of an analytical model for the inflation and printing-down of PDMS film.

FEM Simulation of Balloon Deformation. FIG. 39A illustrates the mechanics model for inflating and transfer printing onto the PDMS balloon of FIG. 11. The initially flat, circular thin film (initial state, upper left frame of FIG. 24A) of radius r is fixed at its outer boundary, and is inflated by air to a spherical cap of height h (inflated state, right frame of FIG. 39A). The radius of the sphere is $R=(h^2+r^2)/(2h)$. The spherical cap is pressed down and flattened during transfer printing, as shown in the lower left frame of FIG. 39A (as-print state). The deformation is uniform along the meridional direction during inflation, while all material points move vertically downward during printing. Therefore, for a point of distance $x_0$ to the film center at the initial state, its position changes to $x_i$ in the inflated state with an arc distance $s_1$ to the film center, and then changes to $x_2$ in the state during printing, where $s_1=(Rx_0/r)\arcsin(r/R)$ and $x_1=x_2=R\sin[(x_0/r)\sin^{-1}(r/R)]$. These give the meridional and circumferential strains of the inflated state as:

$$\varepsilon_{\theta 1} = \frac{R}{r}\arcsin\frac{r}{R} - 1, \quad (S1)$$

$$\varepsilon_{\varphi 1} = \frac{R}{x_0}\sin\left(\frac{x_0}{r}\arcsin\frac{r}{R}\right) - 1. \quad (S2)$$

The meridional and circumferential strains at the state during printing are given by:

$$\varepsilon_{\theta 2} = \frac{R}{r}\cos\left(\frac{x_0}{r}\sin^{-1}\frac{r}{R}\right)\sin^{-1}\frac{r}{R} - 1, \quad (S3)$$

$$\varepsilon_{\varphi 2} = \frac{R}{x_0}\sin\left(\frac{x_0}{r}\sin^{-1}\frac{r}{R}\right) - 1 \quad (S4)$$

Figure 39B:
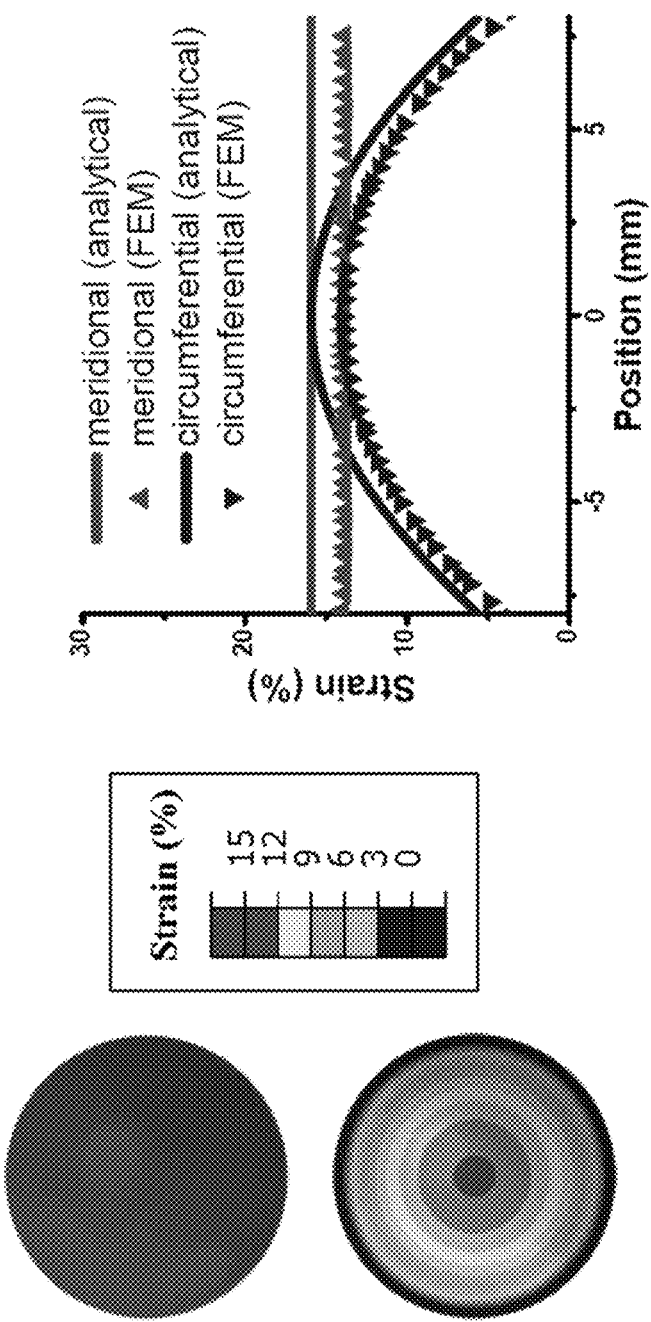
FIGS. 39B and 39C provide results of the FEM models.
Figure 39C:
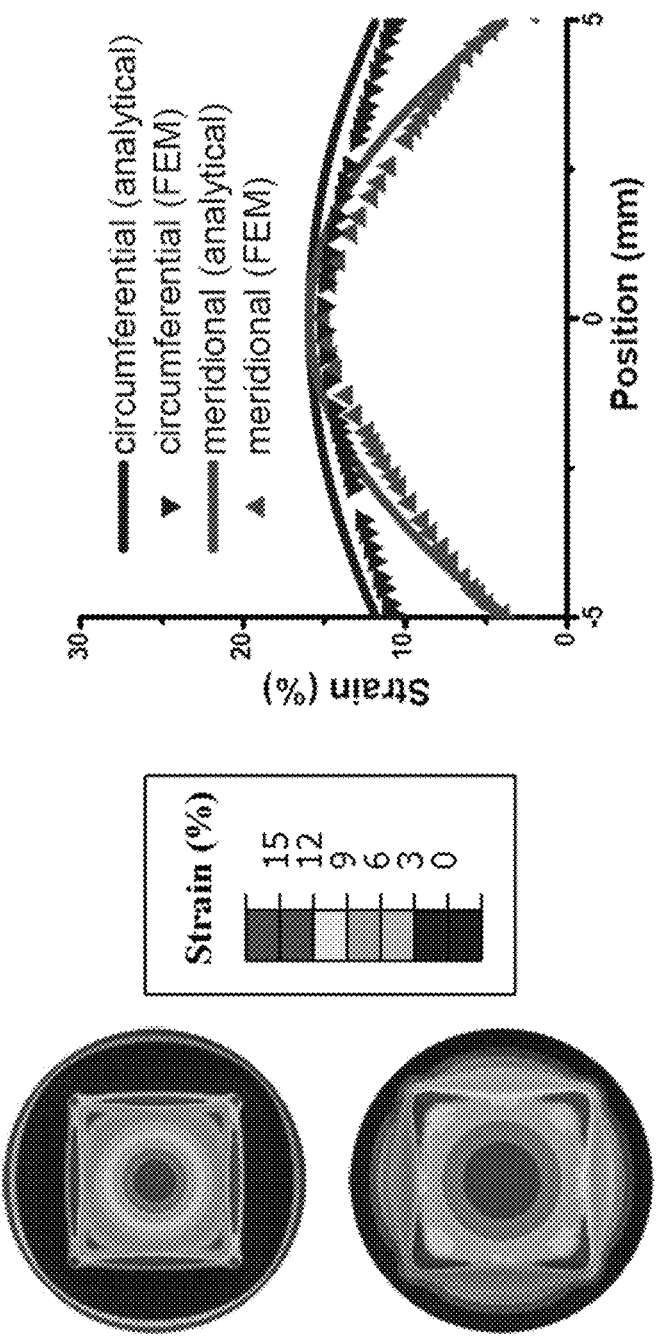

Finite element method (FEM) was used to study this process in order to validate the analytical model above. The contours of meridional and circumferential strains of the inflated state appear in the upper and lower left frames of FIG. 39B, respectively. The results are compared with analytical solutions, Equations (S1) and (S2), in the right frame of FIG. 39B, and show good agreement. Therefore, the analytical formulae, Equations (S1) and (S2), can be used to predict the PDMS strain under different inflation, and further to estimate the strain in devices on the balloon surface. FIG. 39C shows the contours of meridional (upper left frame) and circumferential (lower left frame) strains of the asprint state, and the comparison with analytical solutions from Equations (S3) and (S4) (right frame). The analytical solutions, once again, agree well with FEM simulations without any parameter fitting.

Figure 40:
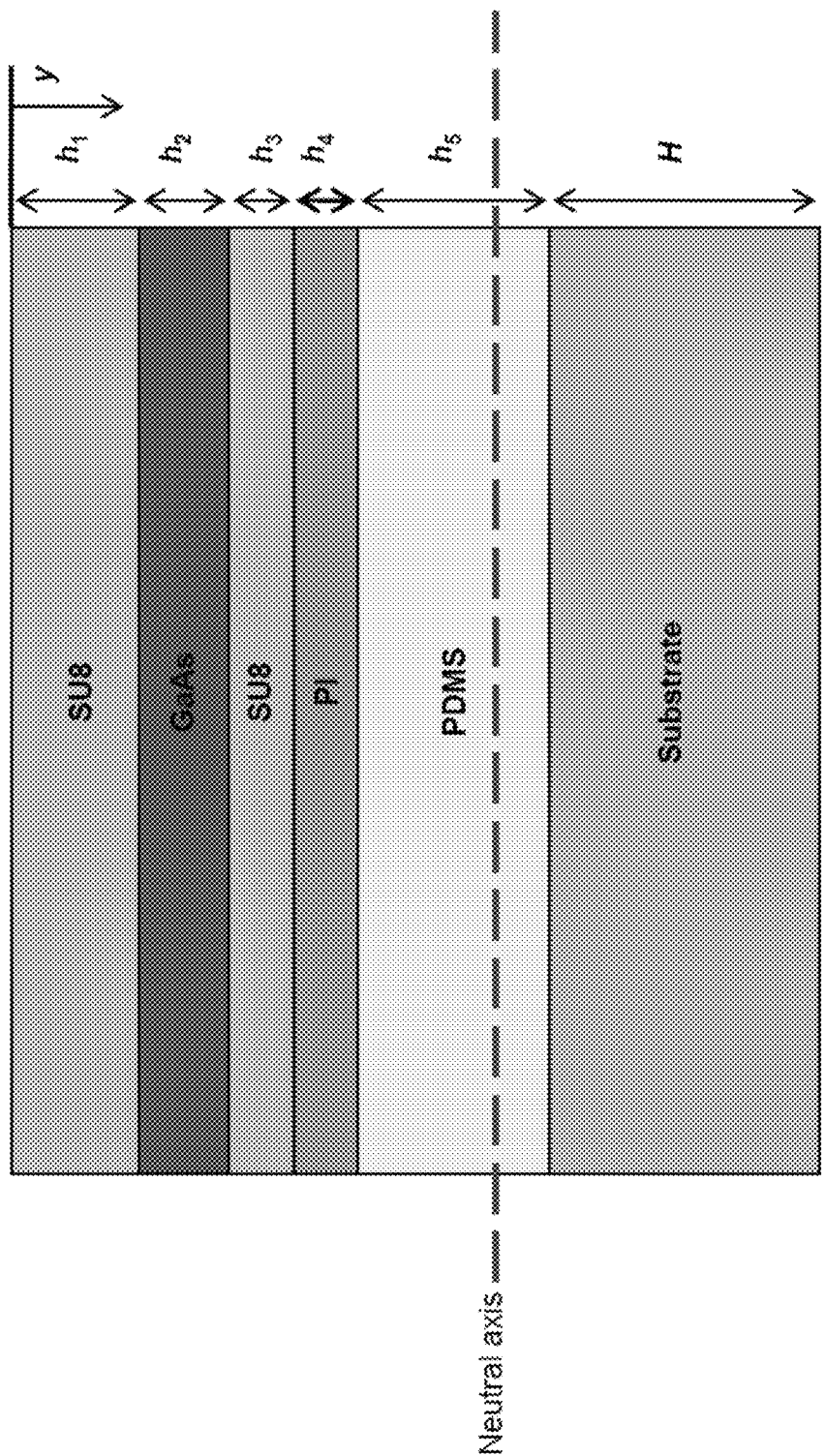
FIG. 40 provides a schematic illustration of the cross section of μ-ILEDs on a substrate.

Bending of LEDs on Various Substrates. The LED, as illustrated in FIG. 40, consists of multiple layers with thicknesses $h_1=3.5$ μm, $h_2=2.5$ μm, $h_3=1.2$ μm and $h_4=1.2$ μm, and Young's moduli are $E_{SUS}=5.6$ GPa, $E_{GaAs}=85.5$ GPa and $E_{Pl}=3.2$ GPa. These layers are modeled as a composite beam with equivalent tensile and bending stiffnesses. The PDMS strain isolation layer has thickness $h_5=50$ um and Young's modulus $E_{PDMS}=0.4$ MPa. The Young's modulus $E_{sub}$ and thickness H of the substrate are 1.2 MPa and 0.8 mm for the fabric, 23.5 MPa and 0.5 mm for the fallen leaf, and 600 MPa and 0.2 mm for the paper. The strain isolation model then gives very small maximum strains in GaAs, 0.043%, 0.082% and 0.23% for the completely folded fabric, leaf and paper, respectively. The minimal bend radii are the same as the corresponding substrate thicknesses H, i.e., 800 μm, 500 μm and 200 μm for the fabric, leaf and paper, respectively. For the Al foil substrate, the minimum bend radius is obtained as 139 μm when the strain in GaAs reaches 1%.

Without the PDMS strain isolation layer, the LED and substrate are modeled as a composite beam. The position of neutral axis (measured from the top surface) is given by:

$$y_0 = \frac{\left\{\begin{array}{l}E_{SUS}[(h_1+h_3)^2+2h_2h_3]+E_{Pl}h_4(2h_1+2h_2+2h_3+h_4)\\+E_{GaAs}h_2(2h_1+h_2)+E_{sub}H(2h_1+2h_2+2h_3+2h_4+H)\end{array}\right\}}{2[E_{SUS}(h_1+h_3)+E_{GaAs}h_2+E_{Pl}h_4+E_{sub}H]}.$$

The maximum strain in GaAs is $$\varepsilon_{GaAs} = \frac{1}{R_b}\max(|y_0-h_1|, |h_1+h_2-y_0|),$$

where $R_b$ is the bending radius. Therefore, the minimum bending radius of LED array on the substrate is $$R_b = \frac{1}{\varepsilon_{failure}}\min(|y_0-h_1|, |h_1+h_2-y_0|),$$

where $\varepsilon_{failure}=1\%$ is the failure strain of GaAs. For the fabric substrate, the maximum strain in GaAs is only 0.34% even when it is completely folded, which gives the minimum bending radius the same as the thickness 0.8 mm. For the fallen leaf and the paper, the minimum bending radii are 1.3 mm and 3.5 mm.

Figure 17B:
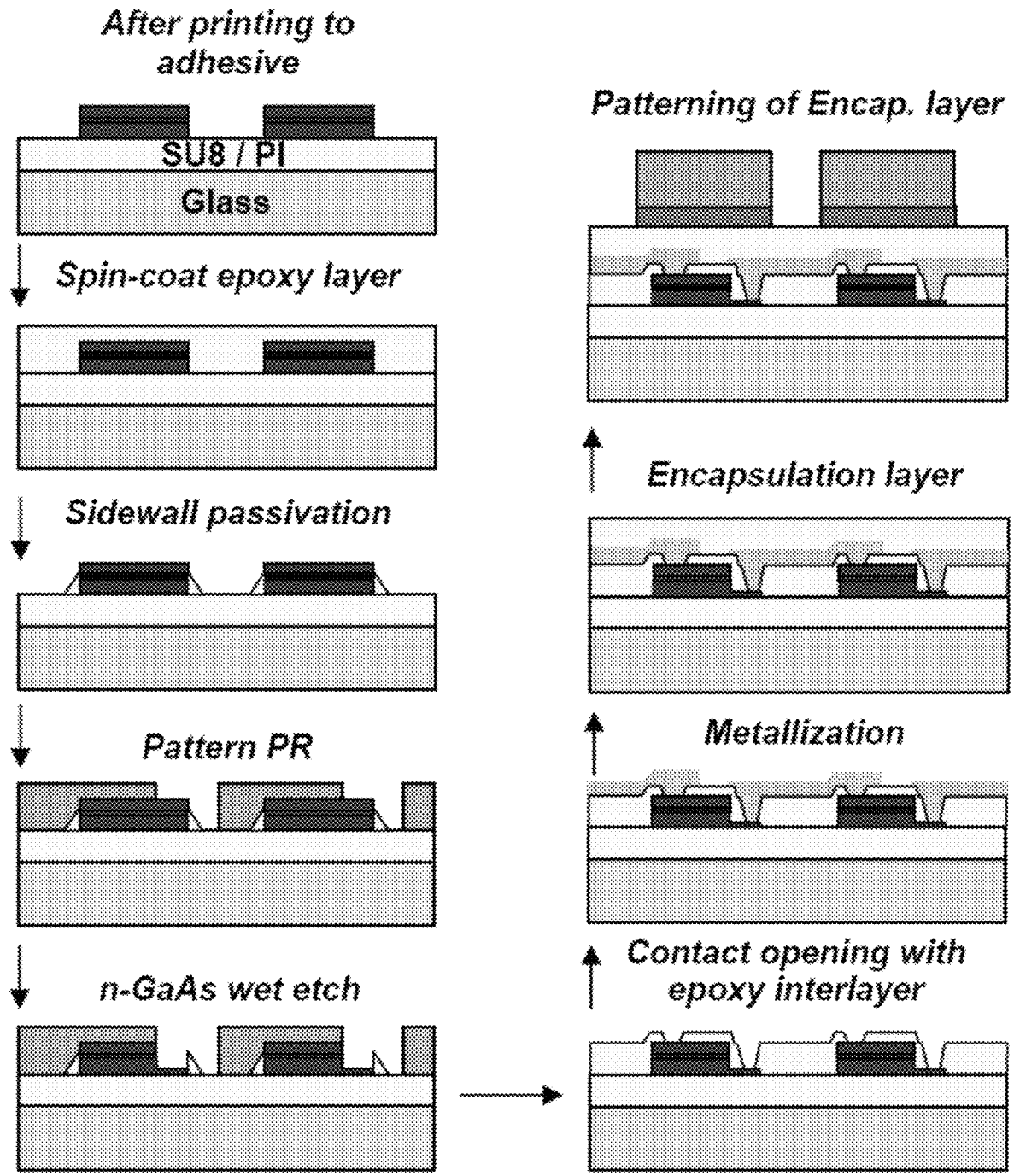
FIG. 17B provides a schematic illustration showing fabrication processes for μ-ILEDs arrays on a carrier glass substrate.

Figure Captions. FIG. 17. Schematic illustration of epitaxial layer (a) and fabrication processes for µ-ILEDs arrays on a carrier glass substrate after transfer printing (b).

FIG. 18. (18A) Schematic illustration (left frame) and corresponding microscope (top right frame) and SEM (bottom right frame) images of a 6×6 µ-ILEDs on a handle glass substrate coated with layers of polymers (epoxy/PI/PMMA). (18B) Schematic illustration (left frame) and corresponding microscope (top right frame) and optical (bottom right frame) images of a 6×6 µ-ILEDs array which is picked up with a PDMS stamp for transfer printing. A shadow mask for selective deposition of Cr/SiO$_2$ (thickness: 3 nm/30 nm) covers the retrieved array on a soft elastomeric PDMS stamp. (18C) Schematic illustration of transfer printing to a pre-strained thin (thickness: ~400 µm) PDMS substrate (left frame) and microscope (top right frame) and SEM (bottom right frame) images of the transferred µ-ILEDs array on a prestrained thin PDMS substrate. Prestrain value was ~20%.

Figure 19A:
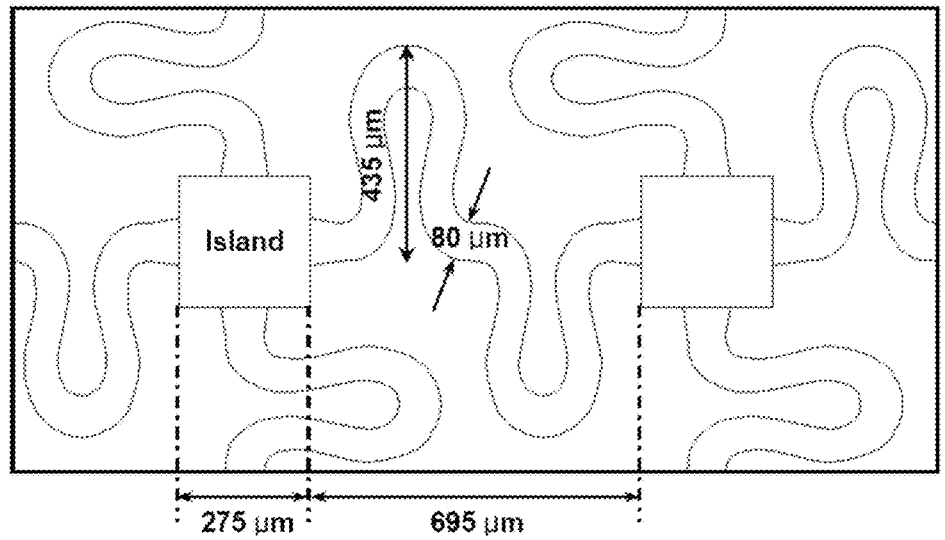
FIG. 19A provides a schematic illustration of a flexible device.
Figure 19B:
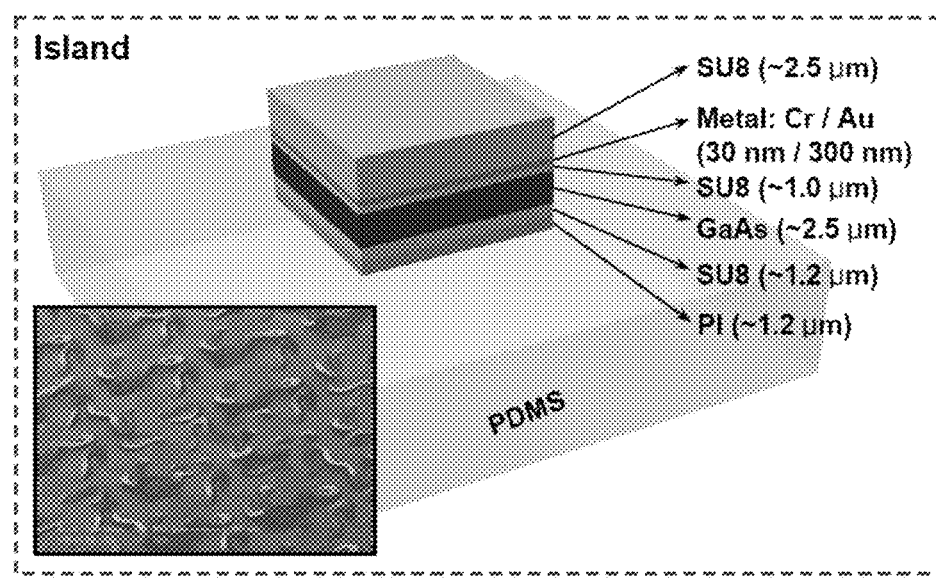
FIG. 19B provides a schematic illustration of the cross sectional structure at an island; the inset shows an SEM image of a μ-ILEDs array after transfer printing to a thin PDMS substrate.
Figure 19C:
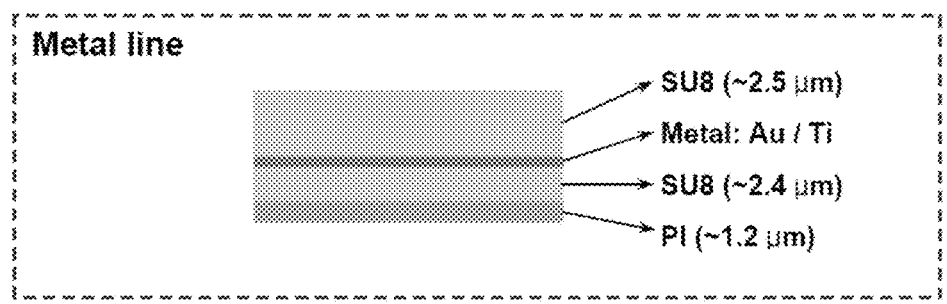
FIG. 19C provides a schematic illustration of the cross sectional structure at metal interconnection bridges.
Figure 20B:
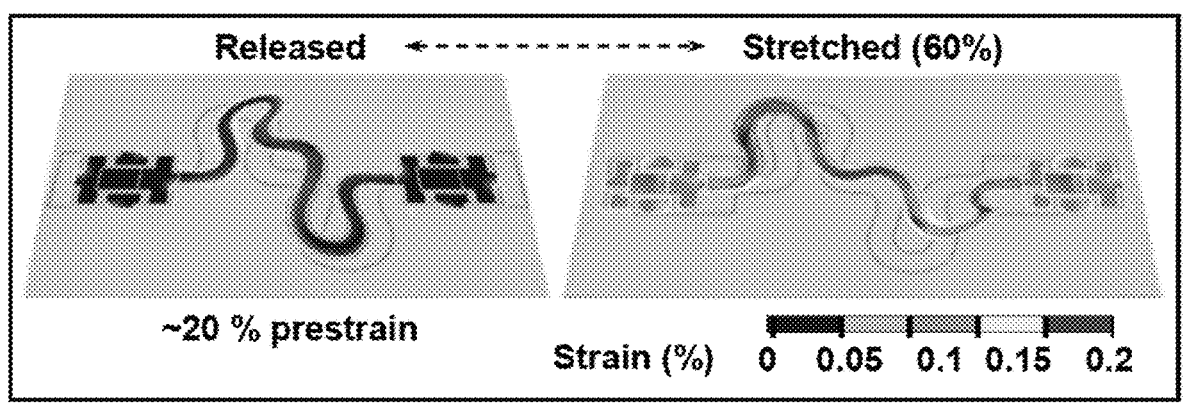
FIG. 20B provides data showing strain distributions determined by 3D-FEM.

FIG. 19. (19A) Schematic illustration of top encapsulation layers indicating some of the key dimensions. (19B) Schematic illustration of the cross sectional structure at an island, with approximate thicknesses for each layer. The inset corresponds to an SEM image of a µ-ILEDs array after transfer printing to a thin PDMS substrate with prestrain of ~20%. (19C) Schematic illustration of the cross sectional structure at metal interconnection bridges, with approximate thicknesses of each layer.

FIG. 20. (20A) Tilted view SEM images of adjacent µ-ILEDs (yellow dashed boxes) before (left, formed with ~20% pre-strain) and after (right) stretching along the horizontal direction (red arrows). (20B) Strain distributions determined by 3D-FEM for the cases corresponding to frames in (20A). The black outlines indicate the positions of the devices and the serpentines before relaxing the pre-strain.

FIG. 21. (21A) Optical microscope images of two pixels in a µ-ILEDs array with a serpentine bridge design before (left frame) and after (right frame) external stretching along the horizontal direction. The upper and lower images show optical micrographs in emission light off (upper) and on (lower) states. The distance between adjacent pixels appears in the lower images and used for calculation of applied strains. The lower images were obtained without external illumination. (21B) Optical micrograph images of two pixels in a µ-ILEDs array before (left frame) and after (right frame) external stretching along the diagonal direction. (21C) FEM simulation under external stretching along the diagonal direction (left frame), and strain contours in the GaAs active island (top right frame) and the metal bridge (bottom right frame).

FIG. 22. Optical images of a 6×6 µ-ILEDs array with a serpentine mesh design with external illumination under the same strain circumstances as FIG. 11B.

FIG. 23. (23A) Optical image of an 8×8 µ-ILEDs array on a thin PDMS substrate in its on state, which is under the same kind of deformed condition as bottom left frame of FIG. 11*d*. (23B) Top view optical images of same array as FIG. 11D in its 'flat' (left frame) and 'inflated' state (right frame) without external illumination. (23C) Spatial distribution of FEM results of the right frame of FIG. 11D and analytical solutions calculated from Equations (S1) and (S2).

FIG. 24. (24A) Schematic illustrations of a 3×8 µ-ILEDs array integrated on a thin PDMS substrate with detailed dimensions (upper frame: registrations of the µ-ILEDs on a PDMS donor substrate, lower frame: entire view of the printed 3×8 µ-ILEDs array). The inset on top represents an optical microscope image of this µ-ILEDs array on a handle glass substrate before transfer printing. (24B) Magnified view of the SEM image in FIG. 12B. The white dotted rectangle highlights the non-coplanar bridge structures. (24C) Voltage at 20 µA current for each twisting cycle of 360°.

Figure 25:
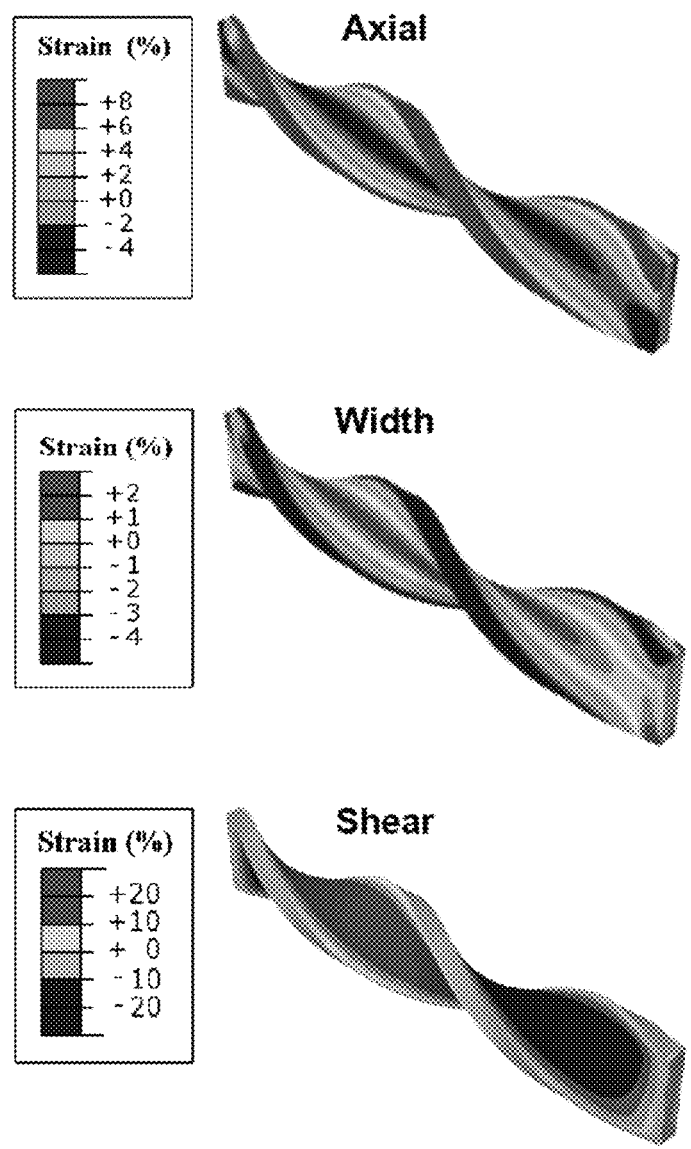
FIG. 25 provides data showing the results of FEM strain contours of axial (top), width (center), and shear (bottom) strains for 360° twisted PDMS substrate.
Figure 26A:
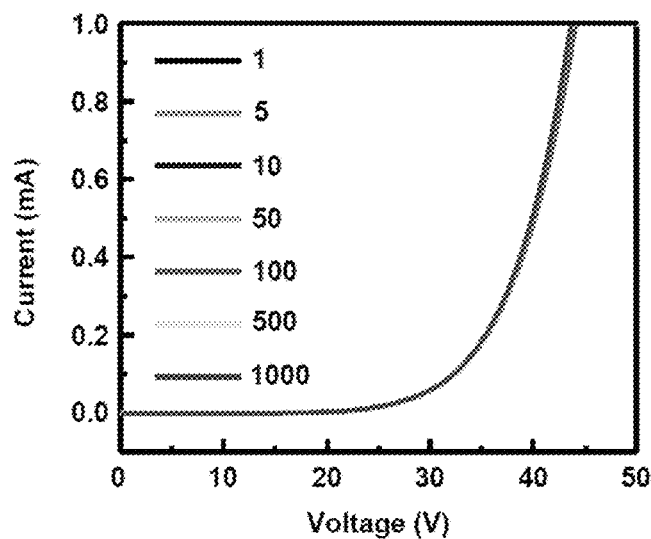
FIG. 26A provides data showing I-V characteristics of a 6×6 μ-ILED array as a function of deformation cycles.
Figure 26B:
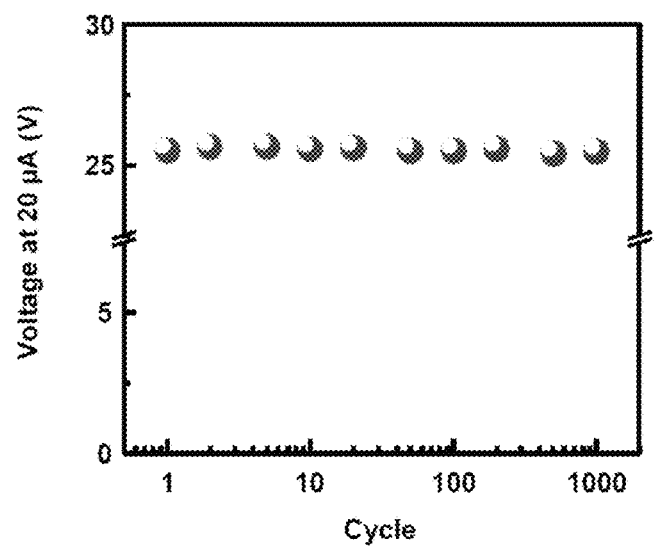
FIG. 26B provides data showing voltage needed to generate a current of 20 μA during a fatigue test.

FIG. 25. FEM strain contours of axial (top), width (center), and shear (bottom) strains for 360° twisted PDMS substrate.

FIG. 26. Fatigue test result of a 6×6 µ-ILEDs array as shown in FIG. 12E. (26A) Plot of I-V characteristics of a 6×6 µ-ILEDs array as a function of deformation cycles. (26B) Plot of voltage needed to generate a current of 20 µA measured after deformation cycles up to 1000 times. Each deformed state is approximately same as shown in FIG. 12E.

FIG. 27. (27A) Schematic illustration of stacked devices describing states of FIG. 13B. (27B) Optical images of stacked devices as shown in FIG. 13B, collected without external illumination.

FIG. 28. (28A) The strain distribution of the two-layer system in the stacked array bent to a radius of curvature 2 mm, as shown in FIG. 13C. The black dashed rectangles demonstrate the positions of µ-ILEDs. (28B) The strain distribution in GaAs layers in the µ-ILEDs island.

FIG. 29. (29A) Optical image of a 6×6 µ-ILEDs array with serpentine metal interconnects, integrated on fabrics, in its bent and on state (bending radius ~4.0 mm). The inset shows the device in its flat and off state. (29B) Plot of I-V characteristics of this array in its bent state. Inset provides a graph of the voltage needed to generate a current of 20 µA, measured after different numbers of cycles of bending deformation. (29C) Optical image of an 8×8 µ-ILEDs array with a human pattern, integrated on a fallen leaf, in its bent and on state. The inset image was collected with external illumination. (29D) Plot of I-V characteristics in the bent state as shown in FIG. 29C. (29E) Optical image of a µ-ILEDs array integrated on a paper in its folded and on state. (29F) Optical image of the same µ-ILEDs array as shown in FIG. 13E in its mildly crumbled state. Inset represents microscope image of adjacent four pixels in their on states.

Figure 29F:
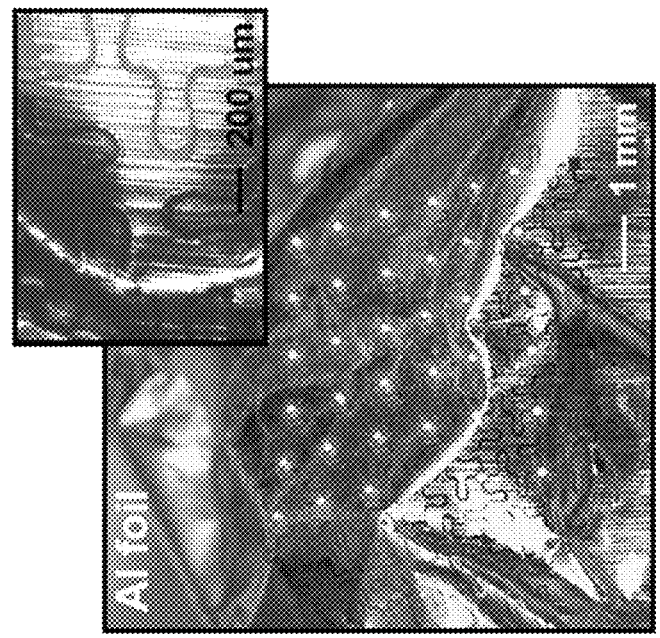
FIG. 29F provides an optical image of a μ-ILED array on crumpled Al foil; the inset shows microscope image of four adjacent pixels in their on states.
Figure 29E:
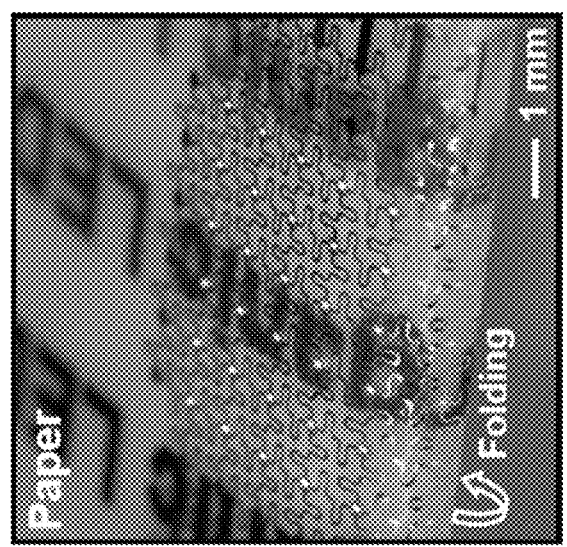
FIG. 29E provides an optical image of a μ-ILED array integrated on paper in its folded and on state.
Figure 30A:
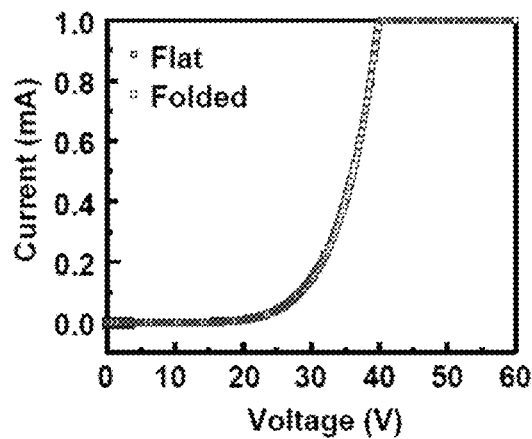
FIG. 30A provides data showing I-V characteristics of a 6×6 μ-ILED array integrated on paper in its flat and folded state.
Figure 30B:
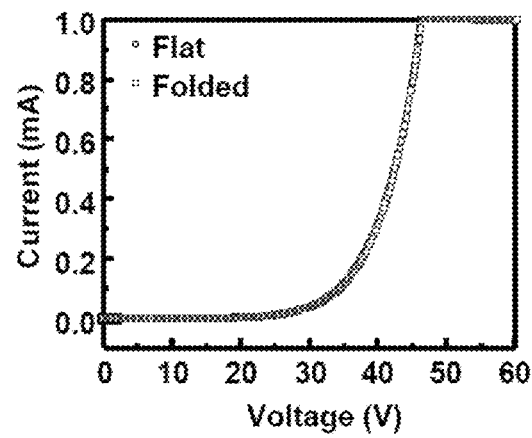
FIG. 30B provides data showing I-V characteristics of a 6×6 μ-ILED array integrated on Al foil in its flat and crumpled state.
Figure 30C:
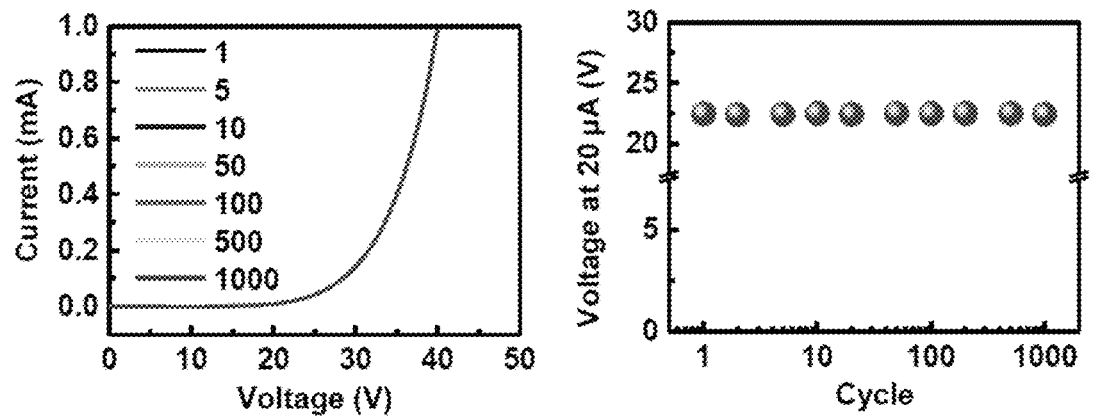
FIG. 30C provides data showing I-V characteristics of a μ-ILED array integrated on paper as a function of deformation cycles (left) and voltage needed to generate a current of 20 μA during a fatigue test (right).
Figure 30D:
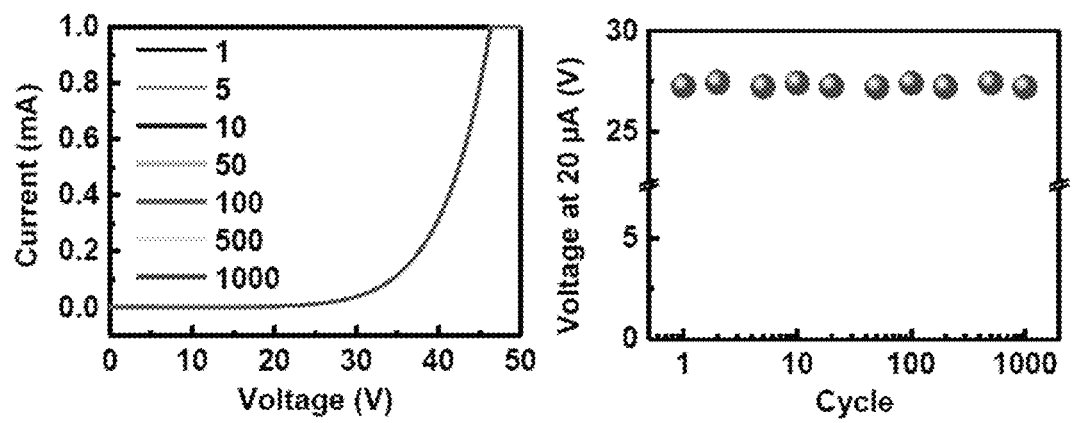
FIG. 30D provides data showing I-V characteristics of a μ-ILED array integrated on Al foil as a function of deformation cycles (left) and voltage needed to generate a current of 20 μA during a fatigue test (right).

FIG. 30. (30A) Plot of I-V characteristics of a 6×6 µ-ILEDs array integrated on paper in its flat (FIG. 13D inset) and folded (FIG. 13D) state. (30B) Plot of I-V characteristics of a 6×6 µ-ILEDs array integrated on aluminum foil in its flat (FIG. 13E inset) and crumbled (the center frame of FIG. 13E) state. (30C) Fatigue tests of arrays of 6×6 µ-ILEDs as shown in FIG. 29E. Plot of I-V characteristics of a µ-ILEDs array integrated on paper as a function of deformation cycles (left frame). Plot of voltage needed to generate a current of 20 µA measured after deformation cycles up to 1000 times (right frame). (30D) Fatigue tests of arrays of 6×6 µ-ILEDs as shown in FIG. 29F. Plot of I-V characteristics of a µ-ILEDs array integrated on aluminum foil as a function of deformation cycles (left frame). Plot of voltage needed to generate a current of 20 µA measured after deformation cycles up to 1000 times (right frame).

Figures 31C, 31D:
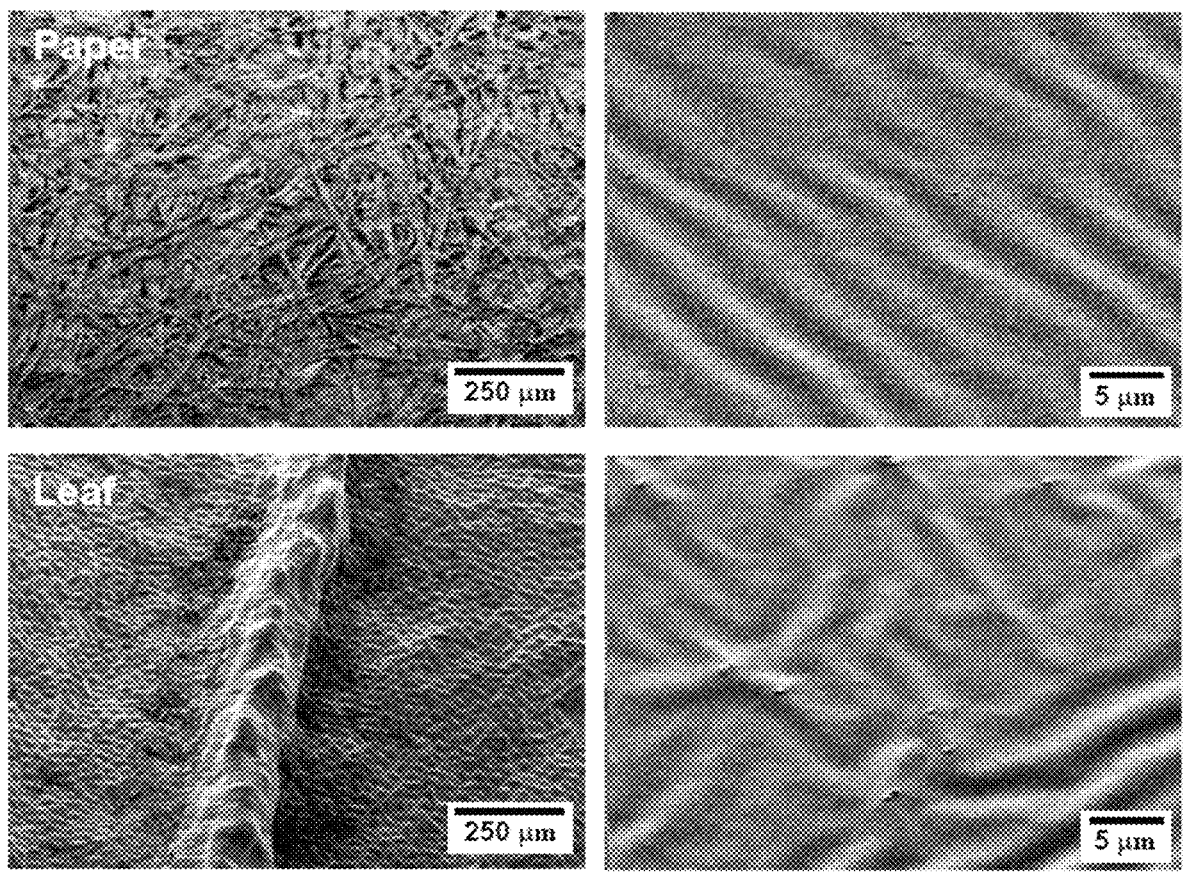
FIG. 31C provides SEM images of paper before (left frame) and after (right frame) coating with a thin layer of PDMS.
FIG. 31D provides SEM images of a fallen leaf before (left frame) and after (right frame) coating with a thin layer of PDMS.

FIG. 31. SEM images of various substrate such as fabrics (31A), Al foils (31B), paper (31C), and fallen leaves (31D) before (left frame) and after (right frame) coating of thin layer of PDMS.

FIG. 32. Optical image of single µ-ILED with long straight interconnects, integrated on a flexible thread with diameter of diameter ~2.5 mm (32A), and diameter ~0.7 mm (32B), respectively. (32C) Optical image of a single LED device with long interconnects, integrated on ~300 µm-wide threads in its bent and un-deformed (inset) states, respectively. (32D) Schematic illustration describing 'rolling method'. (32E) Optical image of a 4×6 µ-ILEDs array with serpentine bridge interconnects integrated on a glass tube using a rolling method for printing. (32F) The suture demonstration using µ-ILEDs array mounted on a thread for radiation therapy with an incision in paper (thread diameter ~700 µm).

FIG. 33. Schematic illustration of the encapsulation of an implantable array of µ-ILEDs as described in FIGS. 14B and 14C.

FIG. 34. (34A) Light intensity spectrum of single µ-ILED, measured with conventional spectrometer (Ocean Optics, USA). (34B) Percent transmittance spectrum through plasmonic nanohole array, measured with conventional spectrometer (CARY, Varian, USA). (34C) Transmitted light intensity spectrum through plasmonic nanohole array at the relevant wavelength range, calculated by multiplying single LED intensity in (34A) and % transmittance in (34B).

FIG. 35. (35A) Measurement results from a representative sensor (top), operated while integrated with a tube, as a sequence of aqueous solutions of PEG (polyethylene glycol) pass through. (35B) The percentage increase in light transmitted from the µ-ILED, through the plasmonic crystal and measured on the opposite side of the tube with a silicon photodiode, as a function of PEG concentration. (35C) Refractive indexes change with different glucose and PEG concentrations.

FIG. 36. (36A) Plot of I-V characteristics of photodiodes at different distances between an optical proximity sensor and an approaching object as explained in FIGS. 16A-C. (36B) Plot of I-V characteristics of 2nd layer (an array of photodiode) as a function of the current level of 1st layer (an array of µ-ILEDs) under negative bias in the stacked device. (36C) Plot of photocurrent of an array of 6×6 p-PDs that is stacked on the layer of a 6×6 µ-ILEDs array as a function of operation current of µ-ILEDs in the stacked device. (36D) Plot of current-voltage characteristics of an array of 6×6 photodiodes as a function of distance between the device and the approaching object in the stacked device. Voltage range of an array of 6×6 µ-PDs was from 0 V to −10 V during the 6×6 µ-ILEDs array was in emission light up state (operation current of µ-ILEDs array: 3 mA). (36E) Replotting of FIG. 36D as a function of distance between approaching object and µ-PDs.

Figure 37A:
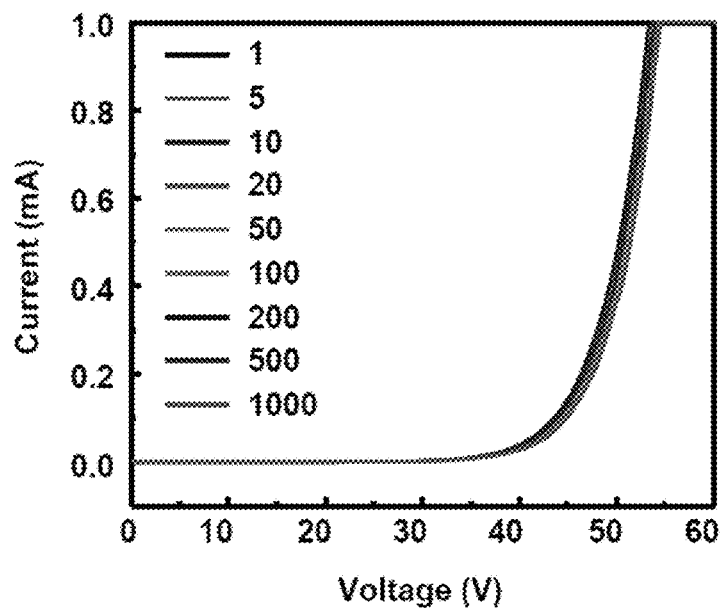
FIGS. 37A and 37B provide data showing IV characteristics of a μ-ILED array at different immersion times.
Figure 37B:
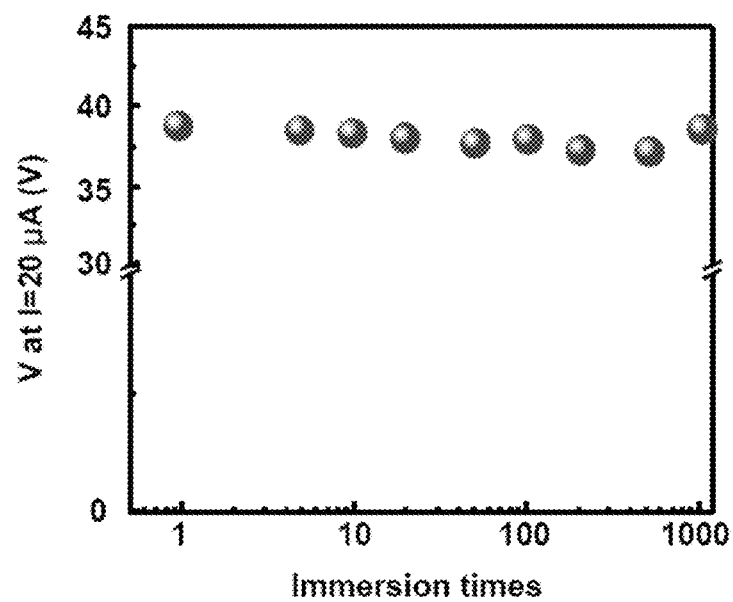

FIG. 37. IV characteristics of the same µ-ILEDs array as shown in FIG. 16C at different immersion times.

FIG. 38. (38A) Result of Luminance (L)—Current (I)—Voltage (V) measurement of an individual pixel with and without applied ohmic contacts. (38B) Applied voltage to generate a current of 20 µA, measured after different operation time. The inset provides I-V characteristics with different operation time.

FIG. 39. (39A) Schematic illustration of analytical model for the inflation and printing-down of PDMS film. (39B) FEM contours of meridional (upper left) and circumferential (lower left) strains of the inflated state and its comparison with analytical solutions calculated from Equations (S1) and (S2). (39C) FEM contours of meridional (upper left) and circumferential (lower left) strains of the as-printed state and its comparison with analytical solutions Equations (S3) and (S4) (right frame).

FIG. 40. Schematic illustration of the cross section of µ-ILEDs on a substrate.

EXAMPLE 2

Smart Sutures

Figure 41A:
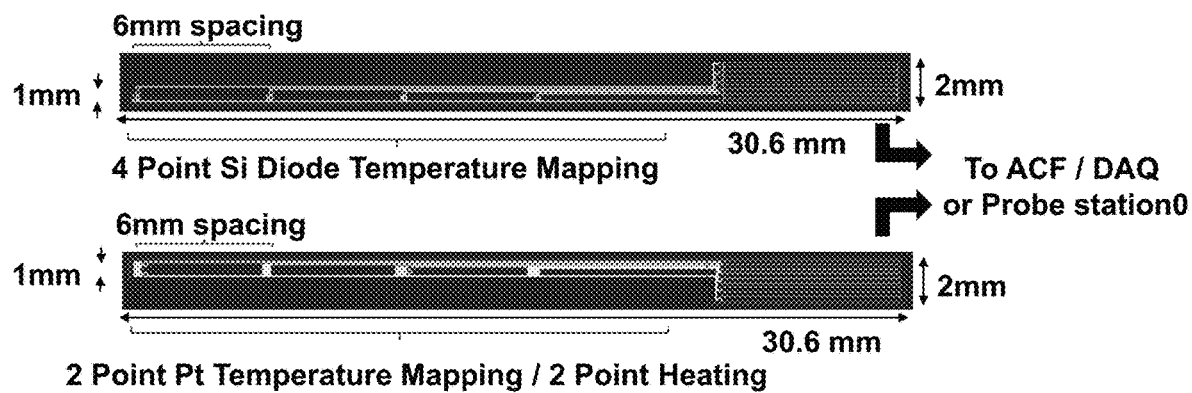
FIG. 41A provides an overview image of two smart sutures.

FIG. 41A provides typical designs smart suture thread embodiments. Thin (~1 mm) and long (~30 mm) threads that include a silicon diode based temperature sensor or a platinum resistor based temperature sensor can be fabricated on a rigid handle substrate, such as a wafer or glass substrate. The top image shows a smart suture design including four individually addressable silicon diode temperature sensors. The bottom image shows a smart suture including two individually addressable platinum resistor temperature sensors and two individually addressable resistive heating elements. Each of these smart sutures thread designs feature a 6 mm inter-element spacing and electrical interconnections to an external controller.

Figure 41B:
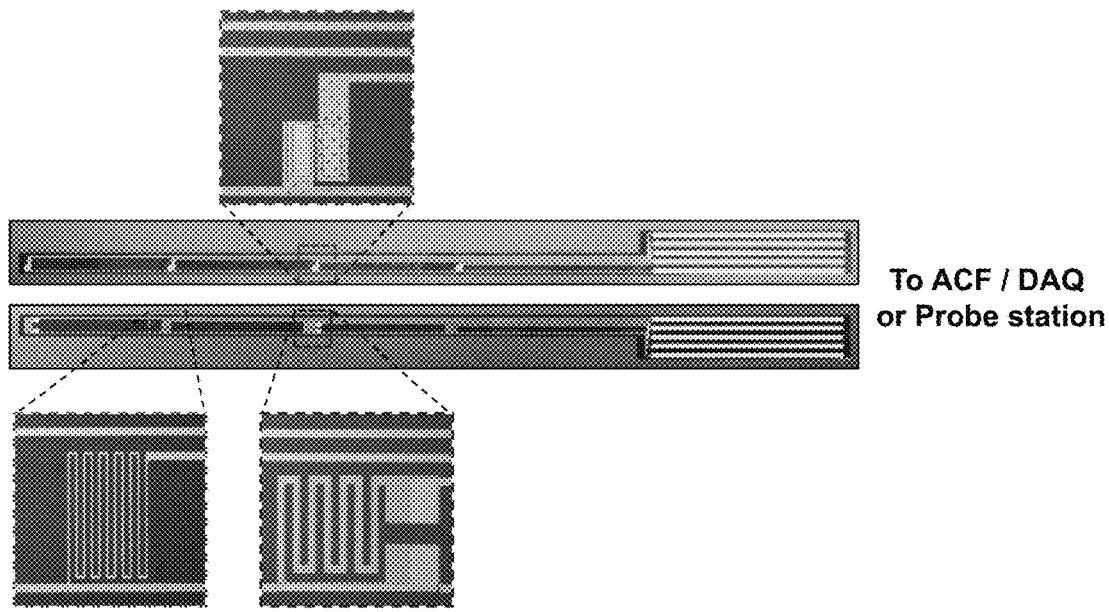
FIG. 41B provides optical images of two smart sutures.

FIG. 41B shows optical images of two smart suture thread embodiments with expanded view images of silicon diode (top) and platinum resistor (bottom right) temperature sensors. Additional functions can also be added beyond temperature sensing. For example, a gold microheater that uses resistive Joule heating can be integrated together for local heating, as shown in the expanded view image (bottom left). Local heating, together with appropriate polymers containing pharmaceutical compositions, can be utilized to selectively release the pharmaceutical compositions controllably at a desired time and location.

Figure 41C:
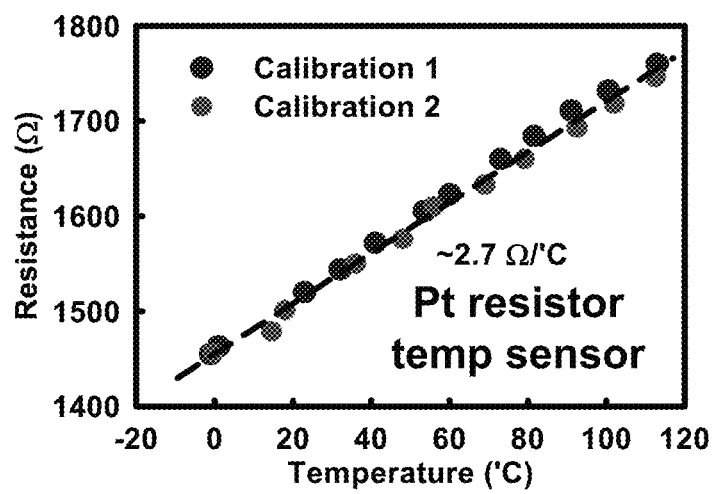
FIG. 41C provides data showing the resistance of a platinum temperature sensor as a function of temperature.
Figure 41D:
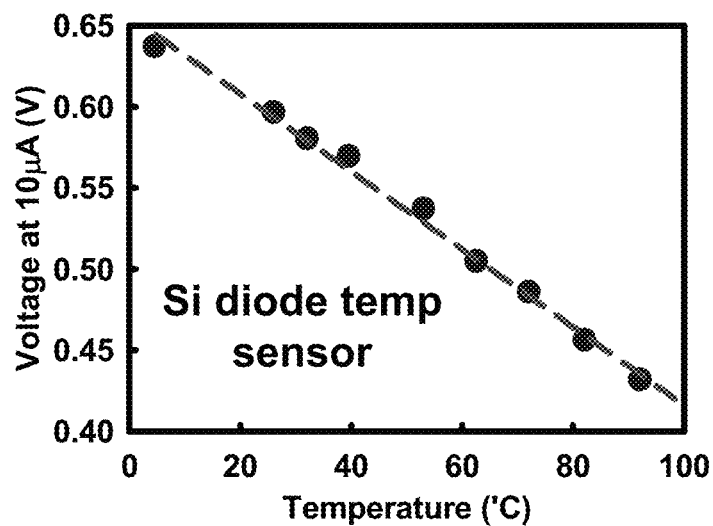
FIG. 41D provides data showing temperature sensitivity of a silicon diode temperature sensor.
Figure 41E:
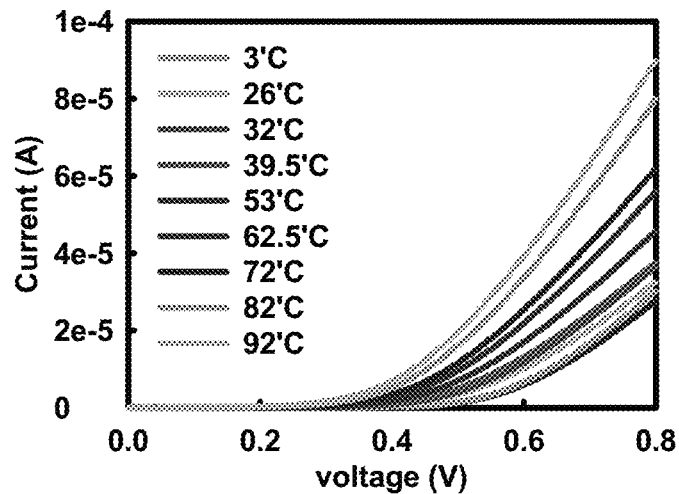
FIG. 41E provides I-V data for a temperature sensor for a number of different temperatures.

FIG. 41E shows typical current-voltage (IV) curves at different temperatures. The voltages at fixed current, for example at 10 µA, can be plotted versus temperature, as shown in FIG. 41D, which shows a linear calibration curve for the temperature sensing. Platinum resistors exhibit different resistance values at different temperatures, as plotted in FIG. 41C. When combined or used separately, these temperature sensors integrated on smart suture threads and sutured around target tissues, can monitor the local temperature to detect abnormal temperature increases, for example as caused by a local inflammation.

Figure 41F:
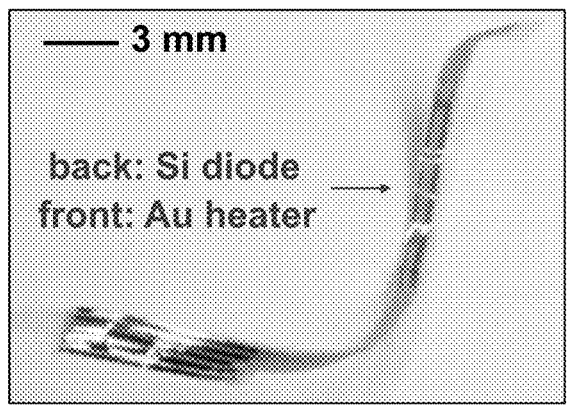
FIG. 41F provides an optical image of a smart suture.

FIG. 41F shows an optical image the resulting smart suture thread including a silicon diode temperature sensor on one side of the suture and a gold heating element on the other side of the suture.

Figure 41G:
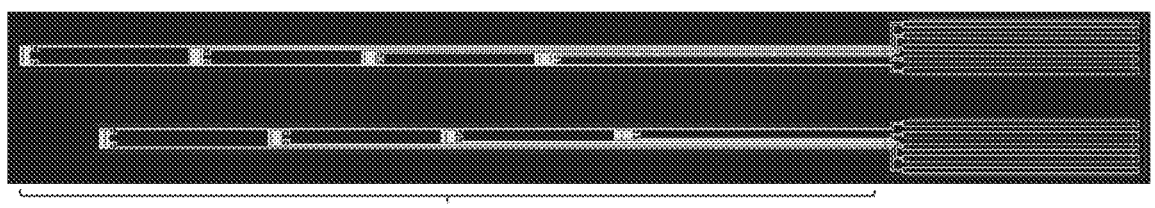
FIG. 41G provides an overview image of a two sided smart suture.

Intentionally offset temperature sensors, as shown in the two sided smart suture thread design shown in FIG. 41G, provides spatially increased detection ability versus a smart suture thread having temperature sensors aligned on opposite sides of the smart suture thread.

EXAMPLE 3

Effect of Bending on Fluid Monitors

Figure 42A:
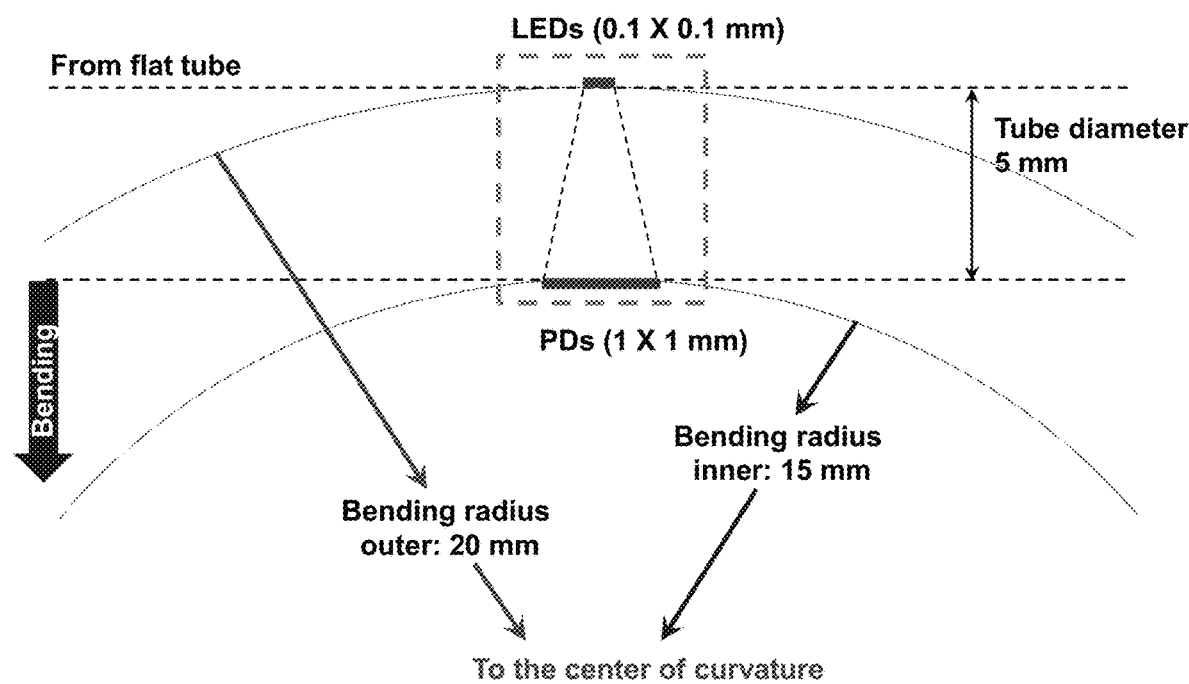
FIG. 42A provides an overview of a model for determining the effect of bending on a plasmonic crystal device and detector in a fluid monitor.

FIG. 42A shows a schematic diagram of a fluid monitor embodiment, shown here as a refractive index micro-sensor which has a thin, molded plasmonic crystal integrated with µ-LEDs on a flexible tube in flat and bent states. In the device shown, the µ-LED array has fixed dimensions of 100 µm×100 µm; the bending radius of the tube as is limited to be smaller than 4× the tube diameter to avoid folding. Additionally, the µ-LEDs and the µ-PDs are in conformal contact on a tube under any bent condition. A simple geometric calculation of collection apertures and outermost light path length based on the illustration shown FIG. 42A establishes the effects of bending on μ-PDs size and separation distance between the μ-LEDs and the μ-PDs (i.e. the outer diameter of the tube) on sensitivity. Here, sensitivity is defined as the difference of light amount that the μ-PDs can collect in flat and bent states.

Figure 42B:
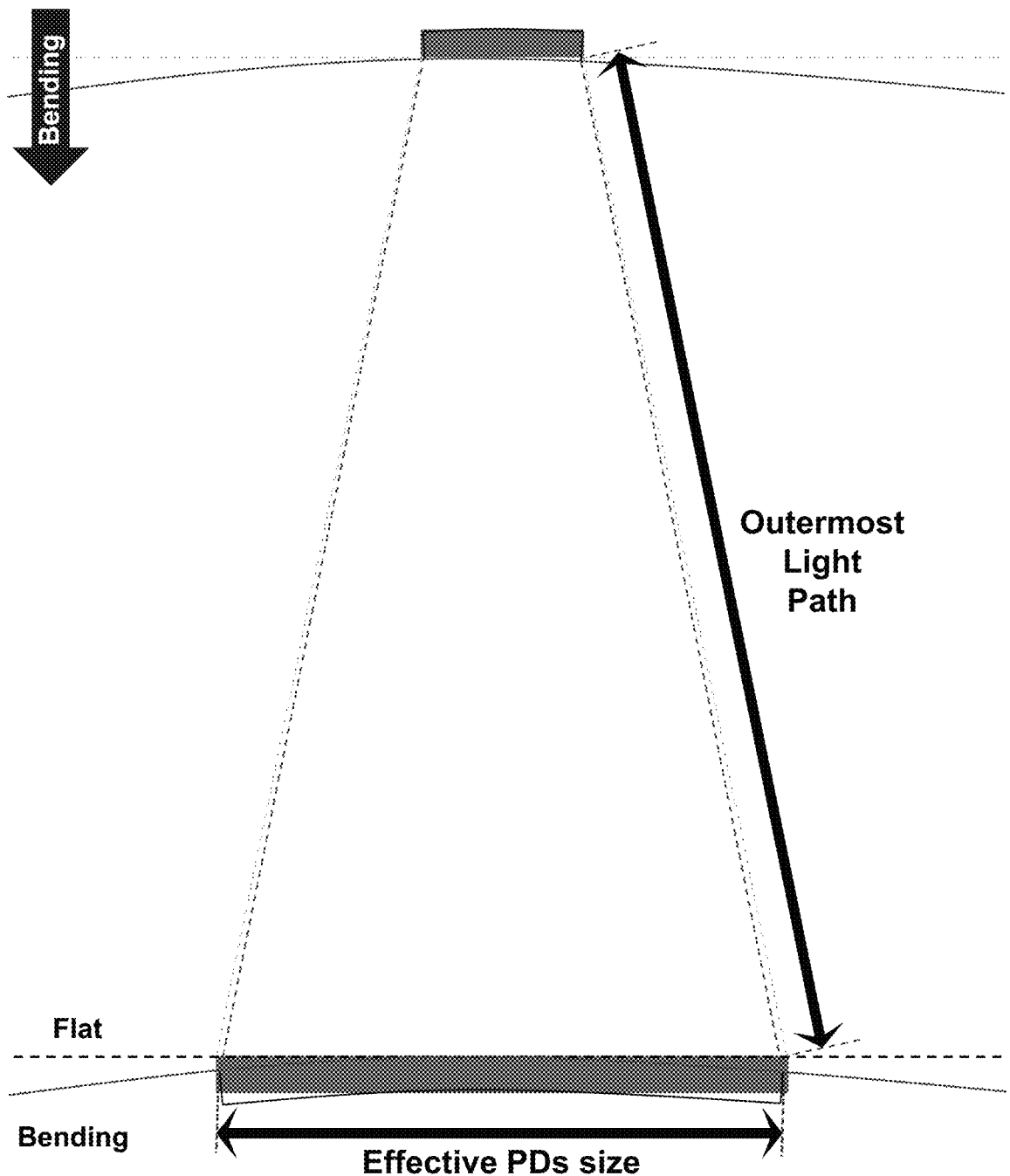
FIG. 42B shows an expanded view of the model.

FIG. 42B shows an enlarged view. The geometric calculation by light tracing reveals that the sensitivity with bending deformation is affected by μ-PDs size and tube diameter but, it change in sensitivity is negligible (<0.5%), partly due to the very small μ-LED array size and invariant solid angle of light from μ-LEDs to μ-PDs. The sensitivity due to bending can be further decreased by use of a small μ-PD array.

For the configuration shown in FIG. 41A, the effective μ-PD array area decreases by 0.22% with an increase in the outermost path of light of 0.2%. For a configuration with a tube of 2.5 mm, a μ-PD array of 1×1 mm, a μ-LED array of 100×100 μm, an outer radius of curvature of 20 mm and inner radius of curvature of 17.5 mm, the effective μ-PD array area decreases by 0.12% with an increase in the outermost path of light of 0.2%. For a configuration with a tube of 2.5 mm, a μ-PD array of 500×500 μm, an LED array of 100×100 μm and an outer radius of curvature of 20 mm and inner radius of curvature of 17.5 mm, the effective μ-PD array area decreases by 0.04% with an increase in the outermost path of light of 0.15%. These latter results demonstrate that the sensitivity to bending deformation is dependent upon the μ-PD array size when all other factors remain constant.

REFERENCES

Reuss, R. H. et al. Macroelectronics: perspectives on technology and applications. Proc. IEEE. 93, 1239-1256 (2005).

Forrest, S. R. The path to ubiquitous and low cost organic electronic appliances on plastic. Nature 428, 911-918 (2004).

Menard, E. et al. Micro- and nanopatterning techniques for organic electronic and optoelectronic systems. Chem. Rev. 107, 1117-1160 (2007).

Loo, Y.-L. & McCulloch, I. Progress and challenges in commercialization of organic electronics, MRS Bull. 33, 653-662 (2008).

So, F., Kido, J. & Burrows, P. Organic light-emitting devices for solid-state lighting, MRS Bull. 33, 663-669 (2008).

Razavi, F. H. et al. Three dimensional nanopillar array photovoltaics on low cost and flexible substrates. Nature Materials 8, 648-653 (2009).

Ko, H. et al. Flexible Carbon Nanofiber Connectors with Anisotropic Adhesion Properties. Small 6, 22-26 (2010).

Cohen-Karni, T., Timko, B. P., Weiss, L. E., & Lieber, C. M. Flexible electrical recording from cells using nanowire transistor arrays. Proc. Natl. Acad. Sci. USA 106, 7309-7313 (2009).

Timko, B. P., Cohen-Karni, T., Yu, G., Qing, Q., Tian, B., & Lieber, C. M. Electrical Recording from Hearts with Flexible Nanowire Device Arrays Nano Lett. 9, 914-918 (2009).

Siegel, A. C., Philips, S. T., Wiley, B. J., & Whitesides, G. M. Thin, lightweight, foldable thermochromic displays on paper. Lab Chip 9, 2775-2781 (2009).

Siegel, A. C. et al. Foldable Printed Circuit Boards on Paper Substrates. Adv. Funct. Mater. 20, 28-35 (2010).

Hu, L. et al. Highly conductive paper for energy-storage devices. Proc. Natl. Acad. Sci. USA 106, 21490-21494 (2009).

Hu, L. et al. Stretchable, Porous, and Conductive Energy Textiles. Nano Lett. 10, 708-714 (2010).

Sekitani, T. et al. Stretchable active-matrix organic light-emitting diode display using printable elastic conductors. Nature Mater. 8, 494-499 (2009).

Jacobs, H. O. & Whitesides, G. M. Submicrometer Patterning of Charge in Thin-Film Electrets. Science 291, 1763-1766 (2001).

Cole, J., Wang, X. & Jacobs, H. O. Patterned Growth and Transfer of ZnO Micro- and Nanocrystals with Size and Location Control. Adv. Mater. 20, 1474-1478 (2008).

Leong, T. G. et al. Tetherless thermobiochemically actuated microgrippers. Proc. Natl. Acad. Sci. USA 106, 703-709 (2009).

Park, S.-I. et al. Printed assemblies of inorganic light-emitting diodes for deformable and semitransparent displays, Science 325, 977-981 (2009).

Dupuis, D. R. & Krames, M. R. History, development, and applications of high-brightness visible light-emitting diodes, IEEE J. Lightwave Tech. 26, 1154-1171 (2008).

Kim, D.-H. et al. Materials and noncoplanar mesh designs for integrated circuits with linear elastic responses to extreme mechanical deformations, Proc. Natl. Acad. Sci. USA 105, 18675-18680 (2008).

Brown, X. Q., Ookawa, K. & Wong, J. Y. Evaluation of polydimethylsiloxane scaffolds with physiologically-relevant elastic moduli: interplay of substrate mechanics and surface chemistry effects on vascular smooth muscle cell response, Biomaterials 26, 3123-3129 (2005).

Kim, D.-H. et al. Optimized structural designs for stretchable silicon integrated circuits, Small 5, 2841-2847 (2009).

Kim, D.-H. et al., Ultrathin silicon circuits with strain-isolation layers and mesh layouts for high-performance electronics on fabric, vinyl, leather, and paper, Adv. Mater. 21, 3703-3707 (2009).

Jeon, B. S., Chun, S. Y. & Hong, C. J. Structural and mechanical properties of woven fabrics employing peirce's model, Textile Research Journal, 73, 929-933 (2003).

Gardner, W. R. & Ehlig, C. F. Physical aspects of the internal water relations of plant leaves, Plant Physiol. 40, 705-710 (1965).

Cox, H. L., The elasticity and strength of paper and other fibrous materials, Br. J. Appl. Phys. 3, 72-79 (1952).

Hayase, M. et al. Photoangioplasty with local motexafin lutetium delivery reduces macrophages in a rabbit post-balloon injury model, Cardiovascular Research 49, 449-455 (2001).

Waksman, R. et al. Photopoint photodynamic therapy promotes stabilization of atherosclerotic plaques and inhibits plaque progression, J. Am. Coll. Cardiol. 52, 1024-1032 (2008).

Woodburn, K. W. et al. Phototherapy of cancer and atheromatous plaque with texaphyrins. J. Clin. Laser Med. Surg. 14, 343-348 (1996).

Overholt, B. F., Panjehpour, M., Denovo, R. C. & Petersen, M. G., Photodynamic therapy for esophageal cancer using a 180° windowed esophageal balloon, Lasers in Surg. Med. 14, 27-33 (2005).

Sum, S., Madden, S., Hendricks, M., Chartier, S. & Muller, J. Near-infrared spectroscopy for the detection of lipid core coronary plaques. Current Cardiovascular Imaging Reports 2, 307-315 (2009).

Waxman, S. et al. In vivo validation of a catheter-based near-infrared spectroscopy system for detection of lipid core coronary plaques: initial results of the spectacl study. J. Am. Coll. Cardiol. Img. 2, 858-868 (2009).

Waxman, S. Near-Infrared Spectroscopy for Plaque Characterization, J Intery Cardiol. 21, 452-458 (2008).

Corazza, A. V., Jorge, J., Kurachi, C. & Bagnato, V. S., Photobiomodulation on the angiogenesis of skin wounds in rats using different light sources, Photomedicine and Laser Surgery 25, 102-106 (2007).

Wong-Riley, M. T. T. et al. Photobiomodulation directly benefits primary neurons functionally inactivated by toxins, J. Biol. Chem. 280, 4761-4771 (2005).

Vinck, E. M., Cagnie, B. J., Cornelissen, M. J., Declercq, H. A. & Cambier, D. C., Increased fibroblast proliferation induced by light emitting diode and low power laser irradiation, Lasers Med. Sci. 18, 95-99 (2003).

Schindl, A. et al. Direct stimulatory effect of low-intensity 670-nm laser irradiation on human endothelial cell proliferation, Br. J. Dermatol. 148, 334-336 (2003).

Amir, A. et al. The influence of helium-neon irradiation on the viability of skin flaps in the rat, Br. J. Plast. Surg. 53, 58-62 (2000).

Yao, J. et al. Functional nanostructured Plasmonic materials, Adv. Mater. 22, 1102-1110 (2010).

Yao, J. et al. Seeing molecules by eye: Surface plasmon resonance imaging at visible wavelengths with high spatial resolution and submonolayer sensitivity, Angew. Chem. 47, 5013-5017 (2008).

Lacour et al., Flexible and stretchable micro-electrodes for in vitro and in vivo neural interfaces, Med. Biol. Eng. Comput., 48:945-954 (2010).

"Guided molecular self-assembly: a review of recent efforts", Jiyun C Huie Smart Mater. Struct. (2003) 12, 264-271.

"Large-Scale Hierarchical Organization of Nanowire Arrays for Integrated Nanosystems", Whang, D.; Jin, S.; Wu, Y.; Lieber, C. M. Nano Lett. (2003) 3(9), 1255-1259.

"Directed Assembly of One-Dimensional Nanostructures into Functional Networks", Yu Huang, Xiangfeng Duan, Qingqiao Wei, and Charles M. Lieber, Science (2001) 291, 630-633.

"Electric-field assisted assembly and alignment of metallic nanowires", Peter A. Smith et al., Appl. Phys. Lett. (2000) 77(9), 1399-1401.

Rogers et al., Sci. Transl. Med. 2, 24ra22.

Greg C. Randall and Patrick S. Doyle, 102(31) p.10813-10818, PNAS

U.S. Pat. Nos. 7,705,280, 7,195,733, 7,557,367, 7,622,367 and 7,521,292.

U.S. Patent Application Publication Numbers 2009/0199960, 2007/0032089, 2008/0108171, 2008/0157235, 2010/0059863, 2010/0052112, 2010/0002402, 2010/0283069 and 2010/0121420.

International Patent Application Publication Numbers WO 2007/016524, WO 2009/114115, WO 2009/155397 and WO 2009/076088.

European Patent and Patent Application Publication Numbers EP 1467224,

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The following references relate generally to flexible and/or stretchable semiconductor materials and devices and are each hereby incorporated by reference in its entirety: U.S. patent application Ser. No. 12/778,588, filed on May 12, 2010, PCT International Application No. PCT/US05/19354, filed Jun. 2, 2005 and published under No. WO2005/122285 on Dec. 22, 2005, U.S. Provisional Patent Application No. 61/313,397, filed Mar. 12, 2010, U.S. patent application Ser. No. 11/851,182, filed Sep. 6, 2007 and published under No. 2008/0157235 on Jul. 3, 2008, and PCT International Application No. PCT/US07/77759, filed Sep. 6, 2007 and published under No. WO2008/030960 on Mar. 13, 2008.

The following references relate generally to bioresorbable substrates and methods of making bioresorbable substrates and are each hereby incorporated by reference in its entirety: PCT Patent Application PCT/US03/19968 filed Jun. 24, 2003, PCT Patent Application PCT/US04/000255 filed 1/7/2004, PCT Patent Application PCT/US04/11199 filed Apr. 12, 2004, PCT Patent Application PCT/US05/20844 filed Jun. 13, 2005, and PCT Patent Application PCT/US06/029826 filed Jul. 28, 2006.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A medical sensor comprising:
   a flexible or stretchable substrate;
   one or more flexible or stretchable light emitting diode (LED) arrays supported by said flexible or stretchable substrate, each flexible or stretchable LED array comprising one or more inorganic LEDs;
   one or more flexible or stretchable photodetector (PD) arrays supported by said flexible or stretchable substrate, each flexible or stretchable PD array comprising one or more inorganic semiconductor elements;
   an optical element in optical communication with the one or more LED arrays and/or the one or more PD arrays;
   one or more barrier layers partially encapsulating said one or more flexible or stretchable LED arrays, and said one or more flexible or stretchable PD arrays, wherein said barrier layer prevents fluid from said environment from contacting at least a portion of said inorganic LEDs of said one or more flexible or stretchable LED arrays and at least a portion of said inorganic semiconductor elements of said one or more flexible or stretchable PD arrays;
   wherein the one or more barrier layers comprise holes formed at selected regions of the one or more barrier layers, the selected regions corresponding to locations of at least some of the inorganic semiconductor elements; and
   a controller configured to measure blood oxygenation in tissue via electromagnetic radiation intensity information received from said one or more flexible or stretchable PD arrays.

2. The medical sensor of claim 1, wherein said one or more flexible or stretchable LED arrays comprises one or more individually encapsulated LED array layers provided in a multilayer stacked geometry.

3. The medical sensor of claim 1, wherein said one or more flexible or stretchable LED arrays comprises 2 to 1,000 individually encapsulated LED array layers provided in a multilayer laminated geometry.

4. The medical sensor of claim 1, wherein said one or more flexible or stretchable PD arrays comprises one or more individually encapsulated PD array layers provided in a multilayer stacked geometry.

5. The medical sensor of claim 1, wherein said one or more flexible or stretchable PD arrays comprises 2 to 1,000 individually encapsulated PD array layers provided in a multilayer laminated geometry.

6. The medical sensor of claim 1, wherein said one or more flexible or stretchable LED arrays comprise a first array of LEDs that emit light of a first wavelength range and a second array of LEDs that emit light of a second wavelength range.

7. The medical sensor of claim 6, wherein the LEDs of said first array are configured to emit red light and wherein the LEDs of said second array are configured to emit infrared light.

8. The medical sensor of claim 6, wherein said first wavelength range includes light having a wavelength of 680 nm, and wherein said second wavelength range includes light having a wavelength of 940 nm.

9. The medical sensor of claim 6, wherein the LEDs of said first array are laterally offset from the LEDs of said second array.

10. The medical sensor of claim 1, wherein the controller is configured to operate said one or more LED arrays in short pulse mode.

11. The medical sensor of claim 1, wherein the optical element comprises a coating, a reflector, a window, an optical filter, a collecting optic, a diffusing optic, a concentrating optic, or a combination thereof.

12. The medical sensor of claim 1, wherein the optical element comprises a molded structure.

13. The medical sensor of claim 1, wherein the optical element comprises a replica molded structure.

14. The medical sensor of claim 1, wherein the optical element comprises a lithographically patterned structure.

15. The medical sensor of claim 1, wherein the optical element comprises a structure patterned by nano-imprint lithography.

16. The medical sensor of claim 1, wherein the optical element comprises a lens, a diffuser, a reflective coating, a reflective coating having a transparent section, a microstructured grating, or a nanostructured grating.

17. The medical sensor of claim 1, wherein the LED arrays comprise p-LEDs and wherein the PD arrays comprise ρ-IPDs.

18. The medical sensor of claim 1, wherein the optical element comprises one or more plasmonic crystals.

19. The medical sensor of claim 1, wherein the optical element comprises a plasmonic structure including a layer of Au sputter-deposited onto a thin polymer film.

20. The medical sensor of claim 1, wherein the one or more barrier layers are mesh-structure barrier layers.

21. The medical sensor of claim 1, wherein said barrier layer provides a net permeability with respect to transport of water in said biological environment to said flexible or stretchable device low enough to prevent an electrical short circuit in said flexible or stretchable electronic circuit or wherein said barrier layer provides a net leakage current from said flexible or stretchable electronic circuit to said tissue of 10 µA or less or 0.1 µA/cm2 or less.

22. The medical sensor of claim 1, wherein said barrier layer is a moisture barrier which provides protection to components from water or other solvents.

23. The medical sensor of claim 1, wherein said barrier layer comprises windows.

\* \* \* \* \*